US008491903B2

(12) United States Patent
Dodel et al.

(10) Patent No.: US 8,491,903 B2
(45) Date of Patent: Jul. 23, 2013

(54) METHOD OF TREATMENT OF NEURODEMENTING DISEASES USING ISOLATED, MONOCLONAL, HUMAN, ANTI-B-AMYLOID ANTIBODY

(75) Inventors: Richard Dodel, Weimar a.d. Lahn (DE); Michael Bacher, Coelbe (DE); Michael Przybylski, Trebur (DE); Raluca Stefanescu, Constance (DE); Marilena Manea, Constance (DE)

(73) Assignee: Philipps-Universitaet Marburg, Marburg (DE)

( * ) Notice: Subject to any disclaimer, the term of this patent is extended or adjusted under 35 U.S.C. 154(b) by 0 days.

(21) Appl. No.: 13/079,852

(22) Filed: Apr. 5, 2011

(65) Prior Publication Data

US 2012/0039897 A1 Feb. 16, 2012

Related U.S. Application Data

(62) Division of application No. 12/013,185, filed on Jan. 11, 2008, now Pat. No. 7,939,075.

(60) Provisional application No. 60/884,526, filed on Jan. 11, 2007, provisional application No. 60/884,513, filed on Jan. 11, 2007, provisional application No. 60/981,675, filed on Oct. 22, 2007, provisional application No. 60/981,667, filed on Oct. 22, 2007.

(30) Foreign Application Priority Data

| Jan. 11, 2007 | (EP) | 07000507 |
| Jan. 11, 2007 | (EP) | 07000521 |
| Oct. 22, 2007 | (EP) | 07119002 |
| Oct. 22, 2007 | (EP) | 07119026 |

(51) Int. Cl.
*A61K 39/395* (2006.01)
(52) U.S. Cl.
USPC .................................. 424/142.1; 424/139.1
(58) Field of Classification Search
None
See application file for complete search history.

(56) References Cited

U.S. PATENT DOCUMENTS

| 6,787,139 B1 | 9/2004 | Schenk |
| 6,787,523 B1 | 9/2004 | Schenk |
| 6,818,218 B2 | 11/2004 | Schenk |
| 6,866,849 B2 | 3/2005 | Schenk |
| 6,866,850 B2 | 3/2005 | Schenk |
| 6,962,707 B2 | 11/2005 | Schenk |
| 6,972,127 B2 | 12/2005 | Schenk |
| 7,195,761 B2 | 3/2007 | Holtzman et al. |
| 8,168,185 B2 * | 5/2012 | Eon-Duval et al. ......... 424/133.1 |
| 2002/0009445 A1 | 1/2002 | Du et al. |
| 2002/0182660 A1 | 12/2002 | Fong |
| 2003/0059937 A1 | 3/2003 | Ruben et al. |
| 2003/0083277 A1 | 5/2003 | Hersh |
| 2004/0170626 A1 | 9/2004 | Shuurman et al. |
| 2005/0019330 A1 | 1/2005 | Schenk |
| 2005/0106626 A1 | 5/2005 | Pieczenik |
| 2006/0039906 A1 | 2/2006 | Holtzman et al. |
| 2006/0246071 A1 | 11/2006 | Green et al. |
| 2010/0028357 A1 * | 2/2010 | Matsubara et al. ......... 424/139.1 |

FOREIGN PATENT DOCUMENTS

| EP | 0 440 619 | 1/1996 |
| EP | 1 172 378 | 1/2002 |
| EP | 1 308 461 | 5/2003 |
| EP | 1 666 061 | 6/2006 |
| GB | 2408508 A * | 6/2005 |
| WO | 94/17197 | 8/1994 |
| WO | 96/15452 | 5/1996 |
| WO | 98/44955 | 10/1998 |
| WO | 01/42306 | 6/2001 |
| WO | 01/62801 | 8/2001 |
| WO | 02/074240 | 9/2002 |
| WO | 03/040183 | 5/2003 |
| WO | 03/051374 | 6/2003 |
| WO | 03/070760 | 8/2003 |
| WO | 03/077858 | 9/2003 |
| WO | 2004/013172 | 2/2004 |
| WO | 2004/024090 | 3/2004 |
| WO | 2004/031400 | 4/2004 |
| WO | 2004/032868 | 4/2004 |
| WO | 2004/056318 | 7/2004 |
| WO | 2004/067561 | 8/2004 |
| WO | 2004/080419 | 9/2004 |
| WO | 2005/025516 | 3/2005 |
| WO | 2005/082939 | 9/2005 |
| WO | 2005/123775 | 12/2005 |

(Continued)

OTHER PUBLICATIONS

Lambert et al. (2007) Monoclonal antibodies that target pathological assemblies of Abeta. J. Neurochem. 100:23-35.*
Lee et al. (2006) Targeting amyloid-beta peptide (Abeta) oligomers by passive immunization with a conformation-selective monoclonal antibody improves learning and memory in Abeta prescursor protein (APP) transgenic mice. J. Biol Chem. 281:4292-99.*
Liscic RM et al. (2007) Clinical and psychometric distinction of frontogemporal and Alzheimer dementias. Arch Neurol. 64:535-540.*
Mitchell et al. (2007) Curr Drug Targets. 8(7):832-838.*
Padlan et al. (1989) Proc Natl Acad Sci USA, 86:5938-5942.*

(Continued)

*Primary Examiner* — Elizabeth C Kemmerer
*Assistant Examiner* — Kimberly A Ballard
(74) *Attorney, Agent, or Firm* — Clark & Brody

(57) ABSTRACT

Isolated, monoclonal, human, anti-β-amyloid antibodies are provided which bind to dimeric forms of Ab with higher affinity than to monomeric forms of Ab and when bound to an Aβ polypeptide comprising Aβ(21-37) shield Aβ(21-37) from proteolytic digestion. The antibodies were shown to inhibit fibril formulation and reduce plaque size in vivo and to not bind brain vessel walls. Accordingly, the antibodies are useful in human and veterinary medicine for the treatment and prophylaxis of Alzheimer's disease and other neurodementing diseases. Methods of detecting or measuring the progression of a neurodementing disease also are provided.

7 Claims, 183 Drawing Sheets

FOREIGN PATENT DOCUMENTS

| | | |
|---|---|---|
| WO | 2006/017173 | 2/2006 |
| WO | 2006/040153 | 4/2006 |
| WO | 2006/047254 | 5/2006 |
| WO | 2006/055178 | 5/2006 |
| WO | 2006/081171 | 8/2006 |
| WO | 2006/081587 | 8/2006 |
| WO | 2006/094724 | 9/2006 |
| WO | 2006/103116 | 10/2006 |
| WO | 2006/118959 | 11/2006 |
| WO | 2007/062088 | 5/2007 |
| WO | 2007/064972 | 6/2007 |
| WO | 2007/068412 | 6/2007 |
| WO | 2007/108756 | 9/2007 |

OTHER PUBLICATIONS

Paul WE, editor. Fundamental Immunology, Third Edition. Raven Press, New York, 1993, pp. 292-295.*
Rudikoff et al. (1982) Proc Natl Acad Sci USA, 79(6):1979-1983.*
Vickers JC (2002) Drugs Aging. 19(7):487-494.*
Bard et al.; "Peripherally administered antibodies against amyloid β-peptide enter the central nervous system and reduce pathology in a mouse model of Alzheimer disease;" Nature Medicine; vol. 6, No. 8; Auq. 2000; pp. 916-919.
Bilkova et al.; "Epitope extraction technique using a proteolytic magnetic reactor combined with Fourier-transform ion cyclotron resonance mass spectrometry as a tool for the screening of potential vaccine lead peptides;" Eur. J. Mass Spectrom., vol. 11; 2005; pp. 489-495 (XP009084150).
Dodel et al.; "Human Antibodies against Amyloid β Peptide: A Potential Treatment for Alzheimer's Disease;" Annals of Nuerology; vol. 52, No. 2; Aug. 2002; pp. 253-256.
Dodel et al.; "Intravenous immunoglobulins containing antibodies against β-amyloid for the treatment of Alzheimer's disease;" J. Neurol. Psychiatry; vol. 75; 2004; pp. 1472-1474.
Du et al.; "Human anti-β-amyloid antibodies block β-amyloid fibril formation and prevent β-amyloid-induced neurotoxicity;" Brain; vol. 126; Jun. 23, 2003; pp. 1935-1939.
Du et al.; "Reduced levels of amyloid β-peptide antibody in Alzheimer disease;" Neurology; vol. 57; 2001; pp. 801-805.
Gruden et al.; "Autoimmune Responses to Amyloid Structures of AB(25-35)Peptide and Human Lysozyme in the Serum of Patients with Progressive Alzheimer's Disease;" Dementia and Geriatric Cognitive Disorders; vol. 18; 2004; pp. 165-171 (XP008056285).
Improta et al.; "Structure and Conformational Behavior of Biopolymers by Density Functional Calculations Employing Periodic Boundary Conditions. 1. The Case of Polyglycine, Polyalanine, and Polyo-aminoisobutyric Acid in Vacuo;" J. Am. Chem. Soc; vol. 123; 2001; pp. 3311-3322 (XP-002434952).
Istrin et al. "Intravenous immunoglobulin Enhances the Clearance of Fibrillar Amyioid-βPeptide," journal of Neuroscience Research; vol. 84; 2006; pp. 434-443.
Koo et al., "Amyloid β-protein as a substrate interacts with extracellular matrix to promote neurite outgrowth," Proc. Natl. Acad. Sci. USA; vol. 90; 1993; pp. 4748-4752 (XP-002434874).
Manea et al., "Synthesis, Solution Conformation, and Antibody Recognition of Oligotuftsin-Based Conjugates Containing a /j-Amyloid (4-10) Plaque-Specific Epitope," Bioconjugate Chem.; vol. 16; 2005; 921-928 (XP-002434951).
Manea et ai., "Polypeptide Conjugates Comprising a β-Amyloid Plaque-Specific Epitope as new Vaccine Structures Against Alzheimer's Disease," Biopolymers (Peptide Science), vol. 76; 2004; pp. 503-511 (XP009043837).
Markaryan et al., "Atypical Processing of Amyloid Precursor Fusion Protein by Proteolytic Activity in *Pichia pastoris*," Biochemical and Biophysical Research Communications; vol. 262; 1999; pp. 263-268 (XP-002441209).
McLaurin et al,, "Therapeutically effective antibodies against amyloid-β peptide target amyloid-βpeptide target amyloid-βresidues 4-10 and inhibit cytotoxicity and fibrillogenesis," Nature Medicine; vol. 8; No. 11; 2002; pp. 1263-1269.
McLean et al., "Amyloid Aβ levels in Alzheimer's disease—A diagnostic tool and the key to understanding the natural history of Aβ," Journal of Alzheimer's Disease; vol. 3; 2001; pp. 305-312 (XP009084295).
Mezo et al., "Synthesis and Structural Characterization of Bioactive Peptide Conjugates using Thioether Linkage Approaches," Journal of Peptide Science; vol. 10; 2004; pp. 701-713 (XP-002434950).
O'Nuallain et al., "Diagnostic of Therapeutic Potential of Amyloid-Reactive IgG Antibodies Contained in Human Sera," The Journal of Immunology; vol. 176; 2006; pp. 7071-7078.
Piket et al., "Amino-terminal Deletions Enhance Aggregation of β-Amyloid Peptides in Vitro," The Journal of Biological Chemistry; vol. 270; 1995; pp. 23895-23898 (XP-002444096).
Portelius et al., "An Alzheimer's disease-specific β-amyloid fragment signature in cerebrospinal fluid," Neuroscience Letters; vol. 409; 2006; pp. 215-219 (XP-002434875).
Selkoe, Dennis J.; "Translating cell biology into therapeutic advances in Alzheimer's disease;" Nature; vol. 399, No. 6738; Jun. 24, 1999; pp. A23-A31.
Solomon, Beka; "Intravenous immunoglobulin and Alzheimer's disease immunotherapy," Current Opinion in Molecular Therapeutics; vol. 9, No. 1; 2007; pp. 79-85.
Solomon, Beka; "Clinical immunologic approaches for the treatment of Alzheimer's disease," Expert Opin. Investig. Drugs; vol. 16, No. 6; 2007; pp. 819-828.
Solomon, Beka; "Antibody-mediated immunotherapy for Alzheimer's disease," Current Opinion in Investigational Drugs; vol. 8, No. 7; 2007; pp. 519-524.
Solomon, Beka: "Alzheimer's disease immunotherapy: From in vitro amyloid immunomodulation to in vivo vaccination," Journal of Alzheimer's Disease: vol. 9; 2006: pp. 433-438.
Tian et al., "Identification and structural characterization of carboxy-terminal polypeptides and antibody epitopes of Alzheimer's amyloid precursor protein using high-resolution mass spectrometry," Eur. J, Mass Spectrum; vol. 11: 2005: pp. 547-555.
Weksler et al., "Patients with Alzheimer disease have lower levels of serum anti-amyloid peptide antibodies than healthy elderly individuals," Experimental Gerontology; vol. 37; 2002; pp. 943-948 (XP002903206).
Wilcock et al., "Passive Amyloid immunotherapy Clears Amyloid and Transiently Activates Microglia in a Transgenic Mouse Model of Amyloid Deposition," The Journal of Neuroscience; vol. 24, No. 27; 2004, pp. 6144-6151
Wilcock et al., "Passive immunotherapy against Aβ in aged APP-transgenic mice reverses cognitive deficits and depletes parenchymal amyloid deposits in spite of increased vascular amyloid and microhemorrhage." Journal of Neuroinflammation: vol. 1. No. 24: 2004: pp. 1-11.
Xu et al,, "Increased incidence of anti-B-amyloid autoantibodies secreted by Epstein-Barr virus transformed B cell lines from patients with Alzheimer's disease," Mechanisms of Ageing and Development: vol. 94: 1997; No. 213-222 (XP-002434873).
Partial European Search Report EP07 00 0507; Date of Completion of the Search : May 24, 2007, 9 pages.
Partial European Search Report (EP 07 00 0521); Date of Completion of the Search: Jul. 6, 2007; 6 pages.
European Search Report (EP 07 00 0521); Date of Completion of the Search: Jul. 6, 2007; 10 pages.
European Search Report (EP 07 00 0507); Date of Completion of the Search: Jul. 31, 2007; 21 pages.
Gaskin, et al., Human Antibodies Reactive with Beta-Amyloid Protein in Alzheimer's Disease, Journal of Experimental Medicine, Tokyo, Japan, 1993, vol. 177, No. 4, pp. 1181-1186.
International Search Report for PCT/IB2008/000456, mailed Feb. 12, 2009.

* cited by examiner

1D SDS-PAGE
(DTT, 56°C)

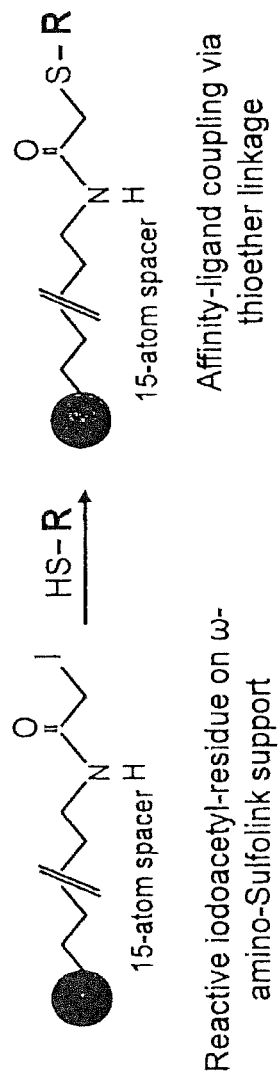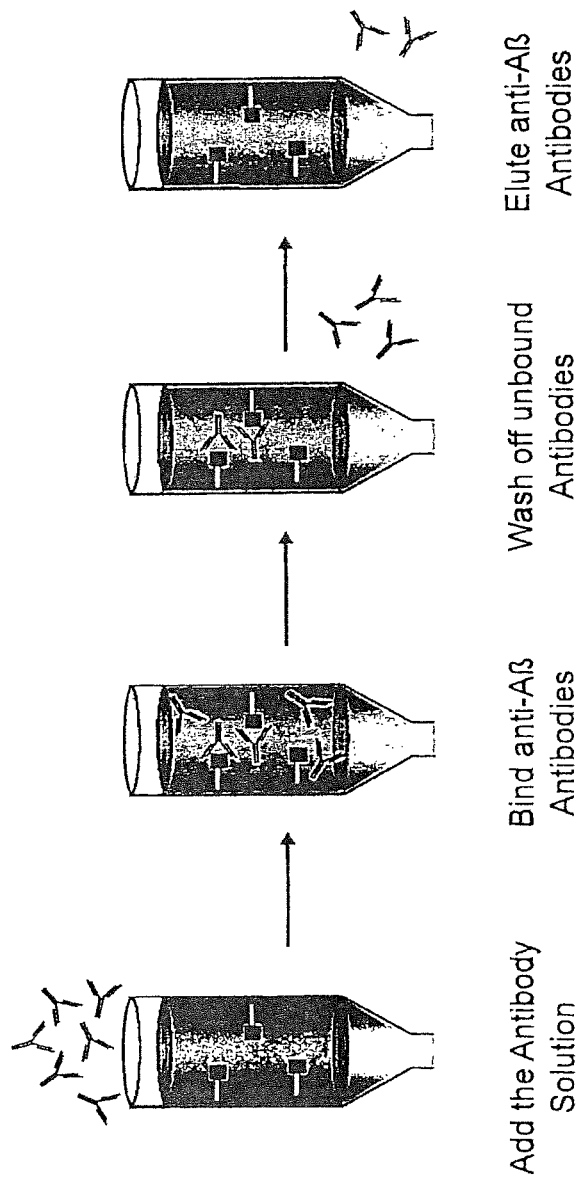
Fig. 9

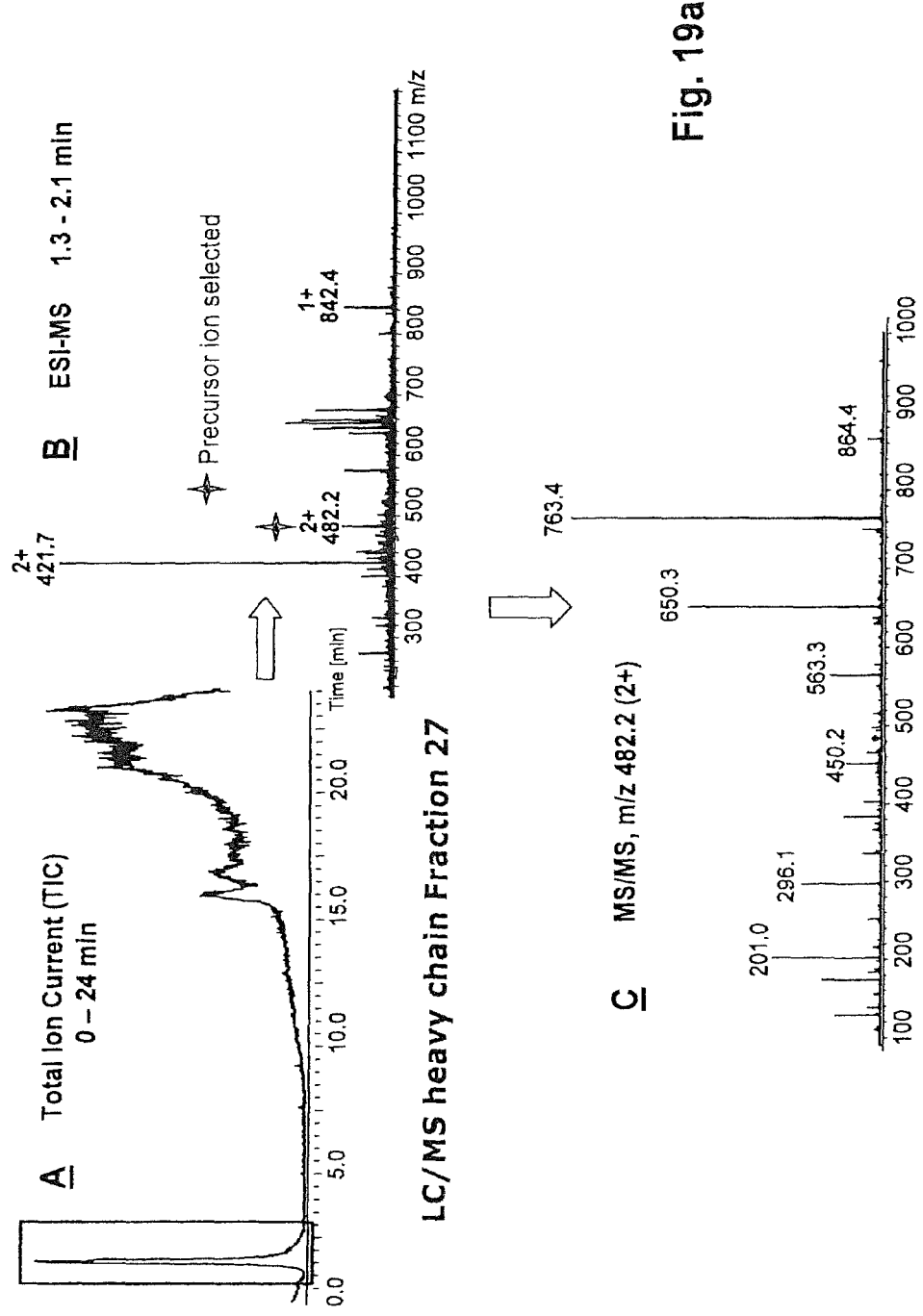

MALDI-TOF-MS / fraction 50
Serum IVIG_G1_HC(2)_1 c(138-151)

STSESTAALGCLVK
SEQ ID NO. 171

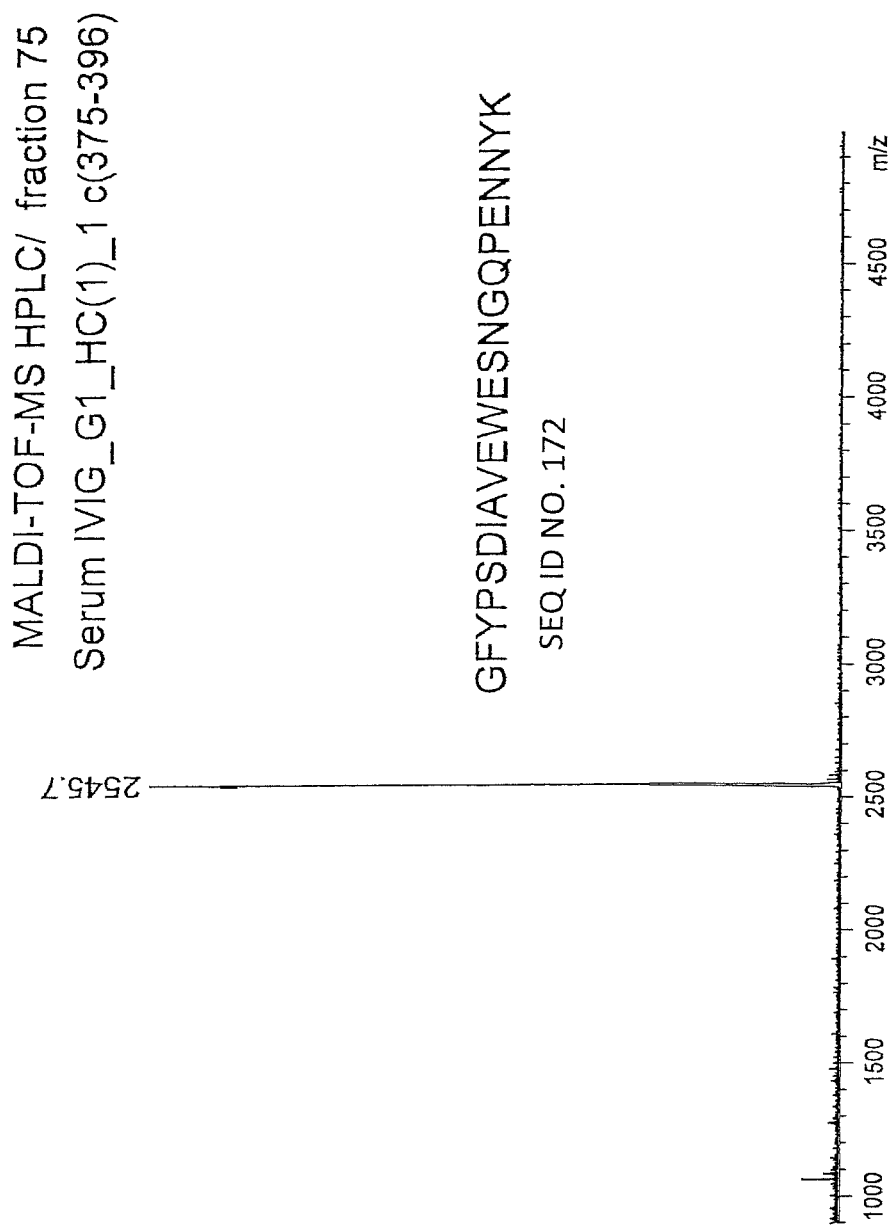

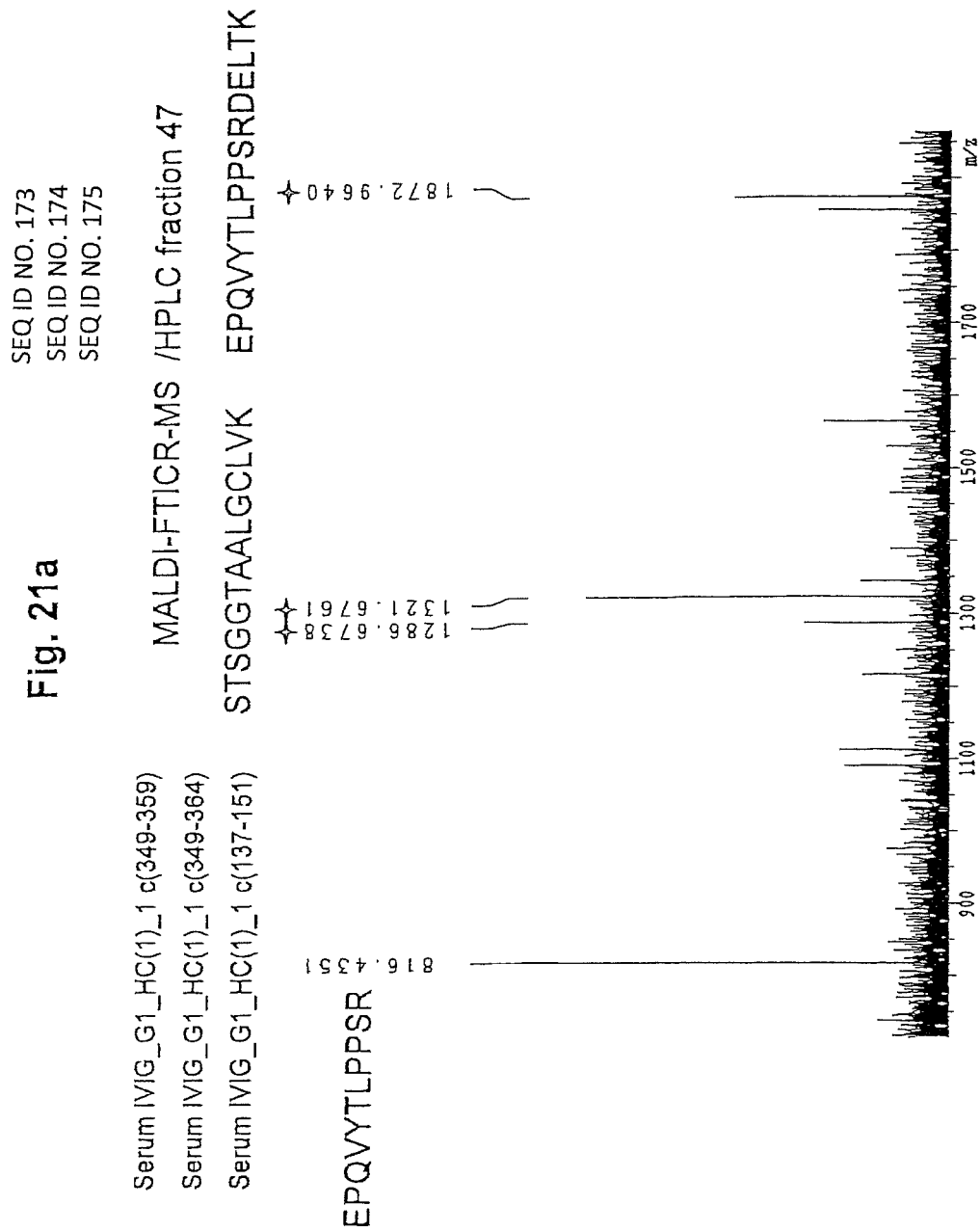

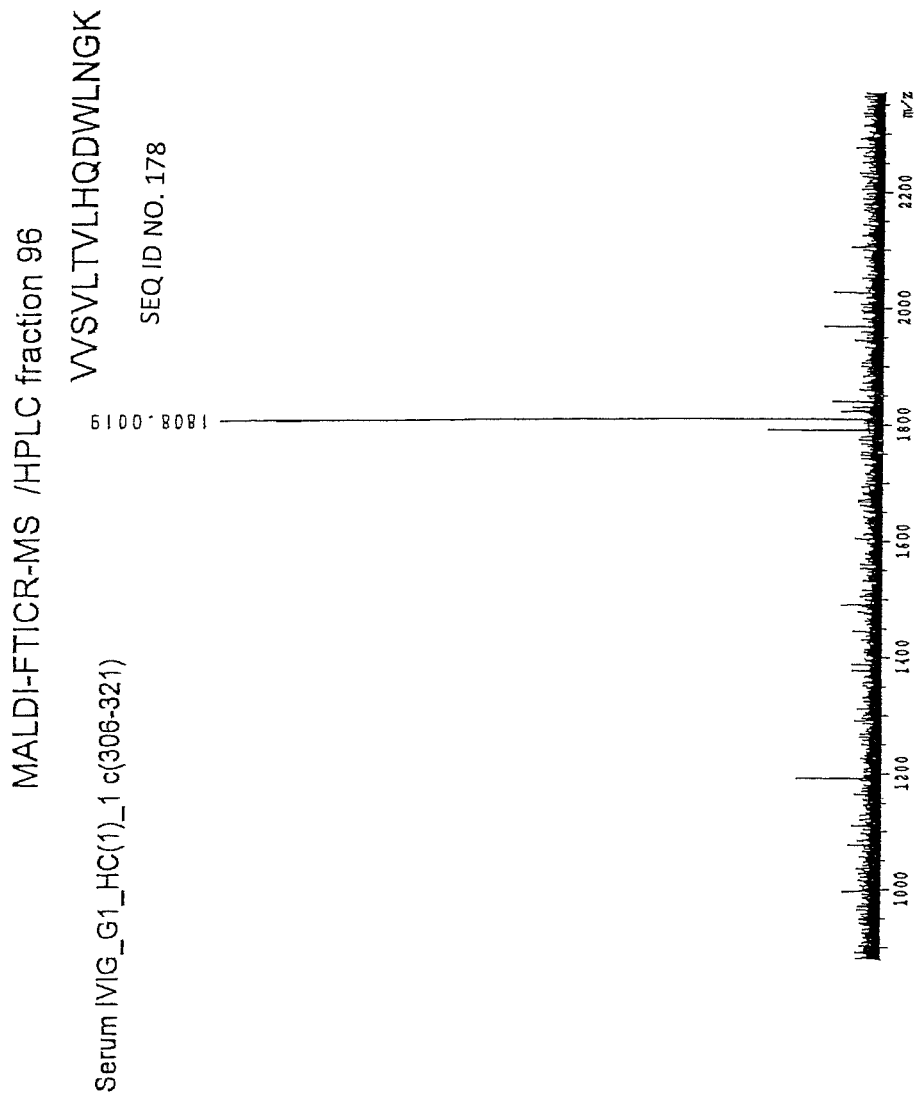

SEQ ID NO. 179, SEQ ID NO.180, SEQ ID NO.181, SEQ ID NO. 182, SEQ ID NO. 183, SEQ ID NO.184, SEQ ID NO. 185, SEQ ID NO. 186

| Name | Source | Type[1] | Connection / isoforms of constant region | CDRs | | |
|---|---|---|---|---|---|---|
| | | | | CDR1 | CDR2 | CDR3 |
| IVIG_(1)_A' | IVIG | LCk | IVIG_(4)_A / 1, 2 | 2 | 1 | 1 |
| IVIG_(2)_B' | IVIG | LCk | IVIG_(5)_B / 1, 2 | 1 | 5 | 1 |
| IVIG_(3) | IVIG | LCλ | IVIG_(4)_A / 1 | 5 | 6 | 3 |
| IVIG_(4)_A | IVIG | HC | IVIG_(1)_A' and IVIG_(3) / 1, 2, 3 | 1 | 1 | 1 |
| IVIG_(5)_B | IVIG | HC | IVIG_(2)_B' / 1, 2, 3 | 2 | 7 | 3 |
| IVIG_(6) | IVIG | LCk | --- / 1, 2 | 2 | 3 | 1 |
| IVIG_(7) | IVIG | LCk | --- / 1, 2 | 3 | 1 | 1 |
| IVIG_(8) | IVIG | LCk | --- / 1, 2 | 1 | 4 | 1 |
| Serum_(9) | Serum[2] | LCk | --- / 1 | 1 | 4 | 2 |
| Serum_(10) | Serum[3] | LCk | --- / 1, 2 | 2 | 1 | 1 |
| Serum_(11) | Serum[3] | LCk | | 4 | 2 | 1 |

[1]k, kappa, λ, lambda, light chain; HC, heavy chain
[2]PI_1, Patient_1 (Ü-30-A)
[3]PI_2, Patient_2 (Ü-30-B)

Fig. 23a

| Name | Source | Type[1] | Connection / isoforms of constant region | CDRs | | |
|---|---|---|---|---|---|---|
| | | | | CDR1 | CDR2 | CDR3 |
| IVIG_(12) | IVIgG | HC | --- / 1, 2, 3 | 1 | 6 | 1 |
| IVIG_(13) | IVIgG | HC | --- / 1, 2, 3 | 2 | 1 | 3 |
| IVIG_(14) | IVIgG | HC | --- / 1, 2, 3 | 3 | 3 | 2 |
| IVIG_(15) | IVIgG | HC | --- / 1, 2, 3 | 3 | 2 | 2 |
| IVIG_(16) | IVIgG | HC | --- / 1, 2, 3 | 8 | 7 | 4 |
| IVIG_(17) | IVIgG | HC | --- / 1, 2, 3 | 6 | 5 | 4 |
| IVIG_(18) | IVIgG | HC | --- / 1, 2, 3 | 6 | 7 | 4 |
| IVIG_(19) | IVIgG | HC | --- / 1, 2, 3 | 2 | 7 | 4 |
| IVIG_(20) | IVIgG | HC | --- / 1, 2, 3 | 2 | 1 | 4 |
| IVIG_(21) | IVIgG | HC | --- / 1, 2, 3 | 4 | 1 | 4 |

[1] HC, heavy chain

Fig. 23b

| Name | Source | Type[1] | Connection / isoforms of constant region | CDRs | | |
|---|---|---|---|---|---|---|
| | | | | CDR1 | CDR2 | CDR3 |
| Serum_(22) | Serum[2] | HC | --- / 1, 2 | 7 | 1 | 5 |
| Serum_(23) | Serum[2] | HC | --- / 1, 2 | 4 | 1 | 1 |
| Serum_(24) | Serum[3] | HC | --- / 1, 3 | 5 | 6 | 4 |
| Serum_(25) | Serum2[3] | HC | --- / 1, 3 | 2 | 4 | 1 |

[1] HC, heavy chain
[2] PI_1, Patient_1 (Ü-30-A)
[3] PI_2, Patient_2 (Ü-30-B)

| CDR1 | CDR2 | CDR3 |
|---|---|---|
| (1) SYWMS (SEQ ID NO:13) | (1) SVKQDGSEKYYVDSVKG (SEQ ID NO:21) | (1) DASSWYRDWFDP (SEQ ID NO:28) |
| (2) GYWMS (SEQ ID NO:14) | (2) RIGTAGDRYYAGSVKG (SEQ ID NO:22) | (2) GAGRWAPLGAFDI (SEQ ID NO:29) |
| (3) NYDMH (SEQ ID NO:15) | (3) RIGTAGRTNYNPSLKG (SEQ ID NO:23) | (3) DGSSWYRDWFDP (SEQ ID NO:30) |
| (4) SYWMH (SEQ ID NO:16) | (4) SVKQFFSGKYYAGSVKG (SEQ ID NO:24) | (4) DGSSWYRDWFDP (SEQ ID NO:31) |
| (5) NYWMS (SEQ ID NO:17) | (5) SVKQFFSGSAATGSVKG (SEQ ID NO:25) | (5) DAGRWADLAFDI (SEQ ID NO:32) |
| (6) SYDMS (SEQ ID NO:18) | (6) SVKQFFSGPLATGSVKG (SEQ ID NO:26) | |
| (7) SYDMS (SEQ ID NO:19) | (7) SVKQDGSEKYYVDSVKG (SEQ ID NO:27) | |
| (8) SYWMS (SEQ ID NO:20) | (8) EINRSGATNYNPSLKS (SEQ ID NO:149) | |

Fig. 24b

| | CDR1 | | CDR2 | | CDR3 |
|---|---|---|---|---|---|
| (1) | RESQGIRNYLA (SEQ ID NO:33) | (1) | GASTRAT (SEQ ID NO:38) | (1) | QQYGSSQGT (SEQ ID NO:44) |
| (2) | RASQSVNSYLA (SEQ ID NO:34) | (2) | AASIRAT (SEQ ID NO:39) | (2) | QQANSFPLT (SEQ ID NO:45) |
| (3) | RESQGIRNYLA (SEQ ID NO:35) | (3) | GAASRAT (SEQ ID NO:40) | | |
| (4) | RASQSVSSYLA (SEQ ID NO:36) | (4) | KASSLQS (SEQ ID NO:41) | | |
| | | (5) | AASSRAT (SEQ ID NO:42) | | |
| | | (6) | AASTLQS (SEQ ID NO:150) | | |
| | | (7) | KVSNRFS (SEQ ID NO:151) | | |
| | | (8) | WASTRES (SEQ ID NO:152) | | |
| LC_Lambda | | LC_Lambda | | LC_Lambda | |
| (5) | TLSSEHSTYTIE (SEQ ID NO:37) | (9) | VKSDGSH (SEQ ID NO:43) | (3) | GESHTIDGQC (SEQ ID NO:46) |

Fig. 24c

| | H31 | H32 | H33 | H34 | H35 |
|---|---|---|---|---|---|
| SEQ ID NO: 13 | S | Y | W | M | S |
| SEQ ID NO: 14 | G | Y | W | M | S |
| SEQ ID NO: 15 | N | Y | D | M | H |
| SEQ ID NO: 16 | S | Y | W | M | H |
| SEQ ID NO: 17 | N | Y | D | M | S |
| SEQ ID NO: 18 | S | Y | D | M | S |
| SEQ ID NO: 19 | S | Y | D | M | S |
| SEQ ID NO: 20 | S | Y | W | M | S |
| from SEQ ID NO: 56 | S | Y | W | M | S |
| from SEQ ID NO: 57 | G | Y | W | M | S |
| from SEQ ID NO: 58 | S | Y | W | M | S |
| from SEQ ID NO: 59 | G | Y | D | M | H |
| from SEQ ID NO: 60 | N | Y | D | M | H |
| from SEQ ID NO: 61 | N | Y | W | M | S |
| from SEQ ID NO: 62 | S | Y | D | M | S |
| from SEQ ID NO: 63 | S | Y | D | M | S |
| from SEQ ID NO: 64 | G | Y | D | M | S |
| from SEQ ID NO: 65 | G | Y | W | M | S |
| from SEQ ID NO: 66 | S | Y | W | M | S |
| from SEQ ID NO: 67 | S | Y | W | M | H |
| from SEQ ID NO: 68 | S | Y | D | M | S |
| from SEQ ID NO: 69 | N | Y | W | M | H |
| from SEQ ID NO: 70 | G | Y | W | M | S |
| from SEQ ID NO: 71 | N | Y | D | M | H |
| from SEQ ID NO: 148 | | | | | |

| | H31 | H32 | H33 | H34 | H35 |
|---|---|---|---|---|---|
| SEQ ID NO: 6 | G | | D | | S |
| | N | | M | | H |

Fig. 24d

| | H50 | H51 | H52 | H52a | H53 | H54 | H55 | H56 | H57 | H58 | H59 | H60 | H61 | H62 | H63 | H64 | H65 |
|---|---|---|---|---|---|---|---|---|---|---|---|---|---|---|---|---|---|
| SEQ ID NO: 21 | S | V | K | Q | D | G | S | E | K | Y | Y | V | D | S | V | K | G |
| SEQ ID NO: 22 | R | I | G | - | T | A | G | D | R | Y | Y | A | G | S | L | K | G |
| SEQ ID NO: 23 | R | I | K | Q | F | A | G | R | T | N | Y | N | P | S | V | K | G |
| SEQ ID NO: 24 | S | V | K | Q | F | F | S | G | K | Y | Y | A | G | S | V | K | G |
| SEQ ID NO: 25 | S | V | K | Q | F | F | S | G | P | L | A | T | G | S | V | K | G |
| SEQ ID NO: 26 | S | V | K | - | D | G | S | E | K | Y | Y | V | D | S | V | K | G |
| SEQ ID NO: 27 | S | V | N | - | R | S | G | A | T | N | Y | N | P | S | V | K | G |
| SEQ ID NO:149 | E | I | N | - | R | S | G | A | T | N | Y | N | P | S | L | K | S |
| from SEQ ID NO: 56 | S | V | K | Q | D | G | S | E | K | Y | Y | V | D | S | V | K | G |
| from SEQ ID NO: 57 | S | V | K | Q | D | G | S | E | K | Y | Y | V | D | S | V | K | G |
| from SEQ ID NO: 58 | S | V | K | Q | F | F | S | G | K | Y | Y | T | G | S | V | K | G |
| from SEQ ID NO: 59 | S | V | G | G | D | A | G | E | P | Y | Y | V | P | S | V | K | G |
| from SEQ ID NO: 60 | R | I | K | - | T | A | G | R | T | N | Y | N | P | S | L | K | G |
| from SEQ ID NO: 61 | S | V | K | Q | F | G | S | E | R | Y | Y | A | G | S | V | K | G |
| from SEQ ID NO: 62 | S | V | K | Q | D | G | S | E | K | Y | Y | V | D | S | V | K | G |
| from SEQ ID NO: 63 | S | V | K | Q | F | G | S | E | K | Y | Y | V | D | S | V | K | G |
| from SEQ ID NO: 64 | S | V | K | Q | D | G | S | E | K | Y | Y | V | D | S | V | K | G |
| from SEQ ID NO: 65 | S | V | K | Q | D | G | S | E | K | Y | Y | V | D | S | V | K | G |
| from SEQ ID NO: 66 | S | V | K | Q | D | G | S | E | K | Y | Y | V | D | S | V | K | G |
| from SEQ ID NO: 67 | S | V | K | Q | D | G | S | E | K | Y | Y | V | D | S | V | K | G |
| from SEQ ID NO: 68 | S | V | K | Q | F | F | S | G | P | L | A | T | G | S | V | K | G |
| from SEQ ID NO: 69 | S | V | K | Q | D | G | S | G | K | Y | Y | A | G | S | V | K | G |
| from SEQ ID NO: 70 | S | V | K | Q | D | F | S | A | T | N | Y | T | P | S | V | K | G |
| from SEQ ID NO: 71 | S | V | K | - | R | S | G | A | T | N | Y | N | P | S | L | K | G |
| from SEQ ID NO:148 | E | I | N | - | R | S | G | A | T | N | Y | N | P | S | L | K | S |

| | H50 | H51 | H52 | H52a | H53 | H54 | H55 | H56 | H57 | H58 | H59 | H60 | H61 | H62 | H63 | H64 | H65 |
|---|---|---|---|---|---|---|---|---|---|---|---|---|---|---|---|---|---|
| SEQ ID NO: 7 | S | V | K | - | D | G | S | E | K | Y | Y | V | D | S | V | K | G |
| | R | - | G | | F | A | G | R | P | L | A | T | G | | L | | S |
| | E | I | N | | T | S | | D | S | N | | N | P | | | | |

Fig. 24e

| | H95 | H96 | H97 | H98 | H99 | H100 | H100a | H100b | H100c | H100d | H100e | H101 | H102 |
|---|---|---|---|---|---|---|---|---|---|---|---|---|---|
| SEQ ID NO: 28 | D | A | S | S | W | Y | R | D | W | F | | D | P |
| SEQ ID NO: 29 | G | A | G | R | W | A | P | L | G | A | | D | - |
| SEQ ID NO: 30 | D | G | S | S | W | Y | R | D | W | F | | D | P |
| SEQ ID NO: 31 | D | G | S | S | W | Y | R | D | W | F | | D | P |
| SEQ ID NO: 32 | D | A | G | R | W | A | D | L | A | A | | D | - |
| from SEQ ID NO: 56 | D | A | S | S | W | Y | R | D | W | F | | D | P |
| from SEQ ID NO: 57 | D | G | S | S | W | Y | R | D | W | F | F | D | P |
| from SEQ ID NO: 58 | D | A | S | S | W | Y | R | D | W | F | | D | P |
| from SEQ ID NO: 59 | G | G | S | S | W | Y | R | D | W | F | | D | P |
| from SEQ ID NO: 60 | D | A | G | R | W | A | P | L | G | A | | D | - |
| from SEQ ID NO: 61 | D | A | S | S | W | Y | R | D | W | F | | D | P |
| from SEQ ID NO: 62 | D | G | S | S | W | Y | R | D | W | F | F | D | P |
| from SEQ ID NO: 63 | D | G | S | S | W | Y | R | D | W | F | | D | P |
| from SEQ ID NO: 64 | D | G | S | S | W | Y | P | L | G | A | | D | P |
| from SEQ ID NO: 65 | D | G | G | R | W | A | P | L | G | A | | D | - |
| from SEQ ID NO: 66 | D | A | S | S | W | Y | R | D | W | F | | D | P |
| from SEQ ID NO: 67 | D | G | S | S | W | Y | R | D | W | F | | D | P |
| from SEQ ID NO: 68 | D | A | S | S | W | A | D | L | A | A | | D | - |
| from SEQ ID NO: 69 | D | G | S | S | W | Y | R | D | W | F | | D | P |
| from SEQ ID NO: 70 | D | G | S | S | W | Y | R | D | W | F | F | D | P |
| from SEQ ID NO: 71 | D | A | S | G | W | Y | R | D | W | F | | D | P |
| from SEQ ID NO: 148 | G | G | G | R | W | A | P | L | G | A | | D | - |
| SEQ ID NO: 8 | D | A | S | S | W | Y | R | D | W | F | F | D | P |
| | G | G | G | R | W | A | P | L | G | A | - | D | - |

| | L24 | L25 | L26 | L27 | L28 | L29 | L30 | L31 | L32 | L33 | L34 |
|---|---|---|---|---|---|---|---|---|---|---|---|
| SEQ ID NO: 33 | R | E | S | Q | G | I | R | N | Y | L | A |
| SEQ ID NO: 34 | R | A | S | Q | S | V | N | S | Y | L | A |
| SEQ ID NO: 35 | R | E | S | Q | G | I | R | N | Y | L | A |
| SEQ ID NO: 36 | R | A | S | Q | S | V | S | S | Y | L | A |
| from SEQ ID NO: 47 | R | A | S | Q | S | V | N | S | Y | L | A |
| from SEQ ID NO: 48 | R | E | S | Q | G | I | R | N | Y | L | A |
| from SEQ ID NO: 50 | R | A | S | Q | S | V | N | S | Y | L | A |
| from SEQ ID NO: 51 | R | E | S | Q | G | V | R | N | Y | L | A |
| from SEQ ID NO: 52 | R | E | S | Q | G | I | R | N | Y | L | A |
| from SEQ ID NO: 53 | R | E | S | Q | G | I | R | S | Y | L | A |
| from SEQ ID NO: 54 | R | A | S | Q | S | V | N | N | Y | L | A |
| from SEQ ID NO: 55 | R | A | S | Q | S | V | S | S | Y | L | A |
| from SEQ ID NO: 145 | R | E | S | Q | G | V | R | N | Y | L | A |
| from SEQ ID NO: 146 | R | E | S | Q | G | I | R | N | Y | L | A |
| from SEQ ID NO: 147 | R | E | S | Q | G | I | R | N | Y | L | A |

| | L24 | L25 | L26 | L27 | L28 | L29 | L30 | L31 | L32 | L33 | L34 |
|---|---|---|---|---|---|---|---|---|---|---|---|
| SEQ ID NO: 9 | R | A | S | Q | G | V | N | S | Y | L | A |
| | | E | | | | | R | | | | |
| | | | | | | | S | | | | |

| | L50 | L51 | L52 | L53 | L54 | L55 | L56 |
|---|---|---|---|---|---|---|---|
| SEQ ID NO: 38 | G | A | S | T | R | A | T |
| SEQ ID NO: 39 | A | A | S | I | R | A | T |
| SEQ ID NO: 40 | G | A | A | S | R | A | T |
| SEQ ID NO: 41 | K | A | S | S | L | Q | S |
| SEQ ID NO: 42 | A | A | S | T | R | A | T |
| SEQ ID NO:150 | A | V | S | N | L | Q | S |
| SEQ ID NO:151 | K | A | S | T | R | F | S |
| SEQ ID NO:152 | W | A | S | T | R | E | S |
| from SEQ ID NO: 47 | G | A | S | T | R | A | T |
| from SEQ ID NO: 48 | A | A | S | S | R | A | T |
| from SEQ ID NO: 50 | G | A | A | T | R | A | T |
| from SEQ ID NO: 51 | G | A | S | S | R | A | S |
| from SEQ ID NO: 52 | A | A | S | T | L | Q | S |
| from SEQ ID NO: 53 | K | A | S | I | L | A | T |
| from SEQ ID NO: 54 | G | A | S | T | R | Q | S |
| from SEQ ID NO: 55 | A | A | S | N | R | A | T |
| from SEQ ID NO: 145 | A | V | S | T | L | A | S |
| from SEQ ID NO: 146 | K | A | S | N | R | F | S |
| from SEQ ID NO: 147 | W | A | S | T | R | E | S |

| | L50 | L51 | L52 | L53 | L54 | L55 | L56 |
|---|---|---|---|---|---|---|---|
| SEQ ID NO: 10 | G | A | S | S | R | A | T |
| | W | V | A | T | L | Q | S |
| | A | A | | I | R | F | |
| | K | | | N | | E | |

Fig. 24h

| | L89 | L90 | L91 | L92 | L93 | L94 | L95 | L96 | L97 |
|---|---|---|---|---|---|---|---|---|---|
| SEQ ID NO: 44 | Q | Q | Y | G | S | S | Q | G | T |
| SEQ ID NO: 45 | Q | Q | A | N | S | F | P | L | T |
| from SEQ ID NO: 47 | Q | Q | Y | G | S | S | Q | G | T |
| from SEQ ID NO: 48 | Q | Q | Y | G | S | S | Q | G | T |
| from SEQ ID NO: 50 | Q | Q | Y | G | S | S | Q | G | T |
| from SEQ ID NO: 51 | Q | Q | Y | G | S | S | Q | G | T |
| from SEQ ID NO: 52 | Q | Q | Y | N | S | F | P | L | T |
| from SEQ ID NO: 53 | Q | Q | A | G | S | S | Q | G | T |
| from SEQ ID NO: 54 | Q | Q | Y | G | S | S | Q | G | T |
| from SEQ ID NO: 55 | Q | Q | A | N | S | F | P | L | T |
| from SEQ ID NO: 145 | Q | Q | A | N | S | F | P | L | T |
| from SEQ ID NO: 146 | Q | Q | A | N | S | F | P | L | T |
| from SEQ ID NO: 147 | Q | Q | A | N | S | F | P | L | T |

| | L89 | L90 | L91 | L92 | L93 | L94 | L95 | L96 | L97 |
|---|---|---|---|---|---|---|---|---|---|
| SEQ ID NO: 11 | Q | Q | A/Y | G/N | S | S/F | Q/P | G/L | T |

|  | H31 | H32 | H33 | H34 | H35 |
|---|---|---|---|---|---|
| from SEQ ID NO: 60 | N | Y | D | M | H |
| from SEQ ID NO: 61 | N | Y | D | M | H |
| from SEQ ID NO: 62 | S | Y | W | M | S |
| from SEQ ID NO: 68 | S | Y | D | M | S |
| from SEQ ID NO: 148 | N | Y | D | M | H |

|  | H31 | H32 | H33 | H34 | H35 |
|---|---|---|---|---|---|
| SEQ ID NO: 153 | N | Y | D | M | H |
|  | S |  | W |  | S |

|                    | H31 | H32 | H33 | H34 | H35 |
|--------------------|-----|-----|-----|-----|-----|
| from SEQ ID NO: 60  | N   | Y   | D   | M   | H   |
| from SEQ ID NO: 61  | N   | Y   | D   | M   | H   |
| from SEQ ID NO: 148 | N   | Y   | D   | M   | H   |

|                | H31 | H32 | H33 | H34 | H35 |
|----------------|-----|-----|-----|-----|-----|
| SEQ ID NO: 154 | N   | Y   | D   | M   | H   |

| | H31 | H32 | H33 | H34 | H35 |
|---|---|---|---|---|---|
| from SEQ ID NO: 62 | S | Y | W | M | S |
| from SEQ ID NO: 68 | S | Y | D | M | S |
| | H31 | H32 | H33 | H34 | H35 |
| SEQ ID NO: 155 | S | Y | W<br>D | M | S |

| | H50 | H51 | H52 | H52a | H53 | H54 | H55 | H56 | H57 | H58 | H59 | H60 | H61 | H62 | H63 | H64 | H65 |
|---|---|---|---|---|---|---|---|---|---|---|---|---|---|---|---|---|---|
| from SEQ ID NO: 60 | R | I | G | | T | A | G | R | T | N | Y | N | P | S | L | K | G |
| from SEQ ID NO: 61 | R | I | G | | T | A | G | D | R | Y | Y | A | G | S | V | K | G |
| from SEQ ID NO: 62 | S | V | K | Q | D | G | S | E | K | Y | Y | V | D | S | V | K | G |
| from SEQ ID NO: 68 | S | V | K | Q | D | G | S | E | K | Y | Y | V | D | S | V | K | G |
| from SEQ ID NO: 148 | E | I | N | - | R | S | G | A | T | N | Y | N | P | S | L | K | S |
| | H50 | H51 | H52 | H52a | H53 | H54 | H55 | H56 | H57 | H58 | H59 | H60 | H61 | H62 | H63 | H64 | H65 |
| SEQ ID NO: 156 | R | | G | | D | G | S | D | R | Y | Y | A | G | S | V | K | G |
| | S | V | K | | R | S | | E | K | | | V | D | | V | | S |
| | E | | N | | | | | A | | | | | | | | | |

Fig. 24m

| | H50 | H51 | H52 | H53 | H54 | H55 | H56 | H57 | H58 | H59 | H60 | H61 | H62 | H63 | H64 | H65 |
|---|---|---|---|---|---|---|---|---|---|---|---|---|---|---|---|---|
| from SEQ ID NO: 60 | R | I | G | T | A | G | R | T | N | Y | N | P | S | L | K | G |
| from SEQ ID NO: 61 | R | I | G | T | A | G | D | R | Y | Y | A | G | S | V | K | G |
| from SEQ ID NO: 148 | E | I | N | R | S | G | A | T | N | Y | N | P | S | L | K | S |

| | H50 | H51 | H52 | H53 | H54 | H55 | H56 | H57 | H58 | H59 | H60 | H61 | H62 | H63 | H64 | H65 |
|---|---|---|---|---|---|---|---|---|---|---|---|---|---|---|---|---|
| SEQ ID NO: 157 | E | I | N | R | S | G | D | R | Y | Y | A | G | S | V | K | S |
| | | | | | | A | | | | | | | | | | |

Fig. 24n

| | H50 | H51 | H52 | H52a | H53 | H54 | H55 | H56 | H57 | H58 | H59 | H60 | H61 | H62 | H63 | H64 | H65 |
|---|---|---|---|---|---|---|---|---|---|---|---|---|---|---|---|---|---|
| from SEQ ID NO: 62 | S | V | K | Q | D | G | S | E | K | Y | Y | V | D | S | V | K | G |
| from SEQ ID NO: 68 | S | V | K | Q | D | G | S | E | K | Y | Y | V | D | S | V | K | G |
| | H50 | H51 | H52 | H52a | H53 | H54 | H55 | H56 | H57 | H58 | H59 | H60 | H61 | H62 | H63 | H64 | H65 |
| SEQ ID NO: 158 | S | V | K | Q | D | G | S | E | K | Y | Y | V | D | S | V | K | G |

| | H95 | H96 | H97 | H98 | H99 | H100 | H100a | H100b | H100c | H100d | H100e | H101 | H102 |
|---|---|---|---|---|---|---|---|---|---|---|---|---|---|
| from SEQ ID NO: 60 | G | A | G | R | W | A | P | L | G | A | F | D | I |
| from SEQ ID NO: 61 | G | A | G | R | W | A | P | L | G | A | F | D | I |
| from SEQ ID NO: 62 | D | G | S | S | W | Y | R | D | W | F | | | P |
| from SEQ ID NO: 68 | D | A | G | R | W | A | D | L | A | F | | D | I |
| from SEQ ID NO: 148 | G | A | G | R | W | A | P | L | G | A | F | D | I |

| | H95 | H96 | H97 | H98 | H99 | H100 | H100a | H100b | H100c | H100d | H100e | H101 | H102 |
|---|---|---|---|---|---|---|---|---|---|---|---|---|---|
| SEQ ID NO: 159 | D | G | S | S | W | Y | R | D | W | F | - | D | P |
| | | | | | | | D | | A | | | | |

| | H95 | H96 | H97 | H98 | H99 | H100 | H100a | H100b | H100c | H100d | H100e | H101 | H102 |
|---|---|---|---|---|---|---|---|---|---|---|---|---|---|
| from SEQ ID NO: 60 | G | A | G | R | W | A | P | L | G | A | F | D | I |
| from SEQ ID NO: 61 | G | A | G | R | W | A | P | L | G | A | F | D | I |
| from SEQ ID NO: 148 | G | A | G | R | W | A | P | L | G | A | F | D | I |
| | H95 | H96 | H97 | H98 | H99 | H100 | H100a | H100b | H100c | H100d | H100e | H101 | H102 |
| SEQ ID NO: 160 | G | A | G | R | W | A | P | L | G | A | F | D | I |

Fig. 24q

| | H95 | H96 | H97 | H98 | H99 | H100 | H100a | H100b | H100c | H100d | H101 | H102 |
|---|---|---|---|---|---|---|---|---|---|---|---|---|
| from SEQ ID NO: 62 | D | G | S | S | W | Y | R | D | W | F | D | P |
| from SEQ ID NO: 68 | D | A | G | R | W | A | D | L | A | F | D | I |

| | H95 | H96 | H97 | H98 | H99 | H100 | H100a | H100b | H100c | H100d | H101 | H102 |
|---|---|---|---|---|---|---|---|---|---|---|---|---|
| SEQ ID NO: 161 | D | G | S | S | W | Y | R | D | W | F | D | P |
| | | A | G | R | | A | D | L | A | | | I |

Fig. 25a

```
1   EIVLTQSPAT LSLSPGERVT ITCRASQSVN SYLAWYQQKP GQAPRLLIY
50  GASTRAIGIP DRFSGSGSGT DFTLTISRLE PEDFAVYYCQ QYGSSQGTFG
100 PGTKVDIKR
```

SEQ ID NO: 47

Edman, N-terminal, MALDI-TOF-MS, MALDI-FTMS, MS/MS

▓ = CDRs

Fig. 25b

1   EIVLTQSPAT LSLSPGERVT ITCRASQGIR NYLAWYQQKP GQAPRLLIY

50  AASSRATGIP DRFSGSGSGT DFTLTISRLE PEDFAVYYCQ QYGSSQGTFG

100 PGTKVDIKR

SEQ ID NO: 48

Edman, N-terminal, MALDI-TOF-MS, MALDI-FTMS, MS/MS

▨ = CDRs

Fig. 25c

```
  1 LPVLTQPPSA SALLGASIKL TCTLSSEHSTYTIAWHQQRP GRSPQYIMKV
 51 KSDGSHSKGD GIPDRFMGSS SGADRYLTFS NLQSDDEAEY HCQTWHSNHWV
101 FGGGTK L
```

SEQ ID NO: 49

Edman, N-terminal, MALDI-TOF-MS, MALDI-FTMS, MS/MS  ▓▓▓ = CDRs

Fig. 25e

1   EIVLTQSPAT LSLSPGERVT ITCRESQGIR NYLAWYQQKP GQAPRLLIY

50  GASTRATGIP DRFSGSGSGT DFTLTISRLE PEDFAVYYCQ QYGSSQGTFG

100 PGTKVDIKR

SEQ ID NO: 51

Edman, N-terminal, MALDI-TOF-MS, MALDI-FTMS, MS / MS

▓ = CDRs

```
1   EIVMTQSPAT LSLSPGERVT ITCRASQGIR NYLAWYQQKP GQAPRLLIY
50  AASTLQSGVP SRFSGSGSGT DFTLTISRLE PEDFAVYYCQ QYGSSQGTFG
100 PGTKVDIKR
```

SEQ ID NO: 52

= CDRs

Edman, N-terminal, MALDI-TOF-MS, MALDI-FTMS, MS/MS

Fig. 25g

1   DVVMTQSPSS LSASVGDRVT ITCRESQGIR NYLAWYQQKP GKAPKLLIYK

51  ASSIQSGVPS RFSGSLLGGK AALTLSGVQP EDFATYYCQ QANSFPLTFGG

101 GTKVEIKR

SEQ ID NO: 53

Edman, N-terminal, MALDI-TOF-MS, MALDI-FTMS, MS/MS

▆ = CDRs

Fig. 25h

```
1   DIVLTQSPAT LSLSPGERVT ITCRASQSVN SYLAWYQQKP GQAPRLLIY
50  GASTRATGIP DRFSGSGSGT DFTLTISRLE PEDFAVYYCQ QYGSSQGTFG
100 PGTKVDIKR
```

SEQ ID NO: 54

Edman, ----  N-terminal, — — —  MALDI-TOF-MS, — · —  MALDI-FTMS, — · · —  MS/MS, ······

▓ = CDRs

```
  1 DIQMTQSPGT LSLSPGERAA LSCRASQSVS SYLAWYQQKP GQAPRLLIY
 50 AASTRATGIP DRFSGSGSGT DFTLTISRLE PEDFAVYYCQ QYGSSQGTFG
100 PGTKVDIKR
```

SEQ ID NO: 55

Edman, N-terminal, MALDI-TOF-MS, MALDI-FTMS, MS/MS

= CDRs

Fig. 25j

```
  1 DVVMTQSPSS LSASVGDRVT ITCRESQGIR NYLAWYQQKP GKAPKLLIYA
 51 ASTLQSGVPS RFSGSLIGGK AALTLSGVQP EDFATYYCQ QANSFPLTFGG
101 GTKVEIKR
```

SEQ ID NO: 145

Edman, N-terminal, MALDI-TOF-MS, MALDI-FTMS, MS/MS

= CDRs

Fig. 25k

```
  1 DVVMTQSPSS LSASVGDRVT ITCRESQGIR NYLAWYQQKP GKAPKLLIYK
 51 VSNRFSGVPS RFSGSLLGGK AALTLSGVQP EDFATYYCQ QANSFPLTFGG
101 GTKVEIKR
```

SEQ ID NO: 146

■ = CDRs

Edman, N-terminal, MALDI-TOF-MS, MALDI-FTMS, MS/MS

Fig. 25I

```
  1  DVVMTQSPSS LSASVGDRVT ITCRESQGIRNYLAWYQQKP GKAPKLLIYW
 51  ASTRESGVPS RFSGSLLGGK AALTLSGVQP EDFATYYCQHQANSFPLTFGG
101  GTKVEIKR
```

SEQ ID NO: 147

Edman, N-terminal, MALDI-TOF-MS, MALDI-FTMS, MS/MS

▓ = CDRs

Fig. 26a

1 EVQLVESGGG VVQPGGSLRL SCAASGFTFR SYAMS WVRQA PGKGLEWVAS

51 VKQDGSEKYY VDSVKGRFTI SRDTSKNTLY LQMNSLRAED TAVYYCARDA

101 SSWYRDWFDF WGQGTLVTVS

SEQ ID NO: 56

Edman, N-terminal, MALDI-TOF-MS, MALDI-FTMS, MS/MS

■ = CDRs

Fig. 26b

```
  1 EVQLVESGGG VVQPGGSLRL SCAASGFTFR GVWMSWVRQA PGKGLEWVAS
 51 VKQDGSEKYY VDSVKGRFTI SRDTSKNTLY LQMNSLRAED TAVYYCARDG
101 SSWYRDWFDP WGQGTLVTVS
```

SEQ ID NO: 57

Edman, N-terminal, MALDI-TOF-MS, MALDI-FTMS, MS/MS

▨ = CDRs

```
  1 EVQLVESGGG VVQPGGSLRL SCAASGFTFR SYWMSWVRQA PGKGLEWVAS
 51 VKQEFSGPLA TGSVKGRFTI SRDNAKNTLY LQMNSLRAED TAVYYCARDA
101 SSWYRDWFDP WGQGTLVTVS
```

SEQ ID NO: 58

Edman, N-terminal, MALDI-TOF-MS, MALDI-FTMS, MS/MS

= CDRs

```
  1 EVQLVESGGG VVQPGGSLRL SCAASGFTFR GYWMS WVRQA PGKGLEWVA S
 51 VKQDGSEKYY VDSVKG RFTI SRDNAKNQFS LKLSSVTAAD TAVYYCAR DF
101 SSNYRGNFDP WGQGTLVSVS
```

SEQ ID NO: 59

Edman, N-terminal, MALDI-TOF-MS, MALDI-FTMS, MS / MS

= CDRs

```
  1 EVQLVESGGG VVQPGGSLRL SCAASGFTFR N[FDYM]WVRQG IGKGLEWVG[I]
 51 [IGTAGRTNYAN ESEK]RFTIS RENAKDSLYL QMNSLRVGDA AVYYCAR[GAS]
101 [RWAPHEAFDL] WGQGTLVIVS
```

SEQ ID NO: 60

Edman, N-terminal, MALDI-TOF-MS, MALDI-FTMS, MS/MS  = CDRs

Fig. 26f

```
1   EVQLVESGGG VVQPGGSLRL SCAASGFTFR NYDMHWVRQG IGKGLVWVSR
51  IGTAGDRYYA GSVKGRFTIS RENAKDSLYL QMNSLRVGDA AVYYCARGAG
101 RWAPLGAFDL WGQGTLVIVS
```

SEQ ID NO: 61

Edman, N-terminal, MALDI-TOF-MS, MALDI-FTMS, MS/MS ........ = CDRs

Fig. 26g

```
  1 EVQLVESGGG VVQPGGSLRL SCAASGFTFS SYAMSWVRQA PGKGLEWVA
 51 VRQDGSEKYY VDSVKGRFTI SRDNAKNTLY LQMNSLRAED TAVYYCARDL
101 SSYYRDWFDP WGQGTLVTVS
```

SEQ ID NO: 62

Edman, N-terminal, MALDI-TOF-MS, MALDI-FTMS, MS/MS ▓ = CDRs

1   EVQLVESGGG VVQPGGSLRL SCAASGFTFR SYDMSWVRQA PGKGLEWVAS
51  VKQFFSGSAA TGSVKGRFTI SRDNAKNTLY LQMNSLRAED TAVYYCARDG
101 SISWYRDWHDP WGQGTLVTVS

SEQ ID NO: 63

Edman, N-terminal, MALDI-TOF-MS, MALDI-FTMS, MS/MS

= CDRs

Fig. 26i

```
  1 EVQLVESGGG VVQPGGSLRL SCAASGFTFR SRYDMSWVRQA PGKGLEWVA
 51 VRQDSSEKY VDSVKGRPTI SRDNAKNQLS LKLSSVTAAD TAVYYCAR
101 SSHEREMELF WGQGTLVTVS
```

SEQ ID NO: 64

Edman, N-terminal, MALDI-TOF-MS, MALDI-FTMS, MS/MS

▓ = CDRs

Fig. 26j

```
  1  EVQLVESGGG VVQPGGSLRL SCAASGFTFR ░░░░░ WVRQA PGKGLEWVA░
 51  ░░░░░░░░░░░░░░░░░░░ RITL SVDTSKNQFS LKLSSVTAAD TAVYYCAR░░
101  ░░░░░░░░ WGQGTLVSVS
```

SEQ ID NO: 65

▓ = CDRs

Edman, N-terminal, MALDI-TOF-MS, MALDI-FTMS, MS/MS

Fig. 26k

```
1   EVQLVESGGG VVQPGGSLRL SCAASGFTFR [GYAMS]WVRQA PGKGLEWVA[...]
51  [VKQDGSEKYY VDSVKG]RVTI SVETSKNQFS LKLSSVTAAD TAVYYCAR[DL]
101 [SSTYRGNFDP] WGQGTLVSVS
```

SEQ ID NO: 66

▬ = CDRs

Edman, N-terminal, MALDI-TOF-MS, MALDI-FTMS, MS/MS

Fig. 26I

```
1   EVQLVESGGG VVQPGGSLRL SCAASGFTFR ▇▇▇▇▇WVRQA PGKGLEWVA▇
51  ▇▇▇▇▇▇▇▇▇▇ ▇▇▇▇▇▇▇RVTI SLDTSKNQFS LKLSSVTAAD TAVYYCAR▇▇
101 ▇▇▇▇▇▇▇▇▇▇ WGQGTLVSVS
```

SEQ ID NO: 67

Edman, N-terminal, MALDI-TOF-MS, MALDI-FTMS, MS/MS    ▇▇ = CDRs

Fig. 26m

```
  1 EVQLVESGGG VVQPGGSLRL SCAASGITFR [SYDMH]WVRQA PGKGLEWVA[.]
 51 [VKQDGSEKXY VDSVKG]RFTV SRDNAKNTLY LQMNSLRAED TAVYYCAR[DA]
101 [GRWADIAFDI]WGQGTLVTVS
```

SEQ ID NO: 68

Edman, N-terminal, MALDI-TOF-MS, MALDI-FTMS, MS / MS ▓ = CDRs

Fig. 26n

```
1   EVQLVESGGG VVQPGGSLRL SCAASGFTFR SYGMHWVRQA PGKGLEWVA
51  VKQDESYKYY VESVKGRVTI TADRAKNTLY LQMNSLRAED TAVYYCARDR
101 SSAROWFDP WGQGTLVTVS
```

SEQ ID NO: 69

Edman, N-terminal, MALDI-TOF-MS, MALDI-FTMS, MS/MS

= CDRs

```
  1 EVQLVESGGG VVQPGGSLRL SCAASGFTER NYWMSWVRQA PGKGLEWVAS
 51 VKQFFISGPLA TGSVKGRFTI SRDTSKNTLY LQMNSLRAED TAVYYCARDG
101 SSWYRDWFDP WGQGTLVTVS
```

SEQ ID NO: 70

Edman, N-terminal, MALDI-TOF-MS, MALDI-FTMS, MS/MS

= CDRs

Fig. 26p

1   EVQLVESGGG VVQPGGSLRL SCAASGFTFR ░░░░░ WVRQA PGKGLEWVA░
51  ░░░░░░░░░░ ░░░░░░░░ERVTI SVETSKNQFS LKLSSVTAAD TAVYYCAR░░
101 ░░░░░░WGQGTLVSVS

SEQ ID NO: 71

Edman, N-terminal, MALDI-TOF-MS, MALDI-FTMS, MS/MS

░░░ = CDRs

```
  1  EVQLVESGGG VVQPGGSLRL SCAASGFTFR NYAMHWVRQG IGKGLEWVCR
 51  INRSSGWINAN PSENSRFTIS RENAKDSLYL QMNSLRVGDA AVYYCARGAS
101  RWAPLGALPD WGQGTLVIVS
```

SEQ ID NO: 148

Edman, N-terminal, MALDI-TOF-MS, MALDI-FTMS, MS/MS

= CDRs

Fig. 27a

```
101       T VAAPSVFIFP PSDEQLKSGT ASVVCLLNNF YPREAKVQWK
151 VDNALQSGNS QESVTEQDSK DSTYSLSSTL TLSKADYEKH KVYACEVTHQ
201 GLSSPVTKSF NRGEC
```

SEQ ID NO: 72

Edman, N-terminal, MALDI-TOF-MS, MALDI-FTMS, MS / MS

Fig. 27b

```
101       T VAAPSVFIFP PSDEQLKSGT ASVVCLLNNF YPREAKVQWK
151 VDNALQSGNS QESVTEQDSK DSTYSLSSTL TLSKADYEKH KLYACEVTHQ
201 GLSSPVTKSF NRGEC
```

SEQ ID NO: 73

Edman, N-terminal, MALDI-TOF-MS, MALDI-FTMS, MS/MS

Fig. 27c

```
101       TVLGQPKAA PSVTLFPPSS EELQANKATL VCLISDFYPG
151 AVTVAWKADS SPVKAGVETT TPSKQSNNKY AASSYLSLTP EQWKSHRSYS
201 CQVTHEGSTV EKTVAPTECS
```

SEQ ID NO: 74

Edman, N-terminal, MALDI-TOF-MS, MALDI-FTMS, MS/MS

```
  1 EIVLTQSPAT LSLSPGERVT ITCRASQSVN SYLAWYQQKP GQAPRLLIY
 50 GASTRATGIP DRFSGSGSGT DFTLTISRLE PEDFAVYYCQ QYGSSQCTFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KLYACEVTHQ
200 GLSSPVTKSF NRGEC
```

SEQ ID NO: 79

Edman, N-terminal, MALDI-TOF-MS, MALDI-FTMS, MS/MS

= CDRs

Fig. 29c

1   EIVLTQSPAT LSLSPGERVT IT RESQGIR NMLAWYQQKP GQAPRLLIY
50  AASSRAT GIP DRFSGSGSGT DFTLTISRLE PEDFAVYY Q QYGSSQT FG
100 PGTKVDIKRT VAAPSVFIFP PSDEQLKSGT ASVV LLNNF YPREAKVQWK
150 VDNALQSGNS QESVTEQDSK DSTYSLSSTL TLSKADYEKH KVYA EVTHQ
200 GLSSPVTKSF NRGE

SEQ ID NO: 80

Edman, ——  N-terminal, — ·  MALDI-TOF-MS, — — —  MALDI-FTMS, – – –  MS / MS, ·······  ▓ = CDRs

Fig. 29d

```
1    EIVLTQSPAT LSLSPGERVT ITCRESQGIR NYLAWYQQKP GQAPRLLIY
50   AASSRATGIP DRFSGSGSGT DFTLTISRLE PEDFAVYYCQ QYGSSQGTFG
100  PGTKVDIKRT VAAPSVFIFP PSDEQLKSGT ASVVCLLNNF YPREAKVQWK
150  VDNALQSGNS QESVTEQDSK DSTYSLSSTL TLSKADYEKH KLYACEVTHQ
200  GLSSPVTKSF NRGEC
```

SEQ ID NO: 81

Edman, N-terminal, MALDI-TOF-MS, MALDI-FTMS, MS/MS

= CDRs

```
  1 LPVLTQPPSA SALLGASIKL TCTLSSGHSSYAIAWHQQRP GRSPQYIMKV
 51 KSDGSHSKGD GIPDRFMGSS SGADRYLTFS NLQSDDEAEY HCGTGYVDIG
101 LQGWVFGGGTK LTVLGQPKAA PSVTLFPPSS EELQANKATL VCLISDFYPG
151 AVTVAWKADS SPVKAGVETT TPSKQSNNKY AASSYLSLTP EQWKSHRSYS
201 HQVTHEGSTV EKTVAPTECS
                    HC-LC
```

SEQ ID NO: 82

Edman, N-terminal, MALDI-TOF-MS, MALDI-FTMS, MS/MS     = CDRs

Fig. 29f

```
  1 DIQMTQSPAT LSLSPGERAA LSCRASQSVN SYLAWYQQKP GQAPRLLIY
 50 GAASRATGIP ARFSGSGSGT DFTLTISRLE PEDFAVYYCQ QYGSSQGTFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KVYACEVTHQ
200 GLSSPVTKSF NRGEC
```

SEQ ID NO: 83

Edman, N-terminal, MALDI-TOF-MS, MALDI-FTMS, MS/MS

▓ = CDRs

Fig. 29g

1   DIQMTQSPAT LSLSPGERAA LSCRASQSVN SYLAWYQQKP GQAPRLLIY
50  GAASRATGIP ARFSGSGSGT DFTLTISRLE PEDFAVYYCQ QYGSSQGTFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KLYACEVTHQ
200 GLSSPVTKSF NRGEC

SEQ ID NO: 84

Edman, N-terminal, MALDI-TOF-MS, MALDI-FTMS, MS/MS

■ = CDRs

Fig. 29h

```
1   EIVLTQSPAT LSLSPGERVT ITCRESQGIR NYLAWYQQKP GQAPRLLIY
50  GASTRAIGIP DRFSGSGSGT DFTLTISRLE PEDFAVYYCQ QYGSSQGIFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KVYACEVTHQ
200 GLSSPVTKSF NRGEC
```

SEQ ID NO: 85

Edman, N-terminal, MALDI-TOF-MS, MALDI-FTMS, MS/MS    ▓ = CDRs

```
  1 EIVLTQSPAT LSLSPGERVT ITCRASQGIR NYLAWYQQKP GQAPRLLIY
 50 GASTRAIGIP DRFSGSGSGT DFTLTISRLE PEDFAVYYCQ QYGSSQGTFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KLYACEVTHQ
200 GLSSPVTKSF NRGEC
```

SEQ ID NO: 86

Edman, N-terminal, MALDI-TOF-MS, MALDI-FTMS, MS/MS  = CDRs

Fig. 29j

```
1   EIVMTQSPAT LSLSPGERVT ITCRESQGIR NYLAWYQQKP GQAPRLLIY
50  AASTLQSGVP SRFSGSGSGT DFTLTISRLE PEDFAVYYCQ QYGSSQGIFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KVYACEVTHQ
200 GLSSPVTKSF NRGEC
```

SEQ ID NO: 87

Edman, N-terminal, MALDI-TOF-MS, MALDI-FTMS, MS / MS

▓ = CDRs

```
  1  EIVMTQSPAT LSLSPGERVT ITCRESQGIR NYLAWYQQKP  GQAPRLLIY
 50  AASTLQSGVP SRFSGSGSGT DFTLTISRLE PEDFAVYYCQ QYGSSQGTFG
100  PGTKVDIKRT VAAPSVFIFP PSDEQLKSGT ASVVCLLNNF YPREAKVQWK
150  VDNALQSGNS QESVTEQDSK DSTYSLSSTL TLSKADYEKH KLYACEVTHQ
200  GLSSPVTKSF NRGEC
```

SEQ ID NO: 88

= CDRs

Edman, N-terminal, MALDI-TOF-MS, MALDI-FTMS, MS/MS

```
1   DVVMTQSPSS LSASVGDRVT ITCRESQGIR NYLAWYQQKP GKAPKLLIYK
51  ASSLQSGVPS RFSGSLIGGK AAITLSGVQP EDFATYYCQ QANSFPLTFGG
101 GTKVEIKRT VAAPSVFIFP PSDEQLKSGT ASVVCLLNNF YPREAKVQWK
151 VDNALQSGNS QESVTEQDSK DSTYSLSSTL TLSKADYEKH KVYACEVTHQ
201 GLSSPVTKSF NRGEC
```

SEQ ID NO: 89

Edman, N-terminal, MALDI-TOF-MS, MALDI-FTMS, MS/MS

▓ = CDRs

Fig. 29m

```
  1 DVVMTQSPSS LSASVGDRVT ITCRESQGIR NYLAWYQQKP GKAPKLLIYK
 51 ASSLQSGVPS RFSGSLLGGK AALTLSGVQP EDFATYYCQQ ANSFPLTFGG
101 GTKVEIKRT  VAAPSVFIFP PSDEQLKSGT ASVVCLLNNF YPREAKVQWK
151 VDNALQSGNS QESVTEQDSK DSTYSLSSTL TLSKADYEKH KLYACEVTHQ
201 GLSSPVTKSF NRGEC
```

SEQ ID NO: 90

Edman, N-terminal, MALDI-TOF-MS, MALDI-FTMS, MS/MS

▓ = CDRs

Fig. 29n

```
1    DIVLTQSPAT LSLSPGERVT ITCRASQSVN SYLAWYQQKP GQAPRLLIY
50   GASTRAT GIP DRFSGSGSGT DFTLTISRLE PEDFAVYYCQ QYGSSQGTFG
100  PGTKVDIKRT VAAPSVFIFP PSDEQLKSGT ASVVCLLNNF YPREAKVQWK
150  VDNALQSGNS QESVTEQDSK DSTYSLSSTL TLSKADYEKH KVYACEVTHQ
200  GLSSPVTKSF NRGEC
```

SEQ ID NO: 91

Edman, N-terminal, MALDI-TOF-MS, MALDI-FTMS, MS/MS ▬ = CDRs

```
  1 DIQMTQSPGT LSLSPGERAA LSCRASQSVS SYLAWYQQKP GQAPRLLIY
 50 AASTRATGIP DRFSGSGSGT DFTLTISRLE PEDFAVYYCQ QYGSSQGIFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KVYACEVTHQ
200 GLSSPVTKSF NRGEC
```

SEQ ID NO: 92

Edman, N-terminal, MALDI-TOF-MS, MALDI-FTMS, MS/MS  = CDRs

Fig. 29p

```
  1 DIQMTQSPGT LSLSPGERAA LSCRASQSVS SYLAWYQQKP GQAPRLLIY
 50 AASTRATGIP DRFSGSGSGT DFTLTISRLE PEDFAVYYCQQ YGSSQGIFG
100 PGTKVDIKRT VAAPSVFIFP PSDEQLKSGT ASVVCLLNNF YPREAKVQWK
150 VDNALQSGNS QESVTEQDSK DSTYSLSSTL TLSKADYEKH KLYACEVTHQ
200 GLSSPVTKSF NRGEC
```

SEQ ID NO: 93

Edman, N-terminal, MALDI-TOF-MS, MALDI-FTMS, MS/MS ▬ = CDRs

Fig. 30-1

```
1   EVQLVESGGG VVQPGGSLRL SCAASGFTFR SYNMSWVRQA PGKGLEWVAS
51  VKQDGSEKYY VDSVKGRFTI SRDTSKNTLY LQMNSLRAED TAVYYCARDA
101 SSWYRDWFDP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 94

Edman, N-terminal, MALDI-TOF-MS, MALDI-FTMS, MS/MS

 = CDRs

Fig. 30-2

```
  1 EVQLVESGGG VVQPGGSLRL SCAASGFTFR SYWMS WVRQA PGKGLEWVAS
 51 VKQDGSEKYY VDSVKGRFTI SRDTSKNTLY LQMNSLRAED TAVYYCARDA
101 SSWYARDWFDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 KRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 95

Edman, N-terminal, MALDI-TOF-MS, MALDI-FTMS, MS/MS        ▓ = CDRs

Fig. 30-3

```
  1 EVQLVESGGG VVQPGGSLRL SCAASGFTFR SYAMSWVRQA PGKGLEWVAS
 51 VKQDGSEKYY VDSVKGRFTI SRDTSKNTLY LQMNSLRAED TAVYYCARDA
101 SSWARDWFDE WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ALFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 96

░░ = no N-glycosylation
▓▓ = CDRs

Edman, N-terminal, MALDI-TOF-MS, MALDI-FTMS, MS / MS

Fig. 30-4

```
  1 EVQLVESGGG VVQPGGSLRL SCAASGFTFR GYWMSWVRQA PGKGLEWVAS
 51 VKQDGSEKYY VDSVKGRFTI SRDTSKNTLY LQMNSLRAED TAVYYCARDG
101 SSWYRDWFDE WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVLHQDWLNG KEYKCKVSNK ALPAPIEKTI SKAKGQPREP
351 QVYTLPPSRD ELTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 97

Edman, N-terminal, MALDI-TOF-MS, MALDI-FTMS, MS/MS  = CDRs

Fig. 30-5

```
  1 EVQLVESGGG VVQPGGSLRL SCAASGFTFR GYWMSWVRQA PGKGLEWVAS
 51 VKQDGSEKYY VDSVKGRFTI SRDTSKNTLY LQMNSLRAED TAVYYCARDG
101 SSNYRDWFDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 98

Edman, N-terminal, MALDI-TOF-MS, MALDI-FTMS, MS/MS     = CDRs

Fig. 30-6

```
  1 EVQLVESGGG VVQPGGSLRL SCAASGFTFR GYWMSWVRQA PGKGLEWVAS
 51 VKQDGSEKYY VDSVKGRFTI SRDTSKNTLY LQMNSLRAED TAVYYCARDG
101 SSWYRDWFDP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ASTFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 99

 = no N-glycosylation

 = CDRs

Edman, N-terminal, MALDI-TOF-MS, MALDI-FTMS, MS/MS

Fig. 30-7

```
  1 EVQLVESGGG VVQPGGSLRL SCAASGFTFR  SYTMSWVRQA PGKGLEWVAS
 51 VKQFFSGPIA TGSVKGRFTI SRDNAKNTLY LQMNSLRAED TAVYYCARDA
101 SSWYRDWEDP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 100

 = N-glycosylation    = CDRs

Edman, N-terminal, MALDI-TOF-MS, MALDI-FTMS, MS/MS

Fig. 30-8

```
  1 EVQLVESGGG VVQPGGSLRL SCAASGFTFR SYWMSWVRQA PGKGLEWVAS
 51 VKQFSGPIA TGSVKGRFTI SRDNAKNTLY LQMNSLRAED TAVYYCARDA
101 SISWYRDWFDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 101

▓ = N-glycosylation    ▒ = CDRs

Edman, N-terminal, MALDI-TOF-MS, MALDI-FTMS, MS/MS

Fig. 30-9

```
  1 EVQLVESGGG VVQPGGSLRL SCAASGFTFR SYWMSWVRQA PGKGLEWVAS
 51 VKQFESGPIA TGSVKGRFTI SRDNAKNTLY LQMNSLRAED TAVYYCARDA
101 SSWYRDWEDP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 AGTFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 102

▬ = no N-glycosylation
▓ = CDRs

Edman, N-terminal, MALDI-TOF-MS, MALDI-FTMS, MS/MS

Fig. 30-10

```
1   EVQLVESGGG VVQPGGSLRL SCAASGFTFR GTMHWVRQA PGKGLEWVA VKQPGSEKVY
51  VKQPGSEKVY VADSVKGRPTI SRDNAKNQFS LKLSSVTAAD TAVYYCARIG
101 WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 103

Edman, N-terminal, MALDI-TOF-MS, MALDI-FTMS, MS/MS

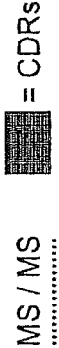 = N-glycosylation    = CDRs

Fig. 30-11

```
1   EVQLVESGGG VVQPGGSLRL SCAASGFTFR  GTMS  WVRQA PGKGLEWVA
51  VKQDESRKYY VASVKGRPTI SRDNAKNQFS LKLSSVTAAD TAVYYCARDY
101 SSNYAJWDF  WGQGTLVSVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 GS THY RVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 104

Edman, N-terminal, MALDI-TOF-MS, MALDI-FTMS, MS/MS

■ = N-glycosylation  ■ = CDRs

Fig. 30-12

```
  1 EVQLVESGGG VVQPGGSLRL SCAASGFTFR  SYAMS WVRQA PGKGLEWVA S
 51 VISQDGSHKYY ADSVKG RPTI SRDNAKNQFS LKLSSVTAAD TAVYYCAR DI
101 SSWYFDY WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTF RVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 105

▨ = no N-glycosylation   ▨ = CDRs

Edman, N-terminal, MALDI-TOF-MS, MALDI-FTMS, MS/MS

Fig. 30-13

```
  1  EVQLVESGGG VVQPGGSLRL SCAASGFTFR  NRDMNWVRQG IGKGLEWVGR
 51  IGWAGRINEYN ESAKGRFTIS RENAKDSLYL QMNSLRVGDA AVYYCARGAG
101  RWAPEGGLDI WGQGTLVIVS SASTKGPSVF PLAPSSKSTS GGTAALGCLV
151  KDYFPEPVTV SWNSGALTSG VHTFPAVLQS SGLYSLSSVV TVPSSSLGTQ
201  TYICNVNHKP SNTKVDKKVE PKSCDKTHTC PPCPAPELLG GPSVFLFPPK
251  PKDTLMISRT PEVTCVVVDV SHEDPEVKFN WYVDGVEVHN AKTKPREEQF
301  FRVVSVL TVLHQDWLNG KEYKCKVSNK ALPAPIEKTI SKAKGQPREP
351  QVYTLPPSRD ELTKNQVSLT CLVKGFYPSD IAVEWESNGQ PENNYKTTPP
401  VLDSDGSFFL YSKLTVDKSR WQQGNVFSCS VMHEALHNHY TQKSLSLSPG
451  K
```

SEQ ID NO: 106

= N-glycosylation     = CDRs

Edman, N-terminal, MALDI-TOF-MS, MALDI-FTMS, MS / MS

Fig. 30-14

```
  1 EVQLVESGGG VVQPGGSLRL SCAASGFTFR ͟S͟Y͟A͟M͟M WVRQQ IGKGLEWVG͟͟A͟
 51 ͟I͟S͟Y͟A͟G͟R͟N͟Y͟A ͟Y͟S͟V͟K͟G RFTIS RENAKDSLYL QMNSLRVGDA AVYYCAR͟G͟Y͟L
101 ͟R͟Y͟A͟P͟L͟G͟A͟H͟D WGQGTLVIVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQ͟Y
301 ͟N͟S͟T͟Y͟RVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 107

■ = N-glycosylation    ■ = CDRs

Edman, N-terminal, MALDI-TOF-MS, MALDI-FTMS, MS / MS

Fig. 30-15

```
  1 EVQLVESGGG VVQPGGSLRL SCAASGFTFR SGYAG-RINYAN P-SDKEG RFTIS RENAKDSLYL QMNSLRVGDA AVYYCAR-AG
 51 NYDMH WVRQG IGKGLEWVG
101 RWADHCALHE WGQGTLIVIVS KDYFPEPVTV SWNSGALTSG VHTFPAVLQS SGLYSLSSVV TVPSSSLGTQ
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ASFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 108

Edman, N-terminal, MALDI-TOF-MS, MALDI-FTMS, MS/MS

▓ = no N-glycosylation
▓ = CDRs

Fig. 30-16

```
  1 EVQLVESGGG VVQPGGSLRL SCAASGFTFR NYDMHWVRQG IGKGLVWVSR
 51 IGTAGDRAYA GSVKGRFTIS RENAKDSLYL QMNSLRVGDA AVYYCARCAG
101 RWAPLGAFDI WGQGTLVIVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 109

■ = N-glycosylation    ■ = CDRs

Edman, N-terminal, MALDI-TOF-MS, MALDI-FTMS, MS/MS

Fig. 30-17

```
  1 EVQLVESGGG VVQPGGSLRL SCAASGFTFR NYDMHWVRQG IGKGLVWVSR
 51 IGTAGDRYYA GSVKGRFTIS RENAKDSLYL QMNSLRVGDA AVYYCARGAG
101 RWAPLGAFDI WGQGTLVIVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 KRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 110          ▨ = N-glycosylation          ▩ = CDRs

Edman, N-terminal, MALDI-TOF-MS, MALDI-FTMS, MS/MS

Fig. 30-18

```
  1 EVQLVESGGG VVQPGGSLRL SCAASGFTFR NYDMHWVRQG IGKGLVWVSR
 51 IGTAGDRVYA GSVKGRFTIS RENAKDSLYL QMNSLRVGDA AVYYCARGAG
101 RWAPLGAFDI WGQGTLVIVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ASTFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 111

Edman, N-terminal, MALDI-TOF-MS, MALDI-FTMS, MS/MS

▨ = no N-glycosylation
▨ = CDRs

Fig. 30-19

```
  1 EVQLVESGGG VVQPGGSLRL SCAASGFTFS RTHWSWVRQA PGKGLEWVA
 51 VKQDGSEKYY VESVKGRFTI SRDNAKNTLY LQMNSLRAED TAVYYCARDL
101 SSYYFDYWGP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 FRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 112

Edman, N-terminal, MALDI-TOF-MS, MALDI-FTMS, MS/MS

 = N-glycosylation       = CDRs

Fig. 30-20

```
  1 EVQLVESGGG VVQPGGSLRL SCAASGFTFS SYAMSWVRQA PGKGLEWVA
 51 VRQIGSEKVV VDSVKGRFTI SRDNAKNTLY LQMNSLRAED TAVYYCARE
101 SSIYERDTIDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 113

Edman, N-terminal, MALDI-TOF-MS, MALDI-FTMS, MS/MS

▨ = N-glycosylation

▧ = CDRs

Fig. 30-21

```
  1 EVQLVESGGG VVQPGGSLRL SCAASGFTFS SAWMSWVRQA PGKGLEWVA
 51 VKQDGSEKYY VDSVKGRFTI SRDNAKNTLY LQMNSLRAED TAVYYCARDL
101 SGWYRDWDY  WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ASTFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 114

Edman, N-terminal, MALDI-TOF-MS, MALDI-FTMS, MS/MS

■ = no N-glycosylation
■ = CDRs

Fig. 30-22

```
  1 EVQLVESGGG VVQPGGSLRL SCAASGFTFR SCAASGFTFR SVDMSWVRQA PGKGLEWVAS
 51 VKQFFSGSAA TGSVKGRFTI SRDNAKNTLY LQMNSLRAED TAVYYCARDG
101 SSMYRDWFDF WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K

SEQ ID NO: 115

▓ = N-glycosylation        ▓ = CDRs

Edman, N-terminal, MALDI-TOF-MS, MALDI-FTMS, MS / MS
```

Fig. 30-23

```
  1 EVQLVESGGG VVQPGGSLRL SCAASGFTFR SYDMSWVRQA PGKGLEWVAS
 51 VKQFESGSAA TGSVKGRFTI SRDNAKNTLY LQMNSLRAED TAVYYCARDG
101 SSWYRDWEDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 116

▓ = N-glycosylation   ▓ = CDRs

Edman, N-terminal, MALDI-TOF-MS, MALDI-FTMS, MS/MS

Fig. 30-25

1   EVQLVESGGG VVQPGGSLRL SCAASGFTFR ...... WVRQA PGKGLEWVA.
51  VK.DGSE.... .SM.....EP RPTI SRDNAKNQLS LKLSSVTAAD TAVYYCAR..
101 ........... WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 FRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K

SEQ ID NO: 118

Edman, N-terminal, MALDI-TOF-MS, MALDI-FTMS, MS/MS

▨ = N-glycosylation    ▨ = CDRs

Fig. 30-26

```
  1 EVQLVESGGG VVQPGGSLRL SCAASGFTFR [SDYAM]S WVRQA PGKGLEWVA
 51 VKQDGSEKKY VDSVKG RPTI SRDNAKNQLS LKLSSVTAAD TAVYYCAR DIG
101 SSMVRDWLDP WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 119    ▓ = N-glycosylation    ▓ = CDRs

Edman, N-terminal, MALDI-TOF-MS, MALDI-FTMS, MS/MS

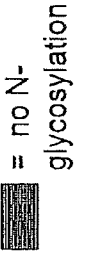

Fig. 30-28

```
1   EVQLVESGGG VVQPGGSLRL SCAASGFTFR SSYAMSWVRQA PGKGLEWVAS
51  VKQDGSRKYY ADSVKGRFTL SVDTSKNQFS LKLSSVTAAD TAVYYCARDL
101 SSNYARDLDF WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 FRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 121

Edman, N-terminal, MALDI-TOF-MS, MALDI-FTMS, MS/MS

▬ = N-glycosylation  ▬ = CDRs

Fig. 30-29

```
  1 EVQLVESGGG VVQPGGSLRL SCAASGFTFR GYAMSWVRQA PGKGLEWVA
 51 VKQDGSEKYY ADSVKGRLTL SVDTSKNQFS LKLSSVTAAD TAVYYCARH
101 SYGMDVWGQG WGQGTLVSVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 122

■ = N-glycosylation     ▓ = CDRs

Edman, N-terminal, MALDI-TOF-MS, MALDI-FTMS, MS/MS

Fig. 30-30

```
  1 EVQLVESGGG VVQPGGSLRL SCAASGFTER ........WVRQA PGKGLEWVA.
 51 VK......................RLTL SVDTSKNQFS LKLSSVTAAD TAVYYCAR..
101 .........WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 A..FRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 123

Edman, N-terminal, MALDI-TOF-MS, MALDI-FTMS, MS/MS

▓ = no N-glycosylation
▓ = CDRs

Fig. 30-31

```
  1 EVQLVESGGG VVQPGGSLRL SCAASGFTFR SYAMSWVRQA PGKGLEWVAS
 51 VKQDGSEKYY VDSVKGRVTI SVETSKNQFS LKLSSVTAAD TAVYYCARDF
101 WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 124

Edman, N-terminal, MALDI-TOF-MS, MALDI-FTMS, MS/MS

▓ = N-glycosylation
▓ = CDRs

Fig. 30-32

```
  1 EVQLVESGGG VVQPGGSLRL SCAASGFTFR SYAMSWVRQA PGKGLEWVA
 51 VISYDGSNKYY ADSVKGRFTI SVETSKNQFS LKLSSVTAAD TAVYYCARD
101 SSYPIWFDP WGQGTLVSVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 125

Edman, N-terminal, MALDI-TOF-MS, MALDI-FTMS, MS/MS

▓ = N-glycosylation
▓ = CDRs

Fig. 30-33

```
  1  EVQLVESGGG VVQPGGSLRL SCAASGFTFR SGAMSWVRQA PGKGLEWVA
 51  VKQDGSEKYY VDSVKGRVTI SVETSKNQFS LKLSSVTAAD TAVYYCARTV
101  SSNYRDWFDP WGQGTLVSVS SASTKGPSVF PLAPSSKSTS GGTAALGCLV
151  KDYFPEPVTV SWNSGALTSG VHTFPAVLQS SGLYSLSSVV TVPSSSLGTQ
201  TYICNVNHKP SNTKVDKKVE PKSCDKTHTC PPCPAPELLG GPSVFLFPPK
251  PKDTLMISRT PEVTCVVVDV SHEDPEVKFN WYVDGVEVHN AKTKPREEQF
301  NSTFRVVSVL TVLHQDWLNG KEYKCKVSNK GLPAPIEKTI SKAKGQPREP
351  QVYTLPPSRD ELTKNQVSLT CLVKGFYPSD IAVEWESNGQ PENNYKTTPP
401  VLDSDGSFFL YSKLTVDKSR WQQGNVFSCS VMHEALHNHY TQKSLSLSPG
451  K
```

SEQ ID NO: 126

Edman, N-terminal, MALDI-TOF-MS, MALDI-FTMS, MS/MS

▨ = no N-glycosylation
▨ = CDRs

Fig. 30-34

```
  1 EVQLVESGGG VVQPGGSLRL SCAASGFTFR SYAMHWVRQA PGKGLEWVA
 51 VISYDGSNKY YADSVKGRVTI SLDTSKNQFS LKLSSVTAAD TAVYYCARDI
101 PSYYRDWDP WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 FRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 127

▓ = N-glycosylation
▓ = CDRs

Edman, N-terminal, MALDI-TOF-MS, MALDI-FTMS, MS / MS

Fig. 30-35

```
  1 EVQLVESGGG VVQPGGSLRL SCAASGFTFR SYAMSWVRQA PGKGLEWVA
 51 VKQDGSEKQY VDSVKGRVTI SLDTSKNQFS LKLSSVTAAD TAVYYCARDG
101 SSWROWLDPW WGQGTLVSVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 128

Edman, N-terminal, MALDI-TOF-MS, MALDI-FTMS, MS/MS

 = N-glycosylation   ▓ = CDRs

Fig. 30-37

```
  1 EVQLVESGGG VVQPGGSLRL SCAASGITFR SSYDMSWVRQA PGKGLEWVAT
 51 VSGDGGSTYYA VDSVKGRFTV SRDNAKNTLY LQMNSLRAED TAVYYCARDY
101 GLWADLFDYW WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 130

Edman, N-terminal, MALDI-TOF-MS, MALDI-FTMS, MS/MS  ▇ = N-glycosylation  ▇ = CDRs

Fig. 30-38

```
  1 EVQLVESGGG VVQPGGSLRL SCAASGITFR SYAMS WVRQA PGKGLEWVA S
 51 VKQDGSEKKY YVDSVK RFTV SRDNAKNTLY LQMNSLRAED TAVYYCAR D
101 GRWADFATFL WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 131 ▓ = N-glycosylation ▓ = CDRs

Edman, N-terminal, MALDI-TOF-MS, MALDI-FTMS, MS/MS

Fig. 30-39

```
  1 EVQLVESGGG VVQPGGSLRL SCAASGFTFR SYAMSWVRQA PGKGLEWVA
 51 VKQDGSEKYY ADESVKGRVTI TADRAKNTLY LQMNSLRAED TAVYYCARDL
101 SSYFDWLLP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 132

Edman, N-terminal, MALDI-TOF-MS, MALDI-FTMS, MS / MS

▨ = N-glycosylation    ▨ = CDRs

Fig. 30-40

```
  1 EVQLVESGGG VVQPGGSLRL SCAASGFTFR SYAMHWVRQA PGKGLEWVA
 51 VISYDGSNKY YADSVKGRFTI TADRAKNTLY LQMNSLRAED TAVYYCAR
101 SSMVRDWEDY WGQGTLVTVS SASTKGPSVF PLAPCSRSTS ESTAALGCLV
151 KDYFPEPVTV SWNSGALTSG VHTFPAVLQS SGLYSLSSVV TVPSSSLGTQ
201 TYTCNVDHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVVHQDWLNG KEYKCKVSNK GLPAPIEKTI SKAKGQPREP
351 QVYTLPPSRE EMTKNQVTLT CLVKGFYPSD IAVEWESNGQ PENNYKTTPP
401 MLDSDGSFFL YSKLTVDKSR WQQGNVFSCS VMHEALHNHY TQKSLSLSPG
451 K
```

SEQ ID NO: 133

■ = N-glycosylation    ■ = CDRs

Edman, N-terminal, MALDI-TOF-MS, MALDI-FTMS, MS/MS

Fig. 30-41

```
  1 EVQLVESGGG VVQPGGSLRL SCAASGFTFR NYWMSWVRQA PGKGLEWVAS
 51 VKQFFSGPLA TGSVKGRFTI SRDTSKNTLY LQMNSLRAED TAVYYCARDG
101 SSMYRDWEDP WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 FRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 134

Edman, N-terminal, MALDI-TOF-MS, MALDI-FTMS, MS/MS

▨ = N-glycosylation
▩ = CDRs

Fig. 30-42

```
  1  EVQLVESGGG VVQPGGSLRL SCAASGFTFR NYWMSWVRQA PGKGLEWVAS
 51  VKQFESGPIA TGSVKGRFTI SRDTSKNTLY LQMNSLRAED TAVYYCARDG
101  SSWYRDWFDP WGQGTLVTVS SASTKGPSVF PLAPSSKSTS GGTAALGCLV
151  KDYFPEPVTV SWNSGALTSG VHTFPAVLQS SGLYSLSSVV TVPSSSLGTQ
201  TYICNVNHKP SNTKVDKKVE PKSCDKTHTC PPCPAPELLG GPSVFLFPPK
251  PKDTLMISRT PEVTCVVVDV SHEDPEVKFN WYVDGVEVHN AKTKPREEQF
301  ASTFRVVSVL TVLHQDWLNG KEYKCKVSNK GLPAPIEKTI SKAKGQPREP
351  QVYTLPPSRD ELTKNQVSLT CLVKGFYPSD IAVEWESNGQ PENNYKTTPP
401  VLDSDGSFFL YSKLTVDKSR WQQGNVFSCS VMHEALHNHY TQKSLSLSPG
451  K
```

SEQ ID NO: 135

Edman, N-terminal, MALDI-TOF-MS, MALDI-FTMS, MS/MS

▓ = no N-glycosylation  ▓ = CDRs

Fig. 30-43

```
  1 EVQLVESGGG VVQPGGSLRL SCAASGFTFR  SYAMSWVRQA PGKGLEWVA
 51 VKQFRSEKAY AGSVKGRVTI SVETSKNQFS LKLSSVTAAD TAVYYCAR
101 SSNFFRDYWRP WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 NSTFRVVSVL TVLHQDWLNG KEYKCKVSNK ALPAPIEKTI SKAKGQPREP
351 QVYTLPPSRD EITKNQVSLT CLVGKFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 136

Edman, N-terminal, MALDI-TOF-MS, MALDI-FTMS, MS/MS  = CDRs

Fig. 30-44

```
  1 EVQLVESGGG VVQPGGSLRL SCAASGFTFR SSYAMSWVRQA PGKGLEWVA
 51 VKQFLSGKAY ACSVKGRVTI SVETSKNQFS LKLSSVTAAD TAVYYCARDL
101 SSYADYWGQG WGQGTLVSVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQF
301 ALFRVVSVL TVLHQDWLNG KEYKCKVSNK GLPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

SEQ ID NO: 137

▨ = no N-glycosylation
▨ = CDRs

Edman, N-terminal, MALDI-TOF-MS, MALDI-FTMS, MS/MS

Fig. 31

| No. | antibody | N-terminal kappa light chain sequence (1-18 aa) | SEQ ID NO: |
|---|---|---|---|
| 1 | IVIG_(1)_LC(1) | EI VLTQSPATLSLSPGER | SEQ ID NO: 138 |
| 2 | IVIG_(8)_LC(5) | EI VMTQSPATLSLSPGER | SEQ ID NO: 139 |
| 3 | IVIG_(6)_LC(3) | DI QMTQSPATLSLSPGER | SEQ ID NO: 140 |
| 4 | Serum_(9)_PI_1_LC(6) | DVVMTQSPSSLSASVGDR | SEQ ID NO: 141 |
| 5 | Serum_(10)_PI_2_LC(7) | DI VLTQSPATLSLSPGER | SEQ ID NO: 142 |
| 6 | Serum_(11)_PI_2_LC(8) | DI QMTQSPGTLSLSPGER | SEQ ID NO: 143 |

Fig. 34c
Supernatant
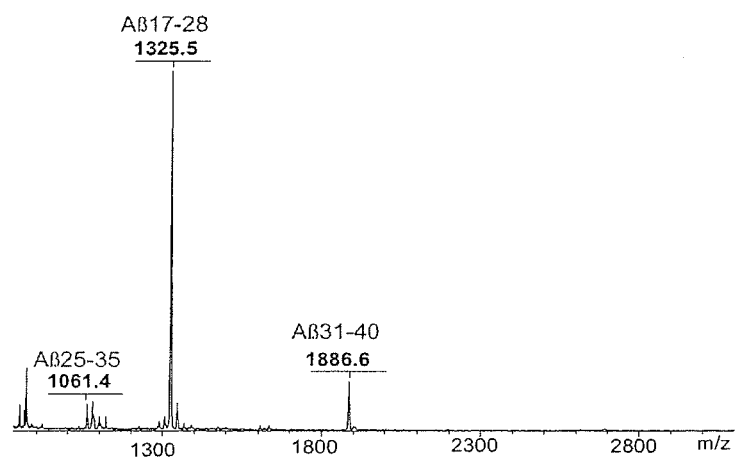
Last Wash
Elution

Fig. 34_e
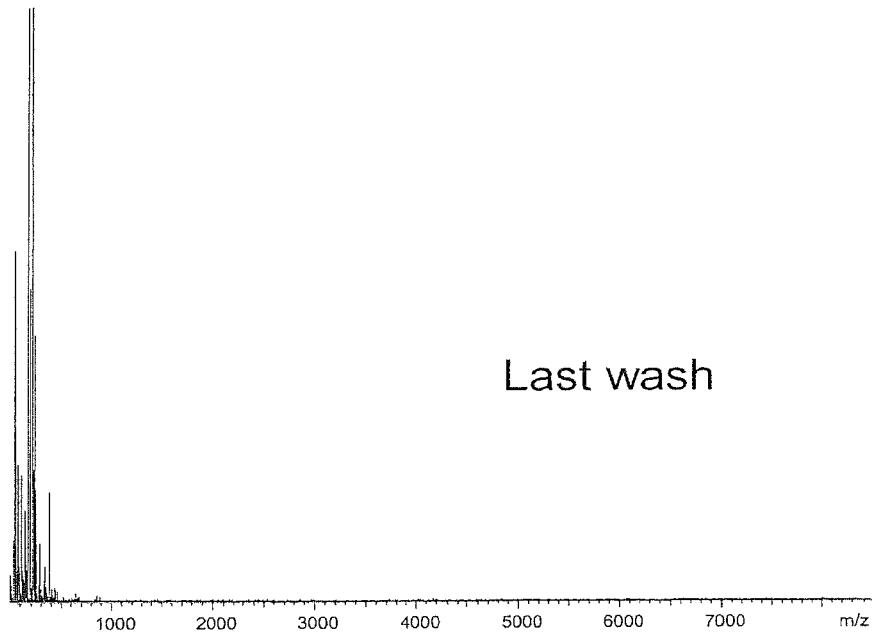
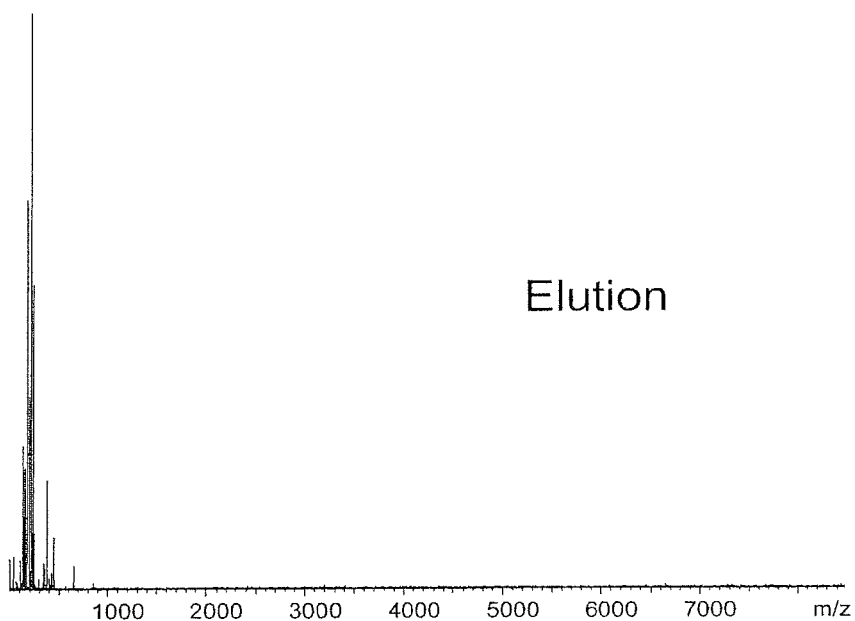
ACA Ab has no affinity for Aß(17-28)

Fig. 34f
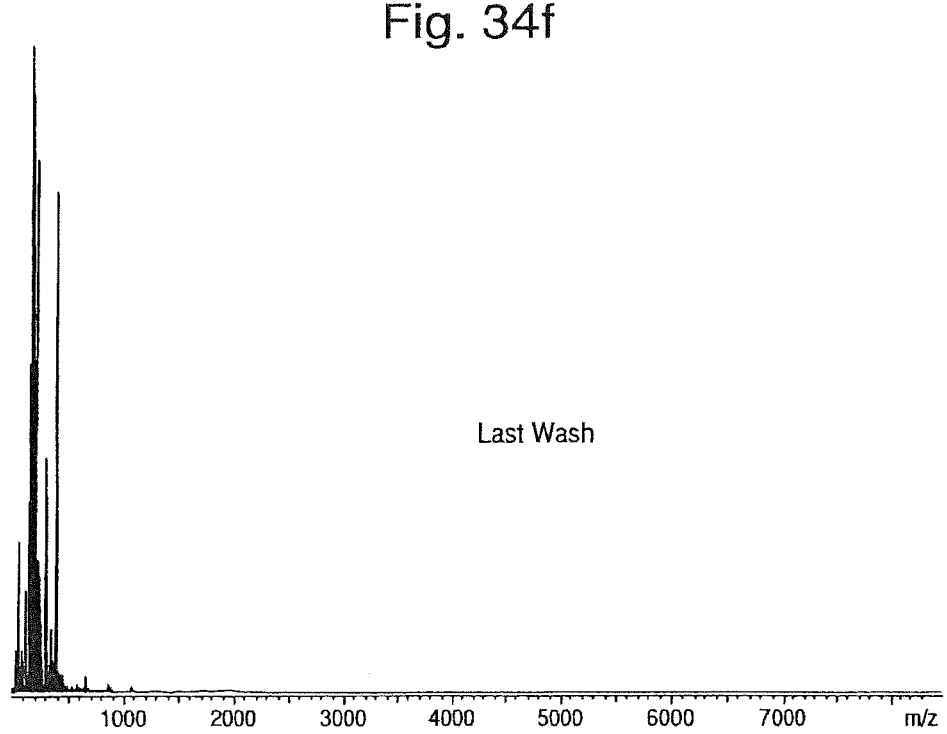
Last Wash
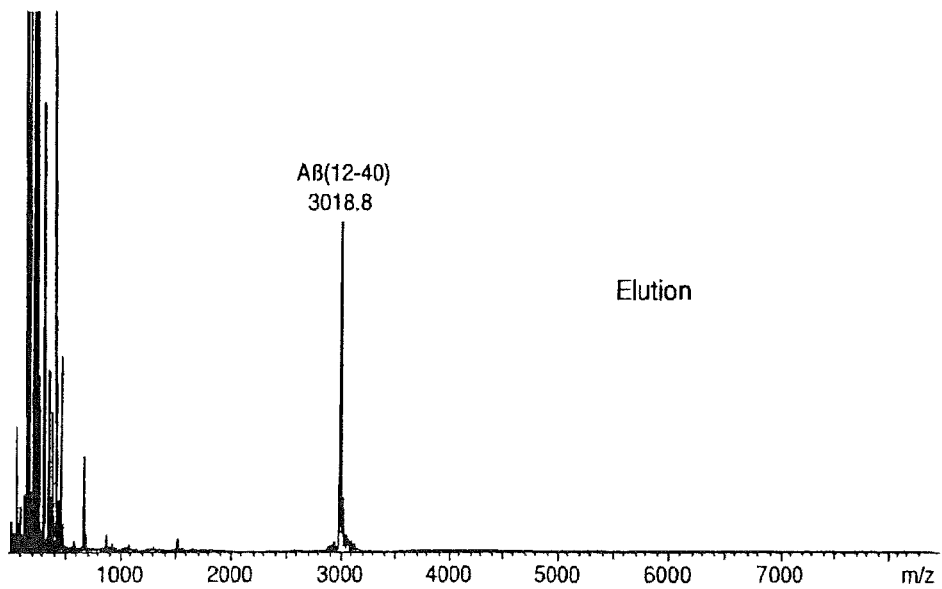
Aβ(12-40)
3018.8
Elution
ACA Ab has no affinity for Aβ(12-40)

Fig. 34_g
Last wash
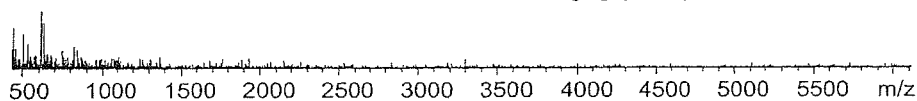
Elution
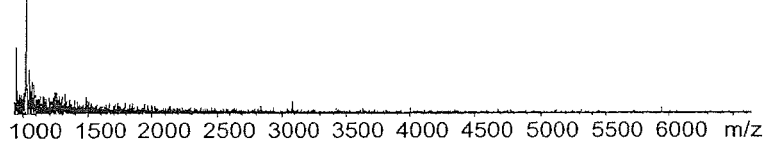
ACA Ab has no affinity for Aß(20-37)

Fig. 34_h
Last wash
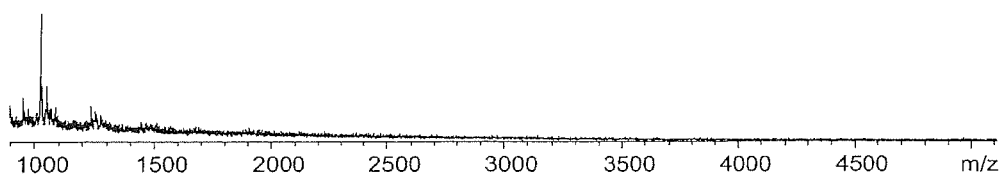
Elution
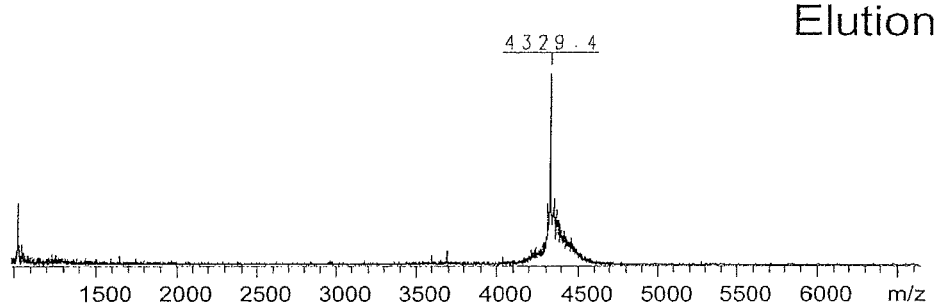
ACA Ab has affinity for Aß(1-40)

Fig. 34_i
Last wash
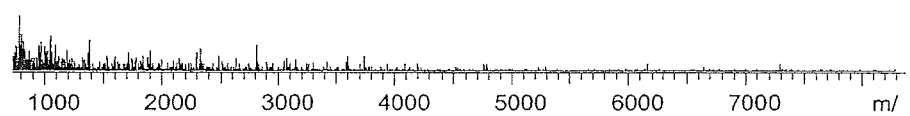
Elution
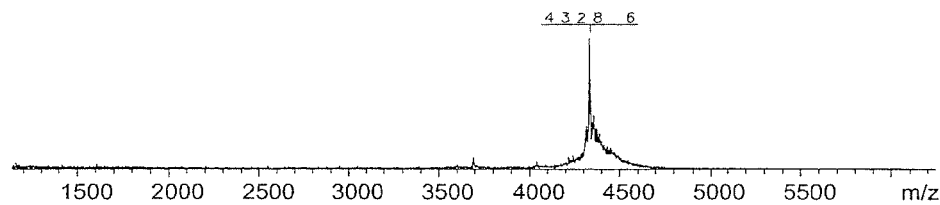
Aß- Ab has affinity for Aß(1-40)

Fig. 34_j
Last wash
Elution
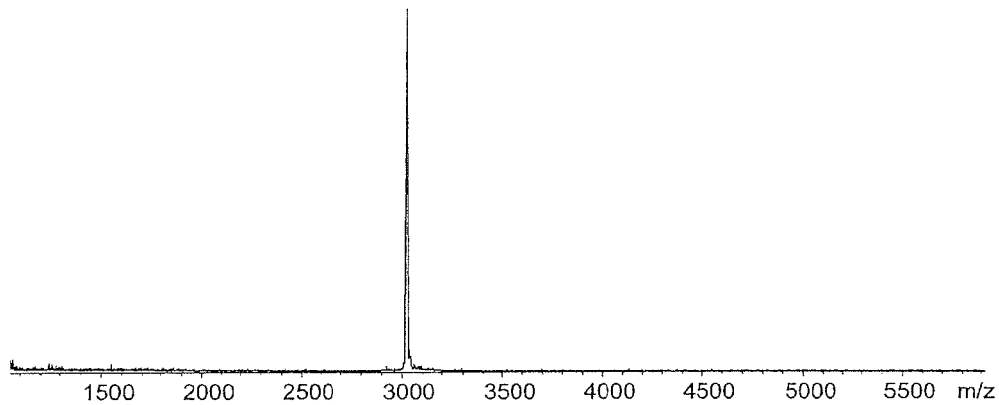
Aß- Ab has affinity for Aß(12-40)

Fig. 34_k
Last wash
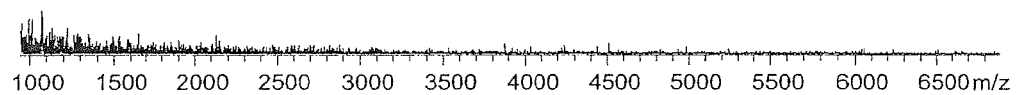
Elution
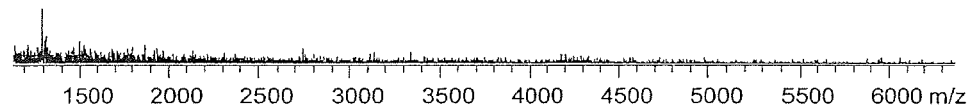
Aß- Ab has no affinity for Aß(17-28)

Fig. 34_I
Last wash
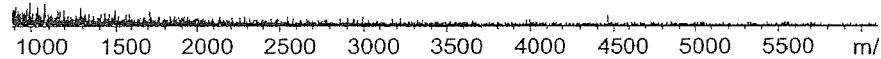
Elution
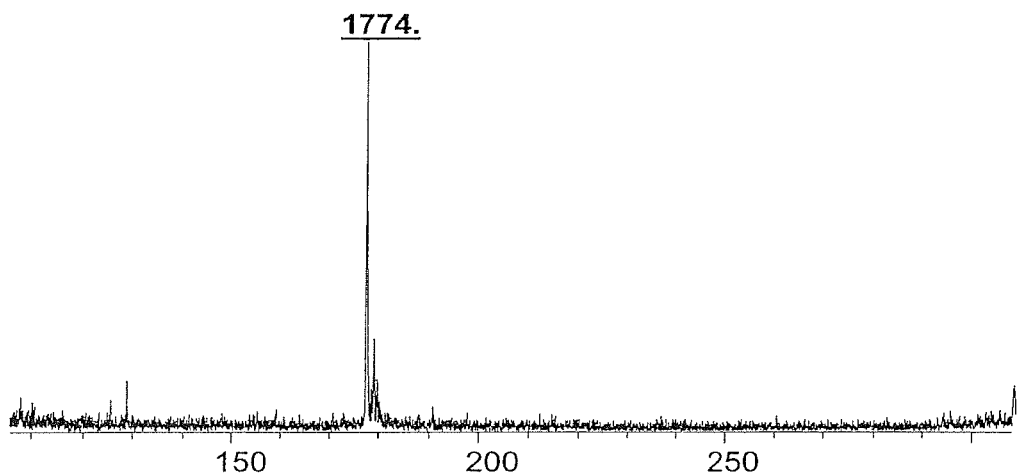
Aß- Ab has affinity for Aß(20-37)

Aß detected by specific binding of anti-Aß mab Bam90.1

1: 6E10
2: Bam90.1
3: CSL-7
4: IVIG
5: ACA
6: sera AD1
7: sera K4

Fig. 43
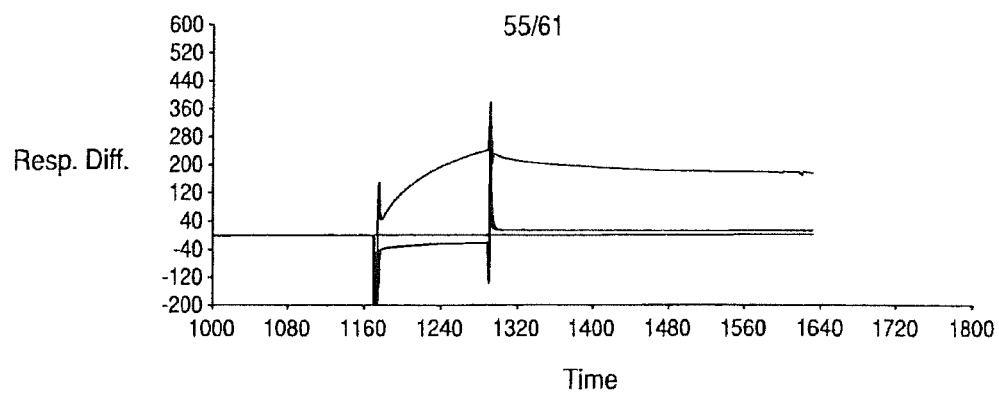
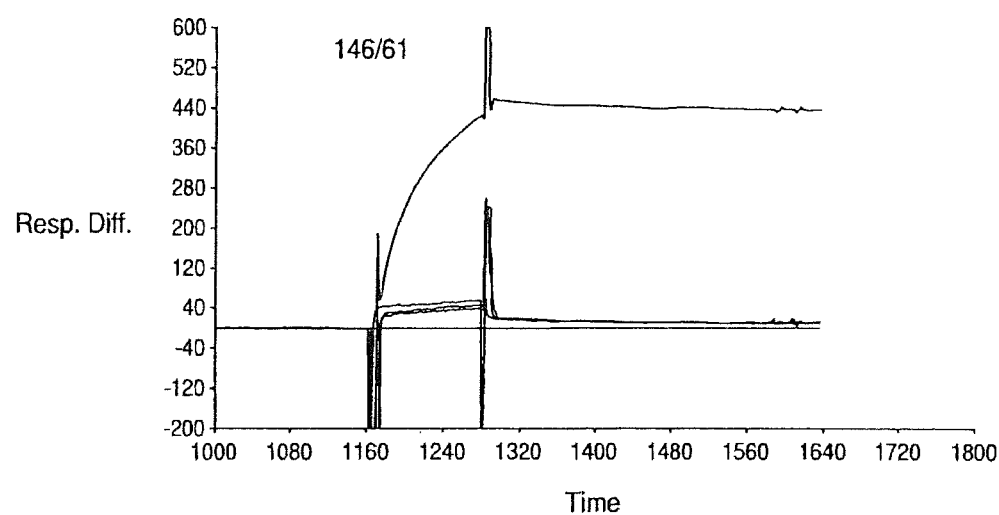
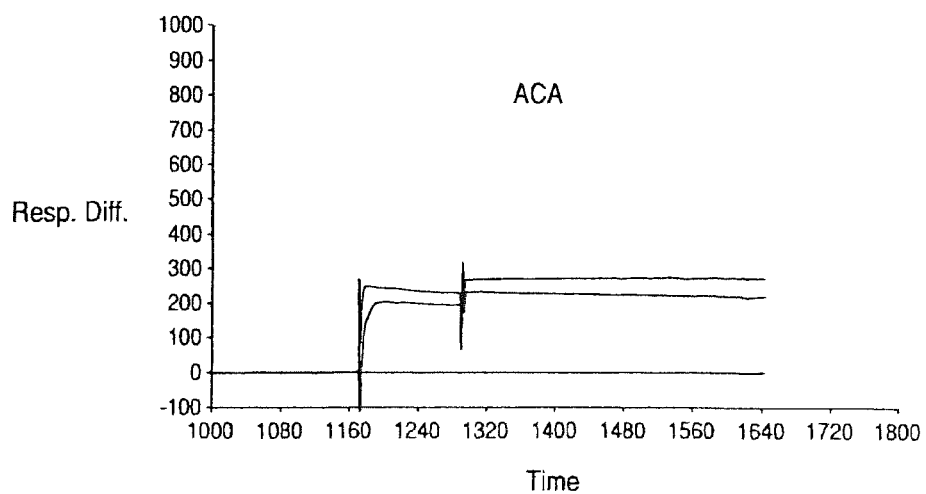

SEQUENCE LISTING

<160> NUMBER OF SEQ ID NOS: 194

<210> SEQ ID NO 1
<211> LENGTH: 40
<212> TYPE: PRT

```
<213> ORGANISM: Homo sapiens
<220> FEATURE:
<221> NAME/KEY: SOURCE
<222> LOCATION: 1..40
<223> OTHER INFORMATION: /mol_type="protein"
      /organism="Homo sapiens"

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 2
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 2

Ala Glu Asp Val Gly Ser Asn Lys Gly Ala Ile Ile Gly Leu Met Val
1               5                   10                  15

Gly

<210> SEQ ID NO 3
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 3

Phe Arg His Asp Ser Gly Tyr
1               5

<210> SEQ ID NO 4
<211> LENGTH: 29
<212> TYPE: PRT
<213> ORGANISM: Homo sapiens
<220> FEATURE:
<221> NAME/KEY: SOURCE
<222> LOCATION: 1..29
<223> OTHER INFORMATION: /mol_type="protein"
      /organism="Homo sapiens"

<400> SEQUENCE: 4

Val His His Gln Lys Leu Val Phe Phe Ala Glu Asp Val Gly Ser Asn
1               5                   10                  15

Lys Gly Ala Ile Ile Gly Leu Met Val Gly Gly Val Val
                20                  25

<210> SEQ ID NO 5
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
```

-continued

/organism="Homo sapiens"

<400> SEQUENCE: 5

Asp Ala Glu Phe Arg His Asp Ser Gly Tyr Glu Val His His Gln Lys
1               5                   10                  15

Leu Val Phe Phe
            20

<210> SEQ ID NO 6
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: Xaa can be Ser or Gly or Asn
<220> FEATURE:
<221> NAME/KEY: SITE
<222> LOCATION: 3..3
<223> OTHER INFORMATION: Xaa can be Trp or Asp
<220> FEATURE:
<221> NAME/KEY: SITE
<222> LOCATION: 5..5
<223> OTHER INFORMATION: Xaa can be Ser or His

<400> SEQUENCE: 6

Xaa Tyr Xaa Met Xaa
1               5

<210> SEQ ID NO 7
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: Xaa can be Ser or Arg or Glu
<220> FEATURE:
<221> NAME/KEY: SITE
<222> LOCATION: 2..2
<223> OTHER INFORMATION: Xaa can be Val or Ile
<220> FEATURE:
<221> NAME/KEY: SITE
<222> LOCATION: 3..3
<223> OTHER INFORMATION: Xaa can be Lys or Gly or Asn
<220> FEATURE:
<221> NAME/KEY: SITE
<222> LOCATION: 4..4
<223> OTHER INFORMATION: Xaa can be Gln or no amino acid
<220> FEATURE:
<221> NAME/KEY: SITE
<222> LOCATION: 5..5
<223> OTHER INFORMATION: Xaa can be Asp or Phe or Thr or Arg
<220> FEATURE:
<221> NAME/KEY: SITE
<222> LOCATION: 6..6
<223> OTHER INFORMATION: Xaa can be Gly or Phe or Ala or Ser
<220> FEATURE:
<221> NAME/KEY: SITE
<222> LOCATION: 7..7
<223> OTHER INFORMATION: Xaa can be Ser or Gly
<220> FEATURE:
<221> NAME/KEY: SITE
<222> LOCATION: 8..8
<223> OTHER INFORMATION: Xaa can be Glu or Gly or Arg or Asp or Ala

```
<220> FEATURE:
<221> NAME/KEY: SITE
<222> LOCATION: 9..9
<223> OTHER INFORMATION: Xaa can be Lys or Pro or Ser or Thr or Arg
<220> FEATURE:
<221> NAME/KEY: SITE
<222> LOCATION: 10..10
<223> OTHER INFORMATION: Xaa can be Tyr or Leu or Ala or Asn
<220> FEATURE:
<221> NAME/KEY: SITE
<222> LOCATION: 11..11
<223> OTHER INFORMATION: Xaa can be Tyr or Ala
<220> FEATURE:
<221> NAME/KEY: SITE
<222> LOCATION: 12..12
<223> OTHER INFORMATION: Xaa can be Val or Thr or Ala or Asn
<220> FEATURE:
<221> NAME/KEY: SITE
<222> LOCATION: 13..13
<223> OTHER INFORMATION: Xaa can be Asp or Gly or Pro
<220> FEATURE:
<221> NAME/KEY: SITE
<222> LOCATION: 15..15
<223> OTHER INFORMATION: Xaa can be Val or Leu
<220> FEATURE:
<221> NAME/KEY: SITE
<222> LOCATION: 17..17
<223> OTHER INFORMATION: Xaa can be Gly or Ser

<400> SEQUENCE: 7

Xaa Xaa Xaa Xaa Xaa Xaa Xaa Xaa Xaa Xaa Xaa Xaa Xaa Ser Xaa Lys
1               5                   10                  15

Gly

<210> SEQ ID NO 8
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: Xaa can be Asp or Gly
<220> FEATURE:
<221> NAME/KEY: SITE
<222> LOCATION: 2..2
<223> OTHER INFORMATION: Xaa can be Ala or Gly
<220> FEATURE:
<221> NAME/KEY: SITE
<222> LOCATION: 3..3
<223> OTHER INFORMATION: Xaa can be Ser or Gly
<220> FEATURE:
<221> NAME/KEY: SITE
<222> LOCATION: 4..4
<223> OTHER INFORMATION: Xaa can be Ser or Arg
<220> FEATURE:
<221> NAME/KEY: SITE
<222> LOCATION: 6..6
<223> OTHER INFORMATION: Xaa can be Tyr or Ala
<220> FEATURE:
<221> NAME/KEY: SITE
<222> LOCATION: 7..7
<223> OTHER INFORMATION: Xaa can be Arg or Pro or Asp
<220> FEATURE:
<221> NAME/KEY: SITE
<222> LOCATION: 8..8
<223> OTHER INFORMATION: Xaa can be Asp or Leu
<220> FEATURE:
<221> NAME/KEY: SITE
<222> LOCATION: 9..9
<223> OTHER INFORMATION: Xaa can be Trp or Gly or Ala
<220> FEATURE:
<221> NAME/KEY: SITE
```

```
<222> LOCATION: 10..10
<223> OTHER INFORMATION: Xaa can be Phe or Ala
<220> FEATURE:
<221> NAME/KEY: SITE
<222> LOCATION: 11..11
<223> OTHER INFORMATION: Xaa can be Phe or no amino acid
<220> FEATURE:
<221> NAME/KEY: SITE
<222> LOCATION: 13..13
<223> OTHER INFORMATION: Xaa can be Pro or Ile

<400> SEQUENCE: 8

Xaa Xaa Xaa Xaa Trp Xaa Xaa Xaa Xaa Xaa Xaa Asp Xaa
1               5                   10

<210> SEQ ID NO 9
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"
<220> FEATURE:
<221> NAME/KEY: SITE
<222> LOCATION: 2..2
<223> OTHER INFORMATION: Xaa can be Glu or Ala
<220> FEATURE:
<221> NAME/KEY: SITE
<222> LOCATION: 5..5
<223> OTHER INFORMATION: Xaa can be Gly or Ser
<220> FEATURE:
<221> NAME/KEY: SITE
<222> LOCATION: 6..6
<223> OTHER INFORMATION: Xaa can be Ile or Val
<220> FEATURE:
<221> NAME/KEY: SITE
<222> LOCATION: 7..7
<223> OTHER INFORMATION: Xaa can be Arg or Asn or Ser
<220> FEATURE:
<221> NAME/KEY: SITE
<222> LOCATION: 8..8
<223> OTHER INFORMATION: Xaa can be Ser or Asn

<400> SEQUENCE: 9

Arg Xaa Ser Gln Xaa Xaa Xaa Xaa Tyr Leu Ala
1               5                   10

<210> SEQ ID NO 10
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: Xaa can be Gly or Trp or Ala or Lys
<220> FEATURE:
<221> NAME/KEY: SITE
<222> LOCATION: 2..2
<223> OTHER INFORMATION: Xaa can be Ala or Val
<220> FEATURE:
<221> NAME/KEY: SITE
<222> LOCATION: 3..3
<223> OTHER INFORMATION: Xaa can be Ser or Ala
<220> FEATURE:
<221> NAME/KEY: SITE
<222> LOCATION: 4..4
<223> OTHER INFORMATION: Xaa can be Thr or Ser or Asn or Ile
<220> FEATURE:
<221> NAME/KEY: SITE
```

```
<222> LOCATION: 5..5
<223> OTHER INFORMATION: Xaa can be Arg or Leu
<220> FEATURE:
<221> NAME/KEY: SITE
<222> LOCATION: 6..6
<223> OTHER INFORMATION: Xaa can be Ala or Gln or Phe or Glu
<220> FEATURE:
<221> NAME/KEY: SITE
<222> LOCATION: 7..7
<223> OTHER INFORMATION: Xaa can be Thr or Ser

<400> SEQUENCE: 10

Xaa Xaa Xaa Xaa Xaa Xaa Xaa
1               5

<210> SEQ ID NO 11
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"
<220> FEATURE:
<221> NAME/KEY: SITE
<222> LOCATION: 3..3
<223> OTHER INFORMATION: Xaa can be Ala or Tyr
<220> FEATURE:
<221> NAME/KEY: SITE
<222> LOCATION: 4..4
<223> OTHER INFORMATION: Xaa can be Gly or Asn
<220> FEATURE:
<221> NAME/KEY: SITE
<222> LOCATION: 6..6
<223> OTHER INFORMATION: Xaa can be Ser or Phe
<220> FEATURE:
<221> NAME/KEY: SITE
<222> LOCATION: 7..7
<223> OTHER INFORMATION: Xaa can be Gln or Pro
<220> FEATURE:
<221> NAME/KEY: SITE
<222> LOCATION: 8..8
<223> OTHER INFORMATION: Xaa can be Gly or Leu

<400> SEQUENCE: 11

Gln Gln Xaa Xaa Ser Xaa Xaa Xaa Thr
1               5

<210> SEQ ID NO 12
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"
<220> FEATURE:
<221> NAME/KEY: SITE
<222> LOCATION: 3..3
<223> OTHER INFORMATION: Xaa can be Tyr or Ala
<220> FEATURE:
<221> NAME/KEY: SITE
<222> LOCATION: 4..4
<223> OTHER INFORMATION: Xaa can be Gly or Asn
<220> FEATURE:
<221> NAME/KEY: SITE
<222> LOCATION: 6..6
<223> OTHER INFORMATION: Xaa can be Ser or Phe
<220> FEATURE:
<221> NAME/KEY: SITE
<222> LOCATION: 7..7
<223> OTHER INFORMATION: Xaa can be Gln or Pro
<220> FEATURE:
<221> NAME/KEY: SITE
```

```
<222> LOCATION: 8..8
<223> OTHER INFORMATION: Xaa can be Gly or Leu

<400> SEQUENCE: 12

Gln Gln Xaa Xaa Ser Xaa Xaa Xaa Thr
1               5

<210> SEQ ID NO 13
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 13

Ser Tyr Trp Met Ser
1               5

<210> SEQ ID NO 14
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 14

Gly Tyr Trp Met Ser
1               5

<210> SEQ ID NO 15
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 15

Asn Tyr Asp Met His
1               5

<210> SEQ ID NO 16
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 16

Ser Tyr Trp Met His
1               5

<210> SEQ ID NO 17
<211> LENGTH: 5
<212> TYPE: PRT
<213> ORGANISM: Homo sapiens
<220> FEATURE:
<221> NAME/KEY: SOURCE
<222> LOCATION: 1..5
```

```
<223> OTHER INFORMATION: /mol_type="protein"
      /organism="Homo sapiens"

<400> SEQUENCE: 17

Asn Tyr Trp Met Ser
1               5

<210> SEQ ID NO 18
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 18

Ser Tyr Asp Met Ser
1               5

<210> SEQ ID NO 19
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 19

Ser Tyr Asp Met Ser
1               5

<210> SEQ ID NO 20
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 20

Ser Tyr Trp Met Ser
1               5

<210> SEQ ID NO 21
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 21

Ser Val Lys Gln Asp Gly Ser Glu Lys Tyr Tyr Val Asp Ser Val Lys
1               5                   10                  15

Gly

<210> SEQ ID NO 22
<211> LENGTH: 17
<212> TYPE: PRT
<213> ORGANISM: Homo sapiens
<220> FEATURE:
```

```
<221> NAME/KEY: SOURCE
<222> LOCATION: 1..17
<223> OTHER INFORMATION: /mol_type="protein"
      /organism="Homo sapiens"

<400> SEQUENCE: 22

Arg Ile Gly Thr Ala Gly Asp Arg Tyr Tyr Ala Gly Ser Val Lys Gly
1               5                   10                  15

Val

<210> SEQ ID NO 23
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"

<400> SEQUENCE: 23

Arg Ile Gly Thr Ala Gly Arg Thr Asn Tyr Asn Pro Ser Leu Lys Gly
1               5                   10                  15

<210> SEQ ID NO 24
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 24

Ser Val Lys Gln Phe Phe Ser Gly Lys Tyr Tyr Ala Gly Ser Val Lys
1               5                   10                  15

Gly

<210> SEQ ID NO 25
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 25

Ser Val Lys Gln Phe Phe Ser Gly Ser Ala Ala Thr Gly Ser Val Lys
1               5                   10                  15

Gly

<210> SEQ ID NO 26
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 26

Ser Val Lys Gln Phe Phe Ser Gly Pro Leu Ala Thr Gly Ser Val Lys
1               5                   10                  15
```

Gly

<210> SEQ ID NO 27
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 27

Ser Val Lys Gln Asp Gly Ser Glu Lys Tyr Tyr Val Asp Ser Val Lys
1               5                   10                  15

Gly

<210> SEQ ID NO 28
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 28

Asp Ala Ser Ser Trp Tyr Arg Asp Trp Phe Asp Pro
1               5                   10

<210> SEQ ID NO 29
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 29

Gly Ala Gly Arg Trp Ala Pro Leu Gly Ala Phe Asp Ile
1               5                   10

<210> SEQ ID NO 30
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 30

Asp Gly Ser Ser Trp Tyr Arg Asp Trp Phe Asp Pro
1               5                   10

<210> SEQ ID NO 31
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 31

```
Asp Ala Gly Arg Trp Ala Asp Leu Ala Phe Asp Ile
1               5                   10
```

<210> SEQ ID NO 32
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 32

```
Asp Ala Gly Arg Trp Ala Asp Leu Ala Phe Asp Ile
1               5                   10
```

<210> SEQ ID NO 33
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 33

```
Arg Glu Ser Gln Gly Ile Arg Asn Tyr Leu Ala
1               5                   10
```

<210> SEQ ID NO 34
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 34

```
Arg Ala Ser Gln Ser Val Asn Ser Tyr Leu Ala
1               5                   10
```

<210> SEQ ID NO 35
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 35

```
Arg Glu Ser Gln Gly Ile Arg Asn Tyr Leu Ala
1               5                   10
```

<210> SEQ ID NO 36
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 36

Arg Ala Ser Gln Ser Val Ser Ser Tyr Leu Ala
1               5                   10

<210> SEQ ID NO 37
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 37

Thr Leu Ser Ser Glu His Ser Thr Tyr Thr Ile Glu
1               5                   10

<210> SEQ ID NO 38
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 38

Ala Gly Ser Thr Arg Ala Thr
1               5

<210> SEQ ID NO 39
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 39

Ala Ala Ser Ile Arg Ala Thr
1               5

<210> SEQ ID NO 40
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 40

Gly Ala Ala Ser Arg Ala Thr
1               5

<210> SEQ ID NO 41
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 41

```
Ala Ser Ser Leu Gln Ser Gly
1               5

<210> SEQ ID NO 42
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 42

Ala Ala Ser Ser Arg Ala Thr
1               5

<210> SEQ ID NO 43
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 43

Val Lys Ser Asp Gly Ser His
1               5

<210> SEQ ID NO 44
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 44

Gln Gln Tyr Gly Ser Ser Gln Gly Thr
1               5

<210> SEQ ID NO 45
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 45

Gln Gln Ala Asn Ser Phe Pro Leu Thr
1               5

<210> SEQ ID NO 46
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 46
```

Gly Glu Ser His Thr Ile Asp Gly Gln Cys
1               5                   10

<210> SEQ ID NO 47
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 47

Glu Ile Val Leu Thr Gln Ser Pro Ala Thr Leu Ser Leu Ser Pro Gly
1               5                   10                  15

Glu Arg Val Thr Ile Thr Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg
            100                 105

<210> SEQ ID NO 48
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 48

Glu Ile Val Leu Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
            20                  25                  30

Leu Ala Trp Tyr Gln Gln Lys Pro Gly Gln Ala Pro Arg Leu Leu Ile
        35                  40                  45

Tyr Ala Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg
            100                 105

<210> SEQ ID NO 49
<211> LENGTH: 111
<212> TYPE: PRT
<213> ORGANISM: Homo sapiens
<220> FEATURE:
<221> NAME/KEY: SOURCE
<222> LOCATION: 1..111

```
<223> OTHER INFORMATION: /mol_type="protein"
     /organism="Homo sapiens"

<400> SEQUENCE: 49

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Cys Trp Val Phe Gly Gly Gly Thr Lys Leu
            100                 105                 110

<210> SEQ ID NO 50
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
     /organism="Homo sapiens"

<400> SEQUENCE: 50

Asp Ile Gln Met Thr Gln Ser Pro Ala Thr Leu Ser Leu Ser Pro Gly
1               5                   10                  15

Glu Arg Ala Ala Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ala Ser Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg
            100                 105

<210> SEQ ID NO 51
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
     /organism="Homo sapiens"

<400> SEQUENCE: 51

Glu Ile Val Leu Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
            20                  25                  30

Leu Ala Trp Tyr Gln Gln Lys Pro Gly Gln Ala Pro Arg Leu Leu Ile
```

```
                    35                  40                  45
Tyr Gly Ala Ser Thr Arg Ala Thr Gly Ile Pro Asp Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Ser Ser Gln Gly
                     85                  90                  95

Thr Phe Gly Pro Gly Thr Lys Val Asp Ile Lys Arg
                100                 105

<210> SEQ ID NO 52
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 52

Glu Ile Val Met Thr Gln Ser Pro Ala Thr Leu Ser Leu Ser Pro Gly
 1               5                  10                  15

Glu Arg Val Thr Ile Thr Cys Arg Glu Ser Gln Gly Ile Arg Asn Tyr
                20                  25                  30

Leu Ala Trp Tyr Gln Gln Lys Pro Gly Gln Ala Pro Arg Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Gln Gly
                     85                  90                  95

Thr Phe Gly Pro Gly Thr Lys Val Asp Ile Lys Arg
                100                 105

<210> SEQ ID NO 53
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 53

Asp Val Val Met Thr Gln Ser Pro Ser Ser Leu Ser Ala Ser Val Gly
 1               5                  10                  15

Asp Arg Val Thr Ile Thr Cys Arg Glu Ser Gln Gly Ile Arg Asn Tyr
                20                  25                  30

Leu Ala Trp Tyr Gln Gln Lys Pro Gly Lys Ala Pro Lys Leu Leu Ile
             35                  40                  45

Tyr Lys Ala Ser Ser Leu Gln Ser Gly Val Pro Ser Arg Phe Ser Gly
         50                  55                  60

Ser Leu Leu Gly Gly Lys Ala Ala Leu Thr Leu Ser Gly Val Gln Pro
 65                  70                  75                  80

Glu Asp Phe Ala Thr Tyr Tyr Cys Gln Gln Ala Asn Ser Phe Pro Leu
                     85                  90                  95

Thr Phe Gly Gly Gly Thr Lys Val Glu Ile Lys Arg
```

<210> SEQ ID NO 54
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
    /organism="Homo sapiens"

<400> SEQUENCE: 54

Asp Ile Val Leu Thr Gln Ser Pro Ala Thr Leu Ser Leu Ser Pro Gly
1               5                   10                  15

Glu Arg Val Thr Ile Thr Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg
            100                 105

<210> SEQ ID NO 55
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
    /organism="Homo sapiens"

<400> SEQUENCE: 55

Asp Ile Gln Met Thr Gln Ser Pro Gly Thr Leu Ser Leu Ser Pro Gly
1               5                   10                  15

Glu Arg Ala Ala Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Ile Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg
            100                 105

<210> SEQ ID NO 56
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
    /organism="Homo sapiens"

<400> SEQUENCE: 56

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Thr Val Ser
        115                 120

<210> SEQ ID NO 57
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 57

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser
        115                 120

<210> SEQ ID NO 58
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 58

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Pro Leu Ala Thr Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Pro Trp Gly
            100                 105                 110

Gln Gly Thr Leu Val Thr Val Ser
        115                 120

<210> SEQ ID NO 59
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 59

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Pro Trp Gly
            100                 105                 110

Gln Gly Thr Leu Val Ser Val Ser
        115                 120

<210> SEQ ID NO 60
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 60

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Glu Trp Val
        35                  40                  45
```

```
Gly Arg Ile Gly Thr Ala Gly Arg Thr Asn Tyr Asn Pro Ser Leu Lys
        50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Val Tyr Tyr Cys Ala
                85                  90                  95

Arg Gly Ala Gly Arg Trp Ala Pro Leu Gly Ala Phe Asp Ile Trp Gly
            100                 105                 110

Gln Gly Thr Leu Val Ile Val Ser
            115                 120

<210> SEQ ID NO 61
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 61

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Val Trp Val
        35                  40                  45

Ser Arg Ile Gly Thr Ala Gly Asp Arg Tyr Tyr Ala Gly Ser Val Lys
    50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Val Tyr Tyr Cys Ala
                85                  90                  95

Arg Gly Ala Gly Arg Trp Ala Pro Leu Gly Ala Phe Asp Ile Trp Gly
            100                 105                 110

Gln Gly Thr Leu Val Ile Val Ser
            115                 120

<210> SEQ ID NO 62
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 62

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser
        115                 120

<210> SEQ ID NO 63
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 63

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
            35                  40                  45

Ala Ser Val Lys Gln Phe Phe Ser Gly Ser Ala Ala Thr Gly Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser
        115                 120

<210> SEQ ID NO 64
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 64

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
            50                  55                  60

Lys Gly Arg Pro Thr Ile Ser Arg Asp Asn Ala Lys Asn Gln Leu Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110
```

```
Gln Gly Thr Leu Val Thr Val Ser
        115                 120

<210> SEQ ID NO 65
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 65

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Leu Thr Leu Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser
        115                 120

<210> SEQ ID NO 66
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 66

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser
        115                 120

<210> SEQ ID NO 67
<211> LENGTH: 120
```

```
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 67

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Ser Leu Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser
        115                 120

<210> SEQ ID NO 68
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 68

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Arg Trp Ala Asp Leu Ala Phe Asp Ile Trp Gly
            100                 105                 110

Gln Gly Thr Leu Val Thr Val Ser
        115                 120

<210> SEQ ID NO 69
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
```

/organism="Homo sapiens"

<400> SEQUENCE: 69

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Thr Ala Asp Arg Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser
        115                 120

<210> SEQ ID NO 70
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 70

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Pro Leu Ala Thr Gly Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser
        115                 120

<210> SEQ ID NO 71
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 71

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Arg Gly Tyr
        20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Lys Tyr Tyr Ala Gly Ser Val
50                      55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Ser Ser Trp Tyr Arg Asp Trp Phe Asp Pro Trp Gly
                100                 105                 110

Gln Gly Thr Leu Val Ser Val Ser
        115                 120

<210> SEQ ID NO 72
<211> LENGTH: 106
<212> TYPE: PRT
<213> ORGANISM: Homo sapiens
<220> FEATURE:
<221> NAME/KEY: SOURCE
<222> LOCATION: 1..106
<223> OTHER INFORMATION: /mol_type="protein"
      /organism="Homo sapiens"

<400> SEQUENCE: 72

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 73
<211> LENGTH: 106
<212> TYPE: PRT
<213> ORGANISM: Homo sapiens
<220> FEATURE:
<221> NAME/KEY: SOURCE
<222> LOCATION: 1..106
<223> OTHER INFORMATION: /mol_type="protein"
      /organism="Homo sapiens"

<400> SEQUENCE: 73

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60
```

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 74
<211> LENGTH: 109
<212> TYPE: PRT
<213> ORGANISM: Homo sapiens
<220> FEATURE:
<221> NAME/KEY: SOURCE
<222> LOCATION: 1..109
<223> OTHER INFORMATION: /mol_type="protein"
      /organism="Homo sapiens"

<400> SEQUENCE: 74

Thr Val Leu Gly Gln Pro Lys Ala Ala Pro Ser Val Thr Leu Phe Pro
1               5                   10                  15

Pro Ser Ser Glu Glu Leu Gln Ala Asn Lys Ala Thr Leu Val Cys Leu
            20                  25                  30

Ile Ser Asp Phe Tyr Pro Gly Ala Val Thr Val Ala Trp Lys Ala Asp
        35                  40                  45

Ser Ser Pro Val Lys Ala Gly Val Glu Thr Thr Thr Pro Ser Lys Gln
50                  55                  60

Ser Asn Asn Lys Tyr Ala Ala Ser Ser Tyr Leu Ser Leu Thr Pro Glu
65                  70                  75                  80

Gln Trp Lys Ser His Arg Ser Tyr Ser Cys Gln Val Thr His Glu Gly
                85                  90                  95

Ser Thr Val Glu Lys Thr Val Ala Pro Thr Glu Cys Ser
            100                 105

<210> SEQ ID NO 75
<211> LENGTH: 331
<212> TYPE: PRT
<213> ORGANISM: Homo sapiens
<220> FEATURE:
<221> NAME/KEY: SOURCE
<222> LOCATION: 1..331
<223> OTHER INFORMATION: /mol_type="protein"
      /organism="Homo sapiens"

<400> SEQUENCE: 75

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
            165                 170                 175

Glu Glu Gln Phe Asn Ser Thr Phe Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 76
<211> LENGTH: 331
<212> TYPE: PRT
<213> ORGANISM: Homo sapiens
<220> FEATURE:
<221> NAME/KEY: SOURCE
<222> LOCATION: 1..331
<223> OTHER INFORMATION: /mol_type="protein"
     /organism="Homo sapiens"

<400> SEQUENCE: 76

Ser Ala Ser Thr Lys Gly Pro Ser Val Phe Pro Leu Ala Pro Cys Ser
1               5                   10                  15

Arg Ser Thr Ser Glu Ser Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Thr Cys Asn Val Asp His Lys Pro Ser Asn Thr Lys Val Asp
            85                  90                  95

Lys Lys Val Glu Pro Lys Ser Cys Asp Lys Thr His Thr Cys Pro Pro
        100                 105                 110

Cys Pro Ala Pro Glu Leu Leu Gly Gly Pro Ser Val Phe Leu Phe Pro
    115                 120                 125

Pro Lys Pro Lys Asp Thr Leu Met Ile Ser Arg Thr Pro Glu Val Thr
130                 135                 140

```
Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Val His Gln Asp Trp Leu Asn Gly Lys Glu Tyr Lys Cys Lys Val Ser
        195                 200                 205

Asn Lys Gly Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Thr Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Met Leu Asp Ser Asp Gly Ser Phe
            275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 77
<211> LENGTH: 331
<212> TYPE: PRT
<213> ORGANISM: Homo sapiens
<220> FEATURE:
<221> NAME/KEY: SOURCE
<222> LOCATION: 1..331
<223> OTHER INFORMATION: /mol_type="protein"
      /organism="Homo sapiens"

<400> SEQUENCE: 77

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
```

```
                165                 170                 175
Glu Glu Gln Phe Ala Ser Thr Phe Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Lys Gly Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 78
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 78

Glu Ile Val Leu Thr Gln Ser Pro Ala Thr Leu Ser Leu Ser Pro Gly
1               5                   10                  15

Glu Arg Val Thr Ile Thr Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
            85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190
```

```
Ala Cys Glu Val Thr His Gln Gly Leu Ser Ser Pro Val Thr Lys Ser
            195                 200                 205

Phe Asn Arg Gly Glu Cys
        210

<210> SEQ ID NO 79
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 79

Glu Ile Val Leu Thr Gln Ser Pro Ala Thr Leu Ser Leu Ser Pro Gly
  1               5                  10                  15

Glu Arg Val Thr Ile Thr Cys Arg Ala Ser Gln Ser Val Asn Ser Tyr
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Gln Gly
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 80
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 80

Glu Ile Val Leu Thr Gln Ser Pro Ala Thr Leu Ser Leu Ser Pro Gly
  1               5                  10                  15

Glu Arg Val Thr Ile Thr Cys Arg Glu Ser Gln Gly Ile Arg Asn Tyr
             20                  25                  30
```

```
Leu Ala Trp Tyr Gln Gln Lys Pro Gly Gln Ala Pro Arg Leu Leu Ile
            35                  40                  45

Tyr Ala Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 81

Glu Ile Val Leu Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
            20                  25                  30

Leu Ala Trp Tyr Gln Gln Lys Pro Gly Gln Ala Pro Arg Leu Leu Ile
            35                  40                  45

Tyr Ala Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 82
<211> LENGTH: 220
<212> TYPE: PRT
<213> ORGANISM: Homo sapiens
<220> FEATURE:
<221> NAME/KEY: SOURCE
<222> LOCATION: 1..220
<223> OTHER INFORMATION: /mol_type="protein"
      /organism="Homo sapiens"

<400> SEQUENCE: 82

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Cys Trp Val Phe Gly Gly Gly Thr Lys Leu Thr
            100                 105                 110

Val Leu Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220

<210> SEQ ID NO 83
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 83

```
Asp Ile Gln Met Thr Gln Ser Pro Ala Thr Leu Ser Leu Ser Pro Gly
1               5                   10                  15

Glu Arg Ala Ala Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ala Ser Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 84

Asp Ile Gln Met Thr Gln Ser Pro Ala Thr Leu Ser Leu Ser Pro Gly
1               5                   10                  15

Glu Arg Ala Ala Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ala Ser Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                  130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Leu Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 85
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 85

Glu Ile Val Leu Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 86
<211> LENGTH: 214
<212> TYPE: PRT
<213> ORGANISM: Homo sapiens
<220> FEATURE:
<221> NAME/KEY: SOURCE
<222> LOCATION: 1..214
```

<223> OTHER INFORMATION: /mol_type="protein"
    /organism="Homo sapiens"

<400> SEQUENCE: 86

```
Glu Ile Val Leu Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 87
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
    /organism="Homo sapiens"

<400> SEQUENCE: 87

```
Glu Ile Val Met Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
            20                  25                  30

Leu Ala Trp Tyr Gln Gln Lys Pro Gly Gln Ala Pro Arg Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 88
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 88

Glu Ile Val Met Thr Gln Ser Pro Ala Thr Leu Ser Leu Ser Pro Gly
1               5                   10                  15

Glu Arg Val Thr Ile Thr Cys Arg Glu Ser Gln Gly Ile Arg Asn Tyr
                20                  25                  30

Leu Ala Trp Tyr Gln Gln Lys Pro Gly Gln Ala Pro Arg Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
                180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 89
<211> LENGTH: 214
```

```
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 89
```

Asp Val Val Met Thr Gln Ser Pro Ser Ser Leu Ser Ala Ser Val Gly
1               5                   10                  15

Asp Arg Val Thr Ile Thr Cys Arg Glu Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Leu Leu Gly Gly Lys Ala Ala Leu Thr Leu Ser Gly Val Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 90
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 90
```

Asp Val Val Met Thr Gln Ser Pro Ser Ser Leu Ser Ala Ser Val Gly
1               5                   10                  15

Asp Arg Val Thr Ile Thr Cys Arg Glu Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Leu Leu Gly Gly Lys Ala Ala Leu Thr Leu Ser Gly Val Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 91
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 91

Asp Ile Val Leu Thr Gln Ser Pro Ala Thr Leu Ser Leu Ser Pro Gly
1               5                   10                  15

Glu Arg Val Thr Ile Thr Cys Arg Ala Ser Gln Ser Val Asn Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys

-continued

```
<210> SEQ ID NO 92
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 92

Asp Ile Gln Met Thr Gln Ser Pro Gly Thr Leu Ser Leu Ser Pro Gly
1               5                   10                  15

Glu Arg Ala Ala Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Ile Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Gln Gly
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 93

Asp Ile Gln Met Thr Gln Ser Pro Gly Thr Leu Ser Leu Ser Pro Gly
1               5                   10                  15

Glu Arg Ala Ala Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Ile Arg Ala Thr Gly Ile Pro Asp Arg Phe Ser Gly
```

```
                 50                  55                  60
Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Gln Gly
                     85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 94
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 94

Glu Val Gln Leu Val Glu Ser Gly Gly Gly Val Val Gln Pro Gly Gly
  1               5                  10                  15

Ser Leu Arg Leu Ser Cys Ala Ala Ser Gly Phe Thr Phe Arg Ser Tyr
                 20                  25                  30

Trp Met Ser Trp Val Arg Gln Ala Pro Gly Lys Gly Leu Glu Trp Val
             35                  40                  45

Ala Ser Val Lys Gln Asp Gly Ser Glu Lys Tyr Tyr Val Asp Ser Val
 50                  55                  60

Lys Gly Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Ser Ser Trp Tyr Arg Asp Trp Phe Asp Pro Trp Gly
                100                 105                 110

Gln Gly Thr Leu Val Thr Val Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 95
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 95

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Thr Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95
Ala Arg Asp Ala Ser Ser Trp Tyr Asp Trp Phe Asp Pro Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Thr Cys Asn Val Asp His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Val His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Thr
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Met Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 96
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 96

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

-continued

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 97
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 97

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                 295                 300
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Thr
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 98
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 98

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
                35                  40                  45

Ala Ser Val Lys Gln Asp Gly Ser Glu Lys Tyr Tyr Val Asp Ser Val
                50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Thr
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 99
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 99

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
        50                  55                  60

Lys Gly Arg Phe Thr Ile Ser Arg Asp Thr Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95
Ala Arg Asp Gly Ser Ser Trp Tyr Arg Asp Trp Phe Asp Pro Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Ala Ser Thr Phe
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 100
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 100

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Pro Leu Ala Thr Gly Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400
```

-continued

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 101
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 101

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Pro Leu Ala Thr Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
              290                 295                 300
Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Thr
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 102
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 102

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
                20                  25                  30

Trp Met Ser Trp Val Arg Gln Ala Pro Gly Lys Gly Leu Glu Trp Val
            35                  40                  45

Ala Ser Val Lys Gln Phe Phe Ser Gly Pro Leu Ala Thr Gly Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Ser Trp Tyr Arg Asp Trp Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Phe Ala Ser Thr Phe
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 103
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 103

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Phe Ser
65                  70                  75                  80

```
Leu Lys Leu Ser Ser Val Thr Ala Ala Asp Thr Ala Val Tyr Tyr Cys
                 85                  90                  95
Ala Arg Asp Gly Ser Ser Trp Tyr Arg Asp Trp Phe Asp Pro Trp Gly
            100                 105                 110
Gln Gly Thr Leu Val Ser Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Asn Ser Thr Phe
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 104
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 104

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 105
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 105

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
```

```
                    290                 295                 300
Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 106
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 106

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Glu Trp Val
        35                  40                  45

Gly Arg Ile Gly Thr Ala Gly Arg Thr Asn Tyr Asn Pro Ser Leu Lys
    50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Ala Val Tyr Tyr Cys Ala
                85                  90                  95

Arg Gly Ala Gly Arg Trp Ala Pro Leu Gly Ala Phe Asp Ile Trp Gly
            100                 105                 110

Gln Gly Thr Leu Val Ile Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
        450

<210> SEQ ID NO 107
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 107

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Glu Trp Val
        35                  40                  45

Gly Arg Ile Gly Thr Ala Gly Arg Thr Asn Tyr Asn Pro Ser Leu Lys
    50                  55                  60

Gly Arg Phe Thr Ile Ser Arg Glu Asn Ala Lys Asp Ser Leu Tyr Leu
65                  70                  75                  80
```

```
Gln Met Asn Ser Leu Arg Val Gly Asp Ala Ala Val Tyr Tyr Cys Ala
                 85                  90                  95
Arg Gly Ala Gly Arg Trp Ala Pro Leu Gly Ala Phe Asp Ile Trp Gly
            100                 105                 110
Gln Gly Thr Leu Val Ile Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Thr Cys Asn Val Asp His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Val His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Thr
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Met Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 108
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 108

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Glu Trp Val
        35                  40                  45

Gly Arg Ile Gly Thr Ala Gly Arg Thr Asn Tyr Asn Pro Ser Leu Lys
    50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Ala Val Tyr Tyr Cys Ala
                85                  90                  95

Arg Gly Ala Gly Arg Trp Ala Pro Leu Gly Ala Phe Asp Ile Trp Gly
            100                 105                 110

Gln Gly Thr Leu Val Ile Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 109
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 109

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Val Trp Val
        35                  40                  45

Ser Arg Ile Gly Thr Ala Gly Asp Arg Tyr Tyr Ala Gly Ser Val Lys
    50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Ala Val Tyr Tyr Cys Ala
                85                  90                  95

Arg Gly Ala Gly Arg Trp Ala Pro Leu Gly Ala Phe Asp Ile Trp Gly
            100                 105                 110

Gln Gly Thr Leu Val Ile Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
```

```
                290                 295                 300
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450

<210> SEQ ID NO 110
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 110

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
                20                  25                  30

Asp Met His Trp Val Arg Gln Gly Ile Gly Lys Gly Leu Val Trp Val
                35                  40                  45

Ser Arg Ile Gly Thr Ala Gly Asp Arg Tyr Tyr Ala Gly Ser Val Lys
                50                  55                  60

Gly Arg Phe Thr Ile Ser Arg Glu Asn Ala Lys Asp Ser Leu Tyr Leu
65                  70                  75                  80

Gln Met Asn Ser Leu Arg Val Gly Asp Ala Ala Val Tyr Tyr Cys Ala
                85                  90                  95

Arg Gly Ala Gly Arg Trp Ala Pro Leu Gly Ala Phe Asp Ile Trp Gly
                100                 105                 110

Gln Gly Thr Leu Val Ile Val Ser Ser Ala Ser Thr Lys Gly Pro Ser
                115                 120                 125

Val Phe Pro Leu Ala Pro Cys Ser Arg Ser Thr Ser Glu Ser Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 111
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 111

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Val Trp Val
        35                  40                  45

Ser Arg Ile Gly Thr Ala Gly Asp Arg Tyr Tyr Ala Gly Ser Val Lys
    50                  55                  60

Gly Arg Phe Thr Ile Ser Arg Glu Asn Ala Lys Asp Ser Leu Tyr Leu
65                  70                  75                  80
```

```
Gln Met Asn Ser Leu Arg Val Gly Asp Ala Ala Val Tyr Tyr Cys Ala
                 85                  90                  95
Arg Gly Ala Gly Arg Trp Ala Pro Leu Gly Ala Phe Asp Ile Trp Gly
            100                 105                 110
Gln Gly Thr Leu Val Ile Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Ala Ser Thr Phe
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 112
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 112

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 113
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 113

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                 295                 300
Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Thr
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 114
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 114

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

Pro Ser Ser Ser Leu Gly Thr Gln Thr Tyr Ile Cys Asn Val Asn His
         195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Phe Ala Ser Thr Phe
     290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
             340                 345                 350

Tyr Thr Leu Pro Pro Ser Arg Asp Glu Leu Thr Lys Asn Gln Val Ser
         355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445

Pro Gly Lys
    450

```
<210> SEQ ID NO 115
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 115
```

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Phe Phe Ser Gly Ser Ala Ala Thr Gly Ser Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Arg Ala Glu Asp Thr Ala Val Tyr Tyr Cys
                85                  90                  95
Ala Arg Asp Gly Ser Ser Trp Tyr Arg Asp Trp Phe Asp Pro Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Asn Ser Thr Phe
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 116
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 116

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Phe Phe Ser Gly Ser Ala Ala Thr Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 117
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 117

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Phe Phe Ser Gly Ser Ala Ala Thr Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
```

```
                        290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 118
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 118

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
                20                  25                  30

Asp Met Ser Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
        50                  55                  60

Lys Gly Arg Pro Thr Ile Ser Arg Asp Asn Ala Lys Asn Gln Leu Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 119
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 119

Glu Val Gln Leu Val Glu Ser Gly Gly Val Gln Pro Gly Gly
1               5                  10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Leu Ser
65                  70                  75                  80
```

Leu Lys Leu Ser Ser Val Thr Ala Ala Asp Thr Ala Val Tyr Tyr Cys
            85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 120
<211> LENGTH: 451
<212> TYPE: PRT
<213> ORGANISM: Homo sapiens
<220> FEATURE:
<221> NAME/KEY: SOURCE
<222> LOCATION: 1..451

<223> OTHER INFORMATION: /mol_type="protein"
/organism="Homo sapiens"

<400> SEQUENCE: 120

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Pro Thr Ile Ser Arg Asp Asn Ala Lys Asn Gln Leu Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 121
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 121

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Leu Thr Leu Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
```

```
                290              295               300
Arg Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450

<210> SEQ ID NO 122
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 122

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
                35                  40                  45

Ala Ser Val Lys Gln Asp Gly Ser Glu Lys Tyr Tyr Val Asp Ser Val
                50                  55                  60

Lys Gly Arg Leu Thr Leu Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
                100                 105                 110

Gln Gly Thr Leu Val Ser Val Ser Ser Ala Ser Thr Lys Gly Pro Ser
                115                 120                 125

Val Phe Pro Leu Ala Pro Cys Ser Arg Ser Thr Ser Glu Ser Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Thr
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 123
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 123

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Leu Thr Leu Ser Val Asp Thr Ser Lys Asn Gln Phe Ser
65                  70                  75                  80
```

```
Leu Lys Leu Ser Ser Val Thr Ala Ala Asp Thr Ala Val Tyr Tyr Cys
             85                  90                  95
Ala Arg Asp Gly Ser Ser Trp Tyr Arg Asp Trp Phe Asp Pro Trp Gly
            100                 105                 110
Gln Gly Thr Leu Val Ser Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Ala Ser Thr Phe
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 124
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 124

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

-continued

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 125
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 125

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                    290                 295                 300

Arg Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                    325                 330                 335

Glu Lys Thr Ile Ser Lys Ala Lys Gly Gln Pro Arg Glu Pro Gln Val
                    340                 345                 350

Tyr Thr Leu Pro Pro Ser Arg Glu Glu Met Thr Lys Asn Gln Val Thr
                    355                 360                 365

Leu Thr Cys Leu Val Lys Gly Phe Tyr Pro Ser Asp Ile Ala Val Glu
                    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
    450

<210> SEQ ID NO 126
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 126

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ala Ser Thr Lys Gly Pro Ser
        115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

-continued

```
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Phe Ala Ser Thr Phe
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 127
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 127

Glu Val Gln Leu Val Glu Ser Gly Gly Gly Val Gln Pro Gly Gly
1               5                   10                  15
Ser Leu Arg Leu Ser Cys Ala Ala Ser Gly Phe Thr Phe Arg Ser Tyr
            20                  25                  30
Trp Met His Trp Val Arg Gln Ala Pro Gly Lys Gly Leu Glu Trp Val
        35                  40                  45
Ala Ser Val Lys Gln Asp Gly Ser Glu Lys Tyr Tyr Val Asp Ser Val
    50                  55                  60
Lys Gly Arg Val Thr Ile Ser Leu Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                 85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 128
<211> LENGTH: 451
<212> TYPE: PRT
<213> ORGANISM: Homo sapiens
<220> FEATURE:
<221> NAME/KEY: SOURCE
<222> LOCATION: 1..451
```

-continued

<223> OTHER INFORMATION: /mol_type="protein"
/organism="Homo sapiens"

<400> SEQUENCE: 128

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Ser Leu Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 129
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 129

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
            35                  40                  45

Ala Ser Val Lys Gln Asp Gly Ser Glu Lys Tyr Tyr Val Asp Ser Val
        50                  55                  60

Lys Gly Arg Val Thr Ile Ser Leu Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
```

```
                    290                 295                 300
Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 130
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 130

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
50                  55                  60

Lys Gly Arg Phe Thr Val Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Arg Trp Ala Asp Leu Ala Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 131
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 131

Glu Val Gln Leu Val Glu Ser Gly Gly Gly Val Gln Pro Gly Gly
1               5                   10                  15

Ser Leu Arg Leu Ser Cys Ala Ala Ser Gly Ile Thr Phe Arg Ser Tyr
            20                  25                  30

Asp Met Ser Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Phe Thr Val Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asp Ala Gly Arg Trp Ala Leu Ala Phe Asp Ile Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Thr
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 132
<211> LENGTH: 451
<212> TYPE: PRT
<213> ORGANISM: Homo sapiens
<220> FEATURE:
<221> NAME/KEY: SOURCE
<222> LOCATION: 1..451
```

<223> OTHER INFORMATION: /mol_type="protein"
/organism="Homo sapiens"

<400> SEQUENCE: 132

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Thr Ala Asp Arg Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 133
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 133

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Trp Met His Trp Val Arg Gln Ala Pro Gly Lys Gly Leu Glu Trp Val
        35                  40                  45

Ala Ser Val Lys Gln Asp Gly Ser Glu Lys Tyr Tyr Val Asp Ser Val
    50                  55                  60

Lys Gly Arg Val Thr Ile Thr Ala Asp Arg Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                 295                 300
Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Thr
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 134
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 134

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
                20                  25                  30

Trp Met Ser Trp Val Arg Gln Ala Pro Gly Lys Gly Leu Glu Trp Val
            35                  40                  45

Ala Ser Val Lys Gln Phe Phe Ser Gly Pro Leu Ala Thr Gly Ser Val
        50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Arg Asp Trp Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 135
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 135

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Asn Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Pro Leu Ala Thr Gly Ser Val
    50                  55                  60

Lys Gly Arg Phe Thr Ile Ser Arg Asp Thr Ser Lys Asn Thr Leu Tyr
65                  70                  75                  80
```

Leu Gln Met Asn Ser Leu Arg Ala Glu Asp Thr Ala Val Tyr Tyr Cys
                 85                  90                  95

Ala Arg Asp Gly Ser Ser Trp Tyr Arg Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 136
<211> LENGTH: 451
<212> TYPE: PRT
<213> ORGANISM: Homo sapiens
<220> FEATURE:
<221> NAME/KEY: SOURCE
<222> LOCATION: 1..451

<223> OTHER INFORMATION: /mol_type="protein"
/organism="Homo sapiens"

<400> SEQUENCE: 136

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Lys Tyr Tyr Ala Gly Ser Val
    50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 137
<211> LENGTH: 451
<212> TYPE: PRT
<213> ORGANISM: Homo sapiens
<220> FEATURE:
<221> NAME/KEY: SOURCE
<222> LOCATION: 1..451
<223> OTHER INFORMATION: /mol_type="protein"
      /organism="Homo sapiens"

<400> SEQUENCE: 137

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ala Ser Val Lys Gln Phe Phe Ser Gly Lys Tyr Tyr Ala Gly Ser Val
    50                  55                  60

Lys Gly Arg Val Thr Ile Ser Val Glu Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Ser Ser Trp Tyr Arg Asp Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Phe Ala Ser Thr Phe
```

```
                    290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 138
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 138

Glu Ile Val Leu Thr Gln Ser Pro Ala Thr Leu Ser Leu Ser Pro Gly
1               5                   10                  15

Glu Arg

<210> SEQ ID NO 139
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 139

Glu Ile Val Met Thr Gln Ser Pro Ala Thr Leu Ser Leu Ser Pro Gly
1               5                   10                  15

Glu Arg

<210> SEQ ID NO 140
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 140
```

Asp Ile Gln Met Thr Gln Ser Pro Ala Thr Leu Ser Leu Ser Pro Gly
1               5                   10                  15

Glu Arg

<210> SEQ ID NO 141
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 141

Asp Val Val Met Thr Gln Ser Pro Ser Ser Leu Ser Ala Ser Val Gly
1               5                   10                  15

Asp Arg

<210> SEQ ID NO 142
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 142

Asp Ile Val Leu Thr Gln Ser Pro Ala Thr Leu Ser Leu Ser Pro Gly
1               5                   10                  15

Glu Arg

<210> SEQ ID NO 143
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 143

Asp Ile Gln Met Thr Gln Ser Pro Gly Thr Leu Ser Leu Ser Pro Gly
1               5                   10                  15

Glu Arg

<210> SEQ ID NO 144
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: Xaa can be Glu or Asp
<220> FEATURE:
<221> NAME/KEY: SITE
<222> LOCATION: 2..2
<223> OTHER INFORMATION: Xaa can be Ile or Val
<220> FEATURE:
<221> NAME/KEY: SITE

```
<222> LOCATION: 3..3
<223> OTHER INFORMATION: Xaa can be  Val or Gln
<220> FEATURE:
<221> NAME/KEY: SITE
<222> LOCATION: 4..4
<223> OTHER INFORMATION: Xaa can be  Leu or Met
<220> FEATURE:
<221> NAME/KEY: SITE
<222> LOCATION: 9..9
<223> OTHER INFORMATION: Xaa can be  Ala, Gly or Ser
<220> FEATURE:
<221> NAME/KEY: SITE
<222> LOCATION: 10..10
<223> OTHER INFORMATION: Xaa can be  Thr or Ser
<220> FEATURE:
<221> NAME/KEY: SITE
<222> LOCATION: 13..13
<223> OTHER INFORMATION: Xaa can be Leu or Ala
<220> FEATURE:
<221> NAME/KEY: SITE
<222> LOCATION: 15..15
<223> OTHER INFORMATION: Xaa can be Pro or Val
<220> FEATURE:
<221> NAME/KEY: SITE
<222> LOCATION: 17..17
<223> OTHER INFORMATION: Xaa can be Glu or Asp

<400> SEQUENCE: 144

Xaa Xaa Xaa Xaa Thr Gln Ser Pro Xaa Xaa Leu Ser Xaa Ser Xaa Gly
1               5                   10                  15

Xaa Arg

<210> SEQ ID NO 145
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 145

Asp Val Val Met Thr Gln Ser Pro Ser Ser Leu Ser Ala Ser Val Gly
1               5                   10                  15

Asp Arg Val Thr Ile Thr Cys Arg Glu Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Leu Leu Gly Gly Lys Ala Ala Leu Thr Leu Ser Gly Val Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 146
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 146
```

-continued

Asp Val Val Met Thr Gln Ser Pro Ser Ser Leu Ser Ala Ser Val Gly
1               5                   10                  15

Asp Arg Val Thr Ile Thr Cys Arg Glu Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Lys Val Ser Asn Arg Phe Ser Gly Val Pro Asp Arg Phe Ser Gly
    50                  55                  60

Ser Leu Leu Gly Gly Lys Ala Ala Leu Thr Leu Ser Gly Val Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 147
<211> LENGTH: 108
<212> TYPE: PRT
<213> ORGANISM: Homo sapiens
<220> FEATURE:
<221> NAME/KEY: SOURCE
<222> LOCATION: 1..108
<223> OTHER INFORMATION: /mol_type="protein"
      /organism="Homo sapiens"

<400> SEQUENCE: 147

Asp Val Val Met Thr Gln Ser Pro Ser Ser Leu Ser Ala Ser Val Gly
1               5                   10                  15

Asp Arg Val Thr Ile Thr Cys Arg Glu Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Trp Ala Ser Thr Arg Glu Ser Gly Val Pro Asp Arg Phe Ser Gly
    50                  55                  60

Ser Leu Leu Gly Gly Lys Ala Ala Leu Thr Leu Ser Gly Val Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 148
<211> LENGTH: 120
<212> TYPE: PRT
<213> ORGANISM: Homo sapiens
<220> FEATURE:
<221> NAME/KEY: SOURCE
<222> LOCATION: 1..120
<223> OTHER INFORMATION: /mol_type="protein"
      /organism="Homo sapiens"

<400> SEQUENCE: 148

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asn Tyr
            20                  25                  30

Asp Met His Trp Val Arg Gln Gly Ile Gly Lys Gly Leu Glu Trp Ile
        35                  40                  45

Gly Glu Ile Asn Arg Ser Gly Ala Thr Asn Tyr Asn Pro Ser Leu Lys
    50                  55                  60

```
Ser Arg Phe Thr Ile Ser Arg Glu Asn Ala Lys Asp Ser Leu Tyr Leu
 65                  70                  75                  80

Gln Met Asn Ser Leu Arg Val Gly Asp Ala Ala Val Tyr Tyr Cys Ala
                 85                  90                  95

Arg Gly Ala Gly Arg Trp Ala Pro Leu Gly Ala Phe Asp Ile Trp Gly
            100                 105                 110

Gln Gly Thr Leu Val Ile Val Ser
        115                 120

<210> SEQ ID NO 149
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"

<400> SEQUENCE: 149

Glu Ile Asn Arg Ser Gly Ala Thr Asn Tyr Asn Pro Ser Leu Lys Ser
 1               5                  10                  15

<210> SEQ ID NO 150
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 150

Ala Ala Ser Thr Leu Gln Ser
 1               5

<210> SEQ ID NO 151
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 151

Lys Val Ser Asn Arg Phe Ser
 1               5

<210> SEQ ID NO 152
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 152

Trp Ala Ser Thr Arg Glu Ser
 1               5

<210> SEQ ID NO 153
<211> LENGTH: 5
```

```
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: X can be Asn or Ser
<220> FEATURE:
<221> NAME/KEY: SITE
<222> LOCATION: 3..3
<223> OTHER INFORMATION: X can be Asp or Trp
<220> FEATURE:
<221> NAME/KEY: SITE
<222> LOCATION: 5..5
<223> OTHER INFORMATION: X can be His or Ser

<400> SEQUENCE: 153

Xaa Tyr Xaa Met Xaa
1               5

<210> SEQ ID NO 154
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 154

Asn Tyr Asp Met His
1               5

<210> SEQ ID NO 155
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"
<220> FEATURE:
<221> NAME/KEY: SITE
<222> LOCATION: 3..3
<223> OTHER INFORMATION: X can be Trp or Asp

<400> SEQUENCE: 155

Ser Tyr Xaa Met Ser
1               5

<210> SEQ ID NO 156
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: X can be Arg or Ser or Glu
<220> FEATURE:
<221> NAME/KEY: SITE
<222> LOCATION: 2..2
<223> OTHER INFORMATION: X can be Ile or Val
<220> FEATURE:
```

```
<221> NAME/KEY: SITE
<222> LOCATION: 3..3
<223> OTHER INFORMATION: X can be Gly or Lys or Asn
<220> FEATURE:
<221> NAME/KEY: SITE
<222> LOCATION: 4..4
<223> OTHER INFORMATION: X can be Gln or no amino acid
<220> FEATURE:
<221> NAME/KEY: SITE
<222> LOCATION: 5..5
<223> OTHER INFORMATION: X can be Thr or Asp or Arg
<220> FEATURE:
<221> NAME/KEY: SITE
<222> LOCATION: 6..6
<223> OTHER INFORMATION: X can be Ala or Gly or Ser
<220> FEATURE:
<221> NAME/KEY: SITE
<222> LOCATION: 7..7
<223> OTHER INFORMATION: X can be Gly or Ser
<220> FEATURE:
<221> NAME/KEY: SITE
<222> LOCATION: 8..8
<223> OTHER INFORMATION: X can be Arg or Asp or Glu or Ala
<220> FEATURE:
<221> NAME/KEY: SITE
<222> LOCATION: 9..9
<223> OTHER INFORMATION: X can be Thr or Arg or Lys
<220> FEATURE:
<221> NAME/KEY: SITE
<222> LOCATION: 10..10
<223> OTHER INFORMATION: X can be Asn or Tyr
<220> FEATURE:
<221> NAME/KEY: SITE
<222> LOCATION: 12..12
<223> OTHER INFORMATION: X can be Asn or Ala or Val
<220> FEATURE:
<221> NAME/KEY: SITE
<222> LOCATION: 13..13
<223> OTHER INFORMATION: X can be Pro or Gly or Asp
<220> FEATURE:
<221> NAME/KEY: SITE
<222> LOCATION: 15..15
<223> OTHER INFORMATION: X can be Leu or Val
<220> FEATURE:
<221> NAME/KEY: SITE
<222> LOCATION: 17..17
<223> OTHER INFORMATION: X can be Gly or Ser

<400> SEQUENCE: 156

Xaa Xaa Xaa Xaa Xaa Xaa Xaa Xaa Xaa Xaa Tyr Xaa Xaa Ser Xaa Lys
1               5                   10                  15

Xaa

<210> SEQ ID NO 157
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: X can be Arg or Glu
<220> FEATURE:
<221> NAME/KEY: SITE
<222> LOCATION: 3..3
<223> OTHER INFORMATION: X can be Gly or Asn
<220> FEATURE:
<221> NAME/KEY: SITE
<222> LOCATION: 4..4
<223> OTHER INFORMATION: X can be Thr or Arg
<220> FEATURE:
<221> NAME/KEY: SITE
<222> LOCATION: 5..5
```

```
<223> OTHER INFORMATION: X can be Ala or Ser
<220> FEATURE:
<221> NAME/KEY: SITE
<222> LOCATION: 7..7
<223> OTHER INFORMATION: X can be Arg or Asp or Ala
<220> FEATURE:
<221> NAME/KEY: SITE
<222> LOCATION: 8..8
<223> OTHER INFORMATION: X can be Thr or Arg
<220> FEATURE:
<221> NAME/KEY: SITE
<222> LOCATION: 9..9
<223> OTHER INFORMATION: X can be Asn or Tyr
<220> FEATURE:
<221> NAME/KEY: SITE
<222> LOCATION: 11..11
<223> OTHER INFORMATION: X can be Asn or Ala
<220> FEATURE:
<221> NAME/KEY: SITE
<222> LOCATION: 12..12
<223> OTHER INFORMATION: X can be Pro or Gly
<220> FEATURE:
<221> NAME/KEY: SITE
<222> LOCATION: 14..14
<223> OTHER INFORMATION: X can be Leu or Val
<220> FEATURE:
<221> NAME/KEY: SITE
<222> LOCATION: 16..16
<223> OTHER INFORMATION: X can be Gly or Ser

<400> SEQUENCE: 157

Xaa Ile Xaa Xaa Xaa Gly Xaa Xaa Xaa Tyr Xaa Xaa Ser Xaa Lys Xaa
1               5                   10                  15

<210> SEQ ID NO 158
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 158

Ser Val Lys Gln Asp Gly Ser Glu Lys Tyr Tyr Val Asp Ser Val Lys
1               5                   10                  15
Gly

<210> SEQ ID NO 159
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"
<220> FEATURE:
<221> NAME/KEY: SITE
<222> LOCATION: 1..1
<223> OTHER INFORMATION: X can be Gly or Asp
<220> FEATURE:
<221> NAME/KEY: SITE
<222> LOCATION: 2..2
<223> OTHER INFORMATION: X can be Ala or Gly
<220> FEATURE:
<221> NAME/KEY: SITE
<222> LOCATION: 3..3
<223> OTHER INFORMATION: X can be Gly or Ser
<220> FEATURE:
<221> NAME/KEY: SITE
<222> LOCATION: 4..4
<223> OTHER INFORMATION: X can be Arg or Ser
<220> FEATURE:
```

```
<221> NAME/KEY: SITE
<222> LOCATION: 6..6
<223> OTHER INFORMATION: X can be Ala or Tyr
<220> FEATURE:
<221> NAME/KEY: SITE
<222> LOCATION: 7..7
<223> OTHER INFORMATION: X can be Pro or Arg or Asp
<220> FEATURE:
<221> NAME/KEY: SITE
<222> LOCATION: 8..8
<223> OTHER INFORMATION: X can be Leu or Asp
<220> FEATURE:
<221> NAME/KEY: SITE
<222> LOCATION: 9..9
<223> OTHER INFORMATION: X can be Gly or Trp or Ala
<220> FEATURE:
<221> NAME/KEY: SITE
<222> LOCATION: 10..10
<223> OTHER INFORMATION: X can be Ala or Phe
<220> FEATURE:
<221> NAME/KEY: SITE
<222> LOCATION: 11..11
<223> OTHER INFORMATION: X can be Phe or no amino acid
<220> FEATURE:
<221> NAME/KEY: SITE
<222> LOCATION: 13..13
<223> OTHER INFORMATION: X can be Ile or Pro

<400> SEQUENCE: 159

Xaa Xaa Xaa Xaa Trp Xaa Xaa Xaa Xaa Xaa Xaa Asp Xaa
1               5                   10

<210> SEQ ID NO 160
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 160

Gly Ala Gly Arg Trp Ala Pro Leu Gly Ala Phe Asp Ile
1               5                   10

<210> SEQ ID NO 161
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"
<220> FEATURE:
<221> NAME/KEY: SITE
<222> LOCATION: 2..2
<223> OTHER INFORMATION: X can be Gly or Ala
<220> FEATURE:
<221> NAME/KEY: SITE
<222> LOCATION: 3..3
<223> OTHER INFORMATION: X can be Ser or Gly
<220> FEATURE:
<221> NAME/KEY: SITE
<222> LOCATION: 4..4
<223> OTHER INFORMATION: X can be Ser or Arg
<220> FEATURE:
<221> NAME/KEY: SITE
<222> LOCATION: 6..6
<223> OTHER INFORMATION: X can be Tyr or Ala
<220> FEATURE:
<221> NAME/KEY: SITE
<222> LOCATION: 7..7
<223> OTHER INFORMATION: X can be Arg or Asp
<220> FEATURE:
```

```
<221> NAME/KEY: SITE
<222> LOCATION: 8..8
<223> OTHER INFORMATION: X can be Asp or Leu
<220> FEATURE:
<221> NAME/KEY: SITE
<222> LOCATION: 9..9
<223> OTHER INFORMATION: X can be Trp or Ala
<220> FEATURE:
<221> NAME/KEY: SITE
<222> LOCATION: 12..12
<223> OTHER INFORMATION: X can be Pro or Ile

<400> SEQUENCE: 161

Asp Xaa Xaa Xaa Trp Xaa Xaa Xaa Xaa Phe Asp Xaa
1               5                   10

<210> SEQ ID NO 162
<211> LENGTH: 30
<212> TYPE: PRT
<213> ORGANISM: artificial sequences
<220> FEATURE:
<221> NAME/KEY: SOURCE
<222> LOCATION: 1..30
<223> OTHER INFORMATION: /mol_type="protein"
      /note="N-Cysteinyl-Abeta (12-40) "
      /organism="artificial sequences"

<400> SEQUENCE: 162

Cys Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 163
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /note="tryptic peptide "
      /organism="Homo sapiens"

<400> SEQUENCE: 163

Glu Glu Gln Tyr Asn Ser Thr Tyr Arg
1               5

<210> SEQ ID NO 164
<211> LENGTH: 20
<212> TYPE: PRT
<213> ORGANISM: artificial sequences
<220> FEATURE:
<221> NAME/KEY: SOURCE
<222> LOCATION: 1..20
<223> OTHER INFORMATION: /mol_type="protein"
      /note="signal peptide for recombinant expression of light chain v
      ariable region of CSL Clone 7 "
      /organism="artificial sequences"

<400> SEQUENCE: 164

Met Glu Ser Gln Thr Gln Val Leu Met Ser Leu Leu Phe Trp Val Ser
1               5                   10                  15

Gly Thr Cys Gly
            20

<210> SEQ ID NO 165
<211> LENGTH: 19
<212> TYPE: PRT
<213> ORGANISM: artificial sequences
```

```
<220> FEATURE:
<221> NAME/KEY: SOURCE
<222> LOCATION: 1..19
<223> OTHER INFORMATION: /mol_type="protein"
      /note="signal peptide for expression of light chain variable
      region of CSL Clone 7 "
      /organism="artificial sequences"

<400> SEQUENCE: 165

Met Gly Trp Ser Trp Ile Phe Leu Phe Leu Val Ser Gly Thr Gly Gly
1               5                   10                  15

Val Leu Ser

<210> SEQ ID NO 166
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="peptide Abeta 20-30 with N-terminal Biotin-G5-Phe
      modification "
      /organism="artificial sequences"

<400> SEQUENCE: 166

Phe Ala Glu Asp Val Gly Ser Asn Lys Gly Ala
1               5                   10

<210> SEQ ID NO 167
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="peptide Abeta 20-37 with N-terminal Biotin-G5-Phe
      modification "
      /organism="artificial sequences"

<400> SEQUENCE: 167

Phe Ala Glu Asp Val Gly Ser Asn Lys Gly Ala Ile Ile Gly Leu Met
1               5                   10                  15

Val Gly

<210> SEQ ID NO 168
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /note="proteolytic peptide fragment of Abeta peptide"
      /organism="Homo sapiens"

<400> SEQUENCE: 168

Asp Ala Glu Phe Arg His Asp Ser Gly Tyr Glu Val His His Gln Lys
1               5                   10                  15

Leu Val

<210> SEQ ID NO 169
<211> LENGTH: 58
<212> TYPE: PRT
<213> ORGANISM: Homo sapiens
<220> FEATURE:
<221> NAME/KEY: SOURCE
<222> LOCATION: 1..58
```

```
<223> OTHER INFORMATION: /mol_type="protein"
     /note="fragment of amyloid precursor protein (APP)"
     /organism="Homo sapiens"

<400> SEQUENCE: 169

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45

Ile Val Ile Thr Leu Val Met Leu Lys Lys
    50                  55

<210> SEQ ID NO 170
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
     /note="heavy chain CDR1 peptide v(20-30)"
     /organism="Homo sapiens"

<400> SEQUENCE: 170

Leu Ser Cys Ala Ala Ser Gly Phe Thr Phe Arg
1               5                   10

<210> SEQ ID NO 171
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
     /note="tryptic peptide, fraction 50, heavy chain (138-151)"
     /organism="Homo sapiens"

<400> SEQUENCE: 171

Ser Thr Ser Glu Ser Thr Ala Ala Leu Gly Cys Leu Val Lys
1               5                   10

<210> SEQ ID NO 172
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
     /note="peptide isolated in fraction 75, heavy chain (375-396)"
     /organism="Homo sapiens"

<400> SEQUENCE: 172

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 173
<211> LENGTH: 11
<212> TYPE: PRT
<213> ORGANISM: Homo sapiens
<220> FEATURE:
<221> NAME/KEY: SOURCE
<222> LOCATION: 1..11
```

```
<223> OTHER INFORMATION: /mol_type="protein"
      /note="peptide isolated in fraction 47 denoted on the molecular
      ion peak (349-359)"
      /organism="Homo sapiens"

<400> SEQUENCE: 173

Glu Pro Gln Val Tyr Thr Leu Pro Pro Ser Arg
1               5                   10

<210> SEQ ID NO 174
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /note="peptide isolated in fraction 47 denoted on the molecular
      ion peak (349-364)"
      /organism="Homo sapiens"

<400> SEQUENCE: 174

Ser Thr Ser Gly Gly Thr Ala Ala Leu Gly Cys Leu Val Lys
1               5                   10

<210> SEQ ID NO 175
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /note="peptide isolated in fraction 47 denoted on the molecular
      ion peak (137-151)"
      /organism="Homo sapiens"

<400> SEQUENCE: 175

Glu Pro Gln Val Tyr Thr Leu Pro Pro Ser Arg Asp Glu Leu Thr Lys
1               5                   10                  15

<210> SEQ ID NO 176
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /note="peptide in fraction 66 (260-278) "
      /organism="Homo sapiens"

<400> SEQUENCE: 176

Phe Asn Trp Tyr Val Asp Gly Val Glu Val His Asn Ala Lys
1               5                   10

<210> SEQ ID NO 177
<211> LENGTH: 19
<212> TYPE: PRT
<213> ORGANISM: Homo sapiens
<220> FEATURE:
<221> NAME/KEY: SOURCE
<222> LOCATION: 1..19
<223> OTHER INFORMATION: /mol_type="protein"
      /note="peptide in fraction 66 (279-292)"
      /organism="Homo sapiens"

<400> SEQUENCE: 177

Thr Pro Glu Val Thr Cys Val Val Val Asp Val Ser His Glu Asp Pro
1               5                   10                  15
```

Glu Val Lys

<210> SEQ ID NO 178
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /note="peptide (306-321) in fraction 96"
      /organism="Homo sapiens"

<400> SEQUENCE: 178

Val Val Ser Val Leu Thr Val Leu His Gln Asp Trp Leu Asn Gly Lys
1               5                   10                  15

<210> SEQ ID NO 179
<211> LENGTH: 26
<212> TYPE: PRT
<213> ORGANISM: Homo sapiens
<220> FEATURE:
<221> NAME/KEY: SOURCE
<222> LOCATION: 1..26
<223> OTHER INFORMATION: /mol_type="protein"
      /note="serum IVIgG1 heavy chain constant region, isolated from 2D
      -gel bands subjected to in-gel tryptic digestion; heavy chain
      (227-252)"
      /organism="Homo sapiens"

<400> SEQUENCE: 179

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 180
<211> LENGTH: 19
<212> TYPE: PRT
<213> ORGANISM: Homo sapiens
<220> FEATURE:
<221> NAME/KEY: SOURCE
<222> LOCATION: 1..19
<223> OTHER INFORMATION: /mol_type="protein"
      /note="serum IVIgG1 heavy chain constant region, isolated from 2D
      -gel bands subjected to in-gel tryptic digestion; heavy chain (2
      60-278)"
      /organism="Homo sapiens"

<400> SEQUENCE: 180

Thr Pro Glu Val Thr Cys Val Val Asp Val Ser His Glu Asp Pro
1               5                   10                  15

Glu Val Lys

<210> SEQ ID NO 181
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /note="serum IVIgG1 heavy chain constant region, isolated from 2D
      -gel bands subjected to in-gel tryptic digestion; heavy chain (2
      79-292)"
      /organism="Homo sapiens"

<400> SEQUENCE: 181

Phe Asn Trp Tyr Val Asp Gly Val Glu Val His Asn Ala Lys
1               5                   10

<210> SEQ ID NO 182
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
    /note="serum IVIgG1 heavy chain constant region, isolated from 2D
    -gel bands subjected to in-gel tryptic digestion; heavy chain (3
    06-321)"
    /organism="Homo sapiens"

<400> SEQUENCE: 182

Val Val Ser Val Leu Thr Val Leu His Gln Asp Trp Leu Asn Gly Lys
1               5                   10                  15

<210> SEQ ID NO 183
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
    /note="serum IVIgG1 heavy chain constant region, isolated from 2D
    -gel bands subjected to in-gel tryptic digestion; heavy chain (3
    49-359)"
    /organism="Homo sapiens"

<400> SEQUENCE: 183

Glu Pro Gln Val Tyr Thr Leu Pro Pro Ser Arg
1               5                   10

<210> SEQ ID NO 184
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
    /note="serum IVIgG1 heavy chain constant region, isolated from 2D
    -gel bands subjected to in-gel tryptic digestion; heavy chain (3
    49-364)"
    /organism="Homo sapiens"

<400> SEQUENCE: 184

Glu Pro Gln Val Tyr Thr Leu Pro Pro Ser Arg Asp Glu Leu Thr Lys
1               5                   10                  15

<210> SEQ ID NO 185
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
    /note="serum IVIgG1 heavy chain constant region, isolated from 2D
    -gel bands subjected to in-gel tryptic digestion; heavy chain (3
    75-396)"
    /organism="Homo sapiens"

<400> SEQUENCE: 185

Gly Phe Tyr Pro Ser Asp Ile Ala Val Glu Trp Glu Ser Asn Gly Gln
1               5                   10                  15

Pro Glu Asn Asn Tyr Lys
            20

```
<210> SEQ ID NO 186
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /note="serum IVIgG1 heavy chain constant region, isolated from 2D
      -gel bands subjected to in-gel tryptic digestion; heavy chain  (4
      21-443)"
      /organism="Homo sapiens"

<400> SEQUENCE: 186

Trp Gln Gln Gly Asn Phe Phe Ser Cys Ser Val Met His Glu Ala Leu
1               5                   10                  15

His Asn His Tyr Thr Gln Lys
            20

<210> SEQ ID NO 187
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /note="serum IVIgG1 heavy chain constant region, isolated from 2D
      -gel bands subjected to in-gel tryptic digestion; heavy chain  (7
      7-87)"
      /organism="Homo sapiens"

<400> SEQUENCE: 187

Asn Thr Leu Tyr Leu Gln Met Asn Ser Leu Arg
1               5                   10

<210> SEQ ID NO 188
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /note="serum IVIgG1 heavy chain constant region, isolated from 2D
      -gel bands subjected to in-gel tryptic digestion; heavy chain  (1
      26-137)"
      /organism="Homo sapiens"

<400> SEQUENCE: 188

Gly Pro Ser Val Phe Pro Leu Ala Pro Ser Ser Lys
1               5                   10

<210> SEQ ID NO 189
<211> LENGTH: 30
<212> TYPE: PRT
<213> ORGANISM: Homo sapiens
<220> FEATURE:
<221> NAME/KEY: SOURCE
<222> LOCATION: 1..30
<223> OTHER INFORMATION: /mol_type="protein"
      /note="serum IVIgG1 heavy chain constant region, isolated from 2D
      -gel bands subjected to in-gel tryptic digestion; heavy chain  (2
      23-252)"
      /organism="Homo sapiens"

<400> SEQUENCE: 189

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
```

```
                    20                  25                  30

<210> SEQ ID NO 190
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /note="serum IVIgG1 heavy chain constant region, isolated from 2D
      -gel bands subjected to in-gel tryptic digestion; heavy chain (2
      93-305)"
      /organism="Homo sapiens"

<400> SEQUENCE: 190

Thr Lys Pro Arg Glu Glu Gln Tyr Asn Ser Thr Tyr Arg
1               5                   10

<210> SEQ ID NO 191
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /note="serum IVIgG1 heavy chain constant region, isolated from 2D
      -gel bands subjected to in-gel tryptic digestion; heavy chain (3
      65-374)"
      /organism="Homo sapiens"

<400> SEQUENCE: 191

Asn Gln Val Ser Leu Thr Cys Leu Val Lys
1               5                   10

<210> SEQ ID NO 192
<211> LENGTH: 27
<212> TYPE: PRT
<213> ORGANISM: Homo sapiens
<220> FEATURE:
<221> NAME/KEY: SOURCE
<222> LOCATION: 1..27
<223> OTHER INFORMATION: /mol_type="protein"
      /note="serum IVIgG1 heavy chain constant region, isolated from 2D
      -gel bands subjected to in-gel tryptic digestion; heavy chain
      fragment "
      /organism="Homo sapiens"

<400> SEQUENCE: 192

Lys Cys Cys Val Glu Cys Pro Pro Cys Pro Ala Pro Pro Val Ala Gly
1               5                   10                  15

Pro Ser Val Phe Leu Phe Pro Pro Lys Pro Lys
                20                  25

<210> SEQ ID NO 193
<211> LENGTH: 26
<212> TYPE: PRT
<213> ORGANISM: Homo sapiens
<220> FEATURE:
<221> NAME/KEY: SOURCE
<222> LOCATION: 1..26
<223> OTHER INFORMATION: /mol_type="protein"
      /note="serum IVIgG1 heavy chain constant region, isolated from 2D
      -gel bands subjected to in-gel tryptic digestion; heavy chain
      fragment"
      /organism="Homo sapiens"

<400> SEQUENCE: 193

Cys Cys Val Glu Cys Pro Pro Cys Pro Ala Pro Pro Val Ala Gly Pro
1               5                   10                  15
```

```
Ser Val Phe Leu Phe Pro Pro Lys Pro Lys
            20                  25

<210> SEQ ID NO 194
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /note="serum IVIgG1 heavy chain constant region, isolated from 2D
      -gel bands subjected to in-gel tryptic digestion; heavy chain HC2
      (306-321)"
      /organism="Homo sapiens"

<400> SEQUENCE: 194

Val Val Ser Val Leu Thr Val Val His Gln Asp Trp Leu Asn Gly Lys
1               5                   10                  15
```

METHOD OF TREATMENT OF NEURODEMENTING DISEASES USING ISOLATED, MONOCLONAL, HUMAN, ANTI-B-AMYLOID ANTIBODY

INFORMATION ON RELATED APPLICATIONS

This application claims priority to U.S. Provisional Application No. 60/884,513, filed Jan. 11, 2007, and to U.S. Provisional Application No. 60/884,526 filed Jan. 11, 2007, and to U.S. Provisional Application No. 60/981,667, filed Oct. 22, 2007, and to U.S. Provisional Application No. 60/981,675, filed Oct. 22, 2007, and to European Patent Application No. 07000507.9, filed Jan. 11, 2007, and to European Patent Application No. 07000521.0, filed Jan. 11, 2007, and to European Patent Application No. 07119002.9, filed Oct. 22, 2007, and to European Patent Application No. 07119026.8, filed Oct. 22, 2007, all of which are hereby incorporated by reference in their entireties.

BACKGROUND

Alzheimer's disease (AD), the most common faun of dementia among elderly population (prevalence: 1000/100,000; >65 years), represents the fourth leading cause of death in the developed world. Cortical atrophy, neuronal loss, region-specific amyloid deposition, neuritic plaques, and neurofibrillary tangles are key neuropathological features in the AD brain. These alterations are thought to be linked to cognitive decline which clinically defines AD. Within these markers, neuritic plaques are amyloid immunoreactive, thioflavin positive, and accompanied by astrogliosis, microgliosis, cytoskeletal changes, and synaptic loss. The degree of neuritic degeneration within plaques correlates with clinical parameters of dementia. Neuritic plaques are spherical, multicellular lesions that are usually found in moderate to large numbers in limbic structures and associated neocortices of the AD brain. These plaques are comprised of extracellular deposits of amyloid-β peptide(s) (Aβ) that include abundant amyloid fibrils intermixed with non-fibrillary forms of the peptide. Such plaques also contain variable numbers of activated microglia that are often situated very near the fibrillar amyloid core, as well as reactive astrocytes surrounding the core.

The major constituent of the neuritic plaque, β-amyloid polypeptide (Aβ), arises from a larger precursor protein, the amyloid precursor protein (APP) (Kang, et al., 1987; Tanzi, et al., 1987). Aβ is produced by normal cells and can be detected as a circulating peptide in the plasma and cerebrospinal fluid (CSF) of healthy humans. Although the physiological role of the amyloid precursor protein (APP) in the brain is not well understood, missense mutations in APP confer autosomal dominant inheritance of AD (FAD), and shed light on potentially important pathogenic mechanism(s). The accumulation of Aβ, a 39-42 amino acid proteolytic product of APP, in neuritic plaques, structures which at autopsy fulfill the neuropathological criteria for a definitive diagnosis of AD, is thought to be causative for disease progression. A major Aβ cleavage product of APP is the Aβ(1-42) polypeptide, but Aβ peptides shorter at the C-terminus (39 to 41) are also produced by the proteolytic (γ-secretase) cleavage in the membrane. The N-terminal part of Aβ(1-42) is localized in the extracellular region of APP, and the major C-terminal part of the Aβ peptide is contained within the transmembrane domain.

Missense mutations, in APP associated with FAD, occur in proximity to the Aβ domain and result in an increase in the production of the 4 kDa Aβ peptide. In AD, it has been postulated that increased synthesis and/or a decreased clearance of Aβ may lead to amyloid plaque deposition and subsequently to the neuropathological changes associated with the disease. In vitro studies, using synthetic Aβ peptide(s), have shown that neurotoxicity is dependent on Aβ being fibrillar and predominantly in a β-pleated sheet conformation.

The accumulation of extracellular plaques containing the neurotoxic amyloid peptide fragment (Aβ) of β-amyloid precursor protein (APP), as the major product, is one of the characteristics of Alzheimer's disease (AD). Although APP has been recognized as a key molecule for AD, the molecular (patho-) physiological degradation and proteolytic pathways of APP, and cellular interactions and biochemical fate of Aβ peptide(s) are still unclear. Despite the lack of details on degradation pathways and cellular transport for the formation and deposition of Aβ-derived plaques, recent studies towards the development of immunisation methods of AD based on therapeutically active antibodies produced from Aβ(1-42) have yielded initial success in transgenic mouse models of Alzheimer's disease. Several reports have demonstrated that antibodies generated by immunization with Aβ(1-42) are capable of inhibiting the formation of Aβ-plaques by disaggregating Aβ-fibrils, and improve the impairments in the spatial memory of mice. The transgenic APPV717F mouse (TG mouse) is a well characterized model of AD-like plaque pathology with age- and region-dependent deposits of Aβ(1-40) and Aβ(1-42) (Games, et al., 1995). Recently, Schenk et al. and others investigated alterations in the deposition of Aβ in APPV717F TG mouse following immunization with pre-aggregated Aβ(1-42) or administration of antibodies against Aβ (Bard, et al., 2000; Schenk, et al., 1999). Both immunization and administration of Aβ antibodies significantly attenuated amyloid plaque deposition, neuritic dystrophy, and astrogliosis. In these studies, increased titers of mouse anti-human Aβ-antibodies were necessary for the observed reduction in plaque burden. These findings raise the possibility that formation and clearance of an Aβ-antigen: antibody complex may decrease brain Aβ deposition either following antibody generation within the central nervous system or by peripheral antibody transport across the blood-brain-barrier (BBB). Furthermore, passive immunization appears to reduce brain Aβ burden by altering Aβ equilibrium between the CNS and plasma (DeMattos, et al., 2001). Remarkably, active or passive immunization significantly reverses behavioral and memory impairment in APPV717F mouse or other APP transgenic mice (Dodart, et al., 2002; Janus, et al., 2000; Morgan, et al., 2000). These results suggest that immunization may prevent memory deficits possibly by altering a soluble pool of Aβ. Thus, treatment of AD patients with active or passive immunization is one of several emerging therapeutic approaches targeting the production, clearance, and aggregation of the Aβ peptide.

Based on these results, a clinical trial using an active immunization procedure [Aβ(1-42) peptide and/or preaggregates thereof; adjuvant: QS21] was initiated for treatment of patients with established AD. Unfortunately, severe side-effects developed ("meningoencephalitis") and the clinical trial was stopped. A subgroup of AD patients (n=30) treated with active immunization in this clinical trial, was analyzed (Hock, et al., 2002; Hock, et al., 2003). The authors demonstrated that (i) immunization induces the production of antibodies against Aβ(1-42) and (ii) in patients where a production of antibodies was observable, the cognitive decline was significantly reduced in comparison to the untreated control group. The authors concluded that immunization may be a therapeutic option for AD.

Recent studies elucidated in more detail the recognition properties of antibodies produced upon immunization with Aβ(1-42). This work resulted in the identification of a specific Aβ-epitope recognized by the antibodies generated in transgenic AD mice (McLaurin et al., 2002; Przybylski et al., 2003). These results have been obtained by using selective proteolytic excision technologies (Epitope-Excision) in combination with high resolution mass spectrometry (FTICR-MS) as bioanalytical tools of high sensitivity and specificity for the identification of antigen epitopes (Macht et al 1996; Suckau et al 1992; Macht et al. 2004; see FIGS. 1, 2)). Using mass spectrometric epitope excision of the immobilized Aβ-antigen-immune complex, the epitope was identified to consist of the residues (4-10) (FRHDSGY) of Aβ(1-42). The selectivity of this recognition structure was ascertained by elucidation of the identical epitope from AD plaques, Aβ(1-42) extracts from Aβ-protofibrils, chemically synthesised Aβ(1-42), and other (Aβ-independent) polypeptides comprising the N-terminal Aβ sequence (Przybylski et al. 2003).

Naturally occurring anti-Aβ autoantibodies (Aβ-autoantibodies) were identified by Du et al. in both the blood and the CSF from non-immunized humans (Du, et al., 2001). These antibodies specifically recognize human Aβ as has been shown by immunoprecipitation (Du, et al., 2001) and ELISA. Furthermore, the antibodies readily recognize synthetic Aβ(1-40) as well as human Aβ deposited in the brain of PDAPP transgenic mice. In addition, fibrillation/oligomerization and neurotoxicity of Aβ-peptides were reduced in the presence of Aβ-autoantibodies (Du, et al., 2003).

Furthermore, it has been investigated whether there is a difference of the Aβ-autoantibody concentration in patients with Alzheimer's disease compared to controls. Interestingly, a significant difference among the two groups was found, resulting in a substantially decreased titer (approximately 15-20-fold) of antibodies against Aβ in patients with Alzheimer's disease. These results have been confirmed recently by other groups (Weksler et al., 2004). Antibodies against Aβ can also be detected in commercially available intravenous IgG preparations (IVIgG). The treatment of patients with different neurological diseases with these intravenous immunoglobulin preparations led to the reduction of Aβ concentration in the CSF (Dodel, et al., 2002). The substantial effect of the Aβ-autoantibodies in preventing, and protecting against Aβ-plaque deposition was also established in young (4 months) APP-transgenic (TgCRND8) mice. Additionally, in a pilot trial with 5 patients with AD, utilizing IVIgG, total Aβ was reduced significantly in the CSF and increased in the serum upon delivery of IVIgG (Dodel, et al., 2004). In the five investigated patients no cognitive deterioration was observed during the six months observation period. These results have been confirmed by a recent pilot study involving 8 AD patients, who were treated with IVIgG (Relkin et al., 2006)

However, administering IVIgG to a patient with AD is not convenient and associated with high costs, as the fraction of therapeutic Aβ autoantibodies is low. The vast majority of IgG in this preparation is not Aβ specific and may result in undesirable effects. Furthermore, the sources for IVIgG are limited, which is an unacceptable disadvantage in view of the prevalence of patients with Alzheimer's disease.

Methods of detecting and monitoring the progression AD and other neurodementing diseases similarly are inadequate. Current AD diagnostics fall into three groups: (i) determinations for genetic risk factors or mutations (mainly for FAD cases, but not for sporadic AD diagnostics); (ii) neuroimaging methods; and (iii) diagnostics based on biochemical/biological markers. Present work on the development of diagnostic procedures based on biomarkers have been mainly focused on CSF, which has the principal disadvantage that such methods require elaborate, invasive material. A major problem associated with brain-derived biomarkers is that clinically examined controls often also include subjects with preclinical AD pathology. Further, current available biomarkers have the major disadvantage of low specificity. Similar disadvantages have been noted for a series of proteins expressed in the frontal cortex, identified by brain proteomics approaches, as potential brain biomarkers arising from presumed alterations of blood brain barrier in AD.

Studies on biomarkers in plasma and serum have been performed mainly with determinations of SP (senile plaques) and NFT (neurofibrillary tangles) components, e.g. the Aβ peptides Aβ(1-40) (SEQ ID NO: 1) and Aβ(1-42) (found with elevated levels) and hyperphosphorylated Tau-protein. However the specificity of Aβ determinations, and application for early and differential diagnostics has been considered uncertain, the same is the case for protein Tau determinations which has been described as a marker of already progressing neurodegeneration.

There exists, therefore, a need for improved methods of treating and detecting neurodementing diseases such as AD.

SUMMARY

In one aspect, isolated, monoclonal, human, anti-β-amyloid antibodies are provided that comprise more than one amino acid sequence selected from at least two consensus amino acid sequences of the group consisting of SEQ ID NO: 6, SEQ ID NO: 7, SEQ ID NO: 8, SEQ ID NO: 9, SEQ ID NO: 10 and SEQ ID NO: 11, wherein each of said more than one amino acid sequence is from a different SEQ ID NO, wherein said antibody binds to dimeric forms of Aβ with higher affinity than to monomeric forms of Aβ.

In one embodiment, the antibody comprises more than two amino acid sequences selected from at least three consensus amino acid sequences of the group consisting of SEQ ID NO: 6, SEQ ID NO: 7, SEQ ID NO: 8, SEQ ID NO: 9, SEQ ID NO: 10 and SEQ ID NO: 11, wherein each of said more than two amino acid sequences is from a different SEQ ID NO. In another, the antibody comprises more than three amino acid sequences selected from at least four consensus amino acid sequences of the group consisting of SEQ ID NO: 6, SEQ ID NO: 7, SEQ ID NO: 8, SEQ ID NO: 9, SEQ ID NO: 10 and SEQ ID NO: 11, wherein each of said more than three amino acid sequences is from a different SEQ ID NO. In still another embodiment, the antibody comprises more than four amino acid sequences selected from at least five consensus amino acid sequences of the group consisting of SEQ ID NO: 6, SEQ ID NO: 7, SEQ ID NO: 8, SEQ ID NO: 9, SEQ ID NO: 10 and SEQ ID NO: 11, wherein each of said more than four amino acid sequences is from a different SEQ ID NO. In another embodiment, the antibody comprises an amino acid sequence from each of the consensus amino acid sequences of SEQ ID NO: 6, SEQ ID NO: 7, SEQ ID NO: 8, SEQ ID NO: 9, SEQ ID NO: 10 and SEQ ID NO: 11.

In one embodiment, the antibody comprises the amino acid sequences of SEQ ID NO: 33, SEQ ID NO: 41; SEQ ID NO: 45 as specific light chain CDRs CDR1, CDR2 and CDR3 respectively and SEQ ID NO: 15; SEQ ID NO: 23 and SEQ ID NO: 29 as specific heavy chain CDRs CDR1, CDR2 and CDR3 respectively, while in another the antibody comprises the amino acid sequences of SEQ ID NO: 53 and SEQ ID NO: 60. In other embodiments, the antibody comprises the amino acid sequences of SEQ ID NO: 145 and SEQ ID NO: 60, SEQ ID NO: 51 and SEQ ID NO: 60, SEQ ID NO: 52 and SEQ ID NO: 60, SEQ ID NO: 146 and SEQ ID NO: 60, SEQ ID NO: 53 and SEQ ID NO: 148, SEQ ID NO: 55 and SEQ ID NO: 61, or SEQ ID NO: 145 and SEQ ID NO: 62. The antibody also can comprise the CDRs from the amino acid sequences of SEQ ID NO: 145 and SEQ ID NO: 60, SEQ ID NO: 51 and SEQ ID NO: 60, SEQ ID NO: 52 and SEQ ID NO: 60, SEQ ID NO: 146 and SEQ ID NO: 60, SEQ ID NO: 53 and SEQ ID NO: 148, SEQ ID NO: 55 and SEQ ID NO: 61, or SEQ ID NO: 145 and SEQ ID NO: 62.

In another aspect the antibody binds to a peptide comprising Aβ(21-37), while in another the antibody shields residues of Aβ(21-37) from proteolytic digestion when being bound to an Aβ polypeptide comprising Aβ(21-37). In another, the antibody binds specifically to Aβ(12-40) or Aβ(20-37) when such antibody is coupled to NHS-activated 6-aminohexanoic acid-coupled sepharose, but does not bind specifically to Aβ(17-28), Aβ(25-35) or Aβ(31-40).

The inventive anti-β-amyloid antibodies also can be formulated as pharmaceutical compositions.

In another aspect, methods of preventing or treating a neurodementing disease in a patient comprise administering to the patient a therapeutically acceptable amount of the inventive anti-β-amyloid antibodies. Such methods can be used in preventing or treating neurodementing diseases selected from the group consisting of Alzheimer's disease, Down's syndrome, dementia with Lewy bodies, fronto-temporal dementia, cerebral amyloid angiopathy and amyloidoses. In a preferred embodiment, the neurodementing disease is Alzheimer's disease.

In another embodiment, the inventive anti-β-amyloid antibodies can be used for the manufacture of a medicament in order to treat a neurodementing disease or to slow or prevent the progression of a neurodementing disease.

In another aspect, methods of detecting or measuring the progression of a neurodementing disease in a patient are provided that comprise (A) measuring in a sample from said patient an antibody titer against a first Aβ peptide, wherein the first Aβ peptide comprises at least the sequence according to Aβ(30-37) and at most the sequence according to Aβ(12-40); (B) measuring in a sample from said patient an antibody titer against a second Aβ peptide wherein the second Aβ peptide comprises at least the sequence according to Aβ(4-10) and at most the sequence according to Aβ(1-20); and (C) comparing the titers from steps (A) and (B). In some embodiments, the first Aβ peptide comprises at least the sequence according to Aβ(21-37). In another embodiment, the methods further comprise comparing the patient titers with titers determined for healthy donors and AD patients whereby a higher titer against the first Aβ peptide correlates with a lower risk of development and/or progression of Alzheimer's disease. The methods also can comprise comparing the patient titers with titers determined for healthy donors and AD patients whereby a higher titer against the first Aβ peptide, relative to the titer against the second Aβ peptide correlates with a lower risk of development and/or progression of Alzheimer's disease. Alternatively, the methods can comprise comparing the patient titers with titers determined for healthy donors and AD patients whereby a higher titer against the second Aβ peptide correlates with a higher risk of development and/or progression of Alzheimer's disease. In another embodiment, the methods further comprise comparing the patient titers with titers determined for healthy donors and AD patients whereby a higher titer against the second Aβ peptide, relative to the titer against the first Aβ peptide, correlates with a higher risk of development and/or progression of Alzheimer's disease.

Methods of detecting or measuring the progression of a neurodementing disease in a patient also are provided that comprise A) obtaining a first sample from said patient at a given time point; B) obtaining a second sample from said patient at later time point; C) measuring in said first and second samples the antibody titer against an epitope comprising at least Aβ(30-37) and at most Aβ(12-40); and D) comparing the titers of said first and second samples. Other such methods comprise A) obtaining a first sample from said patient at a given time point; B) obtaining a second sample from said patient at later time point; C) measuring in said first and second samples the antibody titer against an epitope comprising at least Aβ(4-10) and at most Aβ(1-20); and D) comparing the titers of said first and second samples. In other embodiments, such methods comprise A) obtaining a first sample from said patient at a given time point; B) obtaining a second sample from said patient at later time point; C) measuring in said first and second samples the antibody titer against an epitope comprising Aβ(30-37); and D) comparing the titers of said first and second samples.

In another aspect, there is provided a kit comprising (A) a first Aβ peptide comprising at least the sequence according to Aβ(30-37) and at most the sequence according to Aβ(12-40), and (B) a second Aβ peptide wherein the second Aβ peptide comprising at least the sequence according to Aβ(4-10) and at most the sequence according to Aβ(1-20).

The following figures form part of the present specification and are included to further demonstrate certain aspects of the present invention. The invention may be better understood by reference to one or more of these figures in combination with the detailed description of specific embodiments presented herein.

BRIEF DESCRIPTION OF THE DRAWINGS

FIG. 9: Structure of Aβ(12-40) epitope-specific affinity column and experimental procedure for isolation of anti-Aβ (21-37) autoantibodies. Cys-Aβ(12-40): Cysteine coupled Aβ(12-40) peptide.

FIG. 23a to c: Table giving an overview about the identified and sequenced antibodies specific for a C-terminal part of Aβ-peptide, in particular specific for Aβ(21-37). The table provides the name of the antibody chain sample, the source of the sample, the type of immunoglobulin chain sequenced, verified interactions of light and heavy chains (indicated is the name of the partner chain as connection) as well as confirmed isoforms of the respective immunoglobulin chain and the type of CDR sequence identified for CDR1, CDR2 and CDR3. FIG. 23a: IVIG_(1)_A'; IVIG_(2)_B'; IVIG_(3); IVIG_(4)_A; IVIG_(5)_B; IVIG_(6); IVIG_(7); IVIG_(8); Serum_(9); Serum_(10); Serum_(11); FIG. 23b: IVIG_(12); IVIG_(13); IVIG_(14); IVIG_(15); IVIG_(16); IVIG_(17); IVIG_(18); IVIG_(19); IVIG_(20); IVIG_(21). FIG. 23c: Serum_(22); Serum_(23); Serum_(24); Serum_(25).

FIG. 24a to q: Table indicating the identified CDR types and corresponding consensus sequences for all sequenced antibody chains. The CDR numbers correspond with the numbering as used in FIG. 23 for CDRs. FIG. 24a CDRs of heavy chains; FIG. 24b: CDRs of light chains (lambda chain as well as kappa chain); FIG. 24c: CDR consensus sequence for the CDR1 of the heavy chain, FIG. 24d: CDR consensus sequence for the CDR2 of the heavy chain, FIG. 24e: CDR consensus sequence for the CDR3 of the heavy chain; FIG. 24f: CDR consensus sequences for CDR1 of the kappa light chain, FIG. 24g: CDR consensus sequences for CDR2 of the kappa light chain, FIG. 24h: CDR consensus sequence for CDR3 of the kappa light chain, FIG. 24i: preferred consensus sequence for CDR1 of the heavy chain, FIG. 24j: more preferred consensus sequence for CDR1 of the heavy chain, FIG. 24k: more preferred consensus sequence for CDR1 of the heavy chain. FIG. 24l: preferred consensus sequence for CDR2 of the heavy chain, FIG. 24m: more preferred consensus sequence for CDR2 of the heavy chain, FIG. 24n: more preferred consensus sequence for CDR2 of the heavy chain, FIG. 24o: preferred consensus sequence for CDR3 of the heavy chain, FIG. 24p: more preferred consensus sequence for CDR3 of the heavy chain, FIG. 24q: more preferred consensus sequence for CDR3 of the heavy chain.

FIGS. 25 a to l: Amino acid sequences of light chain variable region sequences of anti-Aβ(21-37) autoantibodies from serum-IVIgG and individual serum anti-Aβ(21-37) autoantibodies (see FIG. 23 for sequence overview). Annotation of codes for sequencing methods employed (Edman; Edman-protein N-terminal; MALDI-TOF-MS; MALDI-FTICR-MS, LC-MS/MS), and of CDR sequences is indicated on the bottom of each sequence. CDRs are indicated by boxes.

FIG. 25a: amino acid sequence of light chain kappa variable region of sample IVIG_(1)_A' (SEQ ID NO:47).

FIG. 25b: amino acid sequence of light chain kappa variable region of sample IVIG_(2)_B' (SEQ ID NO:48).

FIG. 25c: amino acid sequence of light chain lambda variable region of sample IVIG_(3) (SEQ ID NO:49).

FIG. 25d: amino acid sequence of light chain kappa variable region of sample IVIG_(6) (SEQ ID NO:50).

FIG. 25e: amino acid sequence of light chain kappa variable region of sample IVIG_(7) (SEQ ID NO:51).

FIG. 25g: amino acid sequence of light chain kappa variable region of sample Serum_(9) (SEQ ID NO:53).

FIG. 25h: amino acid sequence of light chain kappa variable region of sample Serum_(10) (SEQ ID NO:54).

FIG. 25j: amino acid sequence of light chain kappa variable region of sample Serum_(9) (SEQ ID NO:145).

FIG. 25k: amino acid sequence of light chain kappa variable region of sample Serum_(9) (SEQ ID NO:146).

FIG. 25l: amino acid sequence of light chain kappa variable region of sample Serum_(9) (SEQ ID NO:147).

FIG. 26 a to q: Amino acid sequences of heavy chain variable region sequences of anti-Aβ(21-37) autoantibodies from serum-IVIgG and individual serum anti-Aβ(21-37) autoantibodies (see FIG. 23, sequence overview). Annotation of codes for sequencing methods employed (Edman; Edman-protein N-terminal; MALDI-TOF-MS; MALDI-FTICR-MS, LC-MS/MS), and of CDR sequences is indicated on the bottom of each sequence. CDRs are indicated by boxes.

FIG. 26a: amino acid sequence of heavy chain variable region of sample IVIG_(4)_A (SEQ ID NO:56).

FIG. 26b: amino acid sequence of heavy chain variable region of sample IVIG_(5)_B (SEQ ID NO:57).

FIG. 26f: amino acid sequence of heavy chain variable region of sample IVIG_(15) (SEQ ID NO:61).

FIG. 26g: amino acid sequence of heavy chain variable region of sample IVIG_(16) (SEQ ID NO:62).

FIG. 26i: amino acid sequence of heavy chain variable region of sample IVIG_(18) (SEQ ID NO:64).

FIG. 26j: amino acid sequence of heavy chain variable region of sample IVIG_(19) (SEQ ID NO:65).

FIG. 26k: amino acid sequence of heavy chain variable region of sample IVIG_(20) (SEQ ID NO:66).

FIG. 26l: amino acid sequence of heavy chain variable region of sample IVIG_(21) (SEQ ID NO:67).

FIG. 26m: amino acid sequence of heavy chain variable region of sample Serum_(22) (SEQ ID NO:68).

FIG. 26n: amino acid sequence of heavy chain variable region of sample Serum_(23) (SEQ ID NO:69).

FIG. 26p: amino acid sequence of heavy chain variable region of sample Serum_(25) (SEQ ID NO:71).

FIG. 27a to c: Amino acid sequences of the constant region of kappa and lambda light chains of anti-Aβ(21-37) autoantibody chains. The mutation of the LC-kappa-constant region sequence at V192L is indicated in bold letters.

FIG. 27a: Complete amino acid sequence of constant region light chain kappa isoform 1 (SEQ ID NO:72).

FIG. 27b: Complete amino acid sequence of constant region light chain kappa of isoform 2 (SEQ ID NO:73).

FIG. 27c: Complete amino acid sequence of constant region light chain lambda (SEQ ID NO:74).

FIG. 28a to c: Amino acid sequences and sequence isoforms of the constant region identified for IVIgG-anti-Aβ(21-37) autoantibody heavy chains. Amino acid mutations identified at F300Y, N301A (N-glycosylation site), F304Y, G331A, D360E, L362M, S368T, and V401M are indicated by bold letters. The N-glycosylation consensus sequence and site at, N-301$^{ST}$, are indicated by shaded box and bold grey letter.

FIG. 28a: Complete amino acid sequence of constant region heavy chain of isoform 1 (SEQ ID NO:75).

FIG. 28b: Complete amino acid sequence of constant region heavy chain of isoform 2 (SEQ ID NO:76).

FIG. 28c: Complete amino acid sequence of constant region heavy chain isoform 3 (SEQ ID NO:77).

FIG. 29 a to p: Complete amino acid sequences of light chains of anti-Aβ(21-37) autoantibodies from serum-IVIgG and individual serum (see FIG. 23 for sample overview). Annotation of codes for sequencing methods employed (Edman; Edman-protein N-terminal; MALDI-TOF-MS; MALDI-FTICR-MS, LC-MS/MS), and of CDR sequences is indicated on the bottom of each sequence. CDRs are indicated by boxes. Variable sequence domains, and single amino acid residues in the constant region sequences found with single site mutations are indicated in bold letters.

FIG. 29c: complete amino acid sequence of light chain kappa of sample IVIG_(2)_B', constant region isoform 1 (SEQ ID NO:80).

FIG. 29d: complete amino acid sequence of light chain kappa of sample IVIG_(2)_B', constant region isoform 2 (SEQ ID NO:81).

FIG. 29f: complete amino acid sequence of light chain kappa of sample IVIG_(6), constant region isoform 1 (SEQ ID NO:83).

FIG. 29g: complete amino acid sequence of light chain kappa of sample IVIG_(6), constant region isoform 2 (SEQ ID NO:84).

FIG. 29h: complete amino acid sequence of light chain kappa of sample IVIG_(7), constant region isoform 1 (SEQ ID NO:85).

FIG. 29j: complete amino acid sequence of light chain kappa of sample IVIG_(8), constant region isoform 1 (SEQ ID NO:87).

FIG. 29l: complete amino acid sequence of light chain kappa of sample Serum_(9), constant region isoform 1 (SEQ ID NO:89).

FIG. 29m: complete amino acid sequence of light chain kappa of sample Serum_(9), constant region isoform 2 (SEQ ID NO:90).

FIG. 29n: complete amino acid sequence of light chain kappa of sample Serum_(10), constant region isoform 1 (SEQ ID NO:91).

FIG. 29p: complete amino acid sequence of light chain kappa of sample Serum_(11), constant region isoform 2 (SEQ ID NO:93).

FIGS. 30-1 to 30-44: Complete amino acid sequences of heavy chains of anti-Aβ(21-37) autoantibodies from serum-IVIgG and individual serum (see FIG. 23 for sample overview). Annotation of codes for sequencing methods employed (Edman; Edman-protein N-terminal; MALDI-TOF-MS; MALDI-FTICR-MS, LC-MS/MS), and of CDR sequences is indicated on the bottom of each sequence. CDRs are indicated by boxes. Variable sequence domains, and single amino acid residues in the constant region sequences found with single site mutations are indicated in bold letters. The N-glycosylation site, N-301 is indicated in bold, grey letter.

FIG. 30-1: complete amino acid sequence of heavy chain of sample IVIG_(4)_A, constant region isoform 1 (SEQ ID NO:94).

FIG. 30-2: complete amino acid sequence of heavy chain of sample IVIG_(4)_A, constant region isoform 2 (SEQ ID NO:95).

FIG. 30-3: complete amino acid sequence of heavy chain of sample IVIG_(4)_A, constant region isoform 3 (SEQ ID NO:96).

FIG. 30-4: complete amino acid sequence of heavy chain of sample IVIG_(5) B, constant region isoform 1 (SEQ ID NO:97).

FIG. 30-5: complete amino acid sequence of heavy chain of sample IVIG_(5)_B, constant region isoform 2 (SEQ ID NO:98).

FIG. 30-6: complete amino acid sequence of heavy chain of sample IVIG_(5)_B, constant region isoform 3 (SEQ ID NO:99).

FIG. 30-7: complete amino acid sequence of heavy chain of sample IVIG_(12)_B, constant region isoform 1 (SEQ ID NO:100).

FIG. 30-8: complete amino acid sequence of heavy chain of sample IVIG_(12)_B, constant region isoform 2 (SEQ ID NO:101).

FIG. 30-9: complete amino acid sequence of heavy chain of sample IVIG_(12)_B, constant region isoform 3 (SEQ ID NO:102).

FIG. 30-10: complete amino acid sequence of heavy chain of sample IVIG_(13), constant region isoform 1 (SEQ ID NO:103).

FIG. 30-11: complete amino acid sequence of heavy chain of sample IVIG_(13), constant region isoform 2 (SEQ ID NO:104).

FIG. 30-12: complete amino acid sequence of heavy chain of sample IVIG_(13), constant region isoform 3 (SEQ ID NO:105).

FIG. 30-13: complete amino acid sequence of heavy chain of sample IVIG_(14), constant region isoform 1 (SEQ ID NO:106).

FIG. 30-14: complete amino acid sequence of heavy chain of sample IVIG_(14), constant region isoform 2 (SEQ ID NO:107).

FIG. 30-15: complete amino acid sequence of heavy chain of sample IVIG_(14), constant region isoform 3 (SEQ ID NO:108).

FIG. 30-16: complete amino acid sequence of heavy chain of sample IVIG_(15), constant region isoform 1 (SEQ ID NO:109).

FIG. 30-17: complete amino acid sequence of heavy chain of sample IVIG_(15), constant region isoform 2 (SEQ ID NO:110).

FIG. 30-18: complete amino acid sequence of heavy chain of sample IVIG_(15), constant region isoform 3 (SEQ ID NO:111).

FIG. 30-19: complete amino acid sequence of heavy chain of sample IVIG_(16), constant region isoform 1 (SEQ ID NO:112).

FIG. 30-20: complete amino acid sequence of heavy chain of sample IVIG_(16), constant region isoform 2 (SEQ ID NO:113).

FIG. 30-21: complete amino acid sequence of heavy chain of sample IVIG_(16), constant region isoform 3 (SEQ ID NO:114).

FIG. 30-22: complete amino acid sequence of heavy chain of sample IVIG_(17), constant region isoform 1 (SEQ ID NO:115).

FIG. 30-23: complete amino acid sequence of heavy chain of sample IVIG_(17), constant region isoform 2 (SEQ ID NO:116).

FIG. 30-24: complete amino acid sequence of heavy chain of sample IVIG_(17), constant region isoform 3 (SEQ ID NO:117).

FIG. 30-25: complete amino acid sequence of heavy chain of sample IVIG_(18), constant region isoform 1 (SEQ ID NO:118).

FIG. 30-26: complete amino acid sequence of heavy chain of sample IVIG_(18), constant region isoform 2 (SEQ ID NO:119).

FIG. 30-27: complete amino acid sequence of heavy chain of sample IVIG_(18), constant region isoform 3 (SEQ ID NO:120).

FIG. 30-28: complete amino acid sequence of heavy chain of sample IVIG_(19), constant region isoform 1 (SEQ ID NO:121).

FIG. 30-29: complete amino acid sequence of heavy chain of sample IVIG_(19), constant region isoform 2 (SEQ ID NO:122).

FIG. 30-30: complete amino acid sequence of heavy chain of sample IVIG_(19), constant region isoform 3 (SEQ ID NO:123).

FIG. 30-31: complete amino acid sequence of heavy chain of sample IVIG_(20), constant region isoform 1 (SEQ ID NO:124).

FIG. 30-32: complete amino acid sequence of heavy chain of sample IVIG_(20), constant region isoform 2 (SEQ ID NO:125).

FIG. 30-33: complete amino acid sequence of heavy chain of sample IVIG_(20), constant region isoform 3 (SEQ ID NO:126).

FIG. 30-34: complete amino acid sequence of heavy chain of sample IVIG_(21), constant region isoform 1 (SEQ ID NO:127).

FIG. 30-35: complete amino acid sequence of heavy chain of sample IVIG_(21), constant region isoform 2 (SEQ ID NO:128).

FIG. 30-36: complete amino acid sequence of heavy chain of sample IVIG_(21), constant region isoform 3 (SEQ ID NO:129).

FIG. 30-37: complete amino acid sequence of heavy chain of sample Serum_(22), constant region isoform 1 (SEQ ID NO:130).

FIG. 30-38: complete amino acid sequence of heavy chain of sample Serum_(22), constant region isoform 2 (SEQ ID NO:131).

FIG. 30-39: complete amino acid sequence of heavy chain of sample Serum_(23), constant region isoform 1 (SEQ ID NO:132).

FIG. 30-40: complete amino acid sequence of heavy chain of sample Serum_(23), constant region isoform 2 (SEQ ID NO:133).

FIG. 30-41 complete amino acid sequence of heavy chain of sample Serum_(24), constant region isoform 1 (SEQ ID NO:134).

FIG. 30-42: complete amino acid sequence of heavy chain of sample Serum_(24), constant region isoform 3 (SEQ ID NO:135).

FIG. 30-43 complete amino acid sequence of heavy chain of sample Serum_(24), constant region isoform 1 (SEQ ID NO:136).

FIG. 30-44: complete amino acid sequence of heavy chain of sample Serum_(24), constant region isoform 3 (SEQ ID NO:137).

Figures 24, 30:
Figures 30, 31, 32, 33, 34, 35, 36:
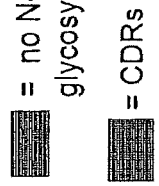

FIG. 31: Table illustrating the conserved nature of the N-terminus of kappa light chain of the antibodies sequenced for the present invention. Indicated are the 6 types of N-terminal sequences, consisting of 18 amino acid residues, which were identified in the kappa light chain sequences of the antibodies of the present invention.

Figure 32A:
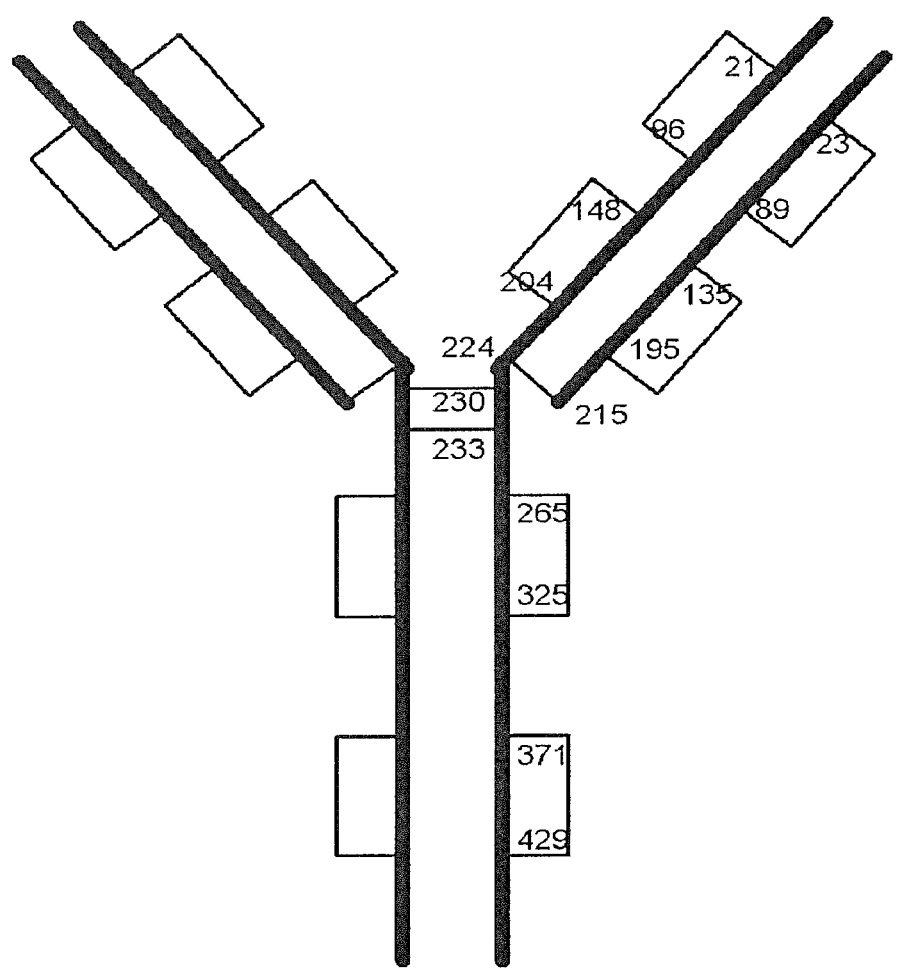
Figure 32B:
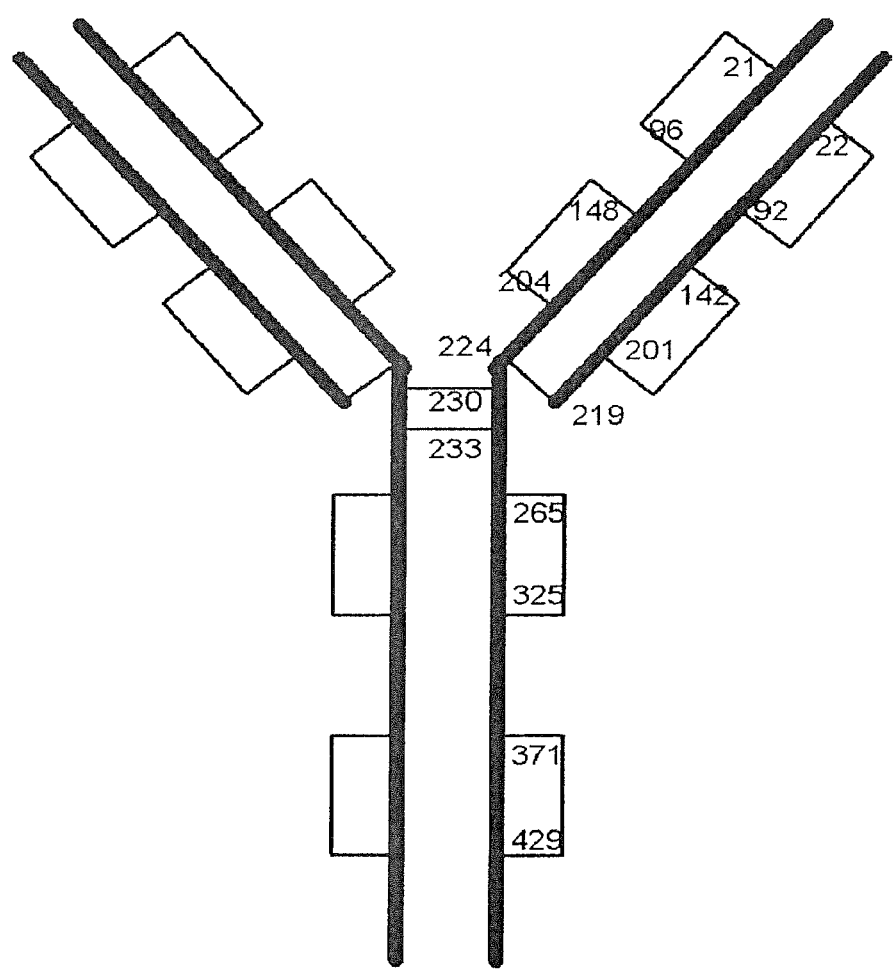
Figure 33:
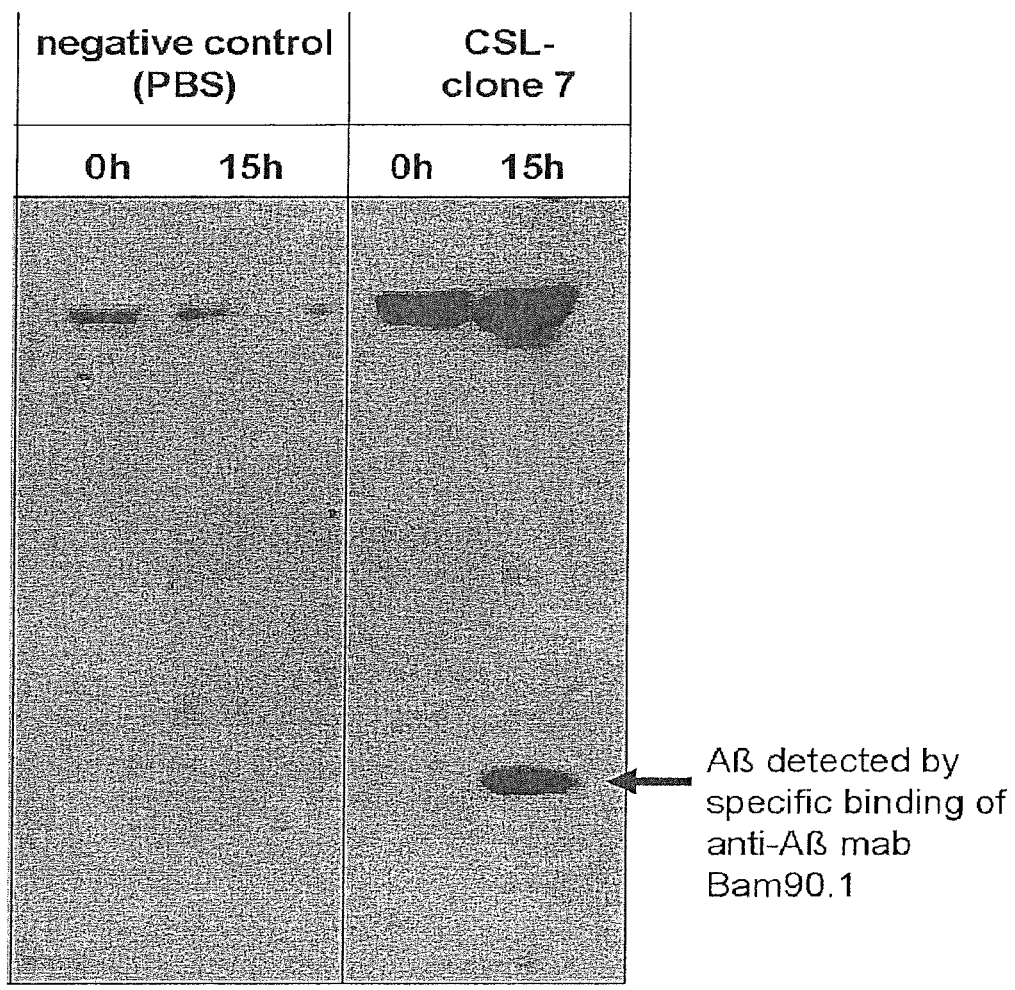

FIGS. 32a and b: Scheme of intra- and inter-disulfide linkages of anti-Aβ(21-37) autoantibodies for HC-LC-kappa and HC-LC-lambda connections. HC intradisulfide linkages are C21-C96, C148-C204, C265-C325, C371-C429; LC-kappa-intradisulfide linkages are C23-C89, C135-C195; LC-lambda-intradisulfide linkages are C22-C92, C142-C201; HC-HC interdisulfide linkages are C230-C230, C233-C33; HC-LC-kappa- and HC-LC-lambda-interdisulfide linkages are C224-C215 and C224-C219, respectively. 32a: IVIgG_LC(1)_HC(1); 32b: IVIG_HC(1)_LCλ(3).

FIG. 33: Western blot showing that the recombinant anti-Aβ(21-37) autoantibody CSL-Clone 7 immunoprecipitates oligomeric forms of Aβ1-40 as described in Example 6. The antibody Bam 90.1 (Sigma Aldrich Cat# A8978 binding to Aβ(13-28)) was used to detect the immunoprecipitated Aβ.

Figure 34A:
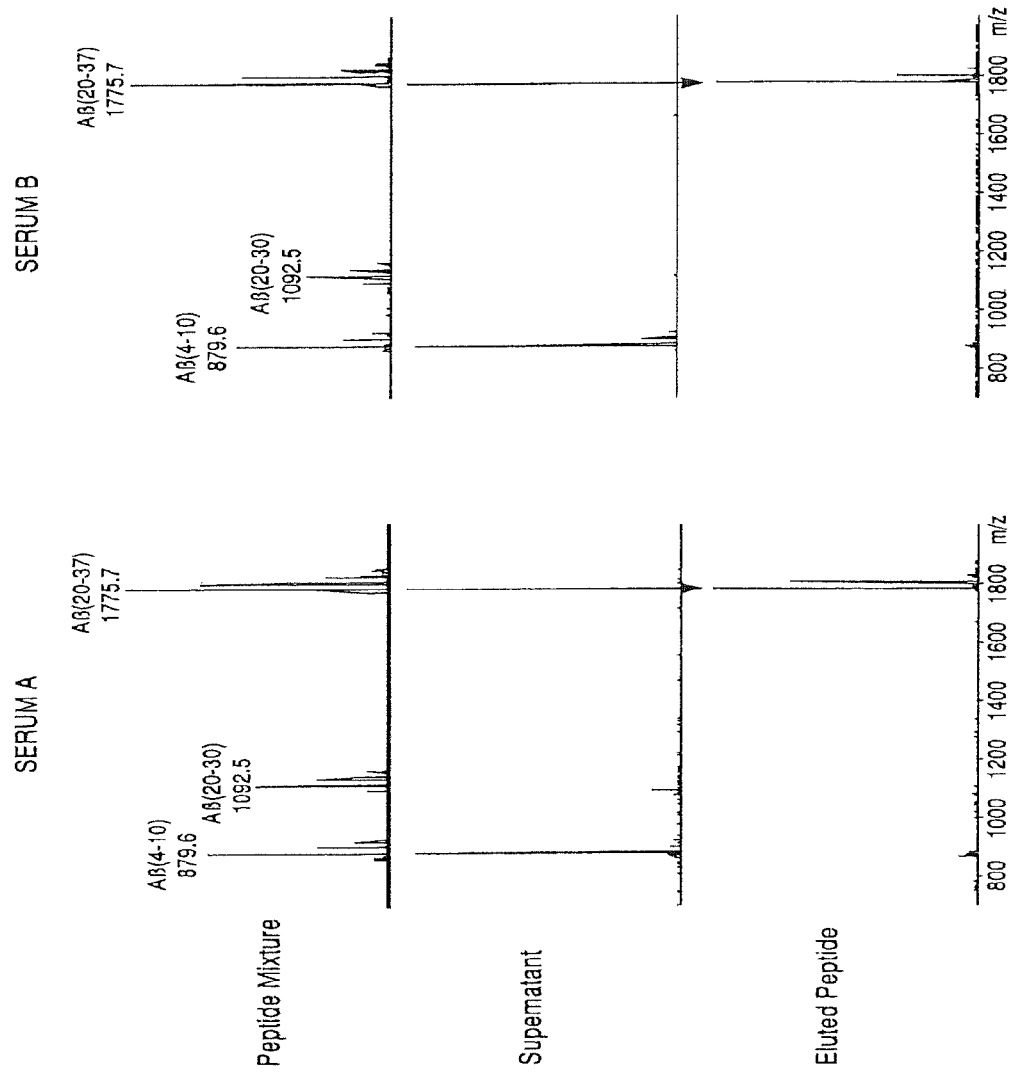

FIG. 34a: Molecular confirmation of epitope recognition specificity of Aβ-autoantibody. Illustrated is the affinity of 3 synthetic Aβ-polypeptides Aβ(4-10), Aβ(20-30) and Aβ(20-37) towards anti-Aβ-autoantibodies isolated from serum of healthy (non-AD control individuals) donors, A and B, by MALDI-mass spectrometry. Affinity-purified antibodies were immobilized on NHS-sepharose as described in Example 2A (A1312-40). Equimolar mixtures (5 μmol mixtures of synthetic Aβ-peptides in aqueous PBS buffer solution, pH 7) were bound to the antibodies after mass spectrometric analysis (MALDI-MS of peptide mixture, upper panel). MALDI-MS of the supernatant washing fraction revealed the N-terminal Aβ(4-10) epitope signal as the predominant ion (confirming the lack of binding of N-terminal Aβ; middle panel), and washing was continued until no MS signal was detectable. After elution with 0.1% trifluoroacetic acid, the Aβ(20-37) peptide was identified as the only polypeptide capable of binding to the autoantibodies (lower panel). All MS determinations were made with a Bruker Bilflex MALDI-TOF spectrometer.

Figure 34B:
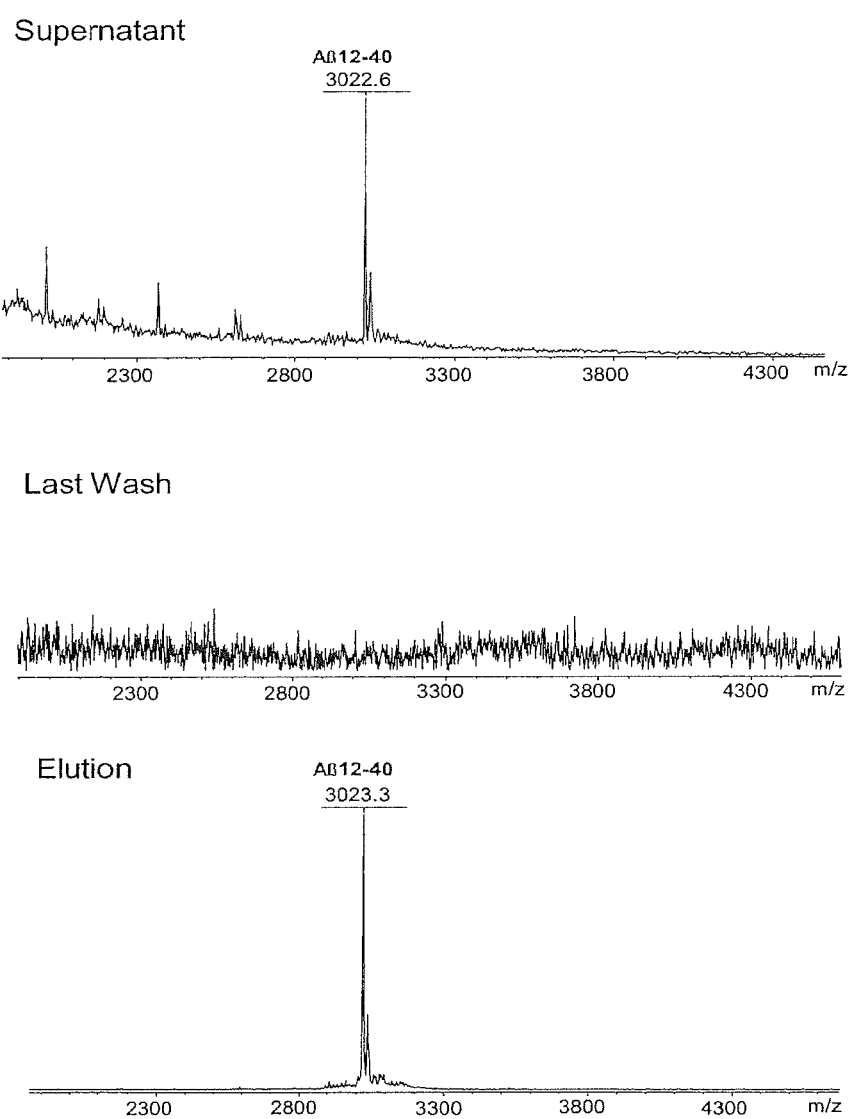
Figure 34D:
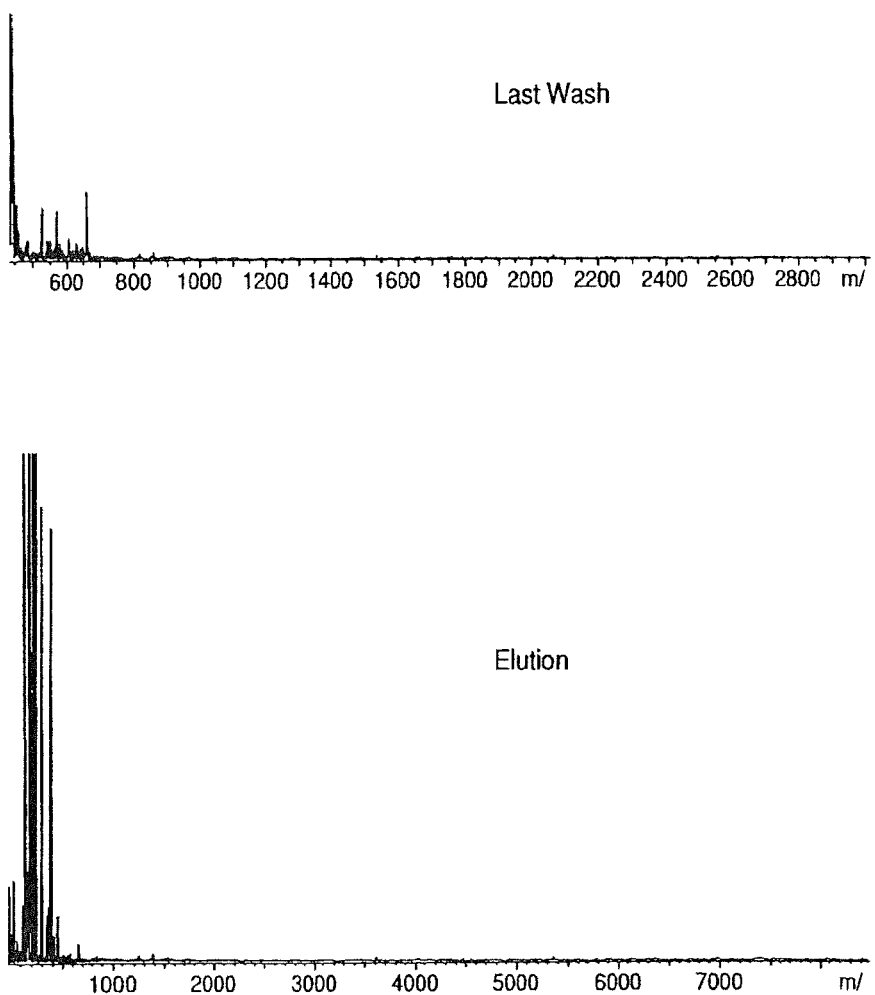
Figure 35:
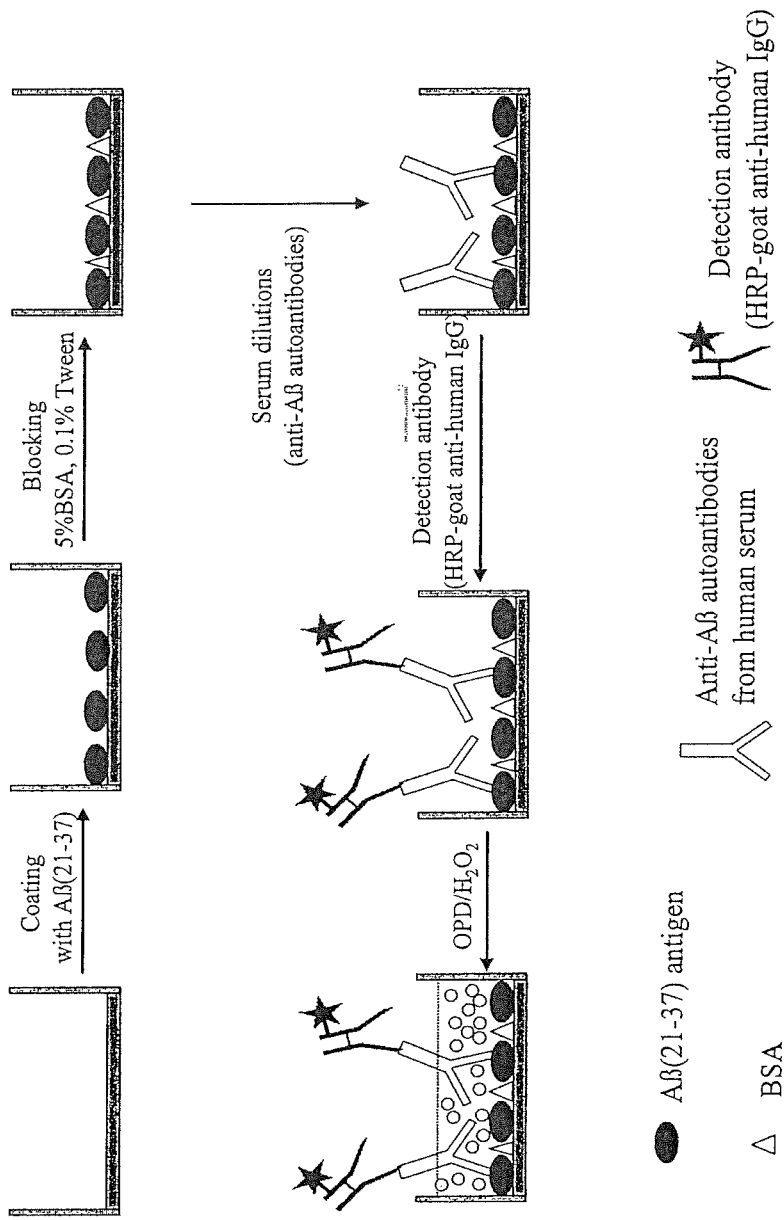
Figure 36:
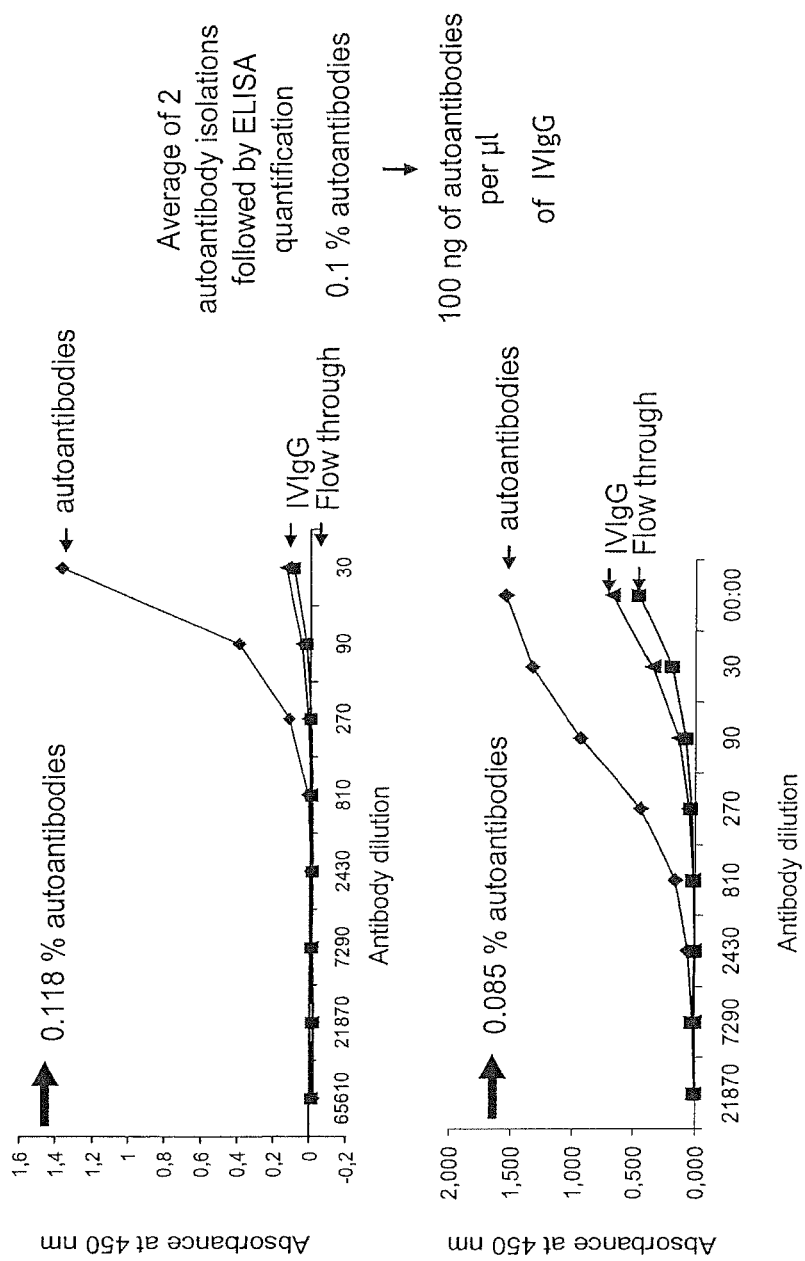

FIG. 34b: Mass spectrograms showing epitope specificity of Aβ-autoantibody. Immobilized Aβ(21-37) autoantibodies purified from IVIgG according to Example 2A were incubated with a synthetic Aβ(12-40) polypeptide. The elution profiles were analyzed via MS as above. The data show that the Aβ(21-37) autoantibodies specifically bound the Aβ(12-40) polypeptide.

FIG. 34c: Mass spectrograms showing epitope specificity of Aβ-autoantibody. Immobilized Aβ(21-37) autoantibodies purified from IVIgG were incubated with synthetic Aβ-polypeptides Aβ(25-35), Aβ(17-28) and Aβ(31-40). The data show that the Aβ(21-37) autoantibodies bound none of the Aβ partial polypeptides.

FIG. 34_d to 34_l: Mass spectrograms showing epitope specificity of Aβ-autoantibody. Immobilized Aβ(21-37) autoantibodies purified from IVIgG and immobilized antibody ACA (see example 5) were incubated with synthetic polypeptides Aβ(4-10), Aβ(17-28), Aβ(12-40) and Aβ(20-37). The data show that both the immobilized ACA antibody and the immobilized Aβ(21-37) autoantibodies bind to Aβ(1-40) and to Aβ(12-40) but that only the immobilized Aβ(21-37) autoantibodies specifically bind to Aβ(20-37). Both immobilized antibodies did not bind Aβ(17-28). Specifically, FIG. 34_d shows that mab ACA does not bind to Aβ(4-10), FIG. 34_e shows that mab ACA does not bind to Aβ(17-28), FIG. 34_f shows that mab ACA does bind to Aβ(12-40), FIG. 34_g shows that mab ACA does not bind to Aβ(20-37), FIG. 34_h shows that mab ACA does bind to Aβ(1-40), FIG. 34_i shows that Aβ(21-37) autoantibodies do bind to Aβ(1-40), FIG. 34_j shows that Aβ(21-37) autoantibodies do bind to Aβ(12-40), FIG. 34_k shows that Aβ(21-37) autoantibodies do not bind to Aβ(17-28) and FIG. 34_l shows that Aβ(21-37) autoantibodies do bind to Aβ(20-37).

FIG. 35: Serum ELISA for determination of anti-Aβ(21-37) autoantibodies. BSA is bovine serum albumin HRP is horseradish peroxidase. OPD is o-phenylenediamine. IgG stands for immunoglobulin G.

FIG. 36: ELISA determination of Aβ-autoantibody (from IVIgG). IVIgG stands for intravenous IgG preparation. The ELISA was carried out with Aβ(1-40) coated on 96-well plate, and dilutions of Aβ-antibody were added, and determined with anti-human horseradish peroxidase-conjugated secondary antibody. Aβ-antibody quantifications were performed with a 1 µg/µl stock solution, using a BSA reference curve for calibration. The percentage indicated represents the Aβ-antibody concentrations in IVIgG from two separate ELISA determinations.

Figure 37:
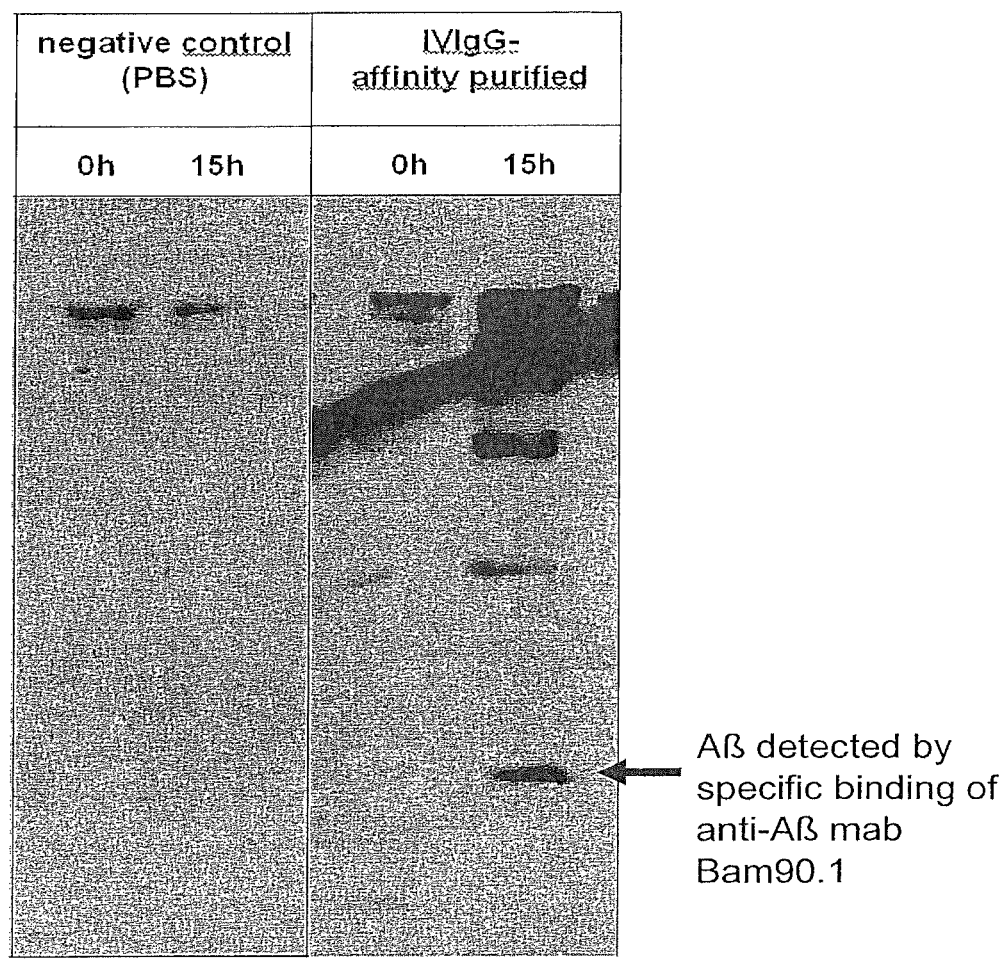

FIG. 37: Western blot showing that affinity purified IVIgG according to Example 4 immunoprecipitates oligomeric forms of Aβ1-40 as described in Example 6. The antibody Bam 90.1 (Sigma Aldrich Cat# A8978 binding to Aβ(13-28)) was used to detect the immunoprecipitated Aβ.

Figure 38:
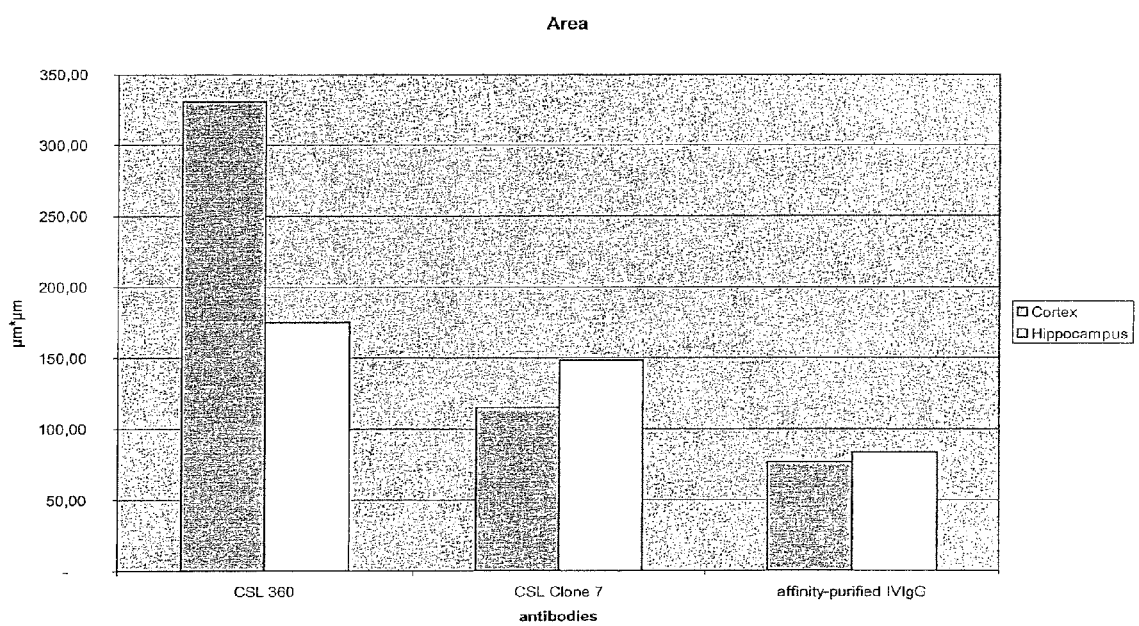

FIG. 38: Bar graph representing the mean total plaque area per antibody used in an AD animal model as described in Example 13. Black columns represent the plaque area in the cortex, white bars represent the plaque area in the hippocampus. Plaque area was measured using the Nikon NIS Elements Software on pictures of immunostained brain slices of the treated animals. The measured plaque area of the CSL 360- or CSL Clone 7-treated animals (N=2) were averaged for both animals for comparison with the affinity-purified IVIgG-treated animal (N=1).

Figure 39:
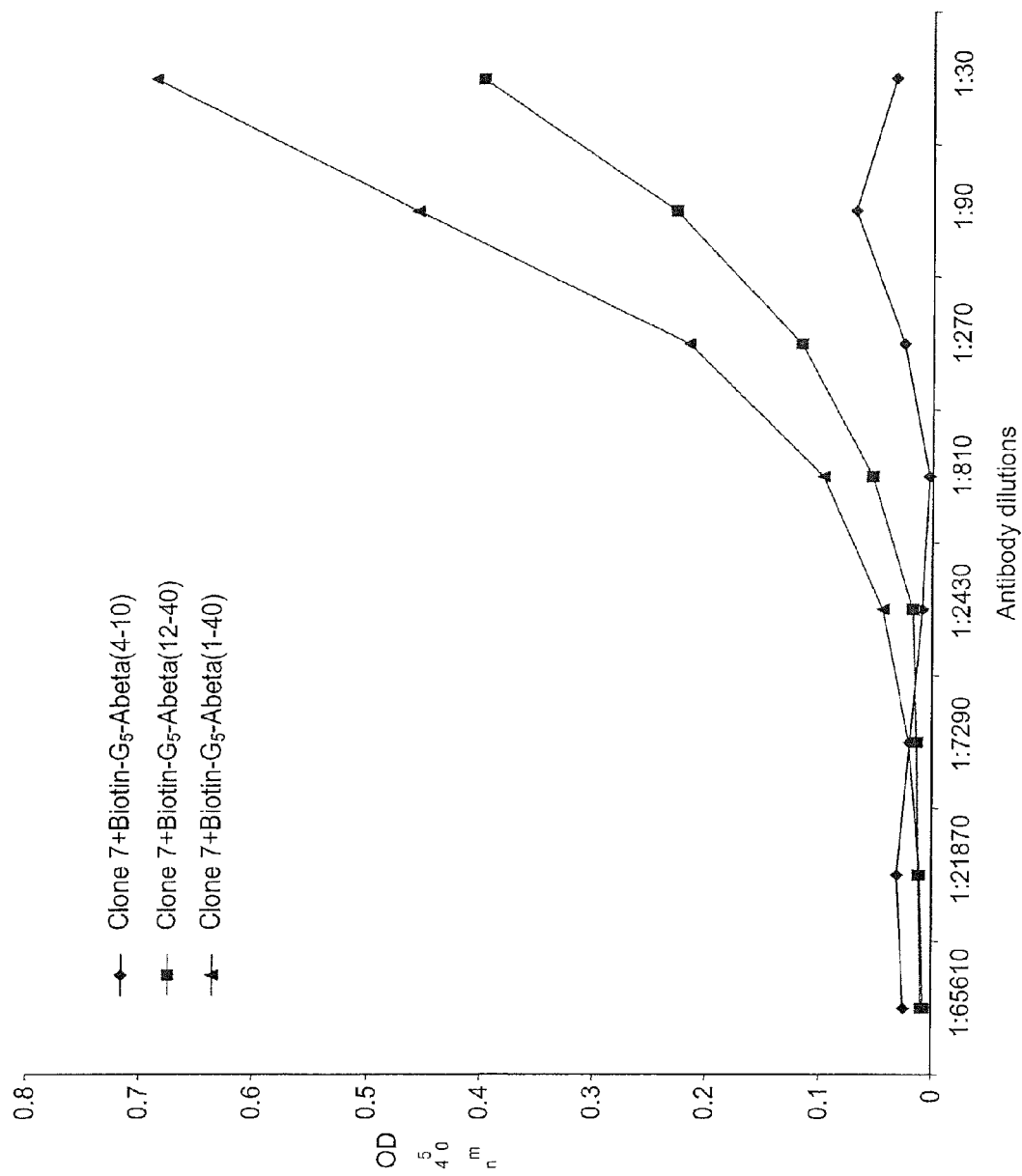

FIG. 39: ELISA data showing that anti-Aβ(21-37) autoantibody CSL-Clone 7 binds to Aβ(1-40) and to Aβ(12-40) peptides but not to Aβ(4-10) as discussed in Example 9D.

Figure 40:
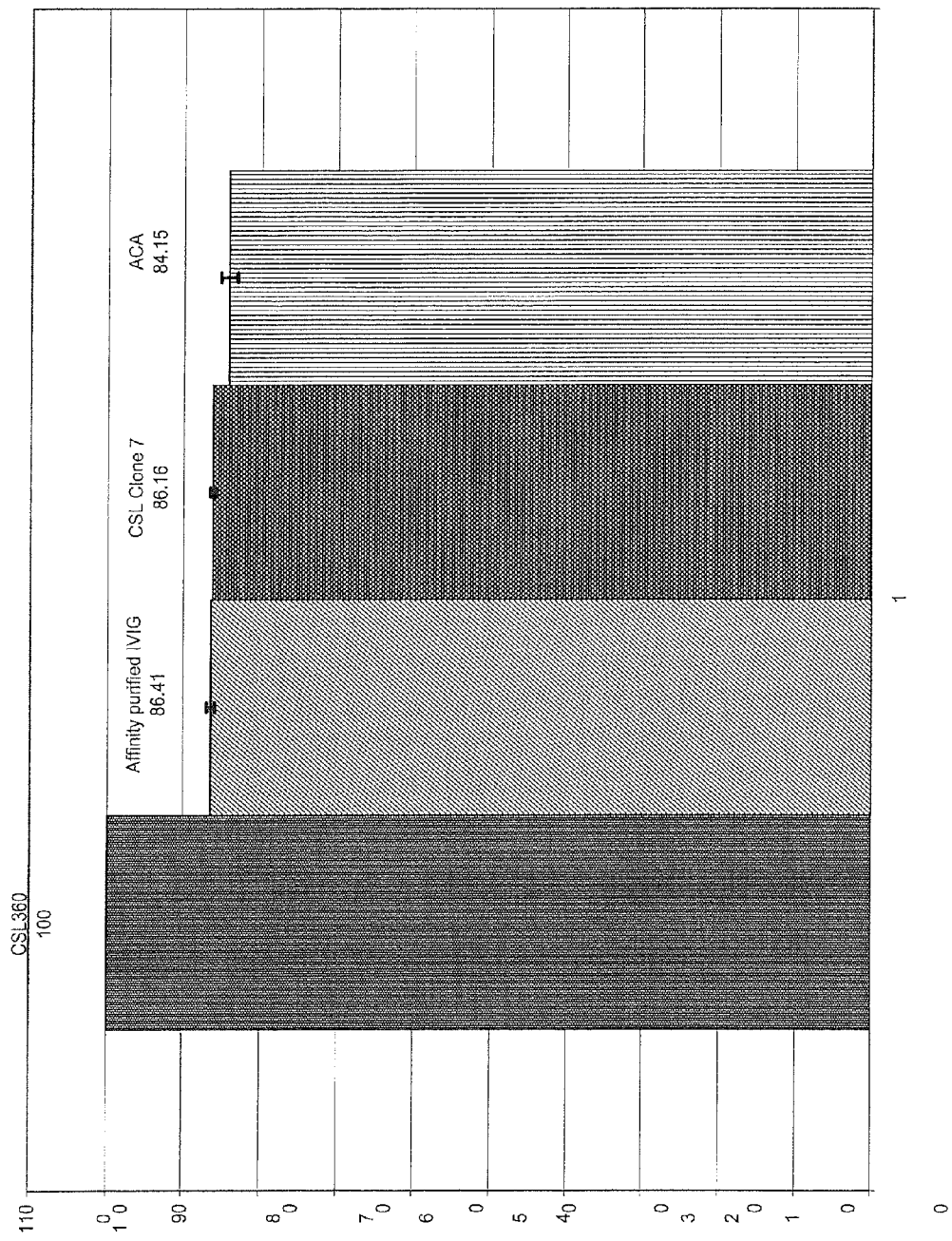

FIG. 40: The effect of 3 different Aβ-specific antibodies: Aβ affinity column purified human IVIgG (as described in Example 4), the human monoclonal Aβ autoantibody CSL Clone 7 (as described in Example 5) and humanized murine monoclonal antibody raised against a midterminal Aβ peptide sequence (AKACA, as described in Example 5) to inhibit Aβ fibril formation as measured by THT fluorescence staining as described in Example 10. The fluorescence of the THT assay is proportional to fibrillar Ab and was used to assess fibril morphology. The fluorescence of Aβ(1-40) incubated in the presence of a nonspecific human monoclonal (CSL360) was set to 100%.

Figure 41:
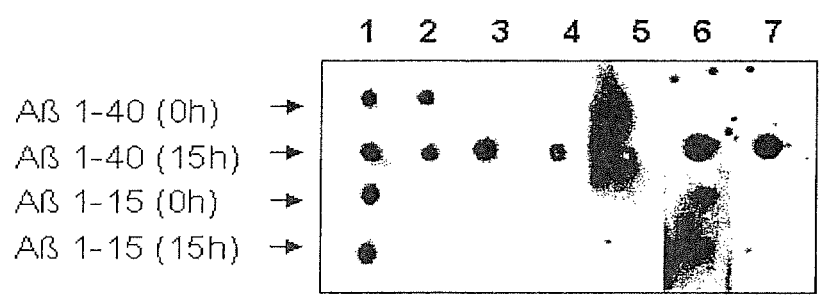

FIG. 41: Dot Blot Analysis as described in Example 11A. Samples were tested with control antibodies (6E10, Bam90.1, CSL Clone 7, affinity purified WIG, ACA), serum from an AD-patient (AD1), serum from an age matched healthy human individual (K4) as described in Example 11A FIG. 42: IgG from serum samples (one AD positive sample and one age-matched control sample) after purification on Protein G (Pierce) were loaded on an Aβ(1-16) column, washed and eluted with 100 mM Glycine pH 2.8. The eluate was analyzed in a Biotin-$G_5$-Aβ(4-10) ELISA as described in Example 11B.

FIG. 43: Binding to Aβ(1-40 Cys) dimer as opposed to Aβ(1-40) monomer as described in Example 12C for the recombinant Aβ(21-37) autoantibodies 55/61, 146/61 and the control antibody ACA FIG. 44: Binding to Aβ(1-40 Cys) dimer as opposed to Aβ(1-40) monomer as described in Example 12C for the recombinant Aβ(21-37) autoantibodies 54/61, 47/56, 51/60 and 53/60.

Figure 45:
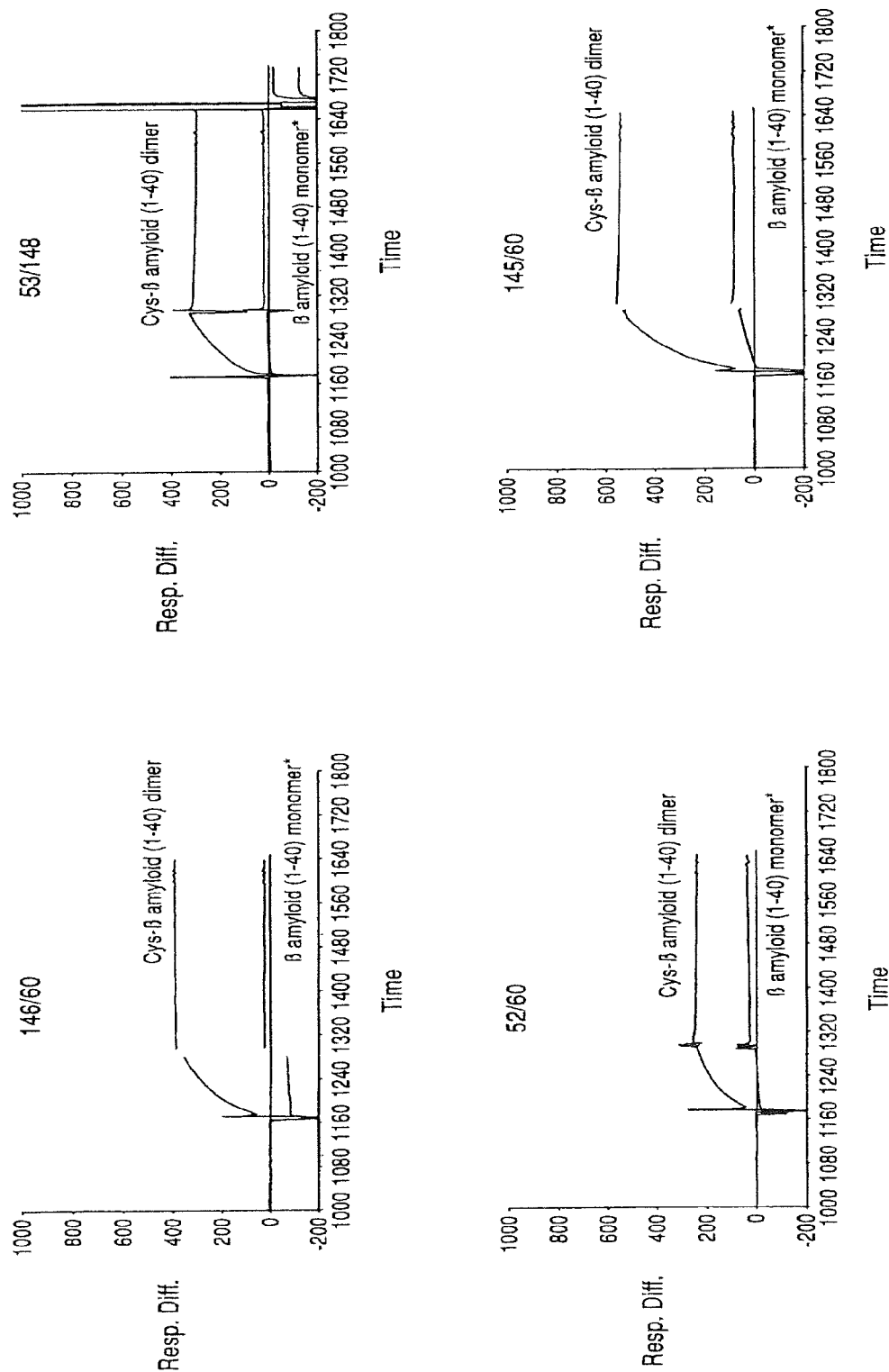

FIG. 45: Binding to Aβ(1-40 Cys) dimer as opposed to Aβ(1-40) monomer as described in Example 12C for the recombinant Aβ(21-37) autoantibodies 146/60, 52/60, 53/148 and 145/60.

Figure 46:
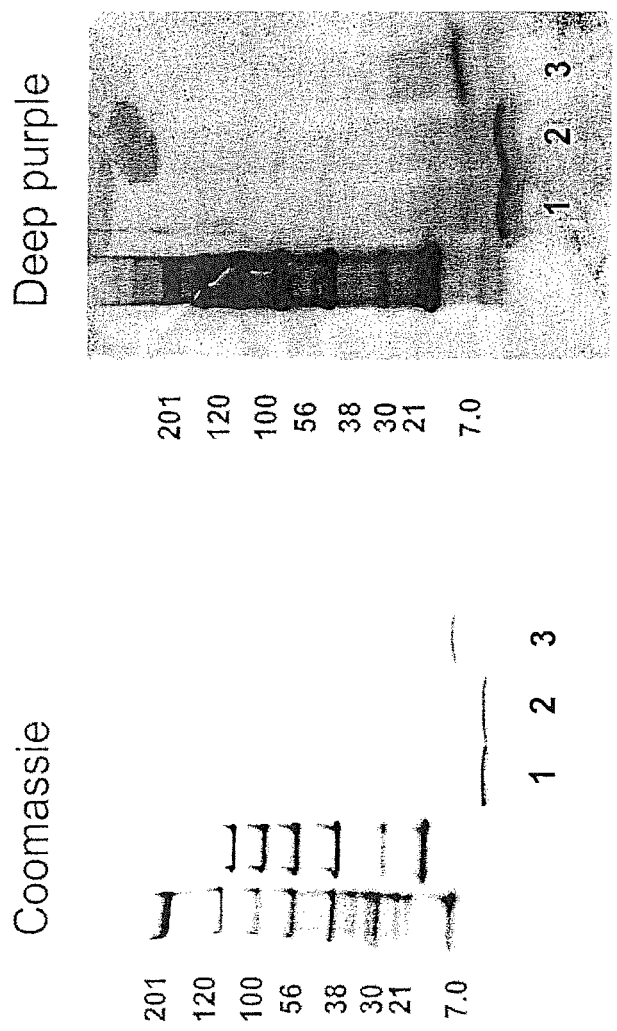

FIG. 46: Tricine Gel protein blot analysis of β amyloid peptides. Protein visualisation of 13 amyloid peptide was done using standard coomassie staining techniques as described in the Novex gel manual (Initrogen) and deep purple reagent for high sensitivity. Deep purple (GE, Sweden) was visualised using a Typhoon scanner as per manufacturer instruction.

Figure 47:
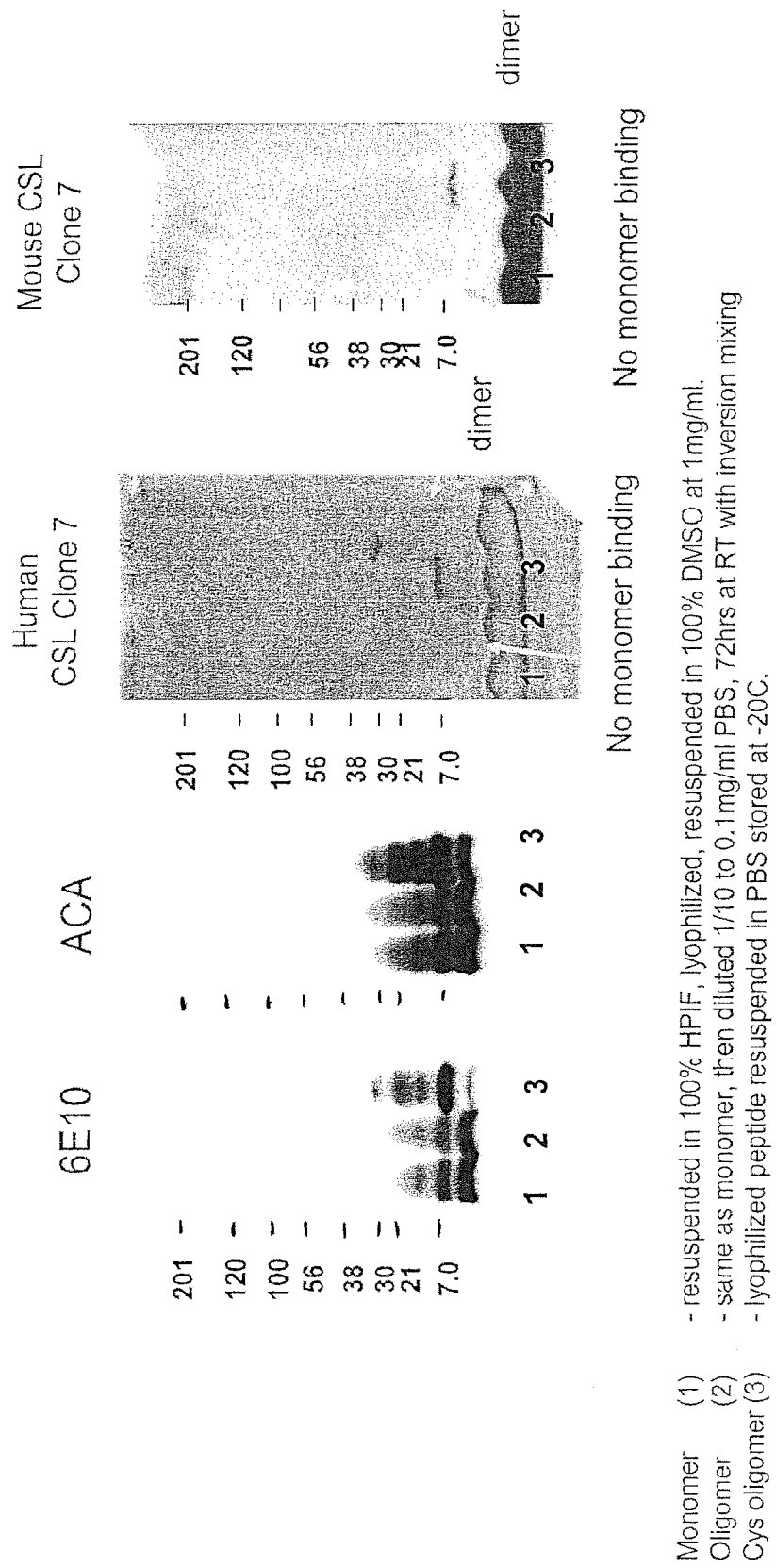

FIG. 47: Western blot comparing the binding of the antibodies 6E10, ACA and CSL Clone 7 to Aβ(1-40) monomer, Aβ(1-40) oligomer and Aβ(1-40 Cys) oligomer as described in Example 12D.

Figure 48A:
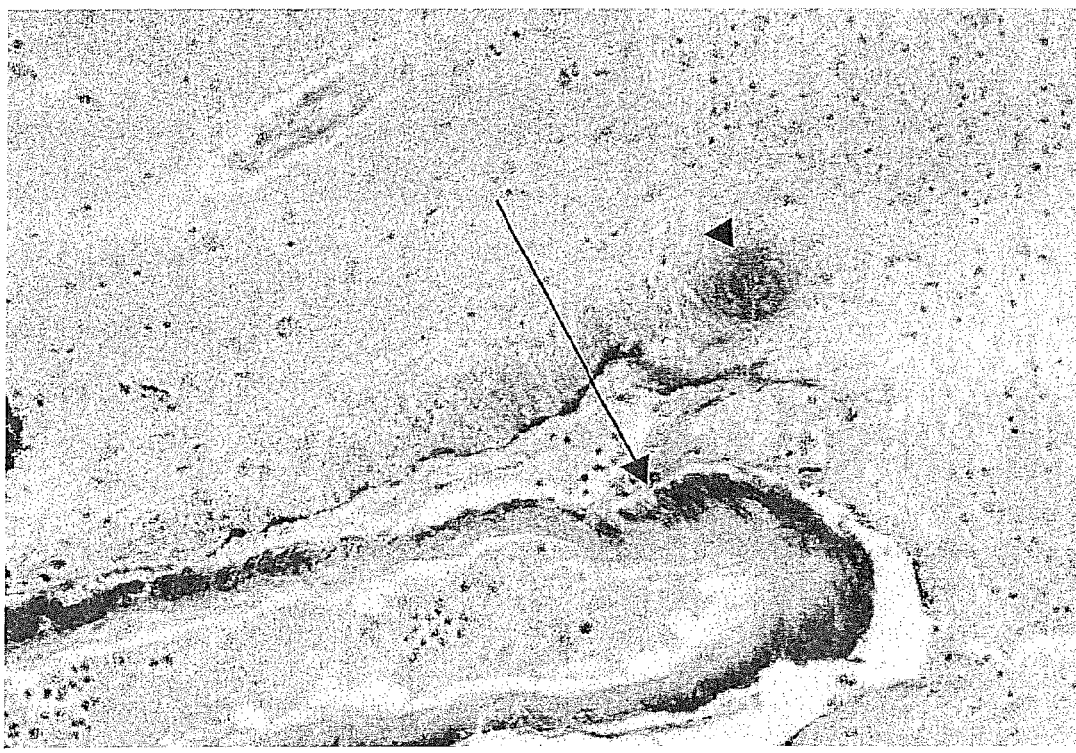

FIG. 48a: Immunohistochemistry of a human brain sample of a patient suffering from Alzheimers disease using the 6F3D anti β-amyloid antibody (Dako) as primary antibody, and the Vectastain® M.O.M.-Kit (HRP anti mouse) as a detection system. A specific immunostaining is detectable in the vessel wall (arrow) as well as the Alzheimer-plaque (arrowheads). This immunostaining serves as positive control.

Figure 48B:
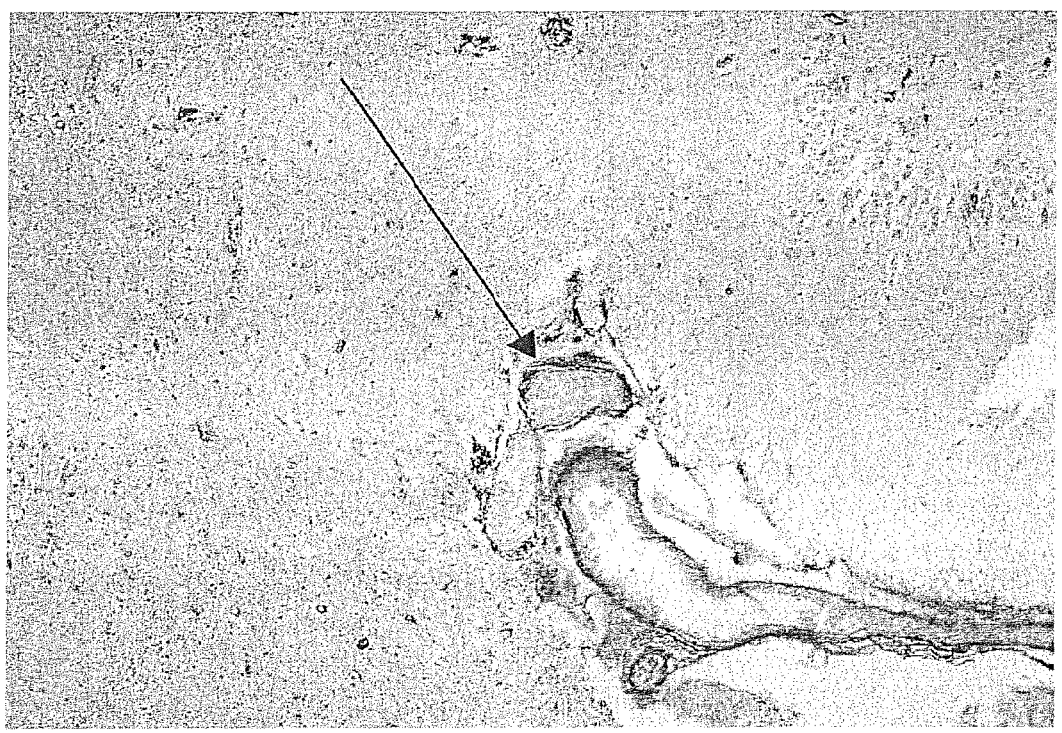

FIG. 48b: Immunohistochemistry of a human brain sample of a patient suffering from Alzheimers disease using the ACA antibody as primary antibody, and the Vectastain® Elite ABC Kit (HRP anti human) as detection system. A specific immunostaining is detectable in the vessel wall (arrow).

Figure 48C:
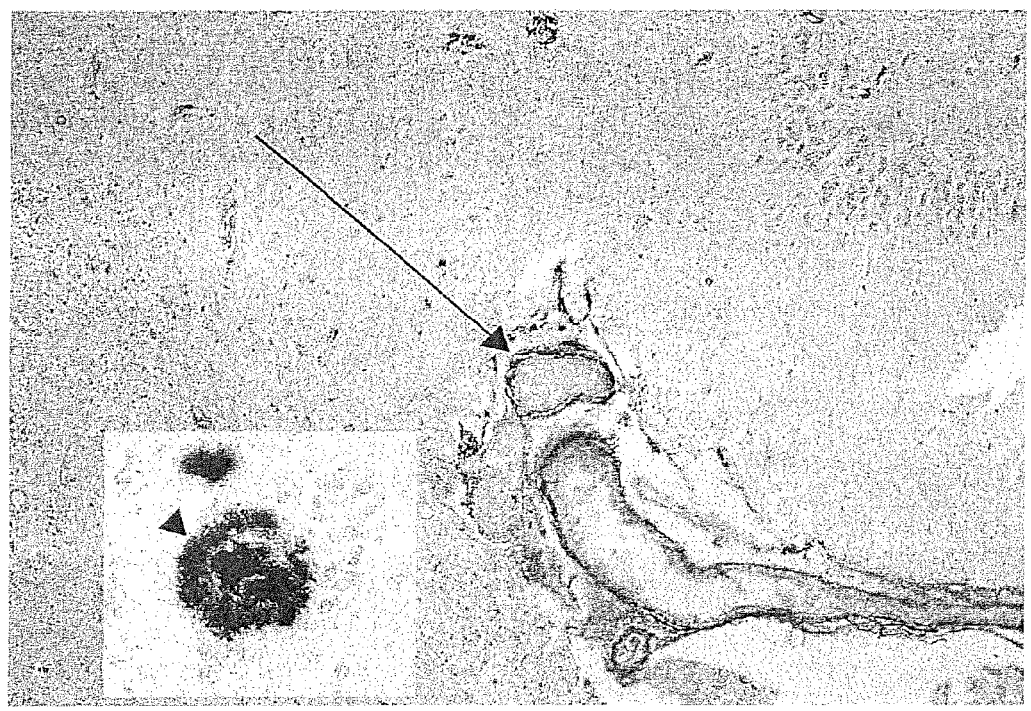

FIG. 48c: Immunohistochemistry of a human brain sample of a patient suffering from Alzheimers disease using the ACA antibody as primary antibody, and the Vectastain® Elite ABC Kit (HRP anti human) as detection system. A specific immunostaining is detectable in the vessel wall (arrow) as well as the Alzheimer-plaque (arrowheads, insert).

Figure 48D:

FIG. 48d: Immunohistochemistry of a human brain sample of a patient suffering from Alzheimers disease and CAA using the affinity purified IVIgG as primary antibody, and the Vectastain® Elite ABC Kit (HRP anti human) as detection system. No specific immunostaining is detectable in the vessel wall (arrow).

Figure 48E:
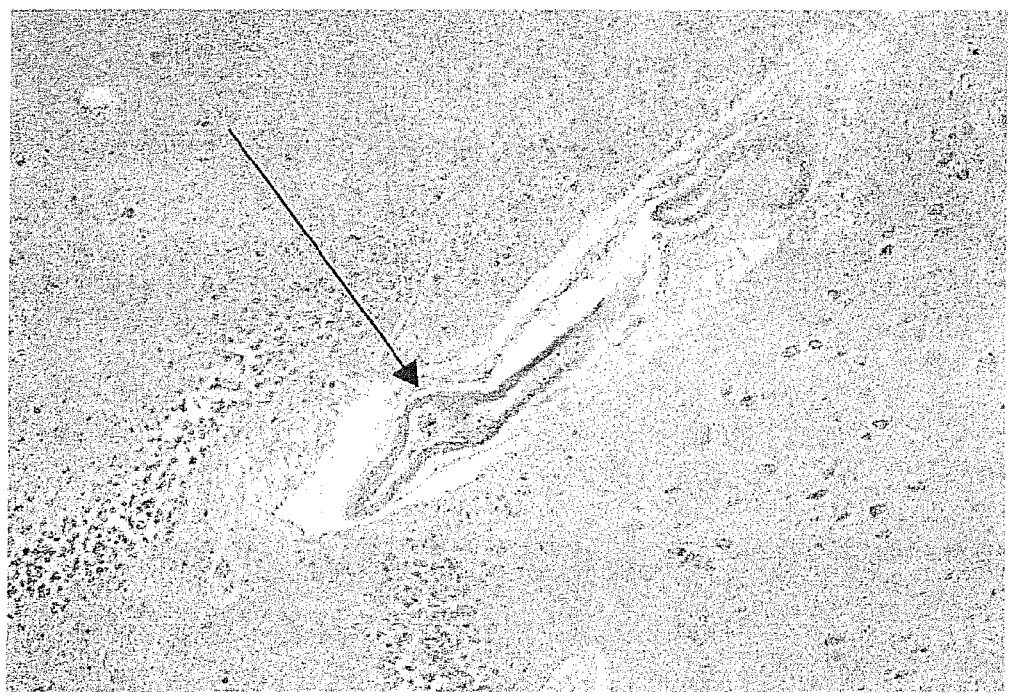

FIG. 48e: Immunohistochemistry of a human brain sample of a patient suffering from Alzheimers disease using the clone 7 antibody as primary antibody, and the Vectastain® Elite ABC Kit (HRP anti human) as detection system. No specific immunostaining is detectable in the vessel wall (arrow).

Figure 48F:
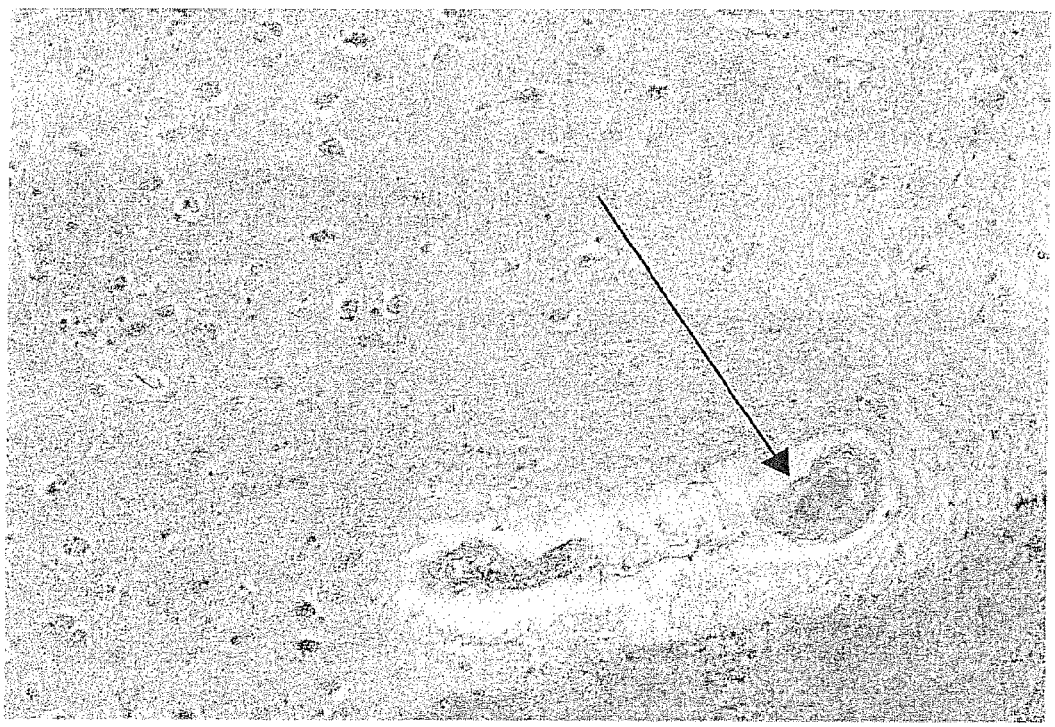

FIG. 48f: Immunohistochemistry of a human brain sample of a patient suffering from Alzheimers disease using the CSL 360 antibody as primary antibody, and the Vectastain®Elite ABC Kit (HRP anti human) as detection system. No specific immunostaining is detectable in the vessel wall (arrow), but the blood in the vessel lumen show unspecific background staining.

Figure 49:
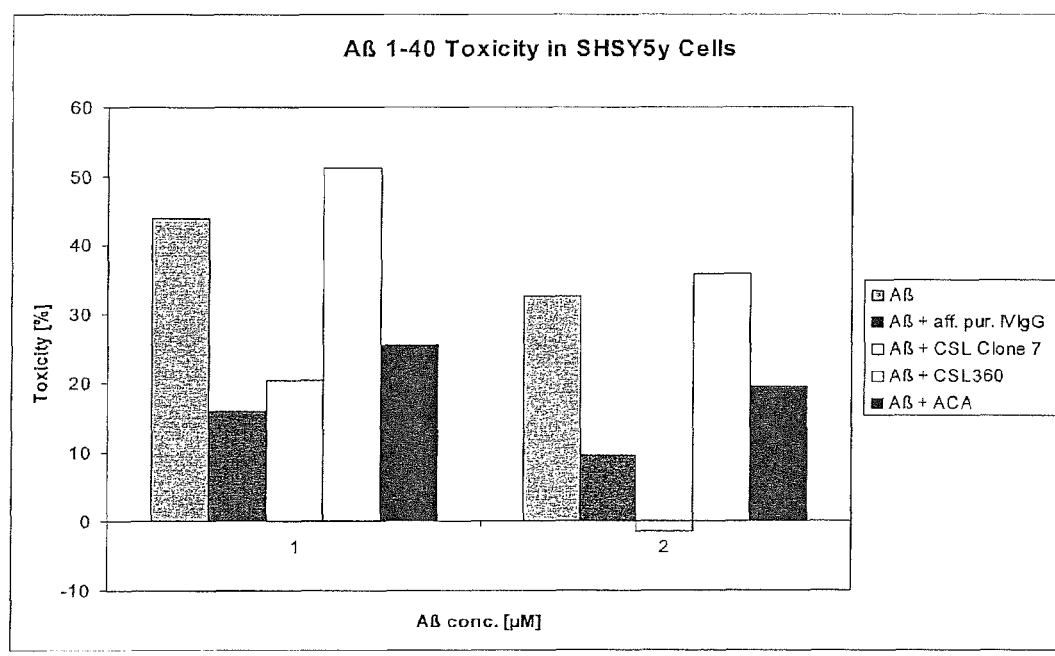

FIG. 49: Toxicity of Aβ-oligomers for human neuroblastoma cells (SH-Sy5y) was tested as described in Example 4. The experiment was repeated with affinity purified IVIgG (purified as described above, mab CSL Clone 7 (see Example 5). As a negative control the antibodies CSL360 (see Example 10) or no antibody was used. A positive control antibody used was ACA (see Example 10). Results clearly show a dose dependent effectiveness of protecting cells from the neurotoxic effects of Aβ oligomers of both the affinity purified mab CSL Clone 7 and affinity purified IVIgG.

DETAILED DESCRIPTION

Aβ-autoantibodies were isolated from the serum of AD patients and healthy controls or pooled commercially obtainable serum immunoglobulin (IVIgG). The cDNA and amino acid sequences of the variable regions of the heavy and light chains were determined and all possible pairings of heavy and light chains were expressed in mammalian cells. A number of these pairings were found to bind with higher affinity to Aβ dimers than to Aβ monomers and one of these, CSL clone 7, was shown to possess biological activities potentially useful for the treatment of AD. The inventors further discovered that the CDRs of anti-Aβ(21-37) autoantibodies are highly homologous. Accordingly, consensus CDRs were determined and used to prepare human anti-β-amyloid antibodies useful for preventing or treating neurodementing diseases like AD. The inventors also surprisingly discovered that AD patients, as compared to healthy controls, have an increased antibody titer against Aβ(4-10) and a decreased antibody titer against Aβ(21-37). Thus, the inventors discovered not only means for detecting and measuring the progression of a neurodementing disease like AD, but also methods for delaying the onset or progression of AD. Kits for detecting and measuring the progression of neurodementing diseases, like AD, also are provided.

Definitions

The term "Aβ polypeptide" as used herein, defines a polypeptide having the amino acid sequence SEQ ID NO:01 or fragments thereof. Such fragments in particular comprise polypeptides having the sequence SEQ ID NO:02.

The term "antibody", as used herein, comprises also derivatives and/or fragments of antibodies. Such derivatives or fragments of antibodies retain the antigen binding properties of the intact antibody, but which lack some sequences of the intact antibody, for example the Fc-domain. Examples for such derivatives or fragments include, but are not limited to, Fab or F(ab')$_2$ fragments, which are obtainable via enzymatic digest of antibodies with papain or pepsin protease, respectively, single chain variable fragments (scFv), Fv fragments, minibodies and diabodies.

The term "autoantibody" or "autoantibodies", as used herein, refers in general to antibodies which are directed against epitopes on proteins of the human body and which can be found in the blood or cerebrospinal fluid of a human subject without prior immunization with the respective antigen. Meanwhile, the term "anti-Aβ(21-37) autoantibody" refers to autoantibodies that bind to an Aβ peptide comprising Aβ(21-37) (SEQ ID NO:2) and shield said SEQ ID NO 2 from proteolytic digestion. Such anti-Aβ(21-37) autoantibodies also bind with a higher affinity to dimers of Aβ than to corresponding monomers of Aβ.

The term "CDR", as used herein, refers to Complementarity Determining Regions. Usually 3 of such CDR-regions (CDR1, CDR2, CDR3) can be found in the variable region on the light chain as well as on the heavy chain of an antibody. Each of these six hypervariable regions can contribute to the antigen specificity of the antibody. However, as used herein, the term CDR does not imply that the molecule referred to is in fact an antibody. Rather, the term is considered to designate a sequence contributing to the specific binding of a polypeptide according to the invention to a C-terminal part of full length Aβ polypeptide (Aβ1-40), in particular contributing to the binding to Aβ(21-37) polypeptide. Consequently, also derivatives of antibodies or other polypeptides engineered for binding to said epitope can exhibit CDRs.

The term "consensus CDR" as used herein refers to a single sequence derived by aligning two or more sequences for a given CDR according to the Kabat numbering system. (see Kabat, E. A., Wu, T. T., Perry, H. M., Gottesman, K. S. & Foeller, C. (1991) Sequences of Proteins of Immunological Interest (Department of Health and Human Services, Public Health Service, National Institutes of Health, Bethesda, Md.) NIH Publ. No 91-3442 5th Ed. and R. Kontermann, S. Dübel (eds.), Antibody Engineering, Springer Lab Manual Series; Springer, Heidelberg 2001, both of which are hereby incorporated by reference.) Accordingly, for each amino acid position of the "consensus CDR", the identity of amino acids which can occur at that position is determined CDR designations as well as amino acid insertions are made according to Kabat numbering.

The term "diabodies" refers to small antibody fragments with two antigen-binding sites, which fragments comprise a heavy chain variable domain (VH) connected to a light chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161.

The term "epitope" or "epitope peptide", as used herein, generally refers to a polypeptide comprising the molecular recognition peptide sequence or structure derived from an antigen, that is bound by a specific antibody. It is an immunological determinant group of an antigen which is specifically recognized by the antibody. An epitope may comprise at least 5, preferably at least 8 amino acids in a spatial or discontinuous conformation. An epitope may also comprise a single segment of a polypeptide chain comprising a continuous linear amino acid sequence with a minimal length of approx. 5 amino acids.

"Fv" is the minimum antibody fragment that contains a complete antigen recognition and binding site. This region consists of a dimer of one heavy and one light chain variable domain in tight, non-covalent association. It is in this configuration that the three CDRs of each variable domain interact to define an antigen binding site on the surface of the VH VL dimer. Collectively, the six CDRs confer antigen binding specificity to the antibody.

The term "moiety", as used herein, refers to a portion of a polypeptide with distinct function(s). Such moieties can provide for a structural or functional feature which is normally not present in the rest of the polypeptide or which feature is enhanced by this moiety. Such functional or structural moieties can for example provide binding, stabilization or detection of the polypeptide. The moiety can be a polypeptide on its own or can be any other compound, which provides the desired function(s) to the polypeptide. Said moiety is stably associated with the polypeptide, in particular covalently coupled to the polypeptide. The term moiety, as used herein, does not confer any information about the size of this portion in comparison to the polypeptide itself. The moiety can be smaller, equally sized or larger than the polypeptide it is coupled to.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a specific antigenic site or epitope, in contrast to polyclonal antibody preparations that typically include different antibodies directed against different epitopes.

The terms "neurodementing diseases", "dementing disorders" or "neurodementia diseases of AD-type", as used herein, refer to diseases selected from Alzheimer's disease, Down's syndrome, Dementia with Lewy bodies, fronto-temporal dementia as well as to disorders such as cerebral amyloid angiopathy and amyloidoses.

The term "oligomerized", "oligomers" and "oligomeric" refers to multimers of Aβ comprising also Aβ dimers, trimers, tetramers and higher oligomers but not to Aβ fibrils.

The term "plaque-specific" antibody, as used herein, refers to an antibody directed against the Aβ(4-10) epitope of Aβ polypeptide.

The term "polypeptide", as used herein, refers to a polypeptide chain of at least 5 amino acid residues. The term also refers to an assembly of more than one polypeptide chain, e.g. an assembly of four polypeptide chains, such as an IgG antibody.

The term "paratope" or "paratope peptide", as used herein, generally defines a molecular recognition peptide sequence derived from a specific monoclonal or polyclonal antibody. This recognition peptide sequence exerts specific binding properties to an antigen epitope, and may comprise variable and/or constant region partial sequences of an antibody.

"Specifically binding to epitope X" as used herein, refers to the property of an antibody to bind to a particular epitope, e.g. epitope X, with a higher affinity than to other epitopes.

"Specifically binding to oligomeric structures of Aβ", as used herein, means that the respective antibody binds to oligomeric structures of Aβ with a higher affinity than to monomeric structures of Aβ.

A "therapeutically effective" amount of Aβ antibody refers to the dosage that provides the specific pharmacological response for which the antibody is administered in a significant number of subjects in need of such treatment. A therapeutically effective amount can be determined by prevention or amelioration of adverse conditions or symptoms of the neurodementing disease being treated. The appropriate dosage will vary depending, for example, on the type, stage, and severity of the disease, as well as on the mode of administration. It is emphasized that a "therapeutically effective amount" administered to a particular subject in a particular instance may not be effective for 100% of patients treated for a specific disease, even though such dosage is deemed a "therapeutically effective amount" by skilled practitioners.

The ter, "titer" denotes a measurement of the amount or concentration of a particular antibody in a sample, typically blood.

The terms "treatment," "treating," "treat," and the like refer to obtaining a desired pharmacological and/or physiologic effect. The effect can be prophylactic in terms of completely or partially preventing a disease or symptom thereof and/or can be therapeutic in terms of a partial or complete stabilization or cure for a disease and/or adverse effect attributable to the disease. "Treatment" covers any treatment of a disease in a mammal, particularly a human, and includes: (a) preventing the disease or symptom from occurring in a subject which can be predisposed to the disease or symptom but has not yet been diagnosed as having it; (b) inhibiting the disease symptom, i.e., arresting its development; or (c) relieving the disease symptom, i.e., causing regression of the disease or symptom.

Antibodies

In one aspect the present invention relates to a polypeptide binding specifically to the epitope Aβ(21-37) (SEQ ID NO 2).

A polypeptide according to the present invention can be for example an antibody, an antibody fragment, or any other polypeptide, binding to a C-terminal part of full length Aβ polypeptide (Aβ1-40), in particular to the epitope denoted in Aβ(21-37) (SEQ ID NO:2).

In one aspect, the inventive polypeptides are capable of binding specifically to a polypeptide comprising the epitope Aβ(21-37) (SEQ ID NO 2) of amyloid beta, in particular under physiological conditions, e.g. pH about 7.4, salt concentrations about 50 to about 150 mM in PBS. In one embodiment, the polypeptides have a relative dissociation constant, under in vitro conditions, (relative KD; reflecting in vitro results but not necessarily identical values under in vivo conditions) of at least about 10-5 M, about 10-6 M, about 10-7 M, about 10-8, about 10-9 M, about 10-10 M, about 10-11 M, about 10-12 M, or higher. For example, the relative dissociation constant of the binding of a polypeptide to the epitope denoted in Aβ(21-37) (SEQ ID NO:2) can be between about 10-8 M to about 10-12 M, in particular around 1 to 50×10-9 M. Such dissociation rate constants can be determined readily using kinetic analysis techniques such as surface plasmon resonance (BIAcore or Biosensor), using general procedures outlined by the manufacturer or other methods known in the art.

In another aspect, it was surprisingly discovered that polypeptides specific for Aβ(21-37) are highly homologous. Thus, polypeptides are provided that comprise sequences selected from consensus CDR sequences. Accordingly, in one embodiment, a polypeptide according to the present invention can comprise a CDR sequence having a sequence as denoted in any of the consensus sequences SEQ ID NOs: 6 to 8.

SEQ ID NOs: 6 to 8 represent consensus sequences for CDR regions of the heavy chain of an antibody having the ability to bind to SEQ ID NO:2. The consensus sequences are derived from the sequence information derived from the antibodies, which have been identified by the inventors to bind specifically to SEQ ID NO:2. In particular, the identified consensus sequences for the CDR regions of both the heavy chain (i.e. SEQ ID NOs: 6 to 8 and SEQ ID Nos 153 to 161) and the light chain (i.e. SEQ ID NOs: 9 to 11) were derived from naturally-occurring, human antibodies isolated as described in Example 2A.

SEQ ID NO:6 represents a CDR1 consensus sequence for the heavy chain, wherein
the amino acid at position 1 of SEQ ID NO:6 which is at the Kabat position H31 can be Ser, Gly or Asn, the amino acid at position 2 of SEQ ID NO:6 which is the amino acid at the Kabat position 8 H32 is Tyr,
the amino acid at position 3 of SEQ ID NO:6 which is the amino acid at the Kabat position H33 can be Trp or Asp,
the amino acid at position 4 of SEQ ID NO:6 which is the amino acid at the Kabat position H34 is Met and
the amino acid at position 5 of SEQ ID NO:6 which is the amino acid at the Kabat position H35 can be Ser or His.

SEQ ID NO:153 represents a preferred CDR1 consensus sequence for the heavy chain, wherein
the amino acid at position 1 of SEQ ID 153 which is at the Kabat position H31 can be Asn or Ser,
the amino acid at position 2 of SEQ ID 153 which is the amino acid at the Kabat position 8 H32 is Tyr,
the amino acid at position 3 of SEQ ID NO: 153 which is the amino acid at the Kabat position H33 can be Asp or Trp,
the amino acid at position 4 of SEQ ID NO: 153 which is the amino acid at the Kabat position H34 is Met and
the amino acid at position 5 of SEQ ID NO: 153 which is the amino acid at the Kabat position H35 can be His or Ser.

SEQ ID NO:154 represents a more preferred CDR1 consensus sequence for the heavy chain, wherein
the amino acid at position 1 of SEQ ID NO: 154 which is at the Kabat position H31 of SEQ ID NO:6 is Asn,
the amino acid at position 2 of SEQ ID NO: 154 which is the amino acid at the Kabat position 8 H32 is Tyr,
the amino acid at position 3 of SEQ ID NO: 154 which is the amino acid at the Kabat position H33 is Asp,
the amino acid at position 4 of SEQ ID NO: 154 which is the amino acid at the Kabat position H34 is Met and
the amino acid at position 5 of SEQ ID NO: 154 which is the amino acid at the Kabat position H35 is His.

SEQ ID NO:155 represents a more preferred CDR1 consensus sequence for the heavy chain, wherein
the amino acid at position 1 of SEQ ID NO: 155 which is at the Kabat position H31 is Ser,
the amino acid at position 2 of SEQ ID NO: 155 which is the amino acid at the Kabat position 8 H32 is Tyr,
the amino acid at position 3 of SEQ ID NO: 155 which is the amino acid at the Kabat position H33 can be Trp or Asp,
the amino acid at position 4 of SEQ ID NO: 155 which is the amino acid at the Kabat position H34 is Met and
the amino acid at position 5 of SEQ ID NO: 155 which is the amino acid at the Kabat position H35 is Ser.

SEQ ID NO:7 represents a CDR2 consensus sequence for the heavy chain, wherein
the amino acid at position 1 of SEQ ID NO:7 which is the amino acid at the Kabat position H50 can be Ser or Arg or Glu,
the amino acid at position 2 of SEQ ID NO:7 which is the amino acid at the Kabat position H51 can be Val or Ile,
the amino acid at position 3 of SEQ ID NO:7 which is the amino acid at the Kabat position H52 can be Lys or Gly or Asn,
the amino acid at position 4 of SEQ ID NO:7 which is the amino acid at the Kabat position H52a can be Gln or no amino acid,
the amino acid at position 5 of SEQ ID NO:7 which is the amino acid at the Kabat position H53 can be Asp or Phe or Thr or Arg,
the amino acid at position 6 of SEQ ID NO:7 which is the amino acid at the Kabat position H54 can be Gly or Phe or Ala or Ser,
the amino acid at position 7 of SEQ ID NO:7 which is the amino acid at the Kabat position H55 can be Ser or Gly,
the amino acid at position 8 of SEQ ID NO:7 which is the amino acid at the Kabat position H56 can be Glu or Gly or Arg or Asp or Ala,
the amino acid at position 9 of SEQ ID NO:7 which is the amino acid at the Kabat position H57 can be Lys or Pro or Ser or Thr or Arg,
the amino acid at position 10 of SEQ ID NO:7 which is the amino acid at the Kabat position H58 can be Tyr or Leu or Ala or Asn,
the amino acid at position 11 of SEQ ID NO:7 which is the amino acid at the Kabat position H59 can be Tyr or Ala,
the amino acid at position 12 of SEQ ID NO:7 which is the amino acid at the Kabat position H60 can be Val or Thr or Ala or Asn,
the amino acid at position 13 of SEQ ID NO:7 which is the amino acid at the Kabat position H61 can be Asp or Gly or Pro,
the amino acid at position 14 of SEQ ID NO:7 which is the amino acid at the Kabat position H62 is Ser,
the amino acid at position 15 of SEQ ID NO:7 which is the amino acid at the Kabat position H63 can be Val or Leu,
the amino acid at position 16 of SEQ ID NO:7 which is the amino acid at the Kabat position H64 is Lys and
the amino acid at position 17 of SEQ ID NO:7 which is the amino acid at the Kabat position H65 can be Gly or Ser.

SEQ ID NO:156 represents a preferred CDR2 consensus sequence for the heavy chain, wherein
the amino acid at position 1 of SEQ ID NO:156 which is the amino acid at the Kabat position H50 can be Arg or Ser or Glu,
the amino acid at position 2 of SEQ ID NO:156 which is the amino acid at the Kabat position H51 can be Ile or Val,
the amino acid at position 3 of SEQ ID NO:156 which is the amino acid at the Kabat position H52 can be Gly or Lys or Asn,
the amino acid at position 4 of SEQ ID NO:156 which is the amino acid at the Kabat position H52a can be Gln or no amino acid,
the amino acid at position 5 of SEQ ID NO:156 which is the amino acid at the Kabat position H53 can be Thr or Asp or Arg,
the amino acid at position 6 of SEQ ID NO:156 which is the amino acid at the Kabat position H54 can be or Ala or Gly or Ser,
the amino acid at position 7 of SEQ ID NO:156 which is the amino acid at the Kabat position H55 can be Gly or Ser,
the amino acid at position 8 of SEQ ID NO:156 which is the amino acid at the Kabat position H56 can be Arg or Asp or Glu or Ala,
the amino acid at position 9 of SEQ ID NO:156 which is the amino acid at the Kabat position H57 can be Thr or Arg or Lys,
the amino acid at position 10 of SEQ ID NO:156 which is the amino acid at the Kabat position H58 can be Asn or Tyr,
the amino acid at position 11 of SEQ ID NO:156 which is the amino acid at the Kabat position 1459 is Tyr,
the amino acid at position 12 of SEQ ID NO:156 which is the amino acid at the Kabat position H60 can be Asn, Ala or Val,
the amino acid at position 13 of SEQ ID NO:156 which is the amino acid at the Kabat position H61 can be Pro or Gly or Asp,
the amino acid at position 14 of SEQ ID NO:156 which is the amino acid at the Kabat position H62 is Ser,
the amino acid at position 15 of SEQ ID NO:156 which is the amino acid at the Kabat position H63 can be Leu or Val,
the amino acid at position 16 of SEQ ID NO:156 which is the amino acid at the Kabat position H64 is Lys and
the amino acid at position 17 of SEQ ID NO:156 which is the amino acid at the Kabat position H65 can be Gly or Ser.

SEQ ID NO:157 represents a more preferred CDR2 consensus sequence for the heavy chain, wherein the amino acid at position 1 of SEQ ID NO:157 which is the amino acid at the Kabat position H50 can be Arg or Glu,
the amino acid at position 2 of SEQ ID NO:157 which is the amino acid at the Kabat position H51 is Ile,
the amino acid at position 3 of SEQ ID NO:157 which is the amino acid at the Kabat position H52 can be Gly or Asn,
the amino acid at position 4 of SEQ ID NO:157 which is the amino acid at the Kabat position H53 can be Thr or Arg,
the amino acid at position 5 of SEQ ID NO:157 which is the amino acid at the Kabat position H54 can be Ala or Ser,
the amino acid at position 6 of SEQ ID NO:157 which is the amino acid at the Kabat position H55 is Gly,
the amino acid at position 7 of SEQ ID NO:157 which is the amino acid at the Kabat position H56 can be Arg or Asp or Ala,
the amino acid at position 8 of SEQ ID NO:157 which is the amino acid at the Kabat position H57 can be Thr or Arg,
the amino acid at position 9 of SEQ ID NO:157 which is the amino acid at the Kabat position H58 can be Asn or Tyr,
the amino acid at position 10 of SEQ ID NO:157 which is the amino acid at the Kabat position H59 is Tyr,
the amino acid at position 11 of SEQ ID NO:157 which is the amino acid at the Kabat position H60 can be Asn or Ala,
the amino acid at position 12 of SEQ ID NO:157 which is the amino acid at the Kabat position H61 can be Pro or Gly,
the amino acid at position 13 of SEQ ID NO:157 which is the amino acid at the Kabat position 1162 is Ser,
the amino acid at position 14 of SEQ ID NO:157 which is the amino acid at the Kabat position 1163 can be Leu or Val,
the amino acid at position 15 of SEQ ID NO:157 which is the amino acid at the Kabat position H64 is Lys and
the amino acid at position 16 of SEQ ID NO:157 which is the amino acid at the Kabat position H65 can be Gly or Ser.

SEQ ID NO:158 represents a more preferred CDR2 consensus sequence for the heavy chain, wherein
the amino acid at position 1 of SEQ ID NO:158 which is the amino acid at the Kabat position H50 is Ser,
the amino acid at position 2 of SEQ ID NO:158 which is the amino acid at the Kabat position H51 is Val,
the amino acid at position 3 of SEQ ID NO:158 which is the amino acid at the Kabat position H52 is Lys,
the amino acid at position 4 of SEQ ID NO:158 which is the amino acid at the Kabat position H52a is Gln,
the amino acid at position 5 of SEQ ID NO:158 which is the amino acid at the Kabat position H53 is Asp,
the amino acid at position 6 of SEQ ID NO:158 which is the amino acid at the Kabat position H54 is Gly,
the amino acid at position 7 of SEQ ID NO:158 which is the amino acid at the Kabat position H55 is Ser,
the amino acid at position 8 of SEQ ID NO:158 which is the amino acid at the Kabat position H56 is Glu,
the amino acid at position 9 of SEQ ID NO:158 which is the amino acid at the Kabat position H57 is Lys,
the amino acid at position 10 of SEQ ID NO:158 which is the amino acid at the Kabat position H58 is Tyr,
the amino acid at position 11 of SEQ ID NO:158 which is the amino acid at the Kabat position H59 is Tyr,
the amino acid at position 12 of SEQ ID NO:158 which is the amino acid at the Kabat position H60 is Val,
the amino acid at position 13 of SEQ ID NO:158 which is the amino acid at the Kabat position H61 is Asp,
the amino acid at position 14 of SEQ ID NO:158 which is the amino acid at the Kabat position H62 is Ser,
the amino acid at position 15 of SEQ ID NO:158 which is the amino acid at the Kabat position H63 is Val,
the amino acid at position 16 of SEQ ID NO:158 which is the amino acid at the Kabat position H64 is Lys and
the amino acid at position 17 of SEQ ID NO:158 which is the amino acid at the Kabat position H65 is Gly.

SEQ ID NO:8 represents a CDR3 consensus sequence for the heavy chain, wherein
the amino acid at position 1 of SEQ ID NO:8 which is the amino acid at the Kabat position H95 can be Asp or Gly,
the amino acid at position 2 of SEQ ID NO:8 which is the amino acid at the Kabat position H 96 can be Ala or Gly,
the amino acid at position 3 of SEQ ID NO:8 which is the amino acid at the Kabat position H97 can be Ser or Gly,
the amino acid at position 4 of SEQ ID NO:8 which is the amino acid at the Kabat position H98 can be Ser or Arg,
the amino acid at position 5 of SEQ ID NO:8 which is the amino acid at the Kabat position H99 is Tip,
the amino acid at position 6 of SEQ ID NO:8 which is the amino acid at the Kabat position H100 can be Tyr or Ala,
the amino acid at position 7 of SEQ ID NO:8 which is the amino acid at the Kabat position H100a can be Arg or Pro or Asp,
the amino acid at position 8 of SEQ ID NO:8 which is the amino acid at the Kabat position H100b can be Asp or Leu,
the amino acid at position 9 of SEQ ID NO:8 which is the amino acid at the Kabat position H100c can be Trp or Gly or Ala,
the amino acid at position 10 of SEQ ID NO:8 which is the amino acid at the Kabat position H100d can be Phe or Ala,
the amino acid at position 11 of SEQ ID NO:8 which is the amino acid at the Kabat position H100e can be Phe or no amino acid,
the amino acid at position 12 of SEQ ID NO:8 which is the amino acid at the Kabat position H101 is Asp and
the amino acid at position 13 of SEQ ID NO:8 which is the amino acid at the Kabat position H102 can be Pro or Ile.

SEQ ID NO:159 represents a preferred CDR3 consensus sequence for the heavy chain, wherein
the amino acid at position 1 of SEQ ID NO:159 which is the amino acid at the Kabat position H95 can be Gly or Asp,
the amino acid at position 2 of SEQ ID NO:159 which is the amino acid at the Kabat position H96 can be Ala or Gly,
the amino acid at position 3 of SEQ ID NO:159 which is the amino acid at the Kabat position H97 can be Gly or Ser,
the amino acid at position 4 of SEQ ID NO:159 which is the amino acid at the Kabat position H98 can be Arg or Ser,
the amino acid at position 5 of SEQ ID NO:159 which is the amino acid at the Kabat position H99 is Trp,
the amino acid at position 6 of SEQ ID NO:159 which is the amino acid at the Kabat position H100 can be Ala or Tyr,
the amino acid at position 7 of SEQ ID NO:159 which is the amino acid at the Kabat position H100a can be Pro or Arg or Asp,
the amino acid at position 8 of SEQ ID NO:159 which is the amino acid at the Kabat position H100b can be Leu or Asp,
the amino acid at position 9 of SEQ ID NO:159 which is the amino acid at the Kabat position H100c can be Gly or Trp or Ala,
the amino acid at position 10 of SEQ ID NO:159 which is the amino acid at the Kabat position H100d can be Ala or Phe,
the amino acid at position 11 of SEQ ID NO:159 which is the amino acid at the Kabat position H100e can be Phe or no amino acid,
the amino acid at position 12 of SEQ ID NO:159 which is the amino acid at the Kabat position H101 is Asp and
the amino acid at position 13 of SEQ ID NO:159 which is the amino acid at the Kabat position H102 can be Ile or Pro.

SEQ ID NO:160 represents a more preferred CDR3 consensus sequence for the heavy chain, wherein the amino acid at position 1 of SEQ ID NO:160 which is the amino acid at the Kabat position H95 is Gly,
the amino acid at position 2 of SEQ ID NO:160 which is the amino acid at the Kabat position H 96 is Ala,
the amino acid at position 3 of SEQ ID NO:160 which is the amino acid at the Kabat position H97 is Gly,
the amino acid at position 4 of SEQ ID NO:160 which is the amino acid at the Kabat position H98 is Arg,
the amino acid at position 5 of SEQ ID NO:160 which is the amino acid at the Kabat position H99 is Trp,
the amino acid at position 6 of SEQ ID NO:160 which is the amino acid at the Kabat position H100 is Ala,
the amino acid at position 7 of SEQ ID NO:160 which is the amino acid at the Kabat position H100a is Pro,
the amino acid at position 8 of SEQ ID NO:160 which is the amino acid at the Kabat position H100b is Leu,
the amino acid at position 9 of SEQ ID NO:160 which is the amino acid at the Kabat position H100c is Gly,
the amino acid at position 10 of SEQ ID NO:160 which is the amino acid at the Kabat position H100d is Ala,
the amino acid at position 11 of SEQ ID NO:160 which is the amino acid at the Kabat position H100e is Phe,
the amino acid at position 12 of SEQ ID NO:160 which is the amino acid at the Kabat position H101 is Asp and
the amino acid at position 13 of SEQ ID NO:160 which is the amino acid at the Kabat position H102 is Ile.

SEQ ID NO:161 represents a more preferred CDR3 consensus sequence for the heavy chain, wherein
the amino acid at position 1 of SEQ ID NO:161 which is the amino acid at the Kabat position H95 is Asp,
the amino acid at position 2 of SEQ ID NO:161 which is the amino acid at the Kabat position H 96 can be Gly or Ala,
the amino acid at position 3 of SEQ ID NO:161 which is the amino acid at the Kabat position H97 can be Ser or Gly,
the amino acid at position 4 of SEQ ID NO:161 which is the amino acid at the Kabat position H98 can be Ser or Arg,
the amino acid at position 5 of SEQ ID NO:161 which is the amino acid at the Kabat position H99 is Trp,
the amino acid at position 6 of SEQ ID NO:161 which is the amino acid at the Kabat position H100 can be Tyr or Ala,
the amino acid at position 7 of SEQ ID NO:161 which is the amino acid at the Kabat position H100a can be Arg or Asp,
the amino acid at position 8 of SEQ ID NO:161 which is the amino acid at the Kabat position H100b can be Asp or Leu,
the amino acid at position 9 of SEQ ID NO:161 which is the amino acid at the Kabat position H100c can be Trp or Ala,
the amino acid at position 10 of SEQ ID NO:161 which is the amino acid at the Kabat position H100d is Phe,
the amino acid at position 11 of SEQ ID NO:161 which is the amino acid at the Kabat position H101 is Asp and
the amino acid at position 12 of SEQ ID NO:161 which is the amino acid at the Kabat position H102 can be Pro or Ile.

In another embodiment, the polypeptide according to the invention comprises as CDRs all three respective consensus CDR sequences as denoted in SEQ ID NO:6 to 8.

In another embodiment, the polypeptide according to the invention comprises at least two of the respective consensus CDR sequences as denoted in SEQ ID NO:6 to 8.

In another embodiment, the polypeptide according to the invention comprises a CDR sequence having at least two of the respective consensus sequences as denoted in any of the consensus sequences SEQ ID NOs: 6 to 11.

SEQ ID NOs: 9 to 11 represent consensus sequences for CDR regions of the light chain of an antibody having the ability to bind to SEQ ID NO:2. The consensus sequences are derived from the sequence information derived from the antibodies, which have been identified by the inventors to bind specifically to SEQ ID NO:2. In particular, the identified consensus sequences for the CDR regions of the light chain were derived from naturally occurring, human antibodies isolated as described in Example 2A.

SEQ ID NO:9 represents a CDR1 consensus sequence for a kappa light chain immunoglobulin CDR1 region, wherein
the amino acid at position 1 of SEQ ID NO:9 which is the amino acid at the Kabat position L24 can be an Arg,
the amino acid at position 2 of SEQ ID NO:9 which is the amino acid at the Kabat position L25 can be Ala or Glu,
the amino acid at position 3 of SEQ ID NO:9 which is the amino acid at the Kabat position L26 can be Ser,
the amino acid at position 4 of SEQ ID NO:9 which is the amino acid at the Kabat position L27 can be Gln,
the amino acid at position 5 of SEQ ID NO:9 which is the amino acid at the Kabat position L28 can be Ser or Gly,
the amino acid at position 6 of SEQ ID NO:9 which is the amino acid at the Kabat position L29 can be Val or Ile,
the amino acid at position 7 of SEQ ID NO:9 which is the amino acid at the Kabat position L30 can be Asn or Arg or Ser,
the amino acid at position 8 of SEQ ID NO:9 which is the amino acid at the Kabat position L31 can be Ser or Asn,
the amino acid at position 9 of SEQ ID NO:9 which is the amino acid at the Kabat position L32 can be Tyr,
the amino acid at position 10 of SEQ ID NO:9 which is the amino acid at the Kabat position L33 can be Leu and
the amino acid at position 11 of SEQ ID NO:9 which is the amino acid at the Kabat position L34 can be Ala.

SEQ ID NO:10 represents a CDR2 consensus sequence for a kappa light chain immunoglobulin CDR2 region, wherein
the amino acid at position 1 of SEQ ID NO:10 which is the amino acid at the Kabat position L50 can be Ala or Gly or Lys or Trp,
the amino acid at position 2 of SEQ ID NO:10 which is the amino acid at the Kabat position L51 can be Val or Ala,
the amino acid at position 3 of SEQ ID NO:10 which is the amino acid at the Kabat position L52 can be Ser or Ala,
the amino acid at position 4 of SEQ ID NO:10 which is the amino acid at the Kabat position L53 can be Thr or Ser or Asn or Ile,
the amino acid at position 5 of SEQ ID NO:10 which is the amino acid at the Kabat position L54 can be Arg or Leu,
the amino acid at position 6 of SEQ ID NO:10 which is the amino acid at the Kabat position L55 can be Ala or Gln or Phe or Glu and
the amino acid at position 7 of SEQ ID NO:10 which is the amino acid at the Kabat position L56 can be Thr or Ser.

SEQ ID NO:11 represents a CDR3 consensus sequence for a kappa light chain immunoglobulin CDR3 region, wherein
the amino acid at position 1 of SEQ ID NO:11 which is the amino acid at the Kabat position L89 can be Gln,
the amino acid at position 2 of SEQ ID NO:11 which is the amino acid at the Kabat position L90 can be Gln,
the amino acid at position 3 of SEQ ID NO:11 which is the amino acid at the Kabat position L91 can be Ala or Tyr,
the amino acid at position 4 of SEQ ID NO:11 which is the amino acid at the Kabat position L92 can be Gly or Asn,
the amino acid at position 5 of SEQ ID NO:11 which is the amino acid at the Kabat position L93 can be Ser,
the amino acid at position 6 of SEQ ID NO:11 which is the amino acid at the Kabat position L94 can be Ser or Phe,
the amino acid at position 7 of SEQ ID NO:11 which is the amino acid at the Kabat position L95 can be Gln or Pro,
the amino acid at position 8 of SEQ ID NO:11 which is the amino acid at the Kabat position L96 can be Gly or Leu and
the amino acid at position 9 of SEQ ID NO:11 which is the amino acid at the Kabat position L97 can be Thr.

In one embodiment, the polypeptide according to the invention comprises as CDRs for the light chain all three respective consensus CDR sequences as denoted in SEQ ID NO:6 to 11.

In one embodiment, the polypeptide according to the invention comprises at least two CDRs for the light chain selected from all three respective consensus CDR sequences as denoted in SEQ ID NO:9 to 11.

Even more preferred is a polypeptide comprising at least two CDR sequences selected from the consensus CDR sequences denoted for the light chain (SEQ ID NO:9 to 11) or at least two of the consensus CDR sequences denoted for the heavy chain (SEQ ID NO:6 to 8) or at least one CDR from the light chain (SEQ ID NO:9 to 11) and at least one CDR from the heavy chain (SEQ ID NO:6 to 8).

In one embodiment, the polypeptide according to the invention comprises as CDRs for the light chain all three respective consensus CDR sequences as denoted in SEQ ID NO:9 to 11.

Even more preferred is a polypeptide comprising at least two CDR sequences selected from the consensus CDR sequences denoted for the light chain (SEQ ID NO:9 to 11) and/or at least two of the consensus CDR sequences denoted for the heavy chain (SEQ ID NO:6 to 8).

In one embodiment, isolated, monoclonal, anti-β-amyloid antibodies are provided that comprise more than one amino acid sequence selected from at least two consensus amino acid sequences of the group consisting of SEQ ID NO: 6, SEQ ID NO: 7, SEQ ID NO: 8, SEQ ID NO: 9, SEQ ID NO: 10 and SEQ ID NO: 11, wherein each of said more than one amino acid sequence is from a different SEQ ID NO, wherein said antibody binds to dimeric forms of with higher affinity than to monomeric forms of Aβ.

In a further embodiment, the polypeptide according to the invention comprises as CDR1 on the heavy chain one of the sequences as denoted in SEQ ID NOs: 13 to 20, as CDR2 on the heavy chain one of the sequence as denoted in SEQ ID NOs: 21 to 27 and 149, and/or as CDR3 on the heavy chain one of the sequences as denoted in SEQ ID NOs: 28 to 32.

In another embodiment the polypeptide according to the invention comprises at least two consensus CDR sequences selected from consensus sequences for CDR 1, CDR 2 and CDR 3 of the heavy chain and CDR 1, CDR 2 and CDR 3 of the light chain, wherein the consensus sequences are derived by aligning the sequences of the following antibody variable regions according to the Kabat numbering:
  a) for CDR1 of the heavy chain, SEQ ID NOs: 56 to 71 and 148
  b) for CDR2 of the heavy chain, SEQ ID NOs: 56 to 71 and 148
  c) for CDR3 of the heavy chain, SEQ ID NOs: 56 to 71 and 148
  d) for CDR1 of the light chain, SEQ ID NOs: 47 to 55 and 145 to 147
  e) for CDR2 of the light chain SEQ ID NOs: 47 to 55 and 145 to 147
  f) for CDR3 of the light chain, SEQ ID Nos: 47 to 55 and 145 to 147

SEQ ID NOs 13 to 20 represent the CDR1 sequences, SEQ ID NOs 21 to 27 and 149 represent the CDR2 sequences and SEQ ID NOs 28 to 32 represent the CDR3 sequences found by the inventors to be present on the heavy chain of antibodies binding to a C-terminal part of Aβ(1-40), in particular to Aβ(21-37).

In a further embodiment, the polypeptide according to the present invention comprises as CDR1 on the light chain one of the sequences as denoted in SEQ ID NOs: 33 to 37, as CDR2 on the light chain one of the sequence as denoted in SEQ ID NOs: 38 to 43 and 150 to 152, and/or as CDR3 on the light chain one of the sequences as denoted in SEQ ID NOs: 44 to 46.

SEQ ID NOs 33 to 37 represent the CDR1 sequences, SEQ ID NOs 38 to 43 and 150 to 152 represent the CDR2 sequences and SEQ ID NOs 44 to 46 represent the CDR3 sequences found by the inventors to be present on the light chain of antibodies binding to a C-terminal part of Aβ(1-40), in particular to Aβ(21-37).

In a preferred embodiment, a polypeptide according to the present invention comprises on the heavy chain a CDR1 sequence selected from SEQ ID NOs: 13 to 20, a CDR2 sequence selected from SEQ ID NOs: 21 to 27 and 148, and/or a CDR3 sequence selected from SEQ ID NOs: 28 to 32, and on the light chain a CDR1 sequence selected from SEQ ID NOs: 33 to 37, a CDR2 sequence selected from SEQ ID NOs: 38 to 43 and 150 to 152 and/or a CDR3 sequence selected from SEQ ID NOs: 44 to 46.

In particular, a polypeptide according to the present invention can comprise on the light chain:
  a) as CDR1 SEQ ID NO:34, as CDR2 SEQ ID NO:38 and as CDR3 SEQ ID NO:44, or
  b) as CDR1 SEQ ID NO:33, as CDR2 SEQ ID NO:42 and as CDR3 SEQ ID NO:44, or
  c) as CDR1 SEQ ID NO:37, as CDR2 SEQ ID NO:43 and as CDR3 SEQ ID NO:46, or
  d) as CDR1 SEQ ID NO:34, as CDR2 SEQ ID NO:40 and as CDR3 SEQ ID NO:44, or
  e) as CDR1 SEQ ID NO:35, as CDR2 SEQ ID NO:38 and as CDR3 SEQ ID NO:44, or
  f) as CDR1 SEQ ID NO:33, as CDR2 SEQ ID NO:41 and as CDR3 SEQ ID NO:44, or
  g) as CDR1 SEQ ID NO:33, as CDR2 SEQ ID NO:41 and as CDR3 SEQ ID NO:45, or
  h) as CDR1 SEQ ID NO:34, as CDR2 SEQ ID NO:38 and as CDR3 SEQ ID NO:44, or
  i) as CDR1 SEQ ID NO:36, as CDR2 SEQ ID NO:39 and as CDR3 SEQ ID NO:44.

In particular, a polypeptide according to the present invention can also comprise on the heavy chain:
  a) as CDR1 SEQ ID NO:13, as CDR2 SEQ ID NO:21 and as CDR3 SEQ ID NO:28, or
  b) as CDR1 SEQ ID NO:14, as CDR2 SEQ ID NO:27 and as CDR3 SEQ ID NO:30, or
  c) as CDR1 SEQ ID NO:13, as CDR2 SEQ ID NO:26 and as CDR3 SEQ ID NO:28, or
  d) as CDR1 SEQ ID NO:14, as CDR2 SEQ ID NO:21 and as CDR3 SEQ ID NO:30, or
  e) as CDR1 SEQ ID NO:15, as CDR2 SEQ ID NO:23 and as CDR3 SEQ ID NO:29, or
  f) as CDR1 SEQ ID NO:15, as CDR2 SEQ ID NO:22 and as CDR3 SEQ ID NO:29, or
  g) as CDR1 SEQ ID NO:20, as CDR2 SEQ ID NO:27 and as CDR3 SEQ ID NO:31, or
  h) as CDR1 SEQ ID NO:18, as CDR2 SEQ ID NO:25 and as CDR3 SEQ ID NO:31, or
  i) as CDR1 SEQ ID NO:18, as CDR2 SEQ ID NO:27 and as CDR3 SEQ ID NO:31, or
  j) as CDR1 SEQ ID NO:14, as CDR2 SEQ ID NO:27 and as CDR3 SEQ ID NO:31, or
  k) as CDR1 SEQ ID NO:14, as CDR2 SEQ ID NO:21 and as CDR3 SEQ ID NO:31, or
  l) as CDR1 SEQ ID NO:16, as CDR2 SEQ ID NO:21 and as CDR3 SEQ ID NO:31, or
  m) as CDR1 SEQ ID NO:19, as CDR2 SEQ ID NO:21 and as CDR3 SEQ ID NO:32, or n) as CDR1 SEQ ID NO:16, as CDR2 SEQ ID NO:21 and as CDR3 SEQ ID NO:28, or
o) as CDR1 SEQ ID NO:17, as CDR2 SEQ ID NO:26 and as CDR3 SEQ ID NO:31, or
p) as CDR1 SEQ ID NO:14, as CDR2 SEQ ID NO:24 and as CDR3 SEQ ID NO:28.

Even more preferred is a polypeptide according to the present invention comprising:
a) on the light chain as CDR1 SEQ ID NO:34, as CDR2 SEQ ID NO:38 and as CDR3 SEQ ID NO:44, and on the heavy chain as CDR1 SEQ ID NO:13, as CDR2 SEQ ID NO:21 and as CDR3 SEQ ID NO:28, or
b) on the light chain as CDR1 SEQ ID NO:33, as CDR2 SEQ ID NO:42 and as CDR3 SEQ ID NO:44, and on the heavy chain as CDR1 SEQ ID NO:14, as CDR2 SEQ ID NO:27 and as CDR3 SEQ ID NO:30.

Even more preferred is a polypeptide according to the present invention comprising a light variable chain having the sequence of SEQ ID NO:53 and a variable heavy chain having the sequence of SEQ ID NO:60, or a polypeptide comprising a light chain having the CDR sequences of SEQ ID NO:33, SEQ ID NO: 41 and SEQ ID NO:45 and a heavy chain having the CDR sequences of SEQ ID NO:15, SEQ ID NO:23 and SEQ ID NO:29, SEQ ID NOs: 47 to 55 and 145 to 147 denote variable regions of the light chain and SEQ ID NOs: 56 to 71 and 148 denote variable regions of the heavy chain of antibodies having the ability to bind specifically to a C-terminal part of Aβ(1-40), in particular to Aβ(21-37), as determined by the inventors. The variable regions of the heavy and light chain are responsible for antigen specificity. Therefore, in a further embodiment, the polypeptide according to the present invention comprises a sequence selected from SEQ ID NOs: 47 to 55 and 145 to 147 and/or a sequence selected from SEQ ID NOs: 56 to 71 and 148. In a particularly preferred embodiment the polypeptide according to the present invention comprises SEQ ID NO:47 and SEQ ID NO:56 or SEQ ID NO:48 and SEQ ID NO:57.

Each of the light chains of SEQ ID NOs: 47 to 55 and 145 to 147 can be combined with any of the heavy chains of SEQ ID NOs: 56 to 71 and 148. Accordingly, anti-β-amyloid antibodies are provided that comprise SEQ ID NO: 47 and SEQ ID NO:56; SEQ ID NO: 47 and SEQ ID NO:57; SEQ ID NO: 47 and SEQ ID NO: 58; SEQ ID NO: 47 and SEQ ID NO: 59; SEQ ID NO: 47 and SEQ ID NO:60; SEQ ID NO: 47 and SEQ ID NO: 61; SEQ ID NO: 47 and SEQ ID NO: 62; SEQ ID NO: 47 and SEQ ID NO: 63; SEQ ID NO: 47 and SEQ ID NO: 64; SEQ ID NO: 47 and SEQ ID NO: 65; SEQ ID NO: 47 and SEQ ID NO: 66; SEQ ID NO: 47 and SEQ ID NO: 67; SEQ ID NO: 47 and SEQ ID NO: 68; SEQ ID NO: 47 and SEQ ID NO: 69; SEQ ID NO: 47 and SEQ ID NO: 70; SEQ ID NO: 47 and SEQ ID NO: 71; SEQ ID NO: 47 and SEQ ID NO: 148; SEQ ID NO: 48 and SEQ ID NO:56; SEQ ID NO: 48 and SEQ ID NO:57; SEQ ID NO: 48 and SEQ ID NO:58; SEQ ID NO: 48 and SEQ ID NO:59; SEQ ID NO: 48 and SEQ ID NO:60; SEQ ID NO: 48 and SEQ ID NO:61; SEQ ID NO: 48 and SEQ ID NO:62; SEQ ID NO: 48 and SEQ ID NO:63; SEQ ID NO: 48 and SEQ ID NO:64; SEQ ID NO: 48 and SEQ ID NO:65; SEQ ID NO: 48 and SEQ ID NO:66; SEQ ID NO: 48 and SEQ ID NO:67; SEQ ID NO: 48 and SEQ ID NO:68; SEQ ID NO: 48 and SEQ ID NO:69; SEQ ID NO: 48 and SEQ ID NO:70; SEQ ID NO: 48 and SEQ ID NO:71; SEQ ID NO: 48 and SEQ ID NO:148; SEQ ID NO: 49 and SEQ ID NO:56; SEQ ID NO: 49 and SEQ ID NO:57; SEQ ID NO: 49 and SEQ ID NO: 58; SEQ ID NO: 49 and SEQ ID NO: 59; SEQ ID NO: 49 and SEQ ID NO: 60; SEQ ID NO: 49 and SEQ ID NO: 61; SEQ ID NO: 49 and SEQ ID NO: 62; SEQ ID NO: 49 and SEQ ID NO: 63; SEQ ID NO: 49 and SEQ ID NO: 64; SEQ ID NO: 49 and SEQ ID NO: 65; SEQ ID NO: 49 and SEQ ID NO: 66; SEQ ID NO: 49 and SEQ ID NO: 67; SEQ ID NO: 49 and SEQ ID NO: 68; SEQ ID NO: 49 and SEQ ID NO: 69; SEQ ID NO: 49 and SEQ ID NO: 70; SEQ ID NO: 49 and SEQ ID NO: 71; SEQ ID NO: 49 and SEQ ID NO: 148; SEQ ID NO: 50 and SEQ ID NO: 56; SEQ ID NO: 50 and SEQ ID NO: 57; SEQ ID NO: 50 and SEQ ID NO: 58; SEQ ID NO: 50 and SEQ ID NO: 59; SEQ ID NO: 50 and SEQ ID NO: 60; SEQ ID NO: 50 and SEQ ID NO: 61; SEQ ID NO: 50 and SEQ ID NO: 62; SEQ ID NO: 50 and SEQ ID NO: 63; SEQ ID NO: 50 and SEQ ID NO: 64; SEQ ID NO: 50 and SEQ ID NO: 65; SEQ ID NO: 50 and SEQ ID NO: 66; SEQ ID NO: 50 and SEQ ID NO: 67; SEQ ID NO: 50 and SEQ ID NO: 68; SEQ ID NO: 50 and SEQ ID NO: 69; SEQ ID NO: 50 and SEQ ID NO: 70; SEQ ID NO: 50 and SEQ ID NO: 71; SEQ ID NO: 50 and SEQ ID NO: 148; SEQ ID NO: 51 and SEQ ID NO: 56; SEQ ID NO: 51 and SEQ ID NO: 57; SEQ ID NO: 51 and SEQ ID NO: 58; SEQ ID NO: 51 and SEQ ID NO: 59; SEQ ID NO: 51 and SEQ ID NO: 60; SEQ ID NO: 51 and SEQ ID NO: 61; SEQ ID NO: 51 and SEQ ID NO: 62; SEQ ID NO: 51 and SEQ ID NO: 63; SEQ ID NO: 51 and SEQ ID NO: 64; SEQ ID NO: 51 and SEQ ID NO: 65; SEQ ID NO: 51 and SEQ ID NO: 66; SEQ ID NO: 51 and SEQ ID NO: 67; SEQ ID NO: 51 and SEQ ID NO: 68; SEQ ID NO: 51 and SEQ ID NO: 69; SEQ ID NO: 51 and SEQ ID NO: 70; SEQ ID NO: 51 and SEQ ID NO: 71; SEQ ID NO: 51 and SEQ ID NO: 148; SEQ ID NO: 52 and SEQ ID NO: 56; SEQ ID NO: 52 and SEQ ID NO: 57; SEQ ID NO: 52 and SEQ ID NO: 58; SEQ ID NO: 52 and SEQ ID NO: 59; SEQ ID NO: 52 and SEQ ID NO: 60; SEQ ID NO: 52 and SEQ ID NO: 61; SEQ ID NO: 52 and SEQ ID NO: 62; SEQ ID NO: 52 and SEQ ID NO: 63; SEQ ID NO: 52 and SEQ ID NO: 64; SEQ ID NO: 52 and SEQ ID NO: 65; SEQ ID NO: 52 and SEQ ID NO:66; SEQ ID NO: 52 and SEQ ID NO: 67; SEQ ID NO: 52 and SEQ ID NO: 68; SEQ ID NO: 52 and SEQ ID NO: 69; SEQ ID NO: 52 and SEQ ID NO: 70; SEQ ID NO: 52 and SEQ ID NO: 71; SEQ ID NO: 52 and SEQ ID NO:148; SEQ ID NO: 53 and SEQ ID NO: 56; SEQ ID NO: 53 and SEQ ID NO: 57; SEQ ID NO: 53 and SEQ ID NO: 58; SEQ ID NO: 53 and SEQ ID NO: 59; SEQ ID NO: 53 and SEQ ID NO: 60; SEQ ID NO: 53 and SEQ ID NO: 61; SEQ ID NO: 53 and SEQ ID NO: 62; SEQ ID NO: 53 and SEQ ID NO: 63; SEQ ID NO: 53 and SEQ ID NO: 64; SEQ ID NO: 53 and SEQ ID NO: 65; SEQ ID NO: 53 and SEQ ID NO: 66; SEQ ID NO: 53 and SEQ ID NO: 67; SEQ ID NO: 53 and SEQ ID NO: 68; SEQ ID NO: 53 and SEQ ID NO: 69; SEQ ID NO: 53 and SEQ ID NO: 70; SEQ ID NO: 53 and SEQ ID NO: 71; SEQ ID NO: 53 and SEQ ID NO: 148; SEQ ID NO: 54 and SEQ ID NO: 56; SEQ ID NO: 54 and SEQ ID NO: 57; SEQ ID NO: 54 and SEQ ID NO: 58; SEQ ID NO: 54 and SEQ ID NO: 59; SEQ ID NO: 54 and SEQ ID NO: 60; SEQ ID NO: 54 and SEQ ID NO: 61; SEQ ID NO: 54 and SEQ ID NO: 62; SEQ ID NO: 54 and SEQ ID NO: 63; SEQ ID NO: 54 and SEQ ID NO: 64; SEQ ID NO: 54 and SEQ ID NO: 65; SEQ ID NO: 54 and SEQ ID NO: 66; SEQ ID NO: 54 and SEQ ID NO: 67; SEQ ID NO: 54 and SEQ ID NO: 68; SEQ ID NO: 54 and SEQ ID NO: 69; SEQ ID NO: 54 and SEQ ID NO: 70; SEQ ID NO: 54 and SEQ ID NO: 71; SEQ ID NO: 54 and SEQ ID NO: 148; SEQ ID NO: 55 and SEQ ID NO: 56; SEQ ID NO: 55 and SEQ ID NO: 57; SEQ ID NO: 55 and SEQ ID NO: 58; SEQ ID NO: 55 and SEQ ID NO: 59; SEQ ID NO: 55 and SEQ ID NO: 60; SEQ ID NO: 55 and SEQ ID NO: 61; SEQ ID NO: 55 and SEQ ID NO: 62; SEQ ID NO: 55 and SEQ ID NO: 63; SEQ ID NO: 55 and SEQ ID NO: 64; SEQ ID NO: 55 and SEQ ID NO: 65; SEQ ID NO: 55 and SEQ ID NO: 66; SEQ ID NO: 55 and SEQ ID NO: 67; SEQ ID NO: 55 and SEQ ID NO: 68; SEQ ID NO: 55 and SEQ ID NO: 69; SEQ ID NO: 55 and SEQ ID NO: 70; SEQ ID NO: 55 and SEQ ID NO: 71; SEQ ID NO: 55 and SEQ ID NO: 148; SEQ ID NO: 145 and SEQ ID NO: 56; SEQ ID NO: 145 and SEQ ID NO: 57; SEQ ID NO: 145 and SEQ ID NO: 58; SEQ ID NO: 145 and SEQ ID NO: 59; SEQ ID NO: 145 and SEQ ID NO: 60; SEQ ID NO: 145 and SEQ ID NO: 61; SEQ ID NO: 145 and SEQ ID NO: 62; SEQ ID NO: 145 and SEQ ID NO: 63; SEQ ID NO: 145 and SEQ ID NO: 64; SEQ ID NO: 145 and SEQ ID NO: 65; SEQ ID NO: 145 and SEQ ID NO: 66; SEQ ID NO: 145 and SEQ ID NO: 67; SEQ ID NO: 145 and SEQ ID NO: 68; SEQ ID NO: 145 and SEQ ID NO: 69; SEQ ID NO: 145 and SEQ ID NO: 70; SEQ ID NO: 145 and SEQ ID NO: 71; SEQ ID NO: 145 and SEQ ID NO: 148; SEQ ID NO: 146 and SEQ ID NO: 56; SEQ ID NO: 146 and SEQ ID NO: 57; SEQ ID NO: 146 and SEQ ID NO: 58; SEQ ID NO: 146 and SEQ ID NO: 59; SEQ ID NO: 146 and SEQ ID NO: 60; SEQ ID NO: 146 and SEQ ID NO: 61; SEQ ID NO: 146 and SEQ ID NO: 62; SEQ ID NO: 146 and SEQ ID NO: 63; SEQ ID NO: 146 and SEQ ID NO: 64; SEQ ID NO: 146 and SEQ ID NO: 65; SEQ ID NO: 146 and SEQ ID NO: 66; SEQ ID NO: 146 and SEQ ID NO: 67; SEQ ID NO: 146 and SEQ ID NO: 68; SEQ ID NO: 146 and SEQ ID NO: 69; SEQ ID NO: 146 and SEQ ID NO: 70; SEQ ID NO: 146 and SEQ ID NO: 71; SEQ ID NO: 146 and SEQ ID NO: 148; SEQ ID NO: 147 and SEQ ID NO: 56; SEQ ID NO: 147 and SEQ ID NO: 57; SEQ ID NO: 147 and SEQ ID NO: 58; SEQ ID NO: 147 and SEQ ID NO: 59; SEQ ID NO: 147 and SEQ ID NO: 60; SEQ ID NO: 147 and SEQ ID NO: 61; SEQ ID NO: 147 and SEQ ID NO: 62; SEQ ID NO: 147 and SEQ ID NO: 63; SEQ ID NO: 147 and SEQ ID NO: 64; SEQ ID NO: 147 and SEQ ID NO: 65; SEQ ID NO: 147 and SEQ ID NO: 66; SEQ ID NO: 147 and SEQ ID NO: 67; SEQ ID NO: 147 and SEQ ID NO: 68; SEQ ID NO: 147 and SEQ ID NO: 69; SEQ ID NO: 147 and SEQ ID NO: 70; SEQ ID NO: 147 and SEQ ID NO: 71; or SEQ ID NO: 147 and SEQ ID NO: 148;

In preferred embodiments, the anti-β-amyloid antibodies comprise SEQ ID NO: 145 and SEQ ID NO:60; SEQ ID NO: 53 and SEQ ID NO:60; SEQ ID NO: 51 and SEQ ID NO:60; SEQ ID NO: 52 and SEQ ID NO:60; SEQ ID NO: 146 and SEQ ID NO:60; SEQ ID NO: 53 and SEQ ID NO:148; SEQ ID NO: 55 and SEQ ID NO:61; SEQ ID NO: 145 and SEQ ID NO:62; SEQ ID NO: 54 and SEQ ID NO:60; SEQ ID NO: 54 and SEQ ID NO:61; SEQ ID NO: 54 and SEQ ID NO:148; SEQ ID NO: 145 and SEQ ID NO:148; or SEQ ID NO: 146 and SEQ ID NO:61.

In addition, SEQ ID NOs 72 to 74 denote constant regions of the light chain and SEQ ID NOs 75 to 77 denote constant regions of the heavy chain of antibodies having the ability to bind specifically to a C-terminal part of Aβ(1-40), in particular to Aβ(21-37). Therefore, in a further embodiment, the polypeptide according to the present invention can comprise a sequence selected from SEQ ID NOs: 72 to 74 and/or a sequence selected from SEQ ID NOs: 75 to 77. In particular, the polypeptide according to the present invention can comprise a sequence selected from SEQ ID NO:72 or 73 and a sequence selected from SEQ ID NOs 75 to 77.

The complete sequences, consisting of variable region and constant region, for the light chain of antibodies having the ability to bind specifically to a C-terminal part of Aβ(1-40), in particular to Aβ(21-37), are denoted in SEQ ID NOs: 78 to 93.

Therefore, in another embodiment of the present invention, the polypeptide according to the present invention comprises a sequence selected from SEQ ID NOs: 78 to 93.

The complete sequences, consisting of variable region and constant region, for the heavy chain of antibodies having the ability to bind specifically to a C-terminal part of Aβ(1-40), in particular to Aβ(21-37), are denoted in SEQ ID NOs: 94 to 137. Therefore, in another embodiment of the present invention, the polypeptide according to the present invention comprises a sequence selected from SEQ ID NOs: 94 to 137.

In an even more preferred embodiment, the polypeptide according to the present invention comprises a sequence as denoted in SEQ ID NO:78 and a sequence as denoted in SEQ ID NO:94 or a sequence as denoted in SEQ ID NO:80 and a sequence as denoted in SEQ ID NO:97. The same applies to the analogous isoforms of respective chains and combinations thereof (as can be taken from FIG. 23a).

Consensus sequences for framework regions also can be identified. If the amino acid sequences of the variable regions of the heavy and light chains are aligned respectively according to the Kabat rules, the so-called framework regions N-terminal to CDR1, between CDR1 and CDR2, between CDR2 and CDR3 and C-terminal to CDR3 can be compared in a way analogous to that described above for the CDR regions, and consensus sequences for the framework of the antibodies of the invention can be derived.

It has to be noted that the inventors found that the N-terminal sequence, about 18 amino acid residues, of kappa light chain of antibodies having the ability to bind specifically to a C-terminal part of Aβ(1-40), in particular to Aβ(21-37), is well conserved. This applies for antibodies derived from IVIgG preparations as well as for antibodies derived from patient serum. In FIG. 31 said sequences are depicted, additionally also denoted as SEQ ID NOs: 138 to 143. It is contemplated, that the conservative nature of the N-terminus of kappa light chain of these antibodies might contribute to antigen specificity and/or prevention of plaque formation when bound to Aβ peptide. Thus, in a preferred embodiment, the polypeptide according to the present invention comprises a sequence as denoted in the consensus sequence of SEQ ID NO: 44, in particular a sequence as denoted in SEQ ID NOs: 138 to 143.

In another embodiment, the inventive polypeptides bind specifically to oligomeric forms of β-amyloid polypeptide. By way of non-limiting example, the polypeptides can bind oligomeric forms of Aβ(1-40) or oligomeric forms of Aβ(12-20) or oligomeric forms of Aβ(21-37). In one aspect, the inventive polypeptides are capable of binding specifically to oligomeric fauns of Aβ(1-40) when incubated overnight at 10 mM sodium phosphate, 150 mM NaCl, pH 7.4 at 4° C.

In another aspect, the inventive autoantibodies bind with a higher affinity to dimers of Aβ than to corresponding monomers of Aβ.

In general, binding affinity is a measure of antibody-antigen combination and concerns the selectivity with which a given antibody binds to an epitope when compared with binding to any other epitope. This preferential or selective binding can be quantified as a binding affinity or titer. Methods of calculating antibody affinity are well-known in the field. See, e.g. Practical Immunology Ch. 3, Frank C Hay & Olwyn M. R. Westwood, Blackwell Publishing (2002); Measuring Immunity: Basic Biology and Clinical Assessment, Ch. 16, Michael T. Lotze & Angus W. Thomson (eds.), Academic Press (2005), both which are incorporated herein by reference.

In a preferred embodiment, where the polypeptide according to the invention is an antibody, said antibody may be a monoclonal antibody. Monoclonal antibodies have the advantage that they exhibit less cross reactivity.

In another preferred embodiment the polypeptides according to the present invention comprises derivatives and/or fragments of antibodies binding to Aβ(21-37) (SEQ ID NO:2). It is well known in the art that antibodies can be treated enzymatically, e.g. with proteases in order to obtain fragments of antibodies which retain the antigen binding properties of the intact antibody, but which lack the Fc-domain. Such fragments are for example Fab or F(ab')$_2$ fragments, which are obtainable via enzymatic digest of antibodies with papain or pepsin protease, respectively. Another fragment of an antibody is a single chain variable fragment (scFv) of an antibody, i.e. a fusion of the variable regions of the heavy and light chains of an antibody via a short flexible linker (usually serine, glycine). Normally, such a chimeric molecule retains the specificity of the original antibody, despite removal of the constant regions and the introduction of a linker peptide. Single chain variable fragments can be obtained by genetic engineering of a respective nucleic acid encoding for such a fusion protein. The advantage of such a fragment is that it consists only of a single polypeptide chain which is more easily expressed and properly folded in artificial expression systems than the whole antibody, which comprises at least 4 polypeptide chains which need a correct assembly in order to function adequately.

If the polypeptide according the invention is an antibody, a human antibody is preferred due to its low immunogenicity in humans. However, the antibody or fragment thereof can be derived from any species suitable for antibody production. Non-human antibodies can be derived in particular from mouse, chicken, rabbit, rat, donkey, camel, dromedary, shark and llamas. Antibodies of camel, dromedary, shark and llamas have the advantage that these animals have antibodies which consist only of a homodimer. Thus, such polypeptides have similar advantages in expression and assembly as described above for single chain variable fragments.

In another preferred embodiment the antibody, derivatives or fragments thereof is a humanized antibody, derivative or fragment thereof, i.e. while the antigen binding domain or parts thereof is/are of non-human origin, the rest of the antibody, derivative or fragment thereof is of human origin. In another preferred embodiment the antibody, derivative or fragment thereof is chimeric, i.e. while the variable domain or parts thereof is/are of non-human origin the constant domain is of human origin. Both embodiments serve the purpose to reduce negative side effects due to immunogenic properties of protein domains of non-human origin. In an even more preferred embodiment, the polypeptide binding to epitope Aβ(21-37) (SEQ ID NO:2) of amyloid-beta peptide (1-40) (SEQ ID NO:1) is an antibody derivative or fragment which comprises only the paratope of an antibody binding to said epitope. Example for such a paratope is, for example, a polypeptide comprising the amino acid sequences for the respective CDR domains of heavy and light chain connected via the intervening sequences or via synthetic linkers.

In one aspect, the antibodies of the present invention embrace allelic variants, conservatively modified variants, and minor recombinant modifications to a specific anti-Aβ (21-37) autoantibody. Amino acid sequence variants of the antibody can be prepared by introducing appropriate nucleotide changes into the encoding DNA, or by peptide synthesis. Such variants include, for example, deletions and/or insertions and/or substitutions of residues within the amino acid sequences of the antibodies. Any combination of deletion, insertion, and substitution is made to arrive at the final construct, provided that the final construct possesses the desired characteristics. The amino acid changes also may alter post-translational processes of antibody, such as changing the number or position of glycosylation sites.

Amino acid sequence insertions can include, for example, amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the specific binding agent or antibody (including antibody fragment) fused to an epitope tag or a salvage receptor epitope. Other insertional variants include a fusion to a polypeptide which increases the serum half-life of the antibody, e.g. at the N-terminus or C-terminus.

Another type of variant is an amino acid substitution variant. These variants have at least one amino acid residue in the antibody molecule removed and a different residue inserted in its place. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class. Example of conservative substitutions include replacing ala with val, leu or ile; arg with lys, gin or asn; asn with gln, his, asp, lys, or gln; asp with glu or asn; cys with ser or ala; gin with asn or glu; glu with asp or gin; gly with ala; his with asn, gln, lys, or arg; ile with leu, val, met, ala or phe; leu with norleucine, ile, val, met, ala, or phe; lys with arg, gly, asn; met with leu, phe, or ile; phe with leu, val, ile, ala, or tyr; pro with ala; ser with thr; thr with ser; trp with tyr or phe; tyr with trp, phe, thr or ser; and val with ile, leu, met, phe, ala, or norleucine.

Any cysteine residue not involved in maintaining the proper conformation of the specific binding agent or humanized or variant antibody also may be substituted, generally with serine, to improve the oxidative stability of the molecule and prevent aberrant crosslinking. Conversely, cysteine bond(s) may be added to the specific binding agent or antibody to improve its stability (particularly where the antibody is an antibody fragment such as an Fv fragment).

Altered glycosylation variants also can be produced that have a modified glycosylation pattern relative to the parent antibody, for example, by deleting one or more carbohydrate moieties found in the antibody, and/or adding one or more glycosylation sites that are not present in the antibody. Glycosylation of polypeptides including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine also may be used. O-linked glycosylation sites may be added to a specific binding agent or antibody by inserting or substituting one or more serine or threonine residues to the sequence of the antibody.

Modifications to increase serum half-life also may desirable, for example, by incorporation of or addition of a salvage receptor binding epitope (e.g., by mutation of the appropriate region or by incorporating the epitope into a peptide tag that is then fused to the antibody at either end or in the middle, e.g., by DNA or peptide synthesis; See, e.g., WO 96/32478) or adding molecules such as PEG or other water soluble polymers, including polysaccharide polymers.

Preparation of Antibodies

Polyclonal Antibodies

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates or derivatives by combining, e.g., 100 μg of the protein or conjugate (for mice) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. At 7-14 days post-booster injection, the animals are bled and the serum is assayed for antibody titer Animals are boosted until the titer plateaus. Preferably, the animal is boosted with the conjugate of the same antigen, but conjugated through a different cross-linking reagent. Conjugates also can be made in recombinant cell culture as protein fusions. Also, aggregating agents such as alum are suitably used to enhance the immune response.

Monoclonal Antibodies

Monoclonal antibodies can be made using the hybridoma method first described by Kohler et al., Nature, 256:495 (1975), or by recombinant DNA methods. In the hybridoma method, a mouse or other appropriate host animal, such as rats, hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can be determined, for example, by BIAcore or Scatchard analysis (Munson et al., Anal. Biochem., 107:220 (1980)).

After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEMO or RPMI 1640 medium. In addition, the hybridoma cells can be grown in vivo as ascites tumors in an animal. The monoclonal antibodies secreted by the subclones are suitably separated from the culture medium, ascites fluid, or serum by conventional immunoglobulin purification procedures such as protein A-Sepharose, hydroxylapatite chromatography, gel electrophoresis, dialysis, or affinity chromatography.

Recombinant Production of Antibodies

The amino acid sequence of an immunoglobulin of interest can be determined by direct protein sequencing, and suitable encoding nucleotide sequences can be designed according to a universal codon table.

Alternatively, DNA encoding the monoclonal antibodies can be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or mRNA encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library can be constructed by reverse transcription of polyA+ mRNA, preferably membrane-associated mRNA, and the library screened using probes specific for human immunoglobulin polypeptide gene sequences. In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be cloned readily into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, PCR is used to amplify cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning The sequence of the amplified or cloned nucleic acid is then determined. Typically the sequence encoding an entire variable region of the immunoglobulin polypeptide is determined, however, sometimes only a portion of a variable region need be sequenced, for example, the CDR-encoding portion. Typically the sequenced portion will be at least 30 bases in length, and more often bases coding for at least about one-third or at least about one-half of the length of the variable region will be sequenced.

Sequencing can be carried out on clones isolated from a cDNA library or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, an artisan can determine readily, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be operably linked to expression control sequences or placed into expression vectors, which are then transfected into host cells such as *E. coli* cells, simian COS cells, Chinese hamster ovary (CHO) cells, or myeloma cells that do not otherwise produce immunoglobulin protein, to direct the synthesis of monoclonal antibodies in the recombinant host cells.

Expression control sequences denote DNA sequences necessary for the expression of an operably linked coding sequence in a particular host organism. The control sequences that are suitable for prokaryotes, for example, include a promoter, optionally an operator sequence, and a ribosome-binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, synthetic oligonucleotide adaptors or linkers can be used in accordance with conventional practice.

Cell, cell line, and cell culture are often used interchangeably and all such designations include progeny. Transformants and transformed cells include the primary subject cell and cultures derived therefrom without regard for the number of transfers. It also is understood that all progeny may not be precisely identical in DNA content, due to deliberate or inadvertent mutations. Mutant progeny that have the same function or biological activity as screened for in the originally transformed cell are included.

Isolated nucleic acids also are provided that encode specific antibodies, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

A variety of vectors are known in the art. Vector components can include one or more of the following: a signal sequence (that, for example, can direct secretion of the antibody), an origin of replication, one or more selective marker genes (that, for example, can confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells. Suitable prokaryotes include eubacteria, such as Gram-negative or Gram-positive organisms, for example, Enterohacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. lichenifonnis, Pseudomonas*, and *Streptomyces*. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-I variant of Autographa californica NPV and the Bm-5 strain of *Bombyx mori* NPV.

However, interest has been greatest in vertebrate cells, and propagation of vertebrate cells in culture (tissue culture) has become routine. Examples of useful mammalian host cell-lines are Chinese hamster ovary cells, including CHOK1 cells (ATCC CCL61) and Chinese hamster ovary cells/–DHFR (DXB-11, DG-44; Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI38, ATCC CCL 75); human hepatoma cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells and FS4 cells.

The host cells can be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 can be used as culture media for the host cells. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements also can be included at appropriate concentrations that would be known to those skilled in the art. The culture conditions, such as temperature, pH, and the like, are those previously used with the host cell selected for expression, and will be apparent to the artisan.

The antibody composition can be purified using, for example, hydroxylapatite chromatography, cation or anion exchange chromatography, or preferably affinity chromatography, using the antigen of interest or protein A or protein G as an affinity ligand. Protein A can be used to purify antibodies that are based on human γ1, γ2, or γ4 heavy chains (Lindmark et al., J. Immunol. Meth. 62: 1-13 (1983)). Protein G is recommended for all mouse isotypes and for human γ3 (Guss et al., 20 EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, 25 NJ.) is useful for purification. Other techniques for protein purification such as ethanol precipitation, Reverse Phase HPLC, chromatofocusing, SDS-PAGE, and ammonium sulfate precipitation are also possible depending on the specific binding agent or antibody to be recovered.

A person skilled in the art with the information of this patent application at hand will readily know how to perform the methods according to the invention. One example would be to coat a sepharose column with a polypeptide having the sequence of SEQ ID NO: 2, followed by incubation with an immunoglobulin fraction (antibody fraction) derived from the sample, performing a washing step and subsequent elution of the Aβ(21-37) specific antibodies bound to the column. For the methods of separation according to the invention the polypeptide, comprising an amino acid sequence of an Aβ polypeptide, wherein the sequence of the Aβ polypeptide has at least the sequence according to SEQ ID NO:2 and at most the sequence according to SEQ ID NO:4, additionally comprises moieties such as tags or markers, in particular biotin, streptavidin, GST, HIS, STREP-tag, Myc, HA, poly-L-lysine, poly-L-lysine-L-alanine copolymers, poly-Aib (alpha-aminoisobutyric acid), poly-β-alanine, poly-L-alanine, poly-D-lysine, poly-D-lysine-D-alanine copolymers, poly-D-alanine, or combinations of poly-L- and D-amino acids. These markers can provide for a facilitated binding of this polypeptide to a carrier. Elution, i.e. separation of polypeptides according to the present invention from the carrier can, for instance, be achieved by applying a short-term pH change to pH 2, by adding excess of a polypeptide comprising the sequence according to SEQ ID NO:2 or by increasing the salt content of the elution buffer. Further, non-limiting examples for isolation of polypeptides from the serum of a subject or from commercially available IVIgG preparations are given in more detail in the examples section of this application.

Antibodies can not only be derived from a human subject but also from an animal. Besides isolating pre-existing anti-Aβ(21-37) autoantibodies from the blood of such an animal in analogy to the methods described above, such animals can be additionally immunized with a polypeptide comprising an amino acid sequence of an Aβ polypeptide, wherein the sequence of the Aβ polypeptide has at least the sequence according to SEQ ID NO:2 and at most the sequence according to SEQ ID NO:4. After several rounds of immunization the corresponding Aβ-specific antibody producing B-cells can be obtained from the blood of the animal by routine methods.

If desired, such B cell clones (of human or animal origin) can be converted into a cell line, for example by isolating cells from the spleen of an animal and immortalizing them by transfection with Epstein Barr Virus or by fusing the cells with myeloma cells (hybridoma technology). The latter is especially useful for producing antibodies in large quantities.

Alternatively, the polypeptides of the present invention can be, if suitable, directly synthesized, either by conventional polypeptide synthesis, by in vitro translation or by any other means for synthesizing polypeptides and proteins. A person skilled in the art will be familiar with a multitude of appropriate techniques and will be readily able to apply them to the subject-matter of the present invention.

Additionally, the polypeptide binding to the epitope Aβ(21-37) (SEQ ID NO:2) of amyloid-beta (1-40) (SEQ ID NO: 1) can originate from other proteins than antibodies. As an example, anticalins can be engineered to bind to certain epitopes i.e. to the epitope as denoted in SEQ ID NO: 2. Anticalins are a class of engineered ligand-binding proteins that are based on the lipocalin scaffold. Using targeted mutagenesis of the loop region and biochemical selection techniques, variants with novel ligand specificities, both for low-molecular weight substances and for macromolecular protein targets, can be generated (see DE 199 26 068; Schlehuber et al., J. Mol. Biol. (2000), 297 (5) p. 1105-1120; Expert Opin Biol Ther. 2005, 5(11), p. 1453-62). Binding of such a polypeptide to an Aβ C-terminal part, in particular to Aβ (21-37) can also provide for an inhibition of polymerization of Aβ peptide and thus provide an efficient means for treatment and or prophylaxis of Alzheimer's Disease and other neurodementing diseases.

The polypeptides according to the invention can also be obtained via a recombinant expression system. In order to express a polypeptide according to the invention, a respective nucleic acid expression construct has to be generated. Therefore, the present invention relates also to a nucleic acid having a sequence encoding for a polypeptide according to the present invention, in particular encoding the light chain or the heavy chain of one of the above mentioned antibodies, derivatives or fragments thereof or encoding for another protein according to the invention such as an anticalin binding to Aβ(21-37). Such a nucleic acid can be for instance obtained by identifying the amino acid sequence of one of the peptides mentioned above, for instance via mass spectrometry means, via Edman sequencing or any other method for protein sequencing known to the skilled artisan. Following the genetic code a nucleic acid sequence can be derived from the amino acid sequence. Preferably, the generated nucleic acid sequence is optimized in regard to the codon usage of the respective expression system of interest. Alternatively, cells expressing such an antibody can be isolated (see above) and the genomic loci or mRNA encoding for the heavy and light chain of the antibody specific for the C-Terminus of Aβ are sequenced. For certain expression systems this nucleic acid sequence might need to be adapted in order to provide for an optimal codon usage. A person skilled in the art with the above mentioned nucleic acid sequences at hand will be readily capable of generating expression constructs for use in a suitable expression system. Therefore, the present invention also relates to an expression construct providing for the expression of the polypeptides of the invention and to an isolated cell, which expresses a polypeptide or a fragment thereof according to the invention. Expression constructs, i.e. vectors include plasmids, cosmids, viruses (bacteriophage, animal viruses, and plant viruses), episomes and artificial chromosomes (e.g., YACs). One of skill in the art would be able to construct a vector by standard recombinant techniques. Said cell can be for example a myeloma cell, a Chinese hamster ovary cell, a Syrian hamster ovary cell, a human embryonic kidney cell, insect cell (baculovirus system), or a transgenic plant cell, which is transformed with an expression vector according to the invention (see Schillberg et al., Cell Mol Life Sci. 2003 60(3): p. 433-445) or a cell, which endogenously expresses a polypeptide according to the invention (hybridoma). The expression of recombinant polypeptides of the invention is not restricted to eukaryotic cells but can also be expressed in prokaryotes. Recombinant polypeptides according to the invention can be obtained from any such cell by purification means which are well known in the art.

In a preferred embodiment, the polypeptide according to the invention is an antibody or a fragment thereof and is optionally encoded by two expression vectors, i.e. one expression vector for the light chain and one for the heavy chain.

In order to bind within the polypeptide fragment Aβ(21-37), an antibody or a fragment thereof requires primarily an intact antigen binding domain (variable domain). The constant region of such an antibody is usually not critical for antigen binding. Thus, it is clear for a person skilled in the art, that if the polypeptide according to the invention is an antibody or a fragment thereof, this antibody/fragment may have any given isotype selected from the group consisting of IgG, IgM, IgA, IgD and IgE, including all respective subclasses of these isotypes. If the polypeptide according to the present invention is expressed as an antibody in an immune cell or hybridoma cell, the isotype can be switched by additional expression or administration of activation induced cytidine deaminase and administration of stimulating factors known to the skilled artisan.

In one embodiment, the polypeptides according to the invention are chemically coupled or fused with substances which prevent plaque aggregation and/or lead to the disintegration of toxic Aβ oligomers. Such a substance could be for example a protease cleaving Amyloid beta polypeptide as used for the experimental characterization of the epitope according to the invention, i.e. Serine-proteases like Trypsin, Chymotrypsin; or Lys-C protease, Arg-C protease, Asp-N-proteases, also unspecific proteases such as proteinase-K, termolysine, subtilisin.

The present invention also relates to a method of isolation and separation of a polypeptide according to the invention from a sample, the method comprising the following steps:
  a) incubating a polypeptide comprising an amino acid sequence of an Aβ polypeptide, wherein the sequence of the Aβ polypeptide has at least the sequence according to SEQ ID NO:2, i.e. Aβ(21-37) and at most the sequence according to SEQ ID NO:4, i.e. Aβ(12-40), which polypeptide is immobilized on a carrier, with a sample,
  b) separating said sample from the carrier.
  c) separating polypeptides according to the invention bound to the polypeptide of step a) from the carrier.

In an alternative approach, a polypeptide according to the invention can be obtained by incubating the sample with the polypeptide comprising an amino acid sequence of an Aβ polypeptide, wherein the sequence of the Aβ polypeptide has at least the sequence according to SEQ ID NO:2 and at most the sequence according to SEQ ID NO:4 prior to incubation with the carrier. Thus, the present invention also relates to a method of separation of a polypeptide according to the invention from a sample, the method comprising the following steps:
  a) incubating a polypeptide, comprising an amino acid sequence of an Aβ polypeptide, wherein the sequence of the Aβ polypeptide has at least the sequence according to SEQ ID NO:2 and at most the sequence according to SEQ ID NO:4, with a sample and subsequently
  b) incubating the sample with a carrier having a binding affinity for the polypeptide of step a), and
  c) separating said sample from the carrier, and,
  d) separating polypeptides according to the invention bound to the polypeptide of step a) from the carrier.

Strategies and techniques are well known in the art to obtain the above mentioned polypeptides, i.e. via genetic engineering and expression of the respective polypeptide in a cell line of interest. Antibody fragments according to the invention do not have to be physically derived from an intact antibody but can also be genetically engineered by conventional means.

The above mentioned polypeptides can be obtained for example by screening antibodies derived from the blood of a human subject for the capacity of binding to amino acid 21 to 37 of SEQ ID NO 1 (i.e. SEQ ID NO: 2).

Methods of Treatment

In another aspect, the present invention relates to the use of the above mentioned polypeptides according to the present invention for use in human and veterinary medicine.

In particular, the polypeptides according to the present invention can be used for the manufacture of a medicament in order to treat and/or prevent the progression of Alzheimer's disease, Down's syndrome, Dementia with Lewy bodies, fronto-temporal dementia, cerebral amyloid angiopathy, and/or amyloidoses.

Furthermore, the present invention relates to the use of a polypeptide comprising an amino acid sequence of an Aβ peptide, wherein the Aβ peptide has at least the sequence according to SEQ ID NO:2 and at most the sequence according to SEQ ID NO:4 for use in human and veterinary medicine, in particular for the manufacture of a medicament for the treatment and/or prevention of Alzheimer's disease, Down's syndrome, Dementia with Lewy bodies, fronto-temporal dementia, cerebral amyloid angiopathy, and amyloidoses.

In this invention, the inventors identified two Aβ epitope sequences recognized by Aβ autoantibodies isolated from serum of AD patients as well as of healthy control individuals. The Aβ autoantibodies of healthy control individuals were found to specifically recognize a C-terminal part of the Aβ sequence, namely Aβ(21-37) (SEQ ID NO:2). Furthermore, Aβ patients have an increased fraction of antibodies recognizing the Aβ(4-10) part of the Aβ polypeptide (SEQ ID NO:3), while having a decreased fraction of the antibodies recognizing the Aβ(21-37) part of Aβ polypeptide. Additionally, the inventors found that in healthy individuals not suffering from AD, the ratio of the amount of Aβ autoantibodies directed against a specific C-terminal epitope of Aβ, namely Aβ(21-37) compared to the amount of Aβ autoantibodies binding to Aβ(4-10), is much higher than in AD patients. The binding to this epitope seems to inhibit the formation of plaques and therefore delay the onset or progression of AD. This provides the basis for a new, therapeutic approach by administration of agents to a human subject or animal, which agents bind to said epitope and thereby prevents the aggregation of Aβ peptide. This delays the onset and/or the progression of Alzheimer's disease and consequently provides a valuable therapeutic/prophylactic pharmaceutical.

The inventors believe to have identified a class of natural human antibodies selected over time by evolution to target the toxic oligomers of Aβ as a natural way the human body prevents neurodementing diseases. Such antibodies would be expected not to have pathological effects caused by the binding to Aβ or related peptides to the brain vessels. Recently, it has been shown that passive immunization with antibodies directed against Aβ's N-terminal part causes bleeding in an animal transgenic mouse model. In these experiments, following 5 months of passive immunization, a significant amyloid reduction was found in the neocortex of the immunized mice compared to sham-treated controls. Immunized mice, however, exhibited a more than twofold increase in the frequency of CAA-associated cerebral hemorrhage in addition to an increase in hemorrhage severity over controls. These adverse events are believed to be caused by Aβ antibodies binding to Aβ deposited in brain vessels (Pfeifer M, et al. 2003. Herzig M C, et al 2004).

Thus, the present invention also relates to the use of the above mentioned polypeptides for the manufacture of a medicament in order to treat and/or prevent the progression of a neurodementing disease, Alzheimer's disease, Down's syndrome, Dementia with Lewy bodies, fronto-temporal dementia, cerebral amyloid angiopathy, and amyloidoses. The treatment/prevention of the above mentioned diseases is provided by prevention of Aβ plaque formation. Depending on the stage of the respective disease this leads to a prevention of the disease (no onset yet) or to a treatment (after onset of the disease), e.g. by preventing further formation of plaques. In a preferred embodiment the medicament is formulated for the treatment and/or prevention of plaques in the brain of a patient.

Alternatively, as already indicated above, the present invention relates also to the use of a polypeptide comprising an amino acid sequence of an Aβ polypeptide, wherein the Aβ polypeptide has at least the sequence according to SEQ ID NO:2 and at most the sequence according to SEQ ID NO:4, for the manufacture of a medicament for the treatment of Alzheimer's disease, Down's syndrome, Dementia with Lewy bodies, fronto-temporal dementia, cerebral amyloid angiopathy, and/or amyloidoses. In such a scenario, this epitope serves for the active immunization of a human or animal subject in order to enhance endogenous antibody production against Aβ(21-37). Such immunization approaches can also utilize DNA vaccines, which have the benefit of avoiding the administration of Aβ protein fragments. Therefore, the present invention also relates to a nucleic acid molecule encoding for a polypeptide comprising an amino acid sequence of an Aβ polypeptide, wherein the Aβ polypeptide has at least the sequence according to SEQ ID NO:2 and at most the sequence according to SEQ ID NO:4. Consequently the present invention also relates to the use of this nucleic acid sequence for the manufacture of a medicament for the treatment and/or prevention of Alzheimer's disease, Down's syndrome, Dementia with Lewy bodies, fronto-temporal dementia, cerebral amyloid angiopathy or amyloidoses.

Administration and Preparation of Pharmaceutical Formulations

The anti-Aβ antibodies can be formulated into pharmaceutical compositions comprising a carrier suitable for the desired delivery method. Suitable carriers include any material which, when combined with the antibody, retains the high-affinity binding of Aβ and is nonreactive with the subject's immune system. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and can include other proteins for enhanced stability, such as albumin, lipoprotein, globulin, etc., subjected to mild chemical modifications or the like.

Exemplary antibody concentrations in the formulation can range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody can be prepared in a pH-buffered solution, for example, at pH ranging from about 4.5 to about 6.5, or from about 4.8 to about 5.5, or alternatively about 5.0. Examples of buffers that are suitable for a pH within this range include, for example, acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which also can stabilize the antibody, can be included in the formulation. Exemplary tonicity agents include sugar alcohols, such as mannitol, sucrose or trehalose. Preferably the aqueous formulation is isotonic, although hypertonic or hypotonic solutions may be suitable. Exemplary concentrations of the sugar alcohol in the formulation may range from about 1% to about 15% w/v.

A surfactant also may be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include: additional buffering agents; co-solvents; antioxidants including ascorbic acid and methionine; chelating agents such as EDTA; metal complexes (e.g. Zn-protein complexes); biodegradable polymers such as polyesters; and/or salt-forming counter-ions such as sodium.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation contains an isotonic buffer such as a phosphate, acetate or TRIS buffer in combination with a tonicity agent such as a sugar alcohol, Sorbitol, sucrose or sodium chloride which tonicities and stabilizes. One example of such a tonicity agent is 5% Sorbitol or sucrose. In addition, the formulation optionally can include a surfactant such as to prevent aggregation and for stabilization at 0.01 to 0.02% w/v. The pH of the formulation can range from 4.5-6.5 or 4.5 to 5.5. Other exemplary descriptions of pharmaceutical formulations for antibodies can be found in US 2003/0113316 and U.S. Pat. No. 6,171,586, each incorporated herein by reference in its entirety.

The formulation herein also can contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients also can be entrapped in microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions or minicells. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. The compositions of the invention can be sterilized by conventional, well known sterilization techniques. For example, sterilization is accomplished readily by filtration through sterile filtration membranes. The resulting solutions may be packaged for use or filtered under aseptic conditions and lyophilized, the lyophilized preparation being combined with a sterile solution prior to administration. The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include sugar alcohols (including mannitol, sorbitol and glycerol); sugars (including glucose and sucrose); and amino acids (including alanine, glycine and glutamic acid).

In addition, sugar alcohols and sugars are often used to protect polypeptides from freezing and drying-induced damage and to enhance the stability during storage in the dried state. In general, sugars, in particular disaccharides are effective in both the freeze-drying process and during storage. Other classes of molecules, including mono- and di-saccharides and polymers such as PVP, also have been reported as stabilizers of lyophilized products.

For injection, the pharmaceutical formulation and/or medicament can be a powder suitable for reconstitution with an appropriate solution as described above. Examples of these include, but are not limited to, freeze-dried, rotary-dried or spray-dried powders, amorphous powders, granules, precipitates, or particulates. For injection, the formulations may optionally contain stabilizers, pH modifiers, surfactants, bioavailability modifiers and combinations of these.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 3TC, resulting in a loss of biological activity and possible changes in immunogenicity or other functional properties. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention can be designed to be short-acting, fast-releasing, long-acting, or sustained-releasing as described herein. Thus, the pharmaceutical formulations also can be formulated for controlled release or for slow release.

Specific dosages can be adjusted depending on conditions of disease, age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The specific binding agent or antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific binding agent or antibody is suitably administered by pulse infusion, particularly with declining doses of the specific binding agent or antibody. Preferably, the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the antibody is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

Administration to Brain

A variety of approaches are known in the art to effect administration of compounds to the brain. For example, a compound can be administered by direct intraventricular or intrathecal injection, preferably via slow infusion to minimize impact on brain parenchyma. The desired drug also can be delivered using a slow release implant in the brain, or (where the drug is a polypeptide) implanted recombinant cells that produce the drug. The blood brain barrier (BBB) can be permeabilized concomitant with drug administration, to permit movement of the drug across the BBB. Permeabilizing agents include osmotic agents, such as hypertonic mannitol, or another permeabilizing agent such as bradykinin, an alkylglycerol, ultrasound, electromagnetic radiation or parasympathetic innervation.

Alternatively, receptor-mediated transport can be utilized to administer drug to the brain. It is known in the art that peptides and proteins that directly cross the BBB may serve as carriers for selective therapeutic agents that allow the therapeutic agents to cross the BBB after delivery into the bloodstream (Pan et al., Brain Research Reviews, 46:32-43, 2004; Misra et al., J. Pharm. Pharmaceut. Sci., 6:252-273, 2003; Begley, Pharmacol Ther. 2004 October; 104(1):29-45; Poduslo, US App. Pub. No. 2003/0082191; Poduslo et al., Biochem., 43:6064-6075, 2004). For example, Poduslo, WO 03/020212 describes conjugation of antibodies to amyloid-beta protein fragments which are then taken up by low-density lipoprotein receptor related protein-1, a transporter at the BBB. Other examples of peptides which cross the BBB include transferrin which binds to the transferrin receptor, a transporter at the BBB; monoclonal antibodies to the transferrin receptor such as OX26; cell-penetrating peptides such as TAT transduction domain, penetratin, or Syn B1; and RAP which binds to low-density lipoprotein receptor related protein-2, another transporter at the BBB (see Pan et al., J Cell Sci. 2004 Oct. 1; 117(Pt 21):5071-8).

Receptor-mediated drug delivery to the brain can employ chimeric peptide technology, wherein a non-transportable drug is conjugated to a BBB transport vector. The latter can be a modified protein or receptor-specific monoclonal antibody that undergoes receptor-mediated transcytosis through the BBB in vivo. Conjugation of drug to transport vector is facilitated with chemical linkers, avidin-biotin technology, polyethylene glycol linkers, or liposomes. Multiple classes of therapeutics have been delivered to the brain with the chimeric peptide technology, including peptide-based pharmaceuticals, anti-sense therapeutics including peptide nucleic acids (PNAs), and small molecules incorporated within liposomes. Alternatively, the drug can be encapsulated in a liposome or nanoparticle which is then linked to the BBB transport vector.

Administration with Other Agents

The antibodies can be concurrently administered with other anti-amyloidgenic therapeutic agents. Concurrent administration includes administration of the two different therapeutic agents at different times and at different routes, as long as there is some overlap in the time during which the agents are exerting their therapeutic effects.

Exemplary anti-amyloidgenic agents known in the art include other anti-amyloid-beta antibodies, anti-inflammatories known in the art (e.g., NSAIDs and Cox-2 inhibitors) that reduce the pathogenic effects of amyloid accumulation, cholesterol lowering drugs, β-secretase inhibitors, or anti-inflammatories that reduce the inflammatory response due to the administration of Aβ antibody or that allow monitoring of the side effects of the anti-Aβ antibody.

Administration of medicaments according to the present invention can be achieved via any common route. Although the intravenous route is a preferred embodiment, other routes of administration are contemplated. This includes oral, nasal, buccal, rectal, vaginal or topical. Alternatively, administration may be by orthotopic, intradermal, subcutaneous, intramuscular or intraperitoneal.

In another preferred embodiment, the medicament according to the present invention comprising a polypeptide according to the invention is formulated for a combined administration with a second medicament for the respective disease. Examples for such therapies would be inhibitors of acetylcholine esterase or NMDA (N-methyl-D-aspartate) receptor antagonists. The administration of the medicament according to the invention can be prior to, simultaneously with or after administration of the second medicament.

In a further aspect the present invention relates to a method of treatment and/or prevention of Alzheimer's disease, Down's syndrome, Dementia with Lewy bodies, fronto-temporal dementia, cerebral amyloid angiopathy or amyloidoses comprising administering one or more of the above mentioned polypeptides of the invention to a subject in need thereof.

The present invention also relates to the use of a polypeptide comprising an amino acid sequence of an Aβ polypeptide, wherein the sequence of the Aβ polypeptide has at least the sequence according to SEQ ID NO:2, i.e. Aβ(21-37) and at most the sequence according to SEQ ID NO:4, i.e. Aβ(12-40) for isolation and separation of a polypeptide according to the present invention from a sample.

Detecting and Measuring the Progression of Disease Peptides

In another aspect, Aβ peptides are provided that are useful for detecting and/or measuring the progression of Alzheimer's and other neurodementing diseases.

The inventors identified two Aβ epitope sequences recognized by Aβ autoantibodies isolated from serum of AD patients as well as of healthy control individuals. The Aβ autoantibodies of healthy control individuals were found to specifically recognize the C-terminal part of the Aβ sequence, namely Aβ(21-37) (SEQ ID NO: 2) or any other sequence comprising Aβ(21-37). Furthermore AD patients have an increased fraction of antibodies recognizing the N-terminus, in particular the Aβ(4-10) epitope of the Aβ polypeptide (SEQ ID NO: 3), while having a decreased fraction of the antibodies recognizing the C-Terminus, in particular the Aβ(21-37) epitope or any other sequence comprising Aβ(21-37) of the Aβ polypeptide. This provides the basis for a new, early AD diagnostic method by determination of Aβ antibodies, wherein an elevated level of Aβ autoantibody (A1321-37) is a positive indicator, i.e. "healthy", while an elevated level of "plaque specific" Aβ(4-10)-antibody is a negative indicator, i.e. "sick", with respect to the prognosis for disease progression in a subject.

In one aspect, the present invention relates therefore to a polypeptide comprising an amino acid sequence of an Aβ peptide, wherein the Aβ peptide has at least the sequence according to SEQ ID NO: 2 and at most the sequence according to SEQ ID NO: 4.

A polypeptide according to the invention having a sequence of Aβ as set forth above may be for instance the Aβ(21-37) fragment of amyloid beta itself. Other possible embodiments could comprise for example Aβ(20-37), Aβ(12-37), Aβ(12-40) (SEQ ID NO: 4), Aβ(20-40), Aβ(21-40) and so forth. This polypeptide fragment can be joined to other moieties. This means that a polypeptide according to the invention can comprise besides the Aβ(21-37) portion other polypeptide sequences or non-polypeptide structures or portions. The moieties attached to the Aβ polypeptide fragments may facilitate the performance of the methods according to the present invention. In other aspects, Aβ polypeptides can form oligomers. Examples of such oligomers include, but are not limited to, oligomeric forms of Aβ(1-40) or oligomeric of Aβ(12-20) or oligomeric forms of Aβ(21-37).

Thus, in a preferred embodiment the polypeptide according to the invention additionally comprises other moieties such as tags or markers, which facilitate in particular the attachment of the polypeptide to a carrier. In particular such tags can provide for the immobilisation of the polypeptide on a carrier coated with the respective antagonist. Examples for such moieties are biotin, streptavidin, GST, HIS, STREP-tag, Myc, HA, poly-L-lysine, poly-L-lysine-L-alanine copolymers, poly-Aib (alpha-aminoisobutyric acid), poly-β-alanine, poly-L-alanine, poly-D-lysine, poly-D-lysine-D-alanine copolymers, poly-D-alanine, or combinations of poly-L- and -D-amino acids. The polypeptide comprising a sequence according to SEQ ID NO 3 and at most the sequence according to SEQ ID NO: 5, as used in some of the methods of the invention, can also comprise such additional moieties.

The above mentioned peptide markers can be directly fused to the polypeptides having e.g. the sequence of SEQ ID NO 2 or 3, respectively. If a higher flexibility between the marker/tag and the e.g. Aβ(21-37) peptide is desired, linkers can be introduced. Such linkers can be for instance polyglycine or—alanine linkers. Biotin, a non-peptidic substance, can be covalently linked to a polypeptide of the present invention. A multitude of possible combinations of markers and carriers for the immobilization of a polypeptide of the present invention is known from the prior art.

In a preferred embodiment the region of the above mentioned polypeptide having e.g. the sequence according to SEQ ID NO: 2 is not in β-sheet conformation. The β-pleated sheet conformation of Aβ has been shown to be responsible for neurotoxicity. Thus, Aβ(21-37) antibodies in a healthy individual recognize in particular the Aβ(21-37) region or any other sequence comprising Aβ(21-37), if it is in random coil or alpha-helix conformation. In another preferred embodiment, therefore, the region of the above mentioned polypeptide having the sequence according to SEQ ID NO: 2 or any other sequence comprising Aβ(21-37) is flanked by amino acid sequences, which prevent or reduce β-sheet formation of the polypeptide region having the sequence according to SEQ ID NO: 2. Preferably said flanking amino acid sequences are located in close proximity to the N- and/or C-terminal ends of the Aβ sequence stretch, e.g. having the sequence according to SEQ ID NO: 2 and/or which flanking amino acid sequences are composed of oligomeric peptides comprising, for example, L-alanine, D-alanine, Aib (alpha-aminoisobutyric acid), β-alanine, D-valine, L-glycine, D-glycine and/or related hydrophobic amino acids. Particularly preferred as flanking amino acid sequences are oligomeric peptides such as -(L-alanine)n-, -(D-Alanine)n-, -(Aib)n-, -(β-alanine)n-, -(D-valine)n-, -(L-glycine)n-, -(D-glycine)n- wherein n ranges preferably from about 2 to about 6. Such flanking regions also ensure, that the epitope Aβ(21-37) of the polypeptides of the invention is not present in β-sheet conformation and thus accessible to the Aβ(21-37) autoantibodies in the samples. In some embodiments, the β-amyloid polypeptide is in oligomeric form.

However, in a particular embodiment, the polypeptide according to the present invention is a minimal polypeptide that has no further sequences than the sequence of Aβ(20-37), Aβ(12-37), Aβ(12-40), Aβ(20-40) or Aβ(21-40). In particular oligomeric forms of said polypeptides are preferred embodiments of the invention.

However, it has to be understood, that other polypeptides than the ones mentioned above, which bind specifically to a first monoclonal antibody, which first antibody is capable of binding specifically to a sequence as denoted in SEQ ID NO 2 or any other sequence comprising Aβ(21-37), but which polypeptides do not bind specifically to a second monoclonal antibody, which second monoclonal antibody is capable of binding specifically to a sequence as denoted in SEQ ID NO 3, can also be used for practicing the methods of the present invention.

In a preferred embodiment the polypeptide according to the invention is directly synthesized by conventional polypeptide synthesis methods (see also Example 5). Similar approaches are suitable for generation of a polypeptide comprising an amino acid sequence of an Aβ peptide, wherein the Aβ peptide has at least the sequence according to SEQ ID NO: 3 and at most the sequence according to SEQ ID NO: 5.

Alternatively, the polypeptide according to the invention can also be obtained by in vitro translation or via a recombinant expression system. In order to express a polypeptide according to the invention a respective nucleic acid expression construct has to be generated. A person skilled in the art will clearly see several ways to construct appropriate expression system harboring a nucleic acid sequence encoding for a polypeptide according to the invention. The construct is subsequently expressed in a suitable host cell and the polypeptide is isolated. For this purification step the above mentioned markers and/or tags can be used as well.

The inventors found in serum of AD patients an additional fraction of antibodies directed against a N-terminal epitope of Aβ peptide, which is not present, or only in low abundance, in healthy individuals. Thus, the detection of such antibodies is indicative for the diagnosis, stage and/or progression of AD. To distinguish between Aβ (21-37) on one hand and Aβ(4-10) or other antibodies directed against the N-terminal part of Aβ, for such diagnosis methods and assays a polypeptide can be used comprising an amino acid sequence of an Aβ peptide, wherein the Aβ peptide has at least the sequence according to SEQ ID NO: 3 (Aβ(4-10)) and at most the sequence according to SEQ ID NO: 5 (Aβ(1-20)).

In one embodiment, the invention relates to a polypeptide comprising an amino acid sequence of an Aβ peptide, wherein the Aβ peptide has at least the sequence according to SEQ ID NO: 2 and at most the sequence according to SEQ ID NO: 4.

The polypeptide according to the invention thus comprises at least a sequence stretch identical to the Aβ peptide amino acid sequence ranging from amino acid 21 to amino acid 37 of SEQ ID NO: 1. This peptide sequence is denoted herein as SEQ ID NO: 2 or Aβ(21-37), respectively. A polypeptide according to the present invention can exhibit also longer sequence stretches of the Aβ peptide sequence, going beyond the Aβ(21-37) sequence. However, the length of the Aβ peptide sequence stretch comprised by the polypeptide according to the invention should not range further than from amino acid 12 to amino acid 40 of the Aβ peptide, also denoted herein as SEQ ID NO:4 or Aβ(12-40). This ensures, that the Aβ sequence stretch of the polypeptide of the invention does not comprise amino acids relevant for the binding of the plaque specific Aβ antibody found in patients with AD. The polypeptide according to the present invention can also comprise other amino acid sequences. For example, tags, markers, binding domains, activation domains or similar functional moieties can be fused to the Aβ sequence stretch, for instance, to provide for a better binding of the polypeptide according to the invention to certain surfaces. Analogous, the polypeptide according to the present invention can be modified for certain purposes, such as covalent coupling to a fluorophor or chromophor, biotin, or the like. In certain cases the non-Aβ sequence stretches of the polypeptide according to the invention provide for a structural stabilisation of the a Aβ(21-37) sequence stretch, preventing or reducing the formation of β-sheet conformation in this region.

In another embodiment, the inventive polypeptides bind specifically to oligomeric forms of β-amyloid polypeptide. By way of non-limiting example, the polypeptides can bind oligomeric forms of Aβ(1-40) or oligomeric forms of Aβ(12-40) or oligomeric forms of Aβ(21-37). In one aspect, the inventive polypeptides are capable of binding specifically to oligomeric forms of Aβ(1-40) when incubated overnight with stirring in 10 mM sodium phosphate, 150 mM NaCl, pH 7.4 at 4° C.

In a preferred embodiment the above mentioned polypeptide additionally comprises one or more moieties such as tags or markers, in particular biotin, streptavidin, GST, HIS, STREP-tag, Myc, HA, poly-L-lysine, poly-L-lysine-L-alanine copolymers, poly-Aib (alpha-aminoisobutyric acid), poly-β-alanine, poly-L-alanine, poly-D-lysine, poly-D-lysine-D-alanine copolymers, poly-D-alanine, or combinations of poly-L- and -D-amino acids.

In a preferred embodiment the region of the above mentioned polypeptide, which has the sequence according to SEQ ID NO: 2 or any other sequence comprising Aβ(21-37) is not in a β-sheet conformation. In an even more preferred embodiment this region is in random coil or exhibits α-helix conformation.

In another preferred embodiment the region of the above mentioned polypeptide having e.g. the sequence according to SEQ ID NO: 2 or any other sequence comprising Aβ(21-37) is flanked by amino acid sequences, which prevent or reduce β-sheet formation of the Aβ polypeptide region having e.g. the sequence according to SEQ ID NO: 2 or any other sequence comprising Aβ (21-37), in particular wherein said flanking amino acid sequences are located in close proximity to the N- and/or C-terminal ends of the Aβ sequence and which flanking amino acid sequences are composed of oligomeric peptides comprising, for example, L-alanine, D-alanine, Aib (alpha-aminoisobutyric acid), β-alanine, D-valine, L-glycine, D-glycine and/or related hydrophobic amino acids. Particularly preferred as flanking amino acid sequences are oligomeric peptides such as -(L-alanine)$_n$-, -(D-Alanine)$_n$-, -(Aib)$_n$-, -(β-alanine)$_n$-, -(D-valine)$_n$-, -(L-glycine)$_n$-, -(D-glycine)$_n$- wherein n ranges preferably from about 2 to about 6. In some embodiments, the β-amyloid polypeptide is in oligomeric Furthermore, the present invention relates to the use of a polypeptide according to the present invention and/or of a polypeptide comprising an amino acid sequence of an Aβ peptide, wherein the Aβ peptide has at least the sequence according to SEQ ID NO: 3 and at most the sequence according to SEQ ID NO: 5, for diagnostic assays. Methods for such diagnostic assays are exemplified below.

Methods

In another aspect the present invention relates to a method for diagnosing a neurodementing disease, the method comprising the following steps:
a) incubating a polypeptide according to the present invention immobilized on a carrier with a sample derived from a subject, subsequently
b) separating said sample from the carrier, and
c) detecting polypeptides bound to the immobilized polypeptide of step a).

The present invention also relates to a method for diagnosing a neurodementing disease, the method comprising the following steps:
a) incubating a polypeptide according to the present invention with a sample derived from a subject, and subsequently b) incubating the sample with a carrier having a binding affinity for the polypeptide according to the present invention, c) separating said sample from the carrier, and
d) detecting polypeptides bound to the polypeptide according to the present invention, said polypeptide being bound to the carrier.

In another aspect the present invention relates to methods of diagnosis of a neurodementing disease, which utilize a polypeptide or protein which comprises at least a sequence stretch identical to the Aβ peptide amino acid sequence ranging from amino acid 4 to amino acid-10 of SEQ ID NO: 1. This peptide sequence is denoted herein as SEQ ID NO: 3 or Aβ(4-10) or the N-terminal peptide, respectively. Such a polypeptide can exhibit also longer sequence stretches of the Aβ peptide sequence, going beyond the Aβ(4-10) sequence. However, the length of the Aβ peptide sequence stretch comprised by such a polypeptide should preferably not range further than from amino acid I to amino acid 20 of the Aβ peptide, also denoted herein as SEQ ID NO:5 or Aβ (1-20). This ensures, that the Aβ sequence stretch of the polypeptide of the invention does not comprise amino acids relevant for the binding of the Aβ autoantibody found in healthy individuals and directed to Aβ(21-37). The N-terminal polypeptide can comprise besides the Aβ sequence stretch other amino acid sequences, moieties and modifications as well, as already mentioned for the polypeptide according to the invention.

Thus, the present invention also relates to a method for diagnosing a neurodementing disease, the method comprising the following steps:
a) incubating a polypeptide immobilized on a carrier with a sample derived from a subject, wherein the polypeptide comprises an amino acid sequence of an Aβ peptide, wherein the Aβ peptide has at least the sequence according to SEQ ID NO: 3 and at most the sequence according to SEQ ID NO: 5, subsequently
b) separating said sample from the carrier, and
c) detecting polypeptides bound to the immobilized polypeptide of step a).

The present invention also relates to a method for diagnosing a neurodementing disease, the method comprising the following steps:
a) incubating a polypeptide with a sample derived from a subject, wherein the polypeptide comprises an amino acid sequence of an Aβ peptide, wherein the Aβ peptide has at least the sequence according to SEQ ID NO: 3 and at most the sequence according to SEQ ID NO: 5, and subsequently
b) incubating the sample with a carrier having a binding affinity for the polypeptide comprising an amino acid sequence of an Aβ peptide, wherein the Aβ peptide has at least the sequence according to SEQ ID NO: 3 and at most the sequence according to SEQ NO: 5,
c) separating said sample from the carrier, and
d) detecting polypeptides bound to the polypeptide, which comprises an amino acid sequence of an Aβ peptide, wherein the Aβ peptide has at least the sequence according to SEQ ID NO: 3 and at most the sequence according to SEQ ID NO: 5, said polypeptide being bound to the carrier.

The present invention also relates to a method for diagnosing a neurodementing disease, the method comprising the following steps:
a) incubating a polypeptide according to the present invention immobilized on a carrier with a cell containing sample derived from a subject,
b) separating said sample from the carrier, and
c) detecting cells bound to the immobilized polypeptide of step a).

The present invention also relates to a method for diagnosing a neurodementing disease, the method comprising the following steps.
a) incubating a polypeptide according to the present invention with a cell containing sample derived from a subject, and subsequently
b) incubating the sample with a carrier having a binding affinity for a polypeptide of the present invention,
c) separating said sample from the carrier, and
d) detecting cells bound to the polypeptide according to the present invention, said polypeptide being bound to the carrier.

The present invention also relates to a method for diagnosing a neurodementing disease, the method comprising the following steps:
a) incubating a polypeptide immobilized on a carrier with a cell containing sample derived from a subject, wherein the polypeptide comprises an amino acid sequence of an Aβ peptide, wherein the Aβ peptide has at least the sequence according to SEQ ID NO: 3 and at most the sequence according to SEQ ID NO: 5,
b) separating said sample from the carrier, and
c) detecting cells bound to the immobilized polypeptide of step a).

The present invention also relates to a method for diagnosing a neurodementing disease, the method comprising the following steps:
a) incubating a polypeptide with a cell containing sample derived from a subject, wherein the polypeptide comprises an amino acid sequence of an Aβ peptide, wherein the Aβ peptide has at least the sequence according to SEQ ID NO: 3 and at most the sequence according to SEQ ID NO: 5, and subsequently
b) incubating the sample with a carrier having a binding affinity for the polypeptide comprising an amino acid sequence of an Aβ peptide, wherein the Aβ peptide has at least the sequence according to SEQ ID NO: 3 and at most the sequence according to SEQ ID NO: 5,
c) separating said sample from the carrier, and
d) detecting cells bound to the polypeptide, which comprises an amino acid sequence of an Aβ peptide, wherein the Aβ peptide has at least the sequence according to SEQ ID NO: 3 and at most the sequence according to SEQ ID NO: 5, said polypeptide being bound to the carrier.

In a further embodiment of the invention the polypeptide, which comprises an amino acid sequence of an Aβ peptide, wherein the Aβ peptide has the sequence according to SEQ ID NO: 3 and at most the sequence according to SEQ ID NO: 5, can comprise, as mentioned above, additional moieties such as tags or markers, in particular biotin, streptavidin, GST, HIS, STREP-tag, Myc, HA, poly-L-lysine, poly-L-lysine-L-alanine copolymers, poly-Aib (alpha-aminoisobutyric acid), poly-β-alanine, poly-L-alanine, poly-D-lysine, poly-D-lysine-D-alanine copolymers, poly-D-alanine, or combinations of poly-L- and -D-amino acids. In a preferred embodiment, a polypeptide of the invention is identical to the polypeptide, which comprises an amino acid sequence of an Aβ peptide, wherein the Aβ peptide has the sequence according to SEQ ID NO: 3 and at most the sequence according to SEQ ID NO: 5, except for the sequence stretch covering the Aβ-sequence.

In a preferred embodiment of the methods of the invention employing a polypeptide according to the invention a solvent is present in the incubation step(s), which prevents or reduces 13-sheet formation of the polypeptide region having e.g. the sequence according to SEQ ID NO: 2. Preferred solvents may be trifluoroethanol (TFE), hexafluoro-isopropanol or similar solvents to stabilize peptide conformations and to prevent or reduce β-sheet formation. Preferably, the solvent is present in an aqueous solution comprising for example 5-10 mM phosphate buffer and 150 mM NaCl. In an even more preferred embodiment the concentration of TFE, hexafluoro-isopropanol and the like in the aqueous solution ranges from about 1 to about 5%, preferably from about 1% to about 2%.

In a preferred embodiment the methods of the invention comprise an additional step, wherein at least one washing step is performed before the detecting step.

In a preferred embodiment of the methods according to the present invention, relating to the detection of cells, the methods are carried out in form of affinity chromatography, in particular immunoaffinity chromatography.

The amount of polypeptides, e.g. antibodies, binding to a polypeptide according to the present invention, e.g. Aβ (21-37) or any other sequence comprising Aβ (21-37), in a sample of a subject is an indicator for the status of the subject with regard to the development and/or progression of AD. The higher the concentration of polypeptides directed against the Aβ (21-37) sequence stretch, the higher the protective capacity and the lower the risk of development and/or progression of AD. The amount of polypeptides, e.g. antibodies, directed against the Aβ(4-10) epitope, in a sample of a subject, is an indicator for the status of the subject with regard to the development and/or progression of AD as well. However, in this case the situation is vice versa. The higher the concentration of polypeptides directed against the Aβ (4-10) sequence stretch, the higher the risk of development and/or progression of AD. For diagnostic reasons, the methods of detection according to the present invention can thus be performed individually, but also in combination in order to provide for a more specific diagnosis.

Thus, in a further embodiment of the invention a method according to the invention employing a polypeptide according to the invention is carried out in combination with a method of the present invention employing a polypeptide comprising an amino acid sequence of an Aβ peptide, wherein the Aβ peptide has at least the sequence according to SEQ ID NO: 3 and at most the sequence according to SEQ ID NO: 5. The method employing a polypeptide of the present invention can be performed simultaneously, prior to or after the second method.

It is also possible to diagnose the neurodementing disease by way of an indirect approach. A method according to the present invention—utilizing either a polypeptide according to the present invention or a polypeptide comprising an amino acid sequence of an Aβ peptide, wherein the Aβ peptide has at least the sequence according to SEQ ID NO: 3 and at most the sequence according to SEQ ID NO: 5—is combined with a similar method, which only differs from the methods of the present invention by utilizing polypeptide comprising a polypeptide having the length of Aβ(1-40) or Aβ(1-42), i.e. full length Aβ peptide instead of the shorter Aβ sequence stretches utilized by the methods of the present invention. In such a scenario, the two methods are carried out independently from each other and the results of the methods are compared. To illustrate this concept, the following example is given:

1) The method utilizing the full length polypeptide sequence yields the amount of all polypeptides (or cells producing such polypeptides, respectively) in the sample directed against full length Aβ (Result A).
2) On the other hand a method of the present invention utilizing a polypeptide of the present invention yields the amount of all polypeptides (or cells producing such polypeptides, respectively) in the sample directed against a polypeptide of the present invention such as Aβ(21-37) or any other sequence comprising Aβ(21-37 (Result B).
3) A person skilled in the art can now easily deduce the amount of polypeptides in the sample directed against an epitope at the N-terminus of Aβ, in particular against epitope Aβ(4-10), by subtracting Result B from Result A.

Analogously, the amount of polypeptides (or cells producing such polypeptides, respectively) in the sample directed against a polypeptide of the present invention such as Aβ(21-37) or any other sequence comprising Aβ(21-37) can be obtained by subtracting the results obtained with a polypeptide comprising an amino acid sequence of an Aβ peptide, wherein the Aβ peptide has at least the sequence according to SEQ ID NO: 3 and at most the sequence according to SEQ ID NO: 5, e.g. Aβ(4-10), from the results obtained with Aβ full length.

Thus, the present invention also refers to a method for diagnosing a neurodementing disease, wherein the methods according to the present invention comprise the following steps:
i) performing a first method according to the present invention as set forth above,
ii) performing a second method according to the present invention proviso that the polypeptide to be incubated in step a) of said second method comprises the full length amino acid sequence of Aβ peptide, and
iii) comparing the result obtained from step i) with the result of step ii).

A person skilled in the art will understand that it does not matter for the above method whether step i) is carried out prior to, simultaneously with or after step ii).

In one embodiment the polypeptides to be detected in the methods of the invention are antibodies, in particular an Aβ(21-37) autoantibody or an Aβ(4-10) autoantibody.

In a preferred embodiment the methods according to the invention are carried out for diagnosing Alzheimer's disease, Down's syndrome, Dementia with Lewy bodies, fronto-temporal dementia, cerebral amyloid angiopathy, and/or amyloidoses.

In a further aspect the present inventions relates to a carrier comprising a polypeptide according to the invention. In a preferred embodiment the carrier additionally comprises a second polypeptide comprising an amino acid sequence of an Aβ peptide, wherein the Aβ peptide of the second polypeptide has at least the sequence according to SEQ ID NO: 3 and at most the sequence according to SEQ ID NO: 5.

The carriers according to the invention and used in the methods of the invention can be of any suitable material capable of binding polypeptides such as beads, in particular magnetic beads or sepharose beads, membranes, in particular polyvinylidene fluoride or nitrocellulose membranes, glass, sepharose matrices, gold surfaces, synthetic surfaces, in particular microtiter plates. For certain embodiments, the surface of the carriers can be coated with agents, which are, for instance, capable of binding to the tags and markers mentioned above.

Detection

A variety of assays can be employed in the inventive methods to detect or measure antibody titer against the Aβ peptides of interest. Exemplary assays include, but are not limited to, ELISA, ELISPOT, Western-Blot, Dot Blot, Protein-Chip, surface plasmon resonance assay, immunoprecipitation or co-immunoprecipitation, or affinity chromatography, in particular immuno affinity chromatography.

In a preferred embodiment, the methods according to the invention comprising the detection of polypeptides in step c) or d), respectively, represent an ELISA. In this case the carrier is for example a microtiter plate. The separation of sample and carrier is achieved by removing the sample liquid from the microtiter plate and/or by washing the microtiter plate after the incubation. Preferably, the bound polypeptide is in this scenario an antibody and this antibody can be detected for example via a secondary antibody, coupled with e.g. alkaline phosphatase (AP), and the addition of a substrate for AP resulting in the turn over of the substrate into, for example, a colored compound detectable by an optical device. A person skilled in the art and familiar with ELISA techniques will know several variations of the ELISA concept, which can be applied to the methods of the present invention as well.

Alternatively, in another preferred embodiment, the methods according to the invention comprising the detection of polypeptides in step c) or d), respectively, represent an ELISPOT assay. In this case the carrier is for example a nitrocellulose plate. The incubation step of the carrier with the sample provides in this scenario enough time for a cell in the sample to produce sufficient amounts of antibody. The separation of sample and carrier is achieved by removing the sample liquid from the nitrocellulose plate and/or by washing the nitrocellulose plate after the incubation. Preferably, the bound polypeptide is an antibody and this antibody can be detected, for example via a secondary antibody, coupled with e.g. alkaline phosphatase (AP), and the addition of a substrate for AP, such as BCIP/NBT (Bromo-chloro-indoryl phosphate/Nitro Blue Tetrazolium) resulting in the turn over of the substrate into, for example, a deep purple stain detectable visually or by an optical device. A person skilled in the art and familiar with ELISPOT techniques will know several variations of the ELISPOT concept, which can be applied to the methods of the present invention as well.

In a further embodiment, the methods according to the invention comprising the detection of polypeptides in step c) or d), respectively, represent a Western Blot or Dot Blot assay. In this case the carrier is for example a nitrocellulose membrane. For the Western Blot, on the nitrocellulose membrane is either immobilized a polypeptide as used in step a) of the methods according to the present invention or a substance with binding affinity for a polypeptide as used in step a) of the methods according to the present invention. The nitrocellulose or similar membrane (PVDF etc.) itself can provide for the binding affinity to the polypeptide as used in step a) of the methods according to the present invention. The separation of sample and carrier is achieved by removing the sample liquid from the nitrocellulose membrane and/or by washing the nitrocellulose membrane after the incubation. Preferably, the bound polypeptide is an antibody and this antibody is for example detected via a labeled secondary antibody, e.g. coupled with horseradish peroxidase, and subsequent luminescent reaction and detection. A person skilled in the art and familiar with Western Blot/Dot blot techniques will know several variations of the Western Blot/Dot blot concept, which can be applied to the methods of the present invention as well.

In a further embodiment, the methods according to the invention comprising the detection of polypeptides in step c) or d), respectively, represent a Protein chip, i.e. protein microarray. In this case the carrier is for example a glass surface functionalized for binding proteins. The separation of sample and carrier is achieved by removing the sample liquid from the glass carrier and/or by washing the glass carrier after the incubation. Preferably, the bound polypeptide is an antibody and this antibody is detected via a labelled secondary antibody, coupled with e.g. a fluorescent dye, which can be detected by an optical device. A person skilled in the art and familiar with protein chip techniques will know several variations of the protein chip concept, which can be applied to the methods of the present invention as well.

In a further embodiment, the methods according to the invention comprising the detection of polypeptides in step c) or d), respectively, represent a surface plasmon resonance analysis. In this case the carrier is for example a metal surface such as a gold surface. The separation of sample and carrier is achieved by removing the sample liquid from the metal carrier and/or by washing the metal carrier after the incubation. Preferably, the bound polypeptide is an antibody and the binding of the antibody is detected via measuring the intensity of the reflected light at a specific incident angle with an optical device. A person skilled in the art and familiar with plasmon resonance analysis techniques will know several variations of the surface plasmon resonance concept, which can be applied to the methods of the present invention as well.

In a further embodiment, the methods according to the invention comprising the detection of polypeptides in step c) or d), respectively, represent a pull down or immunoprecipitation experiment. In this case the carrier may consist of sepharose beads. These sepharose beads are coated for example with glutathione (for pull down assays) or with an antibody (immunoprecipitation assays). Separation of sample and carrier is achieved by removing the sample liquid from the sepharose beads and/or by washing the sepharose beads after the incubation. Preferably, the bound polypeptide is an antibody and this antibody is detected via a subsequent Western Blot analysis of the precipitated protein complexes. A person skilled in the art and familiar with Pull down/ Immunoprecipitation techniques will know several variations of these concepts, which can be applied to the methods of the present invention as well. One such variation would be the application of a co-immunoprecipitation approach, wherein the carrier has only an indirect binding affinity for the polypeptide as used in step a) of the methods according to the present invention.

In a further embodiment, the methods according to the invention comprising the detection of polypeptides in step c) or d), respectively, are carried out in form of an affinity chromatography. In this case the carrier is the matrix, e.g. sepharose within a conventional chromatography column, to which is either linked a polypeptide as used in step a) of the methods according to the present invention or a substance with binding affinity for a polypeptide as used in step a) of the methods according to the present invention. The incubation of the sample with the carrier comprises the time frame the sample needs to pass through the column. The separation of sample and carrier is achieved by eluting the sample liquid from the column and/or by washing the column after the incubation. Preferably, the bound polypeptide is an antibody and this antibody is for example detected by elution of the bound antibody, for instance with a buffer having a high salt content, and subsequent detection of eluted polypeptide, for example by direct optical determination or by subsequent Western blot or similar analyses. A person skilled in the art and familiar with affinity chromatography techniques will know several variations of the affinity chromatography concept, which can be applied to the methods of the present invention as well. One such variation would be the application of an immunoaffinity chromatography approach, wherein the carrier is coated with antibodies directed against a polypeptide as used in step a) of the methods according to the present invention.

In one embodiment, the methods according to the invention comprising the detection of cells in step c) or d), respectively, are carried out in form of an affinity chromatography. In this case, for example, magnetic beads coated with sepharose represent the carrier, to which either a polypeptide as used in step a) of the methods according to the present invention is linked or a substance with binding affinity for a polypeptide as used in step a) of the methods according to the present invention. The separation of sample and carrier is achieved by eluting the sample liquid from the column and/or by washing the column after the incubation. The cells bound to the matrix are for example B- or T-cells, which can be detected, after elution of the cells from the matrix, for example by way of flow cytometry. A person skilled in the art and familiar with affinity chromatography and flow cytometry techniques will know several variations of these concepts, which can be applied to the methods of the present invention as well.

Thus, the methods according to the present invention can be carried out in particularly preferred embodiments as ELISA, ELISPOT, Western-Blot, Protein-Chip, surface plasmon resonance assay, immunoprecipitation or co-immunoprecipitation, or affinity chromatography, in particular immunoaffinity chromatography. These are all exemplifications of diagnostic assays. Examples for ELISA's or affinity chromatography can be found in the examples section. In diagnostic procedures based on surface plasmon resonance (SPR) the detection, and quantification and analysis of binding kinetics of Aβ-epitope specific antibodies can be performed by binding of (i) a biotinylated Aβ(21-37)- or Aβ(4-10)-peptide to a avidin/streptavidin-coated SPR chip surface, or by binding (ii) Aβ(21-37)- or Aβ(4-10)-peptides with an N-terminal Thiol-group containing carboxylic acid spacer to a gold-chip surface; followed by binding and determination of the Aβ-autoantibodies. A person skilled in the art will readily know how to incorporate the methods according to the present invention into one of these standard techniques and procedures mentioned above.

It has to be understood, that although the methods according to the present invention can be carried out in form of one of the above mentioned detection techniques per se (ELISA, ELISPOT, Western-Blot, Dot Blot, Protein-Chip, surface plasmon resonance assay, immunoprecipitation, affinity chromatography, etc.), it is also possible to combine these detection techniques or to apply them only for the detection step according to the invention, i.e. step c) or d), respectively, while the other steps are carried out in other formats. It is also obvious to a person skilled in the art, that the information/signals obtained in the detection steps in the methods of the present invention can provide the basis for quantification of this information/signals.

In some cases it might be of higher diagnostic value, if, instead of or in addition to the detection of polypeptides, e.g. antibodies, cells producing said polypeptides are detected. For example, it could be of importance, if in an AD patient the overall number of cells producing an Aβ(21-37) autoantibody is lower than in healthy individuals, or if the amount of antibody secreted by the respective antibody producing cells is reduced. Depending on the result this can lead to different therapeutic approaches. Thus, the present invention also relates to the detection of cells producing polypeptides binding to a polypeptide according to the invention or binding to a polypeptide comprising an amino acid sequence of an Aβ peptide, wherein the Aβ peptide has at least the sequence according to SEQ ID NO: 3 and at most the sequence according to SEQ ID NO: 5.

As used in this invention, an immobilized polypeptide refers in this regard to a polypeptide, which is coupled to a carrier. The coupling can be covalently or non-covalently, it can be directly to the carrier or via a linker/linking substance. If the immobilization occurs non-covalently, then the carrier or the linking substance exhibits a specific binding affinity for the polypeptide according to the invention and vice versa. Binding affinity refers to a property of a substance, in particular a polypeptide, to associate with (an) other substance(s) and to form a stable specific dimeric or multimeric complex. Such associations rely usually on van der Waals- or hydrogen-bonds.

The incubating step(s) serves the purpose whereby two partners of a binding pair, i.e. having a binding affinity for each other, can associate and form a stable complex. The temperature of the incubation step may vary, but is usually from about 0° C. to about 40° C., preferably from about 4 to about 37° C., even more preferred about 4° C., about 16° C., about 21° C. or about 37° C. The higher the temperature, the shorter the time of incubation might be. For example, if the incubation temperature is 4° C. it should last for at least 12 h or over night, while 1 h is usually enough for an incubation at 37° C. If suitable, the carrier can be blocked prior to the method with a suitable blocking agent, reducing the likelihood of unspecific binding events. Blocking agents can be for example milk powder, BSA, fetal calf sera, or any other blocking reagent.

The detection of polypeptides bound to an immobilized polypeptide of the invention or to a polypeptide comprising an amino acid sequence of an Aβ peptide, wherein the Aβ peptide has at least the sequence according to SEQ ID NO: 3 and at most the sequence according to SEQ ID NO: 5, can be performed by several means. One possibility would be for example the identification via mass spectrometrical means, for example MALDI-TOF, ESI-MS, MS-FTICR. To this purpose, immunoglobulins are first isolated from, for example, a serum sample of an AD patient by protein G affinity chromatography, and subsequently Aβ-autoantibodies and Aβ-plaque specific antibodies are e.g. isolated by Aβ-epitope-chromatography, respectively. The antibodies are then immobilized, for example, on a sepharose carrier as described in the examples. The specific Aβ-epitopes, Aβ(21-37) and Aβ(4-10), are then identified after binding of full-length-Aβ-polypeptide (for example Aβ(1-40) or Aβ(1-42)), followed by proteolytic epitope-excision mass spectrometric analysis using one or several of the proteases, trypsin, chymotrypsin, Glu-C protease, Asp-N-protease. After washing the affinity-bound Aβ-epitope(s) until no signal is detected in the supernatant, the specific Aβ-epitope is eluted from the column by treatment with, typically, 0.1% trifluoroacetic acid, and identified by accurate determination of its protonated molecular ions; the latter molecular ion mass accuracy is entirely sufficient for identification, but can be further ascertained by collision-induced fragmentation and tandem-MS analysis of fragment ions.

For certain embodiments, secondary antibodies labeled with a fluorescent dye or moiety (e.g. GFP) or labeled with an enzymatically active substance such as horseradish peroxidase, alkaline phosphatase, β-galactosidase or other related enzymes able to convert a colorless substrate to a suitable dye or fluorescent product can be applied. The detection can also be accomplished by detecting the amount of occupied binding sites, i.e. utilizing a labeled Aβ(21-37) antibody, which is incubated with the carrier after the removal of the sample. The amount of bound Aβ(21-37) is in this scenario an indicator for the amount of prior bound polypeptide. The lower the amount of subsequently bound Aβ(21-37) antibody is, the more Aβ(21-37) binding polypeptides contained in the sample. The mentioned examples of detection are not to be considered limiting, as a person skilled in the art will readily know a plurality of methods of detection which can be used in the present invention.

Usually, the polypeptides bound to the immobilized polypeptide, which are detected in step c) or d), respectively, in the methods of the present invention will be antibodies, in particular an Aβ(21-37) autoantibody or an Aβ(4-10) autoantibody, respectively. However, other substances in the human body may also bind for instance to Aβ(21-37) or Aβ(4-10) polypeptide.

Likewise, the detection of cells producing a polypeptide binding to a polypeptide of the present invention or binding to a polypeptide comprising an amino acid sequence of an Aβ peptide, wherein the Aβ peptide has at least the sequence according to SEQ ID NO: 3 and at most the sequence according to SEQ ID NO: 5, is accomplished by standard techniques known to a person skilled in the art. One example would be the analysis via flow cytometry. Another approach would be the lysis of the cells, DNA/RNA isolation and subsequent PCR amplification of specific nucleotide sequences. Besides this, in the prior art there are plurality of further possibilities published, which can be employed to detect the cells in the methods of the present invention.

In a preferred embodiment the sample or the cell containing sample, respectively, used for the methods of the present invention is derived from blood, plasma, urine or cerebrospinal fluid (CSF) of a subject. In an even more preferred embodiment the cell containing sample is derived from blood and the cells are of the B-cell lineage. The sample, i.e. the subject can be of human, rodent, bovine, porcine, canine or avian origin. In particular the sample or the cell containing sample can be derived from human, mouse, rat, rabbit, cow, pig, dog, chicken and so forth.

A sample derived from a subject is derived from tissue or body fluid of a subject. The subject can be a healthy individual, i.e. not suffering from AD, or a "patient" suffering from a neurodementing disorder. In a preferred embodiment the sample or the cell containing sample, respectively, used for the methods of the present invention is obtained from blood, plasma, urine or cerebrospinal fluid (CSF) of a subject. In an even more preferred embodiment the cell containing sample is obtained from blood and the cells are of the B-cell lineage. The sample, i.e. the subject can be of human, rodent, bovine, porcine, canine or avian origin. In particular the sample or the cell containing sample can be derived from human, mouse, rat, rabbit, cow, pig, dog, chicken and so forth. Possible preparation procedures of such samples are well known from the prior art.

In a preferred embodiment of the methods of the present invention employing a polypeptide of the present invention a solvent is present in the incubation step(s), which prevents or reduces β-sheet formation of the polypeptide region having the sequence according to SEQ ID NO: 2. As mentioned above, the β-pleated sheet conformation of Aβ has been shown to be responsible for neurotoxicity. Thus, Aβ(21-37) antibodies in a healthy individual recognize in particular the Aβ(21-37) region or any other sequence comprising Aβ(21-37), if it is in random coil or α-helix conformation. Analogous to flanking amino acid sequences, solvents can influence the conformational state of the polypeptides of the invention. In particular, TFE, hexafluoro-isopropanol and so forth can be used in the methods of the present invention, for example in the incubation step, to prevent or reduce a β-sheet conformation of the important epitope Aβ(21-37), thus keeping it accessible to the Aβ(21-37) autoantibodies in healthy individuals. Preferably, TFE is present in a concentration ranging from about 1% to about 5%, preferably about 1 to about 2%.

In a preferred embodiment the methods of the invention comprise an additional step, wherein at least one washing step with a washing solution is performed before the detecting step. A washing step can increase the specificity of the later detection signal and reduces background signals. Preferably, the washing solution is water. More preferably buffers like PBS or TBS are used to ensure a constant pH. The washing solution can contain small amounts of detergent to increase the specificity of the signal. If the specificity of the signal is low, the salt concentration or the concentration of the detergent can be increased in the washing solution.

In a further embodiment of the invention a method according to the invention employing a polypeptide of the invention, i.e. Aβ(21-37) polypeptide, is carried out in combination with a method of the present invention employing a polypeptide comprising an amino acid sequence of an Aβ peptide, wherein the Aβ peptide has at least the sequence according to SEQ ID NO: 3 and at most the sequence according to SEQ ID NO: 5, i.e. Aβ (4-10). The method employing a polypeptide of the present invention can be performed simultaneously, prior to or after the second method. The comparison of the abundance of Aβ(21-37) specific polypeptides with the abundance of Aβ(4-10) specific polypeptides will provide for a more detailed assessment of the stage and progression of AD.

The detecting step in the methods of the present invention provides for the possibility to quantify the amount of polypeptides bound to Aβ(21-37) or Aβ(4-10). The determined values are a measure for the stage and progression of AD. For instance, a human subject can be considered healthy in regard to AD, if its serum contains about 1 to 100 ng/µl of Aβ(21-37) specific polypeptides and/or about 0 ng/µl (i.e. below the detection limit) of the Aβ(4-10) specific polypeptides. As reference for a healthy individual might serve the average concentrations of the respective polypeptides in the serum of people in the age of 20 to 35. In contrast, a subject might suffer from a neurodementing disease or be endangered to develop a neurodementing disease, for instance, if its serum contains about 0.01 to 5 ng/µl of Aβ(4-10) specific polypeptides, preferably about 0.05 to 1 ng/µl or even more preferably about 0.01 ng/µl or if the ratio of the concentration of the plaque specific polypeptide vs. the concentration of the Aβ(21-37) specific polypeptides in the serum raises above 0, preferably if it is higher than 0.001, 0.002, 0.003, 0.004, 0.005, 0.010, 0.015, 0.020, 0.030 or even higher than 0.050. With aging the amount of immunoglobulin produced in a human body decreases naturally. Therefore, in particular cases it might be necessary to consider the age of the subject before the results obtained with the methods according to the present invention are evaluated. In particular a person about 20 to about 35 years of age might be considered healthy, if its, for instance, serum contains about 30 to 100 ng/µl or more of Aβ(21-37) specific polypeptide, while a subject about 70 to about 80 years of age can still be considered equally healthy with regard to AD with "only" 2 to 5 ng/µl of Aβ(21-37) specific polypeptide in its serum.

In a preferred embodiment the methods according to the invention are carried out for diagnosing a neurodementing disease, Alzheimer's disease, Down's syndrome, Dementia with Lewy bodies, fronto-temporal dementia, cerebral amyloid angiopathy, and/or amyloidoses. All diseases have in common, that the concentration of Aβ-autoantibody and Aβ-plaque specific antibody is affected by the respective disease as given above for AD.

In a further aspect the present invention relates to a carrier comprising a polypeptide according to the invention. In a preferred embodiment the carrier additionally comprises a second polypeptide comprising an amino acid sequence of an Aβ peptide, wherein the Aβ peptide of the second polypeptide has at least the sequence according to SEQ ID NO: 3 and at most the sequence according to SEQ ID NO: 5.

The carriers according to the invention and used in the methods of the invention can be of any suitable material capable of binding polypeptides such as beads, in particular magnetic beads or sepharose beads, membranes, in particular polyvinylidene fluoride or nitrocellulose membranes, glass, sepharose matrices, gold surfaces, synthetic surfaces, in particular microliter plates. For certain embodiments, the surface of the carriers can be coated with agents, which are, for instance, capable of binding to the tags and markers mentioned above. A person skilled in the art will readily know a broad variety of different carriers and possible coatings, which can be applied for the methods according to the invention.

Kits

In another aspect the present invention relates to a kit for the diagnosis of a neurodementing disease, wherein the kit comprises a polypeptide according to the invention. In one embodiment, a kit comprises a second polypeptide comprising an amino acid sequence of an Aβ peptide, wherein the Aβ peptide of the second polypeptide has at least the sequence according to SEQ ID NO: 3 and at most the sequence according to SEQ ID NO: 5. In another embodiment the kit comprises a carrier, in particular a carrier as mentioned above. In another embodiment, a kit comprises a first Aβ peptide comprising at least the sequence according to Aβ(30-37) and at most the sequence according to Aβ(12-40), and a second Aβ peptide wherein the second Aβ peptide comprising at least the sequence according to Aβ(4-10) and at most the sequence according to Aβ(1-20). Such kits can be used for example for routine diagnostics in hospitals and nursing homes, for example to monitor the progression of AD or to monitor the effectiveness of an AD therapy.

In another aspect the present invention relates to a kit for the diagnosis of a neurodementing disease, wherein the kit comprises a polypeptide according to the invention.

In a preferred embodiment the above mentioned kit comprises a second polypeptide comprising an amino acid sequence of an Aβ peptide, wherein the Aβ peptide of the second polypeptide has at least the sequence according to SEQ ID NO: 3 and at most the sequence according to SEQ ID NO: 5. In an even more preferred embodiment the kit comprises a carrier, in particular a carrier as mentioned above.

The kit can include one or more containers for the Aβ peptides. In some embodiments, the kit contains separate containers, dividers or compartments for the Aβ peptides and informational material. For example, each Aβ peptide can be contained in a bottle, vial, or syringe, and the informational material can be contained in a plastic sleeve or packet. In other embodiments, the separate elements of the kit are contained within a single, undivided container. For example, each peptide is contained in a bottle, vial, or syringe that has attached thereto the informational material in the form of a label.

The following examples explain the invention but are not considered to be limiting. Unless indicated differently, molecular biological standard methods were used, as e.g., described by Sambrock and Russel, 2001, Molecular cloning: A Laboratory Manual, 3. edition, Cold Spring Harbor Laboratory Press, Cold Spring Harbor, N.Y.

EXAMPLES

Example 1

Isolation of Aβ-Antibody from an AD Patient

Figure 5:
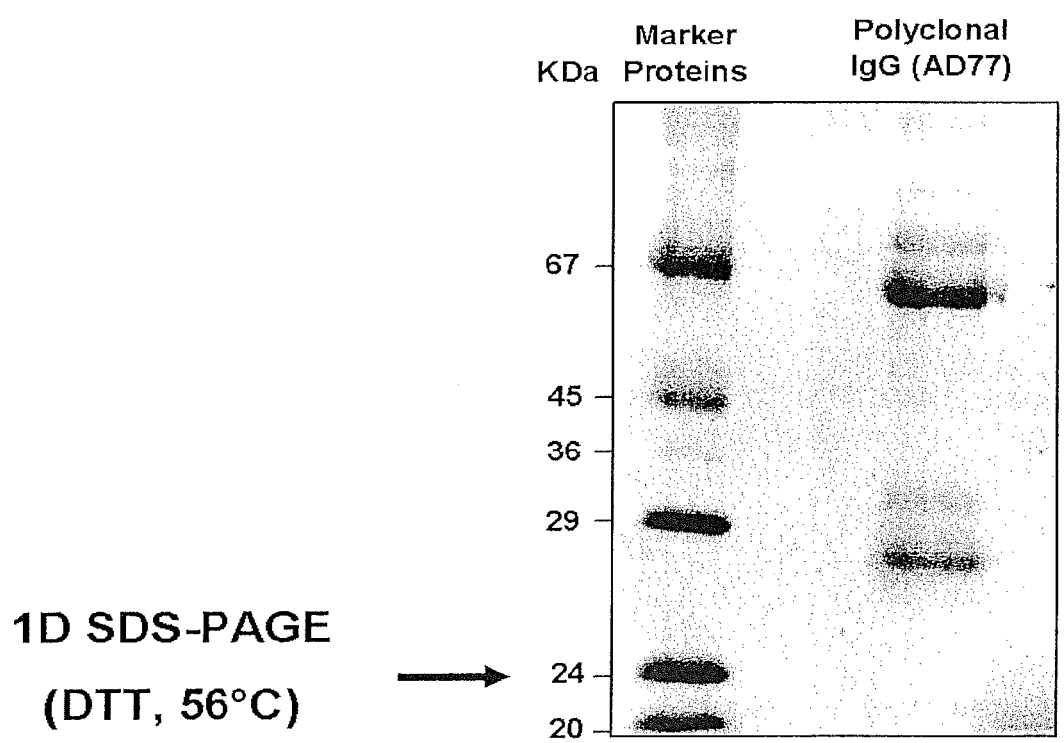
FIG. 5: 1D-Gel electrophoretic separation of polyclonal plaque-specific antibodies from an AD patient (AD77), isolated by Aβ(4-10) epitope-specific affinity chromatography as described in Example 1. KDa: Molecular weight in kilodalton. IgG: Immunoglobulin G. DTT: Dithiothreitol.

Immuno-isolation of the serum Aβ-antibody from an AD patient by epitope-specific affinity-chromatography was performed on a Sepharose-G5Aβ(4-10) affinity matrix column. The Sepharose-G5Aβ(4-10) affinity matrix was washed with 10 ml of PBS (5 mmol L$^{-1}$ Na$_2$HPO$_4$, 150 mmol L$^{-1}$ NaCl, pH 7.5) and transferred into a 1.7 ml vial using 300 µl of PBS. 800 µl (1 µg/µl) of two different Aβ autoantibodies (isolated from the sera of Alzheimer patients) were added and the sample was slowly rotated overnight at 4° C. The suspension was transferred to a 0.8 ml micro-column (Mobitec, Gottingen, Germany) providing the possibility of extensive washing without significant loss of material. The first 2 ml were collected as flow through fraction. The column was washed with 20 ml of PBS and the last 1 ml was collected for one-dimensional electrophoresis. The affinity bound IgG was eluted with 6×0.5 ml 0.1% TFA; the column was shaken gently for 15' and the released antibody molecules collected in a microreaction cup. The samples were lyophilized and stored until 1D-SDS-PAGE analysis (shown in FIG. 5).

Serum samples from healthy controls from all age ranges investigated were also tested for the presence of plaque-antibodies (N-terminal epitope), using the Aβ(4-10) epitope column. In all investigated samples, non-AD control samples were devoid of detectable plaque-specific antibody.

Example 2

Isolation of Anti-Aβ(21-37)-Autoantibodies from Healthy Individuals

A. Affinity Isolation and Purification of Anti-Aβ(21-37)-Autoantibodies

The anti-Aβ(21-37)-autoantibodies were isolated from (i), commercially obtainable serum immunoglobulin and (ii) from serum of healthy individuals (HI). Isolation of antibodies was performed by Aβ-epitope-specific affinity chromatography by a procedure that employed a N-cysteinyl-Aβ(12-40) column which was immobilized on Ultralink-iodoacetyl-solid phase carrier as described below.

N-Cysteinyl-Aβ(12-40) (H-CVHHQKLVFFAEDVG-SNKGAIIGLMVGGVV-COOH) (SEQ ID No: 162) was synthesized by solid phase peptide synthesis using 9-fluorenylmethoxycarbonyl/t-butyl (Fmoc/tBu) chemistry on a NovaSyn TGR resin (0.23 mmole/g coupling capacity) on a semi-automated Peptide Synthesizer EPS-221 (INTAVIS, Langenfeld, Germany). The following side-chain protected amino acid derivatives were used: Fmoc-Lys(Boc)-OH, Fmoc-Asn(Trt)-OH, Fmoc-Ser(tBu)-OH, Fmoc-Asp(OtBu)-OH, Fmoc-Glu(OtBu)-OH, Fmoc-Gln(Trt)-OH, Fmoc-His(Trt)-OH, Fmoc-Cys(Trt)-OH. The synthesis was performed according to the following protocol: (i) DMF washing; (ii) Fmoc deprotection with 2% DBU, 2% piperidine in DMF (5+10 min), (iii) DMF washing, (iv) coupling of 5 equiv of Fmoc amino acid:PyBOP:NMM in DMF (40 min), (v) coupling of 5 mol-equivalents of Fmoc amino acid:PyBOP:NMM in DMF (40 min) (vi) DMF washing (3×1 min) Due to the hydrophobic character of the C-terminal sequence of Aβ, double coupling of each amino acid was employed throughout the synthesis. After completion of the synthesis cycles, the peptide was cleaved from the resin for 3 h using a mixture containing 95% TFA, 2.5% triisopropylsilan and 2.5% deionized water. The crude product was precipitated with cold tert-butylmethylether, washed three times with diethyl ether and solubilized in 10% acetic acid (aqueous solution) prior to freeze-drying. Purification of the peptides was performed by semipreparative HPLC; subsequent characterization by HPLC and MALDI-TOF mass spectrometric analysis ensured molecular homogeneity of the peptide.

i) Immobilisation of CysAβ(12-40) on Ultralink Iodoacetyl Gel

Since the Aβ(12-40) sequence contains two internal lysine residues which might lead to side reactions in immobilization procedures using amino groups, a specific affinity column was prepared using a cysteine residue attached to the Aβ-N-terminus, to ensure homogeneous orientation of peptide molecules on the column support by immobilization through cysteinyl-S-thioether linkage. The azlactone-activated support contains an iodoacetyl group (UltraLink; Perbio, Bonn, Germany) at the end of a hexadecyl-spacer group, which was reacted with the cysteinyl-sulfhydryl group to yield a stable thioether linkage, in order to reduce steric hindrance and provide maximum binding capacity of the antibodies. For covalent attachment of the Cys-Aβ(12-40), 3.7 mg of peptide were dissolved in 50 mM Tris, 5 mM EDTA-Na coupling buffer (pH 8.5) to a final concentration of 0.37 mg/ml. The solution was added to 1 ml of drained Ultralink-Iodoacetyl gel and the coupling reaction was performed for 1 hr at 25° C. under gentle mixing, followed by 30 min reaction time without mixing. An aliquot of 0.5 ml of the Cys-Aβ(12-40) coupled support was packed into a column (2.5 ml, MoBiTec, Gottingen, Germany) allowing the solution to drain. The column was washed with 3 ml of coupling buffer, and nonspecific binding sites on the gel were blocked for 2×45 min by reaction with 1 ml of 50 mM L-Cysteine.HCl in coupling buffer. Subsequently the column was washed with 5 ml of 1 M NaCl and 5 ml of 0.1 M Na-phosphate, 0.15 M NaCl (pH 7.2) and stored at 4° C. The gel support (0.5 ml) was transferred into a 15 ml Falcon vial using 5 ml PBS and mixed with 5 ml IVIgG. After gentle shaking overnight at 4° C., the suspension was transferred to the column using the effluent to completely rinse the matrix back into the column. The column was washed eight times with 10 ml of PBS followed by 2 wash cycles with 10 ml ultrapure water. The affinity-bound antibodies were eluted from the column with 10×0.5 ml 0.1% trifluoroacetic acid (TFA). Subsequent isolation and preparation of IgG for structural characterization and affinity studies was performed using two different protocols:

(a) The first procedure involved adjustment to neutral pH for each fraction collected using 0.5 M NaH$_2$PO$_4$ (pH 8) in order to maintain integrity of the antibodies for use in affinity studies. The bound antibodies were eluted from the column with 10×0.5 ml 0.1 M glycine buffer, pH 2.8. Each fraction was collected in a microreaction tube containing 35 μl 1 M Tris-HCl, pH 9. To maintain integrity of the antibodies neutral pH was adjusted immediately after elution by adding the appropriate amount of Tris-HCl or glycine buffer. To regenerate the column for further use, the column was washed once with 10 ml 10 mM sodium-phosphate buffer pH 6.8, followed by two wash cycles with 10 ml of PBS containing 1M sodium chloride and finally two wash cycles with 10 ml PBS. Protein concentrations were determined by the BCA method (Pierce; Perbio, Bonn, Germany). This procedure yielded the elution of single, defined antibody.

Figure 12:
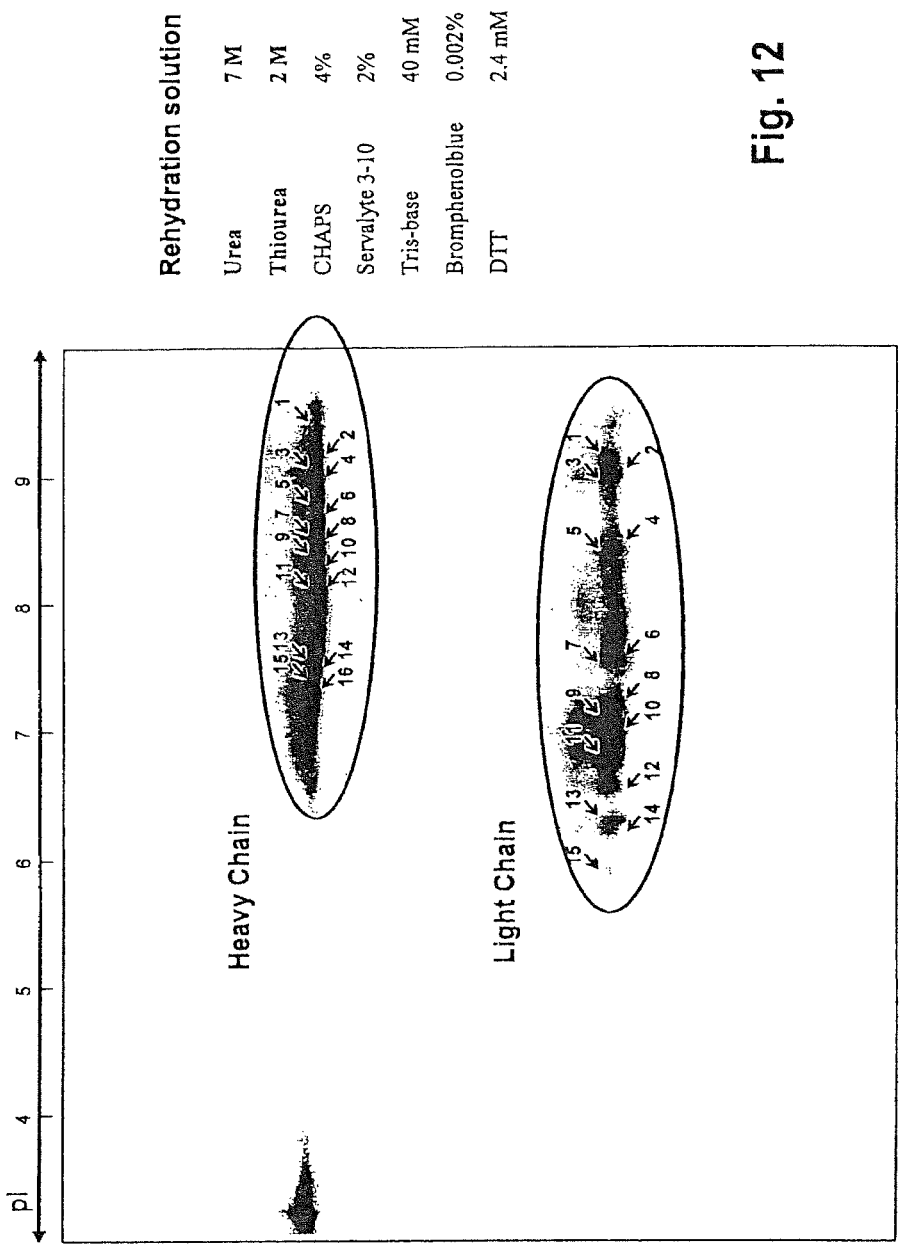
FIG. 12: 2-Dimensional SDS-gel electrophoretic separation of polyclonal anti-Aβ(21-37) autoantibodies isolated from IVIgG; see FIG. 22 (a-c) for identification and sequence determination of Aβ-antibody isoforms. DTT: Dithiothreitol. CHAPS: 3-[(3-Cholamidopropyl)-dimethyl-ammonio]-1-propanesulfonate.

(b) The bound antibodies were eluted from the column with 10×0.5 ml 0.1 M glycine buffer, pH 2.8. For separation by gel electrophoresis the elution of affinity-bound antibodies was not performed by subsequent pH adjustment, in order to reduce the salt content of the samples subjected to isoelectric focusing. Gel electrophoretic separations provided a set of defined bands of antibodies (see numbering in FIG. 12).

ii) Antibody Quantification

Antibody concentrations in the elution fractions were determined by the Micro BCA™ Protein Assay Kit method (Pierce; Perbio, Bonn, Germany). The stock solution of 2 mg/ml of bovine albumin supplied within the Micro BCA™ Kit was used to prepare fresh standard dilutions within the range 40-0.5 μg/ml. The antibodies eluted between fractions 1 to 6, with highest concentrations in fractions 1 and 3. For quantification of each set of 10 elution fractions, fresh albumin standard dilutions were prepared. Results were read at 562 nm with the ELISA reader.

B. Determination of the Epitope Recognized by the Anti-Aβ (21-37)-Autoantibodies Via Epitope Excision Autoantibodies isolated as described in Example 2A from the serum of healthy individuals were immobilized using a solution of 100 μg Aβ(21-37) autoantibodies in 500 μl 0.2 M NaHCO$_3$/0.5 M NaCl (pH 8.3), which was added to n-hydroxysuccinimidyl (NHS)-activated 6-aminohexanoic acid-coupled sepharose (Sigma, St Louis, USA) and allowed to bind for 60 min at 20° C. before transferring onto a microcapillary (MoBiTec, Goettingen, Germany). The column was washed five times with 6 ml blocking buffer (0.1M ethanolamine, 0.5 NaCl-pH=8.3) and between the blocking steps with 6 ml washing buffer (0.2M NaOAc, 0.5M NaCl-pH=4) each with one drop per second. Then the column was incubated for 1 h in blocking buffer, followed by another wash step: washed seven times alternatively with 6 ml washing buffer (0.2M NaOAc, 0.5M NaCl— pH=4) and with 6 ml blocking buffer (0.1M ethanolamine, 0.5 NaCl— pH=8.3). Finally, the column was washed with 20 ml PBS (5 mM Na2HPO4, 150 mM NaCl, pH=7.5). Then the peptides to be analyzed were applied in a molar ratio of about two peptides per coupled antibody. Then the columns were washed with 10 ml PBS wash and then 10 ml double desalted H$_2$O (MilliQ) to remove unspecifically bound peptides. Then elution was done by applying 500 μl 0.1% TFA and incubating it for 15 minutes under gentle agitation. Then the TFA solution containing specifically bound peptides is eluted and TFA solution is applied again 2 to 4 times. These eluates are pooled and lyophilized then measured by MS.

Epitope excision was performed by application of 2-5 μg Aβ-antigen in PBS in a molar ratio of about two peptides per coupled antibody to the antibody microcolumn produced as described in the paragraph above for 60 min at room temperature (20-25° C.). After washing, digestion was performed on the column for 2 h at 37° C. with 0.2 μg protease in 200 μl PBS. Unbound peptides were removed and the epitope was dissociated from the antibody using 500 μl 0.1% trifluoroacetic acid. After incubation for 15 min at 20° C., this step was repeated 5 times, the epitope eluate was lyophilized and reconstituted in 10 μl 0.1% TFA or MALDI solvent (3:2 AcCN: 0.1% TFA-better) for mass spectrometric analysis.

Figure 6:
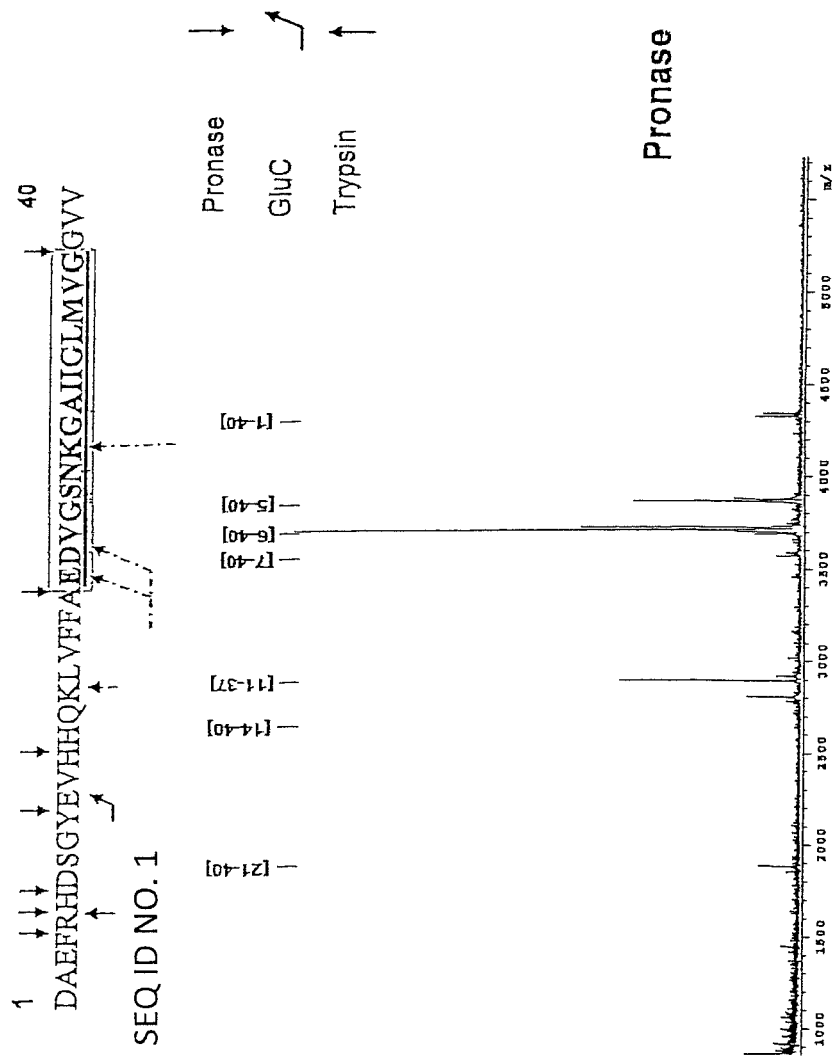
FIG. 6: Identification of Aβ(21-37) as the epitope recognized by human anti-Aβ(21-37)-autoantibodies by epitope excision-mass spectrometry. The upper graph shows the sequence of Aβ(1-40), with cleavages by different proteases indicated by black arrows. Peptide fragments denoted by solid black arrows above the Aβ-sequence were identified after epitope excision using pronase; peptide fragments denoted by black dotted arrows underneath the Aβ sequence were found by epitope excision using trypsin and Glu-C-protease (R5, E11, K16); note that Arg-5 is completely shielded in the immune complex with the plaque-specific antibody, while completely amenable to cleavage in the immune complex with the anti-Aβ(21-37)-autoantibody. Cleavage positions, observed in free Aβ, indicated by broken arrows were found shielded after binding of anti-Aβ(21-37)-autoantibody (Glu-C: E22, D23; trypsin: K28). The MALDI-MS analysis upon partial digestion (2 hrs) with pronase is shown here for illustration.
Figure 7:
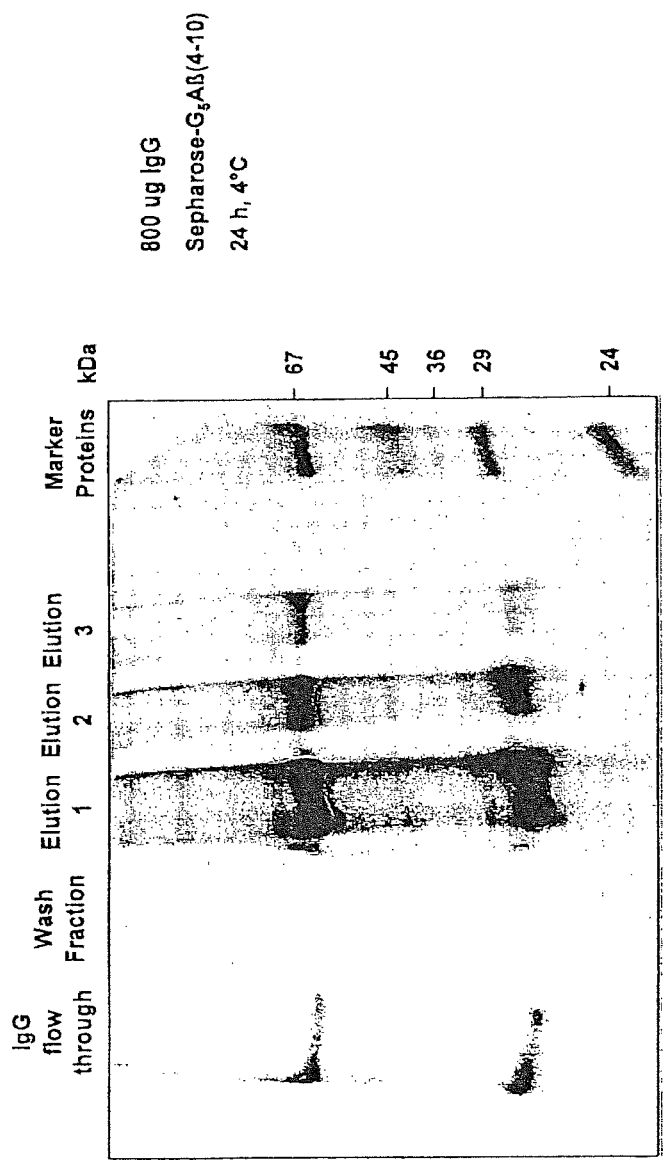
FIG. 7: Isolation of "plaque-specific" antibodies recognizing the N-terminal Aβ(4-10) epitope from the serum Aβ-autoantibodies of an Alzheimer patient, isolated by Aβ(4-10)-epitope specific chromatography. IgG stands for immunoglobulin G. AD signifies Alzheimer's Disease. Affinity column: G5Aβ(4-10). kDa: Molecular weight in kilodalton.

Epitope extraction was performed in an analogous manner, however, proteolytic digestion was performed first with the unbound antigen and the proteolytic digest was applied directly to the antibody column. As shown in FIG. 6, the carboxy-terminal Aβ(21-37) sequence was found to be specifically recognized (proteolytically shielded), while N-terminal residues of Aβ were accessible for cleavage. The extracted Epitope bound by the Aβ-autoantibody isolated from the healthy individuals exhibited thus the amino acid sequence of Aβ(21-37). Therefore, the antibodies of the invention were called Aβ(21-37) autoantibodies.

Figure 1:
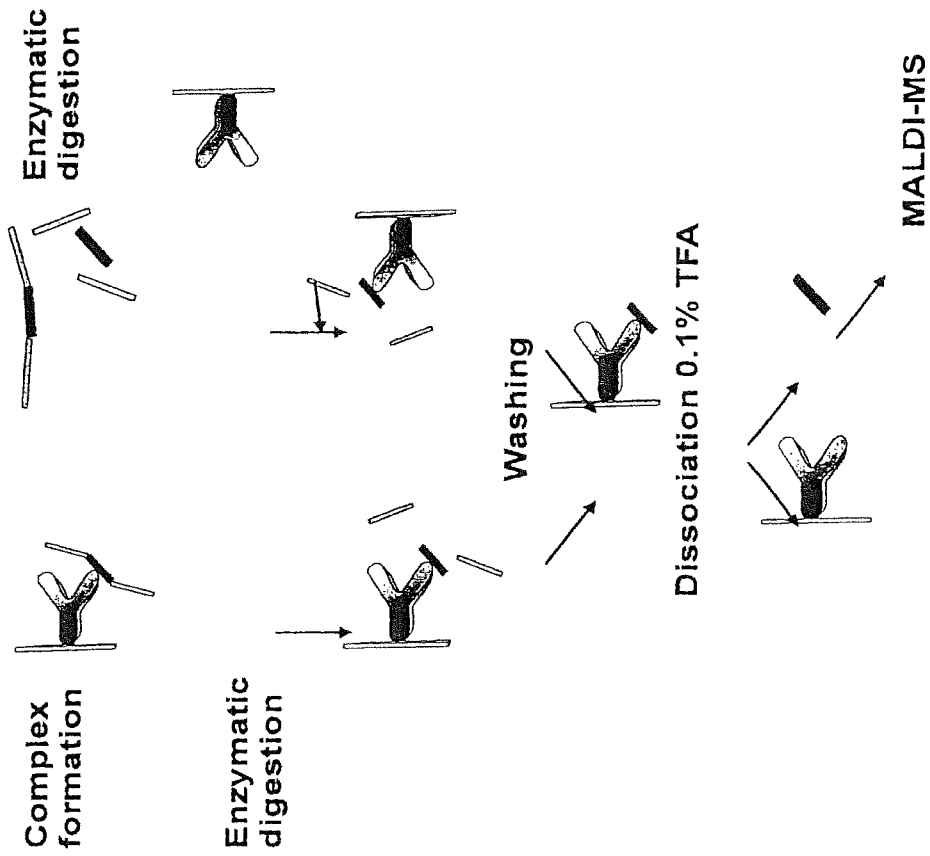
FIG. 1: Principle of epitope-excision and epitope extraction for mass spectrometric epitope identification. Antibody immunoglobulin with native, disulfide-bonding is generally highly resistant to proteolytic digestion by endoproteases (e.g., trypsin, chymotrypsin, AspN-protease), and the epitope region of antigen polypeptides comprising the epitope-paratope interaction structure is generally protected from proteolytic degradation in the immune complex, while the free nonbinding regions are amenable to digestion. Thus, the epitope sequence remaining bound to the antibody after proteolytic removal and washing away nonbinding structures is then dissociated from the antibody and identified by mass spectrometry. Both electrospray-ionization (ESI) and matrix-assisted laser desorption-ionization (MALDI) have been found useful mass spectrometric methods, and have been applied successfully for epitope identifications. "TFA" means trifluoroacetic acid. "MALDI-MS" stands for matrix-assisted laser desorption-ionisation mass spectrometry.
Figure 2:
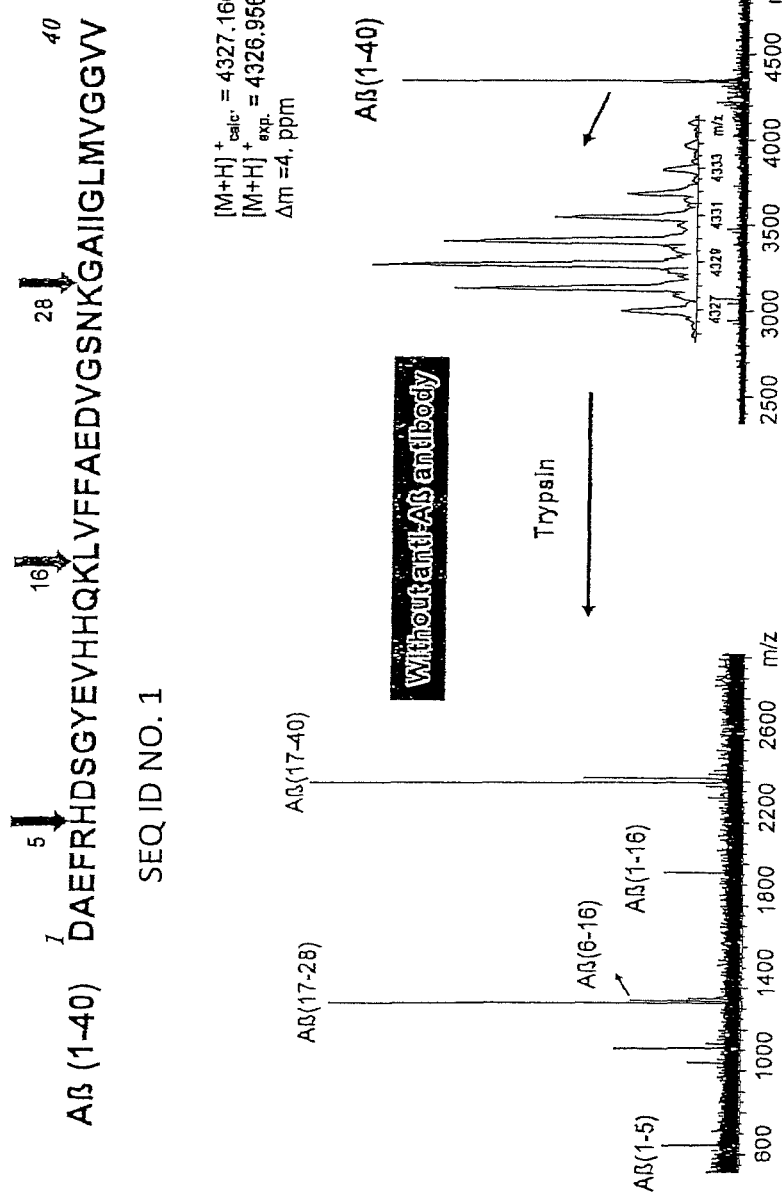
FIG. 2: Mass spectrometric identification of proteolytic peptide fragments of free soluble Aβ peptide. Without the complexation by antibody binding, digestion of Aβ(1-40) by trypsin leads to formation of all peptide fragments expected according to the proteolytic cleavage specificity (Aβ(1-5), Aβ(6-16), Aβ(17-28), Aβ(17-40), Aβ(1-16)). Mass spectrometric analysis is performed by high resolution MALDI-Fouriertransform-ion cyclotron resonance (MALDI-FTICR-MS), which provides spectra at approximately 100,000 mass resolution with complete isotope resolution of ions and mass determination accuracies of typically 1-5 ppm. All FTICR- MS spectra were obtained with a Bruker (Bruker Daltonik, Bremen, Germany) Apex II 7T FT-ICR mass spectrometer equipped with an Apollo H electrospray/nanoelectrospray multiportion source and an external Scout 100 fully-automated X-Y target stage MALDI source with pulsed collision gas. The pulsed nitrogen laser is operated at 337 nm. Ions generated by laser shots were accumulated in the hexapole for 0.5-1 sec at 15 V and extracted at −7 V into the analyzer cell. A 100 mg/ml solution of 2,5-dihydroxybenzoic acid (DHB, Aldrich, Germany) in acetonitrile: 0.1% TFA in water (2:1) was used as the matrix. 0.5 μl of sample solution were mixed on the stainless-steel MALDI sample target and allowed to dry. Typical ESI conditions were ~2 kV needle voltage and 100 nA spray current. Ions were accumulated in a hexapole for 2 sec and then transferred into the cylindrical ICR cell. "ppm" stands for parts per million. "m/z" indicates the mass-to-charge-ratio.
Figure 3:
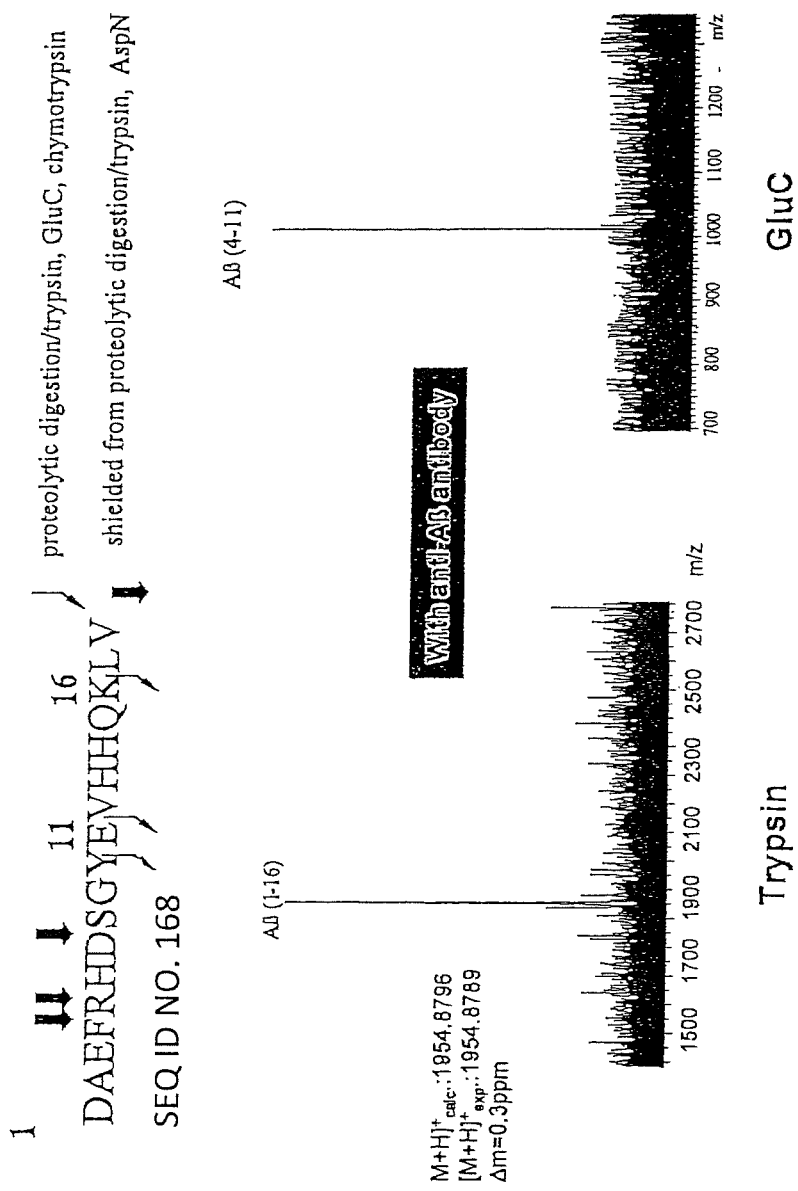
FIG. 3: Epitope Identification of Amyloid Plaque Specific Antibody by MALDI-FTICR-MS: Mass spectrometric identification of N-terminal Aβ-epitope recognized by plaque-specific antibody produced upon active immunization of transgenic mice with Aβ(1-42) or Aβ(1-42)-derived aggregates. The immobilized, purified antibody was incubated with Aβ(1-40), Aβ(1-42), and the immune complex subjected to epitope excision by proteases trypsin, chymotrypsin, Glu-C protease and Asp-N-protease. The left spectrum shows the fragment, Aβ(1-16) remaining bound after trypsin digestion, the right spectrum shows Aβ(1-11) after epitope excision using Glu-C-protease. Black small arrows shown in the Aβ sequence shown denote cleavages identified by epitope excision, fat grey arrows denote substrate cleavage sites on Aβ that were found shielded upon antibody binding. Identical Aβ(4-10) epitope sequences were identified with soluble Aβ-plaques and -protofibrils bound as antigens, and from a mouse anti-Aβ(1-16) peptide monoclonal antibody (Bachem-Peninsula Laboratories, San Francisco).

FIG. 3 shows a similar experiment in which it was shown that the plaque specific antibodies directed against Aβ(4-10) were able to shield the amino acids F4, R5, D7 from proteolytic digestion.

The specificity of the inventive antibodies was further investigated using Aβ(21-37) autoantibodies purified as described in Example 2A from IVIgG. The anti-Aβ antibody ACA (based on U.S. Pat. No. 7,195,761 see example 5) also was evaluated. The antibodies were incubated with different partial Aβ peptides as specified below and washed as described above in Example 2B. The elution profiles were analyzed via MS as above.

FIGS. 34 (a-d) show that antibodies of the invention specifically bind in this experimental setting to Aβ(12-40) and Aβ(20-37) but do not bind Aβ(25-35), Aβ(17-28) or Aβ(31-40).

FIG. 34 (b) shows that the Aβ(21-37) autoantibodies specifically bound the Aβ(12-40) polypeptide FIG. 34(c) shows that Aβ(21-37) antibodies did not bind to Aβ-polypeptides Aβ(25-35), Aβ(17-28) or Aβ(31-40).

FIGS. 34(d) to 34(l) show that both the immobilized ACA antibody and the immobilized Aβ(21-37) autoantibodies bind to Aβ(1-40) and to Aβ(12-40) but that only the immobilized Aβ(21-37) autoantibodies specifically bind to Aβ(20-37) and the ACA antibody does not. Neither immobilized antibody bound Aβ(17-28). In addition the immobilized antibody ACA did not bind to Aβ(4-10).

Therefore the antibodies of the invention are unique in that they are characterized by specifically binding to Aβ(12-40) and Aβ(20-37), whereas they do not bind to Aβ(25-35), Aβ(17-28) or Aβ(31-40) under the experimental conditions specified above.

The structure and conformational properties, binding affinity and specificity of the Aβ-autoantibody epitope were further characterized by investigation of synthetic peptides comprising the Aβ(21-37) epitope sequence, and by fine-structure mapping using Alanine sequence mutations, H-D exchange and high resolution mass spectrometry, ELISA studies and CD spectroscopic conformational analysis in different solvents. Biotinylated Aβ(21-37) peptides and peptides derivative flanked with oligo-Glycine and -(D-Ala) spacer groups were synthesized by solid-phase peptide synthesis according to previously described procedures for Aβ-peptides, and were purified by reversed-phase HPLC and characterized by MALDI- and ESI-mass spectrometry for molecular homogeneity (Manea et al., 2004; Mezo et al., 2004). Comparative binding studies were performed with Aβ-epitope peptides comprising different C-terminal sequence lengths, using an ELISA system (see below, 3). These results established an essential function for antibody affinity of the carboxyterminal sequence end of Aβ, comprising residues 30-37; this partial sequence is critically involved in 3-sheet formation and aggregation of Aβ. Thus, full binding affinity is obtained in Aβ(12-40). In contrast the shortened Aβ(20-30) peptide showed almost completely abolished affinity Mass spectrometric studies of peptides upon H-D equilibrium exchange showed rapid deuterium incorporation of peptide backbone hydrogens only for the Aβ sequence (20-30), but only little backbone deuteration for residues (30-37), suggesting increased shielding in this part due to conformational or aggregation effects. Control binding studies of the epitope peptide Aβ(20-37) with antibodies that recognized the N-terminal, Aβ(1-16) peptide (plaque-specific mono- and polyclonal antibodies) did not show any binding affinity.

C. Affinity Evaluation of Purified Anti-Aβ(21-37)-Autoantibodies

To assess the quality of the affinity purified antibodies, ELISA was performed using the flow through of the affinity-purification column (immobilized Aβ12-40) as a control. The 96-well plate was incubated with 200 ng/well of Aβ(1-40) in PBS buffer for 2 hrs at 20° C. The plate was washed 4 times with 200 μl of PBS containing 0.05% Tween-20 and blocked for 2 hours with 5% BSA containing 0.05% Tween-20 in PBS buffer. The plate was then incubated for 2 hrs at 20° C. under gentle shaking with the affinity-purified antibodies obtained as described in example 2A in 5% BSA, 0.05% Tween-20 using the IVIgG flow through as a control. After washing, anti-human horse-radish peroxidase (HRP) conjugated antibodies were added to the wells and incubated for 1 hr. After adding the substrate OPD the optical density was determined at 450 nm. Affinities were determined by competitive ELISA, with IQ-values ranging between about 8 to about $15 \times 10^{-9}$ M.

D. Electrophoretic Separation for Sequence Determinations of Anti-Aβ(21-37)-Autoantibodies Electrophoretic separation and isolation by isoelectric focusing of the anti-Aβ(21-37)-autoantibodies obtained as described in example 2A was carried out by 1D- and 2D-SDS-PAGE. Samples were equilibrated for 30 min in 6 M urea, 30% glycerol, 2% w/v SDS, 0.05 M Tris-HCl (pH 8.8), 1% DTT and a trace of bromophenol blue, then for 30 min in the same solution except that DTT was replaced by 4.5% (w/v) iodoacetamide Isoelectric focusing (IEF) was carried out with a Multiphor II horizontal electrophoresis system (Amersham Pharmacia Biotech) using 17 cm immobilized pH gradient (IPG) strips (pH range 3-10 linear). The second-dimensional separation was carried out with a Bio-Rad Protean II xi cell vertical electrophoresis system using 10% SDS-PAGE gels of 1.5 mm thickness. The IPG strips were rehydrated overnight in a solution containing about 100 μg lyophilized anti-Aβ(21-37)-autoantibody for Coomassie and 30 μg for silver staining solubilised in 7 M urea, 2 M thiourea, 4% CHAPS, 0.3% DTT, 2% Servalyt pH 3-10 and a trace of bromophenol blue. The samples were applied using the in-gel rehydration method. Rehydrated strips containing the sample were run in the first dimension for about 30 kVh at 20° C.

Figure 13:
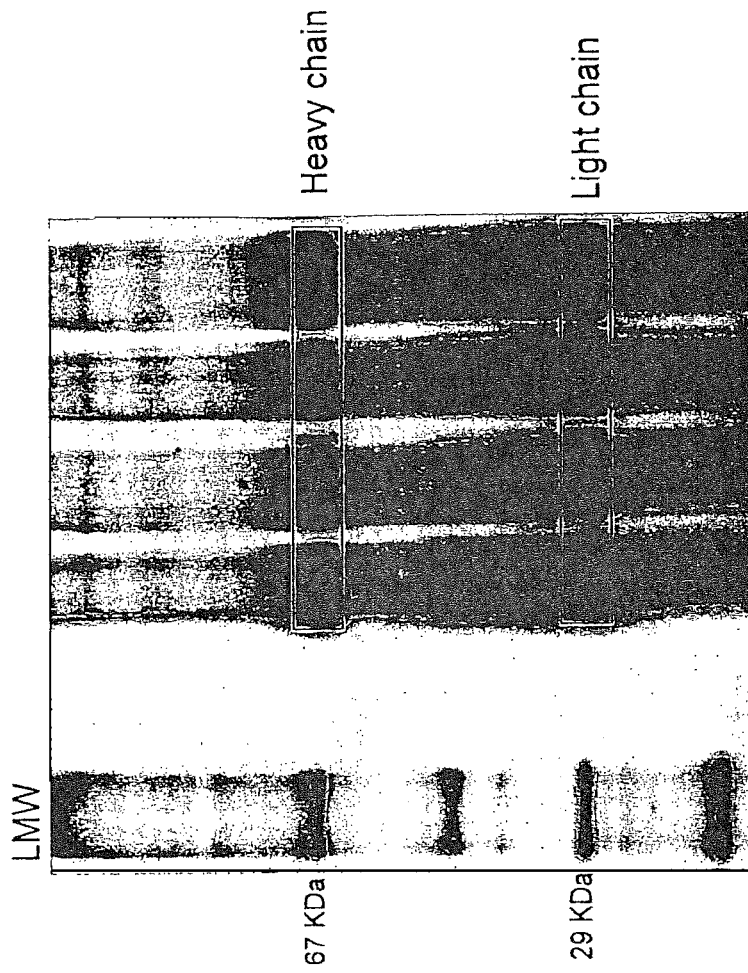
FIG. 13: 1D-SDS-PAGE isolation of heavy and light chains of serum IVIgG anti-Aβ(21-37) autoantibody. a) Reduction (10000×DTT); b) Alkylation (3× iodoacetamide/DTT), LMW: low molecular weight protein standard.
Figure 14:
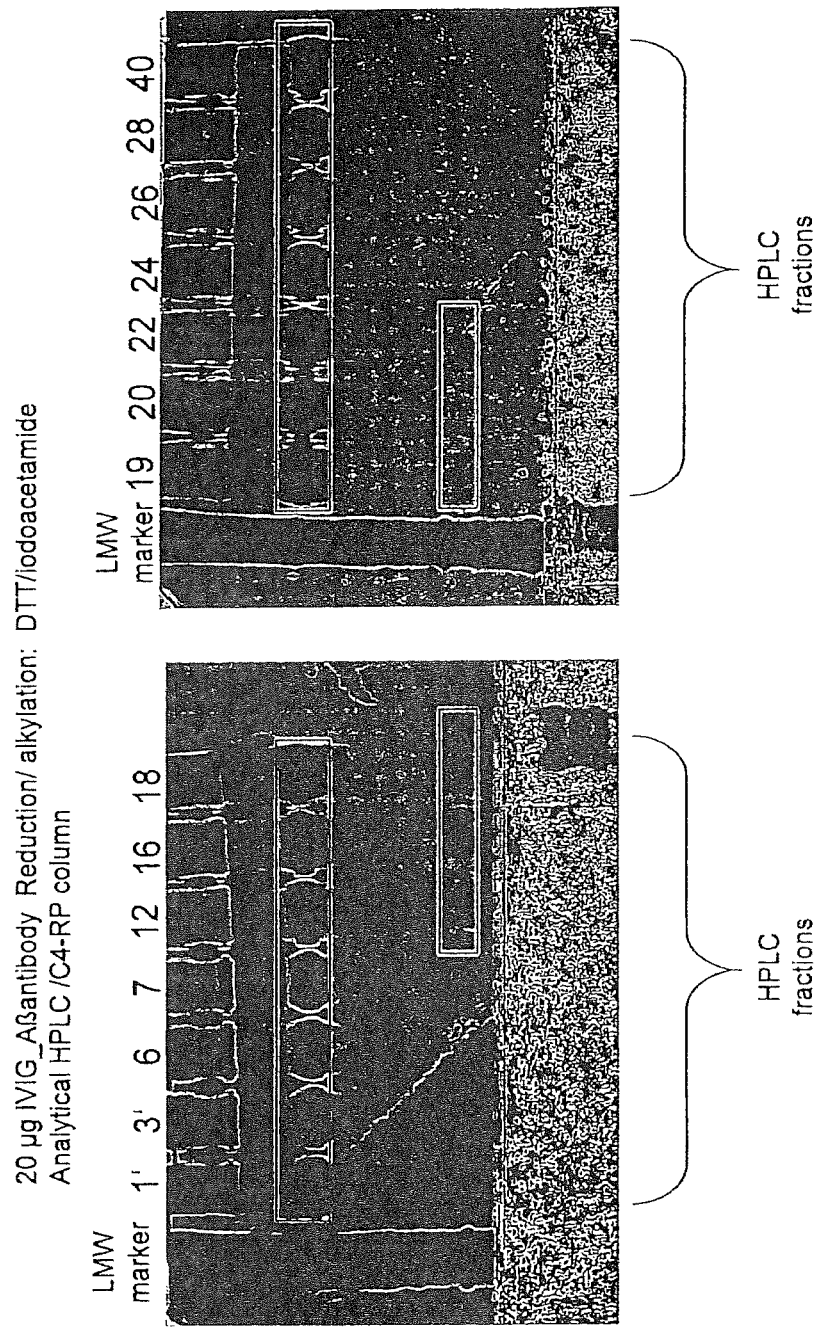
FIG. 14: 1D-Gel electrophoretic separation of HPLC-isolated heavy and light chains of anti-Aβ (21-37) autoantibodies (serum-IVIgG) used for Edman sequence determinations. LMW: low molecular weight protein standard.
Figure 15:
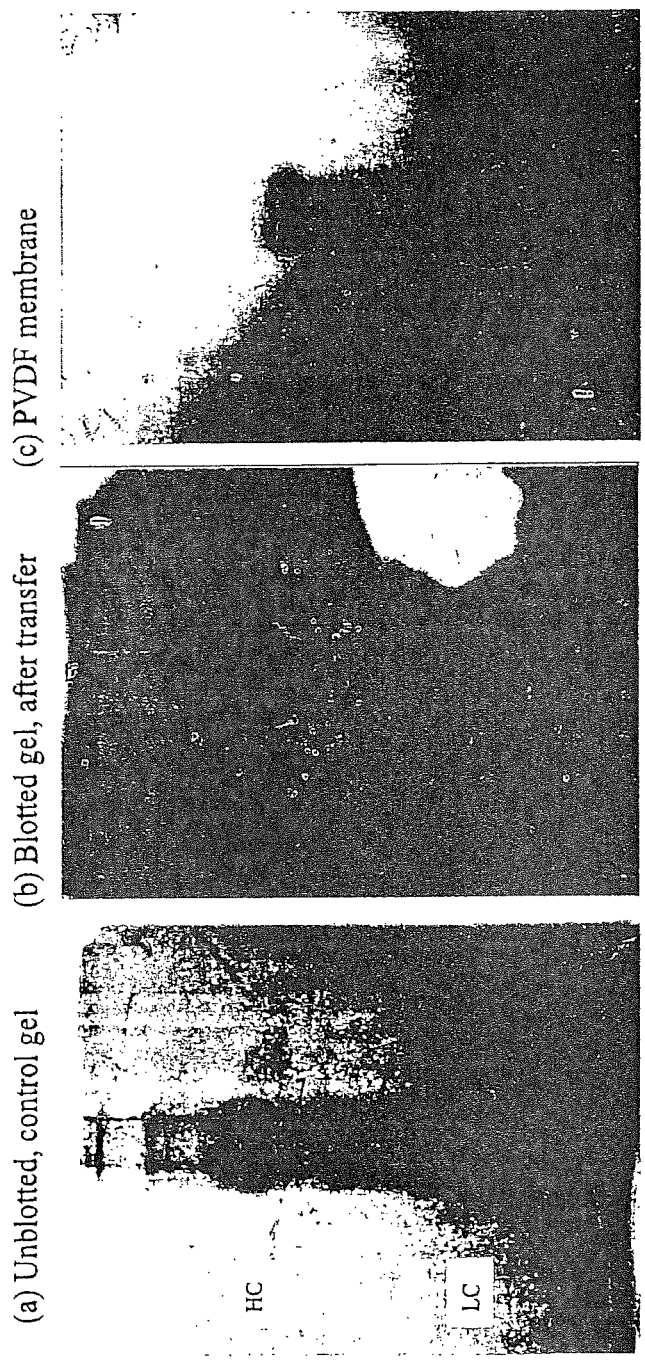
FIG. 15: 1D-Gel electrophoretic separation and blotting of serum IVIgG anti-Aβ(21-37) autoantibody heavy and light chains on PVDF membranes for Edman sequence determination.
Figure 16:
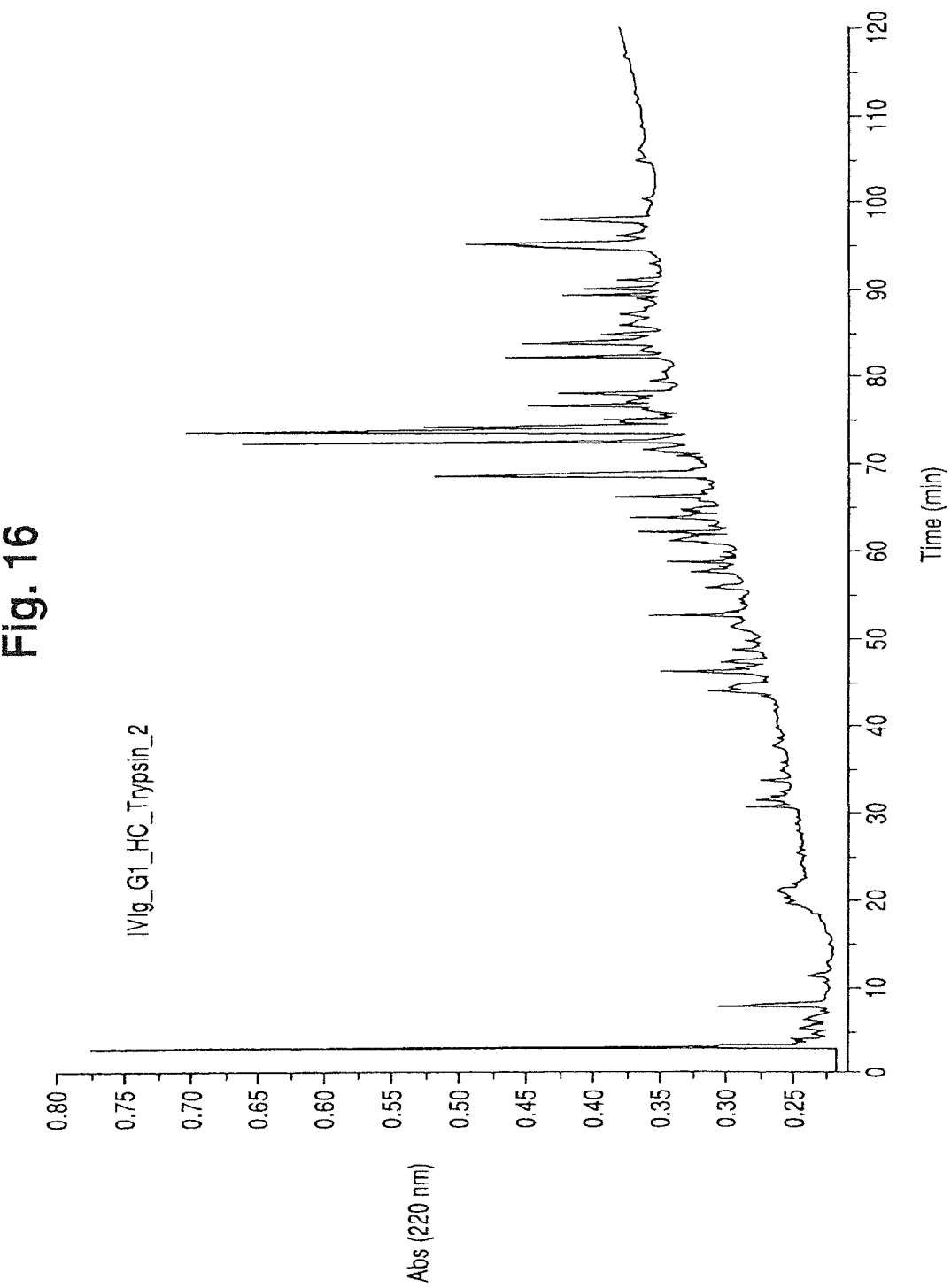
FIG. 16: HPLC separation of heavy chain tryptic peptides. Isolated peptide fractions were subjected to a) Edman sequence analysis, b) LC-MS/MS sequence determination, c) direct MALDI-TOF-MS and d) MALDI-FTICR-MS analysis.
Figure 17:
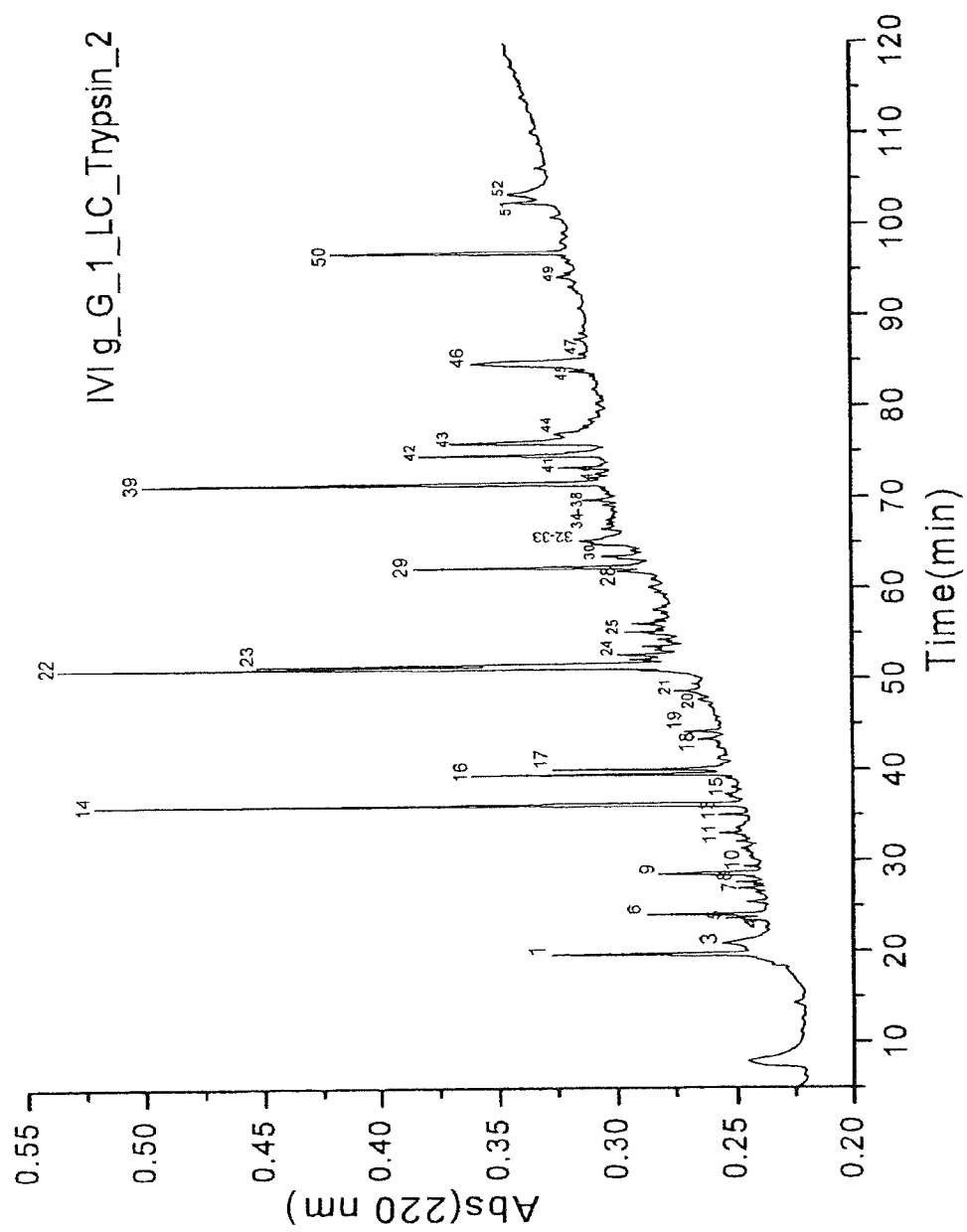
FIG. 17: HPLC separation of light chain tryptic peptides. Isolated peptide fractions were subjected to a) Edman sequence analysis, b) LC-MS/MS sequence determination, c) direct MALDI-TOF-MS and d) and MALDI-FTICR-MS analysis.
Figure 18A:
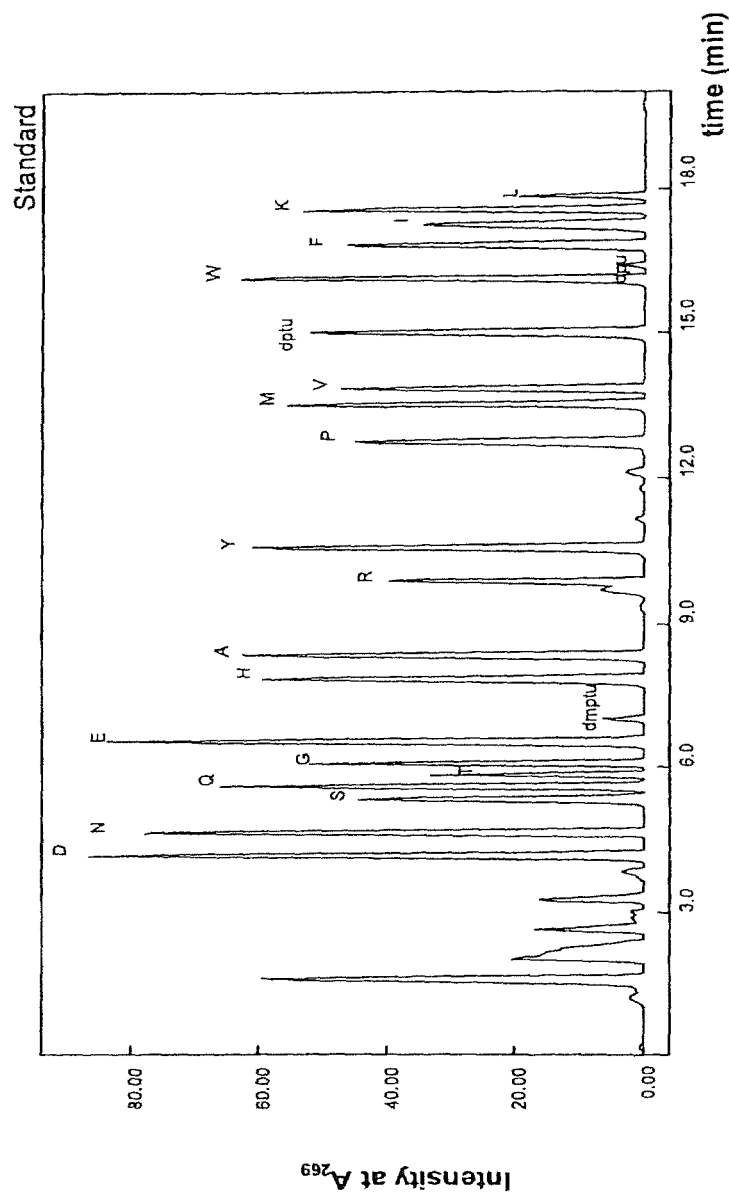
FIG. 18 (a-d): Edman sequence determination of HPLC-isolated heavy chain tryptic peptide, Serum_IVIG_G1_HC (1)_1 c(348-359; EPQVYTLPPSR). 18a: Standard. 18b: Residue 1. 18c: Residue 9. 18d: Residue 11.
Figure 18B:
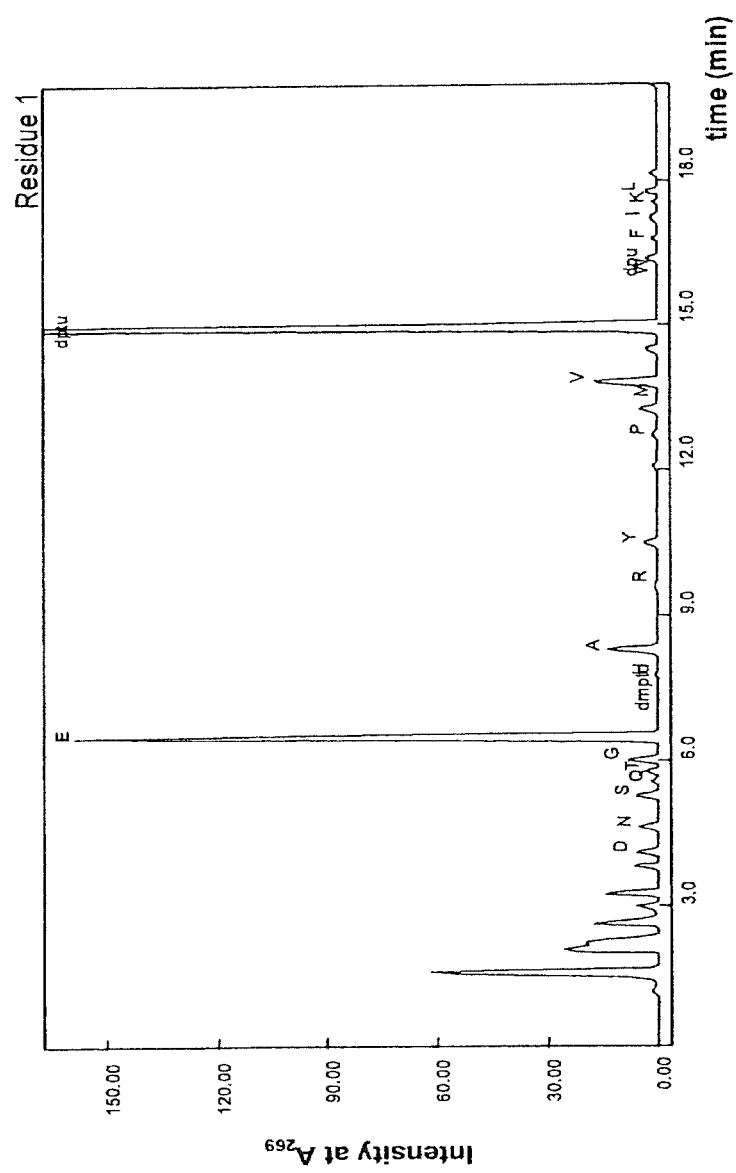
Figure 18C:
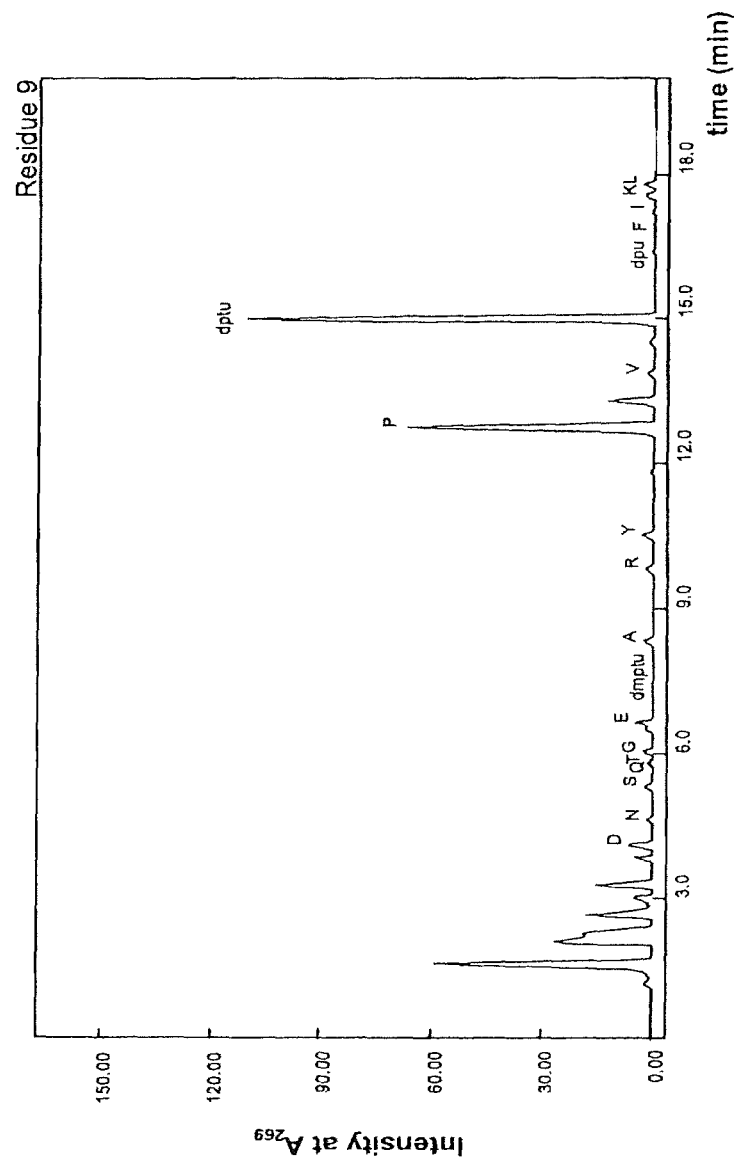
Figure 18D:
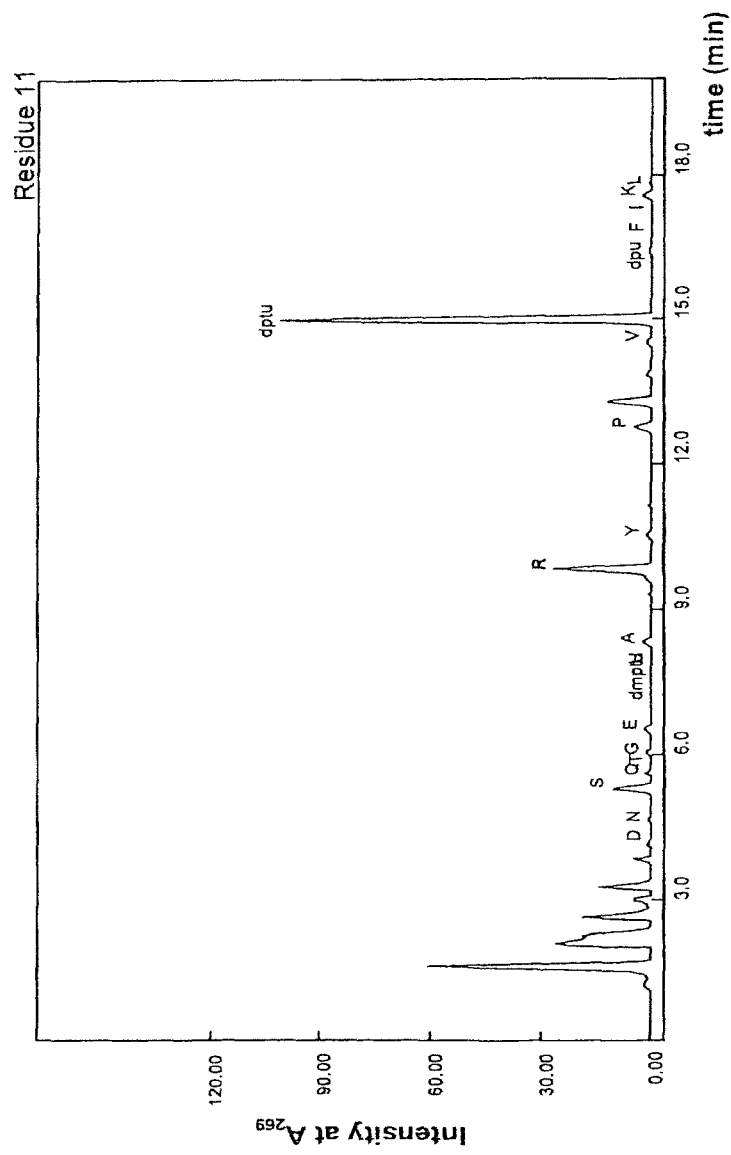
Figure 19B:
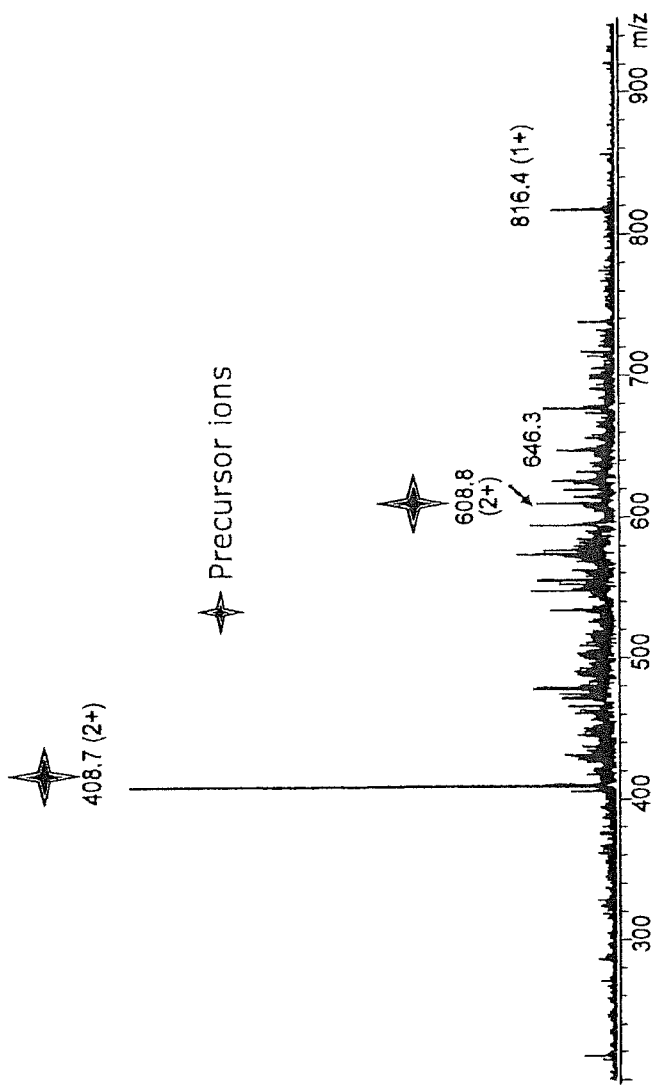
FIG. 19 (a-c): LC-MS/MS sequence determination of heavy chain tryptic HPLC peptides, fraction 27 (a) and HPLC fraction 39, heavy chain CDR1 peptide v(20-30).
FIG. 19a shows the total ion chromatogram, the peptide fraction isolated at 1.3-2.1 min elution time is encircled in red. (b) ESI-mass spectrum of the peptide fraction isolated at 1.3-2.1 min; (c) MS/MS fragment ion analysis of the doubly charged precursor ion selected, m/z 482.2.
Figure 19C:
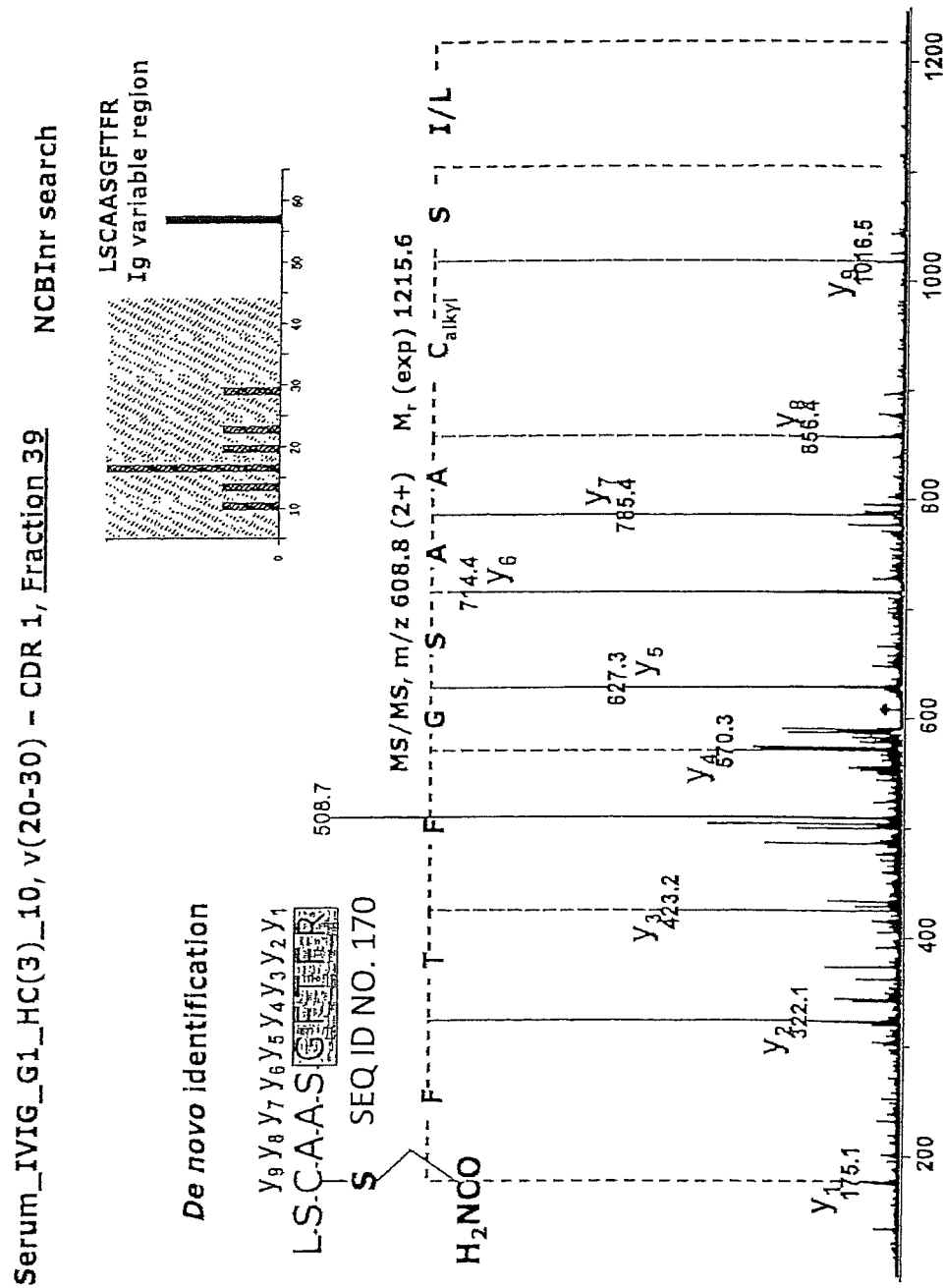
Figure 20A:
FIG. 20 (a, b): MALDI-TOF-MS Identification of tryptic HPLC peptides. a) identification of tryptic peptide, fraction 50, heavy chain (138-151), mol. mass 1423; b) identification of peptide isolated in fraction 75, heavy chain (375-396), mol. mass 2544 Da.
Figure 21B:
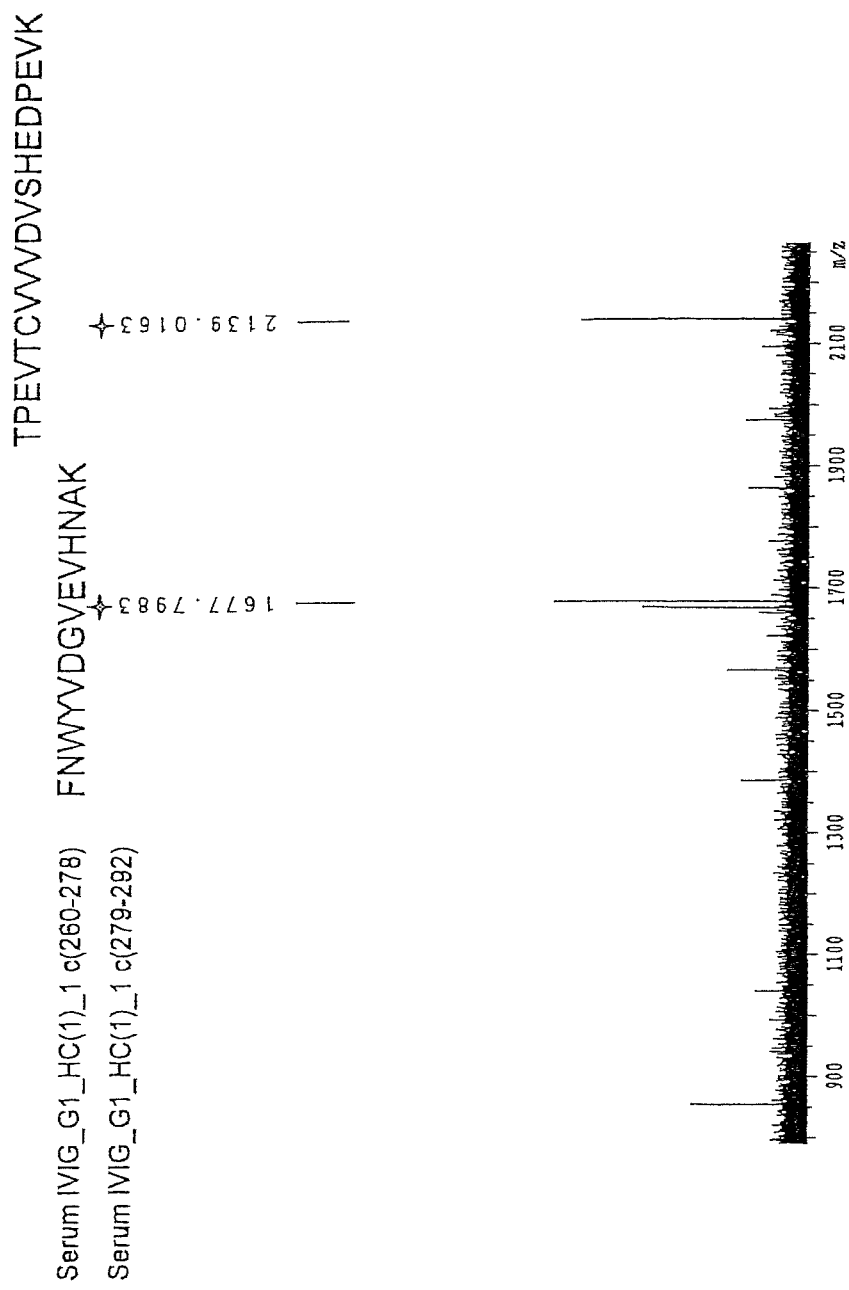
FIG. 21 (a-c): MALDI-FTICR-Mass spectrometric identification of heavy chain constant region tryptic peptides from HPLC fractions 47, 66, and 96. (a) identification of 3 peptides isolated in fraction 47 denoted on the molecular ion peaks, (349-359); (349-364); (137-151); (b) identification of 2 peptides in fraction 66, (260-278) and 279-292); (c) identification of peptide (306-321) in fraction 96.
Figure 22A:
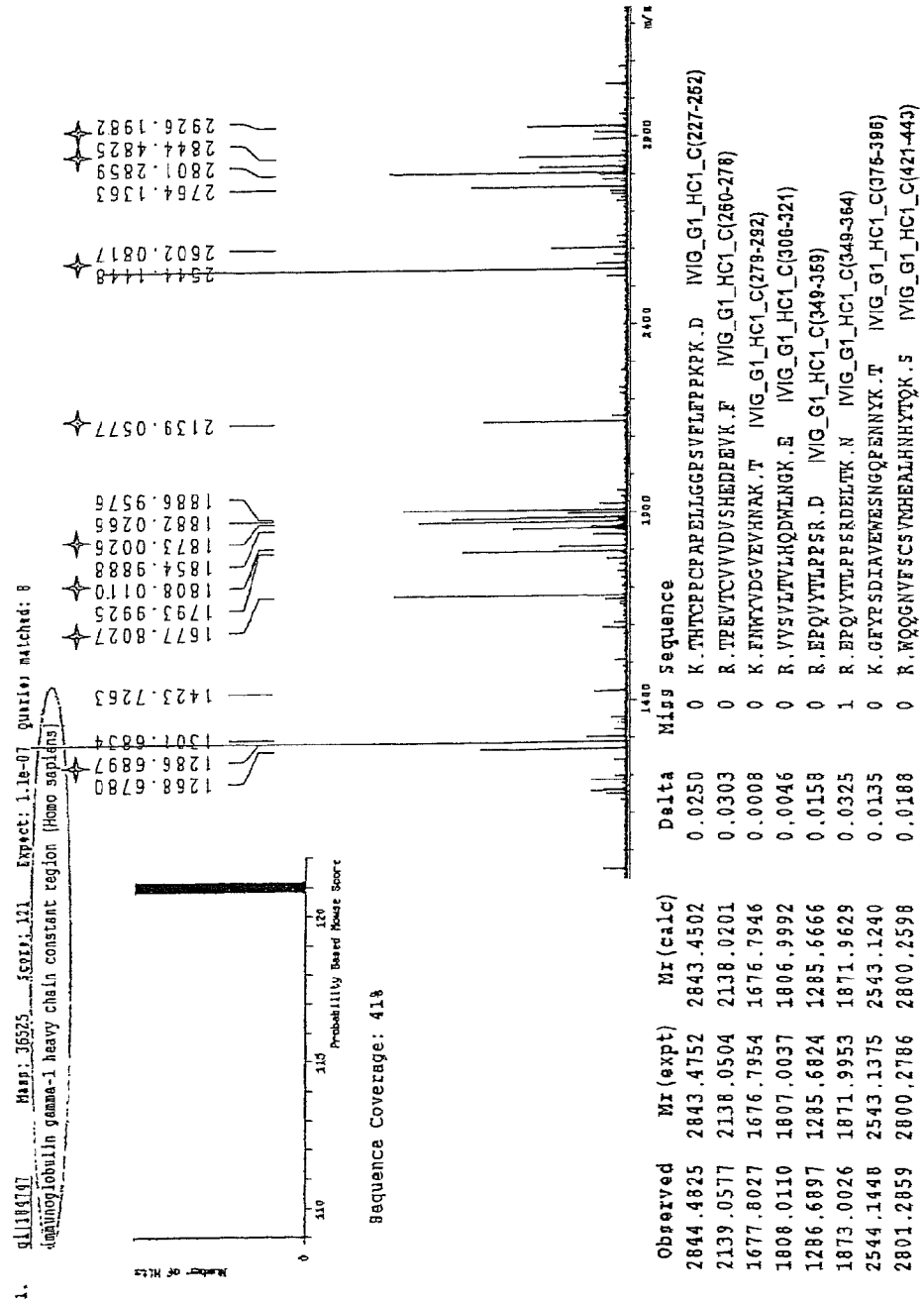
FIG. 22 (a-c): MALDI-FT-ICR Identification of sequences comprising the serum IVIgG1 heavy chain constant regions, isolated from 2D-gel bands subjected to in-gel tryptic digestion; spot 4 heavy chain (22a), spot 12 heavy chain (22b) and spot 13 heavy chain (22c) as illustrated in FIG. 12. Sequence determinations were performed using the NCBI data base, at a mass accuracy threshold of 5-10 ppm.
Figure 22B:
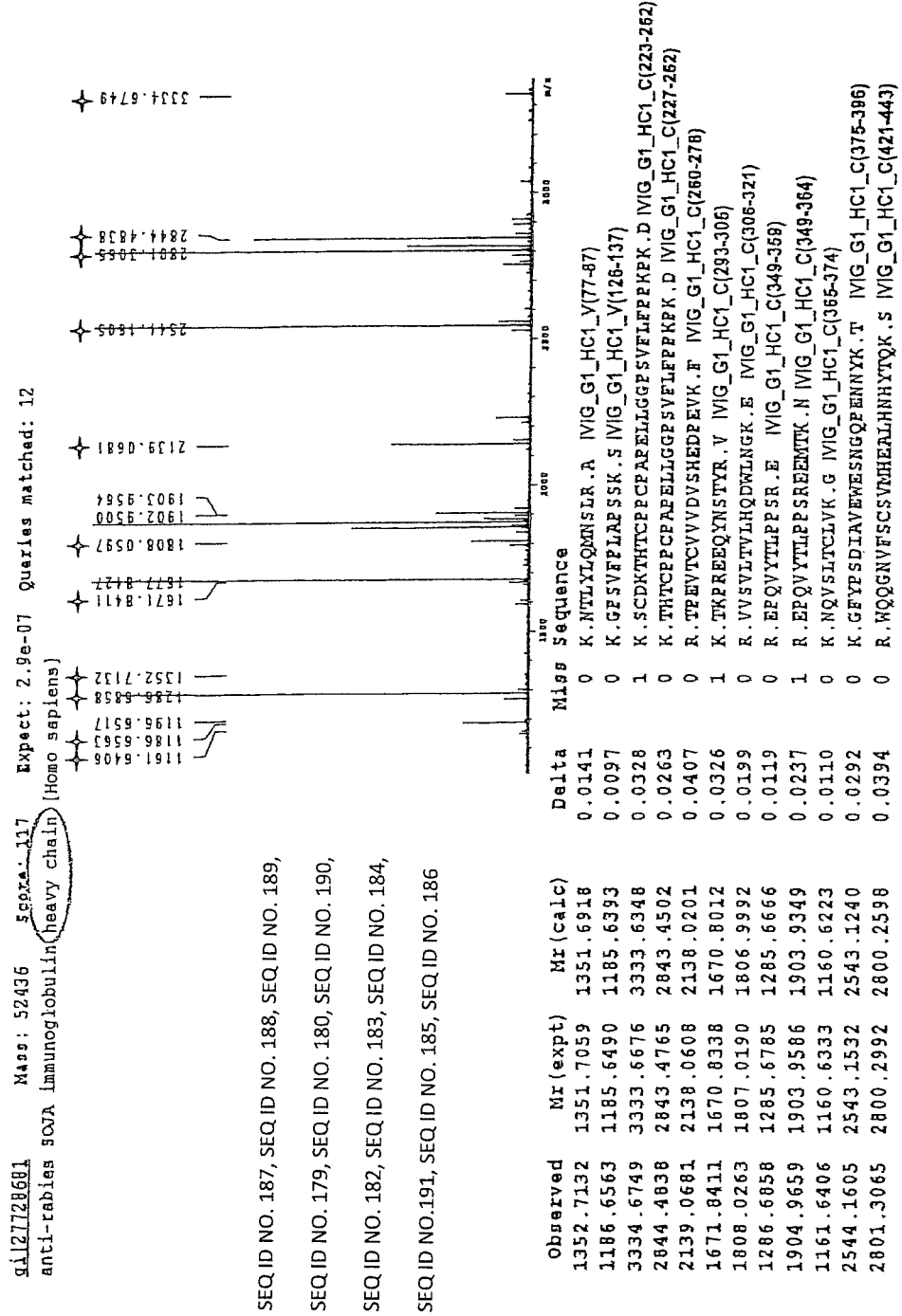
Figure 22C:
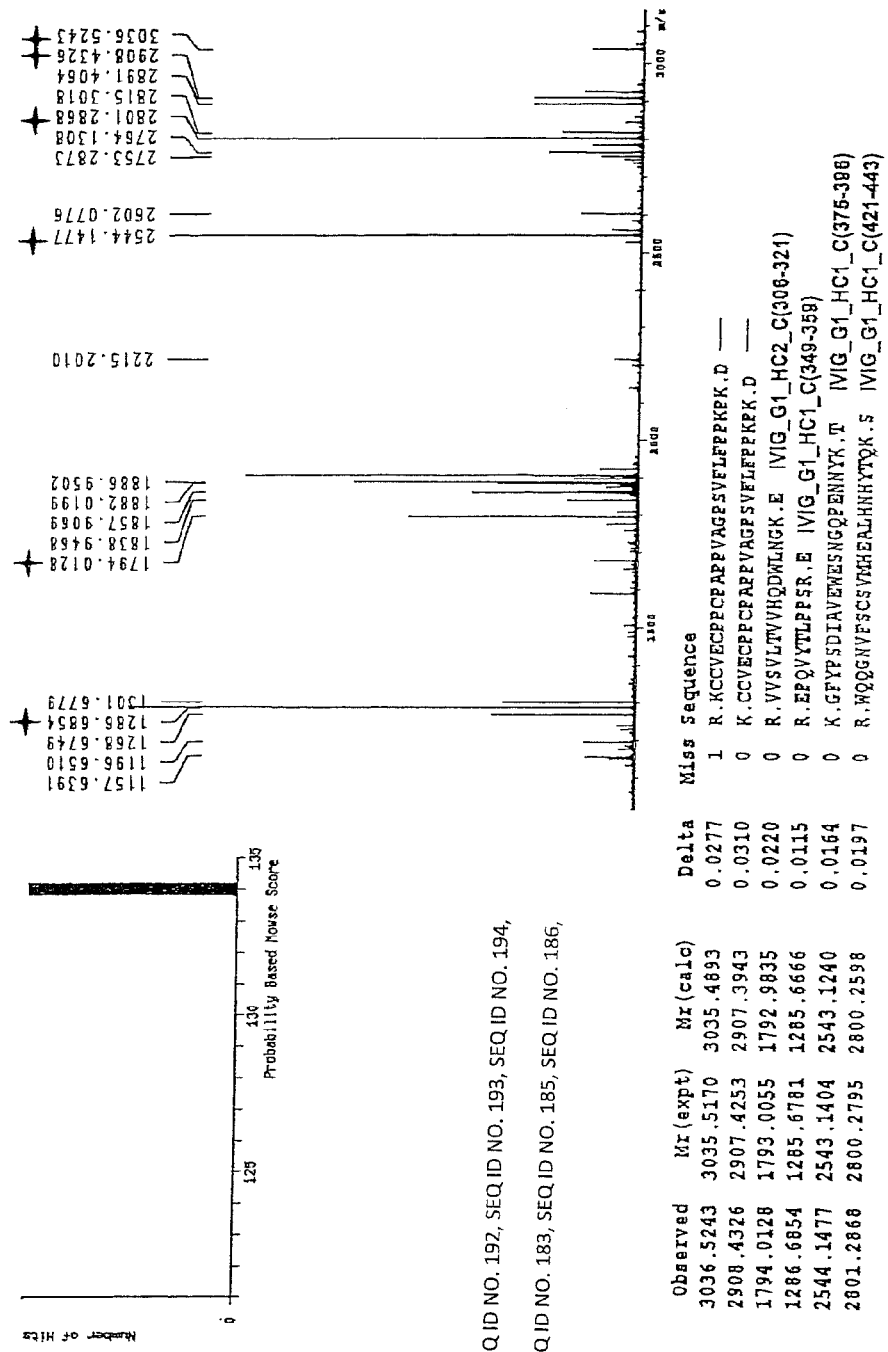

Strips placed on the vertical gels were overlayed with 1% agarose in SDS running buffer (25 mM Tris-HCl, 192 mM glycine and 0.1% w/v SDS) and subjected to electrophoresis at 25 mA/gel for 30 min and 40 mA/gel until the tacking dye reached the anodic end of gels. After separation in SDS-PAGE gels, the proteins were visualized by silver staining or by sensitive colloidal Coomassie staining and scanned using a GS-710 Calibrated Imaging Densitometer (Bio-Rad) (see FIGS. 12 and 13).

Heavy and Light Chain Isolation

Isolation of light chains and heavy chains of antibodies was made using 1D gel electrophoresis. The samples (50-200 μg) were dissolved in sample buffer (4% SDS, 25% glycerol, 50 mM Tris-buffer, 0.02% Coomassie-blue, 6 M urea, pH 6.8) with repeated agitation, sonication and centrifugation to ensure maximum solubilization of the antibodies. Reduction of the disulfide bridges was performed by reaction with dithiothreitol (DTT) at a 1000-x molar excess for 90 min at 20° C. Subsequently, alkylation of reduced cysteinyl-sulfhydryl groups was performed by reaction with a 3-x molar excess of iodoacetamide (IAA)/DTT concentration for 60 min at 20° C. ID-SDS-PAGE isolation of heavy and light chain bands was performed on a 12% acrylamide gel, using a BIO-RAD Protean-(II) Electrophoresis cell, by application of approximately 20 μg antibody per band. The PDQuest software from Bio-Rad was employed for imaging and analyzing 1-D and 2-D gels. After the gels had been stained and scanned, separate algorithms of the PDQuest software were used to reduce background noise levels, gel artifacts, and horizontal or vertical streaking from the image. The PDQuest software was then used to automatically detect the protein spots separated on 2-D gels, and for comparison of different gels. Approximately 20 bands were detected as discerned spots, of which 16 heavy chain and 15 light chain spots were analysed and identified by mass spectrometric analysis.

Figure 10:
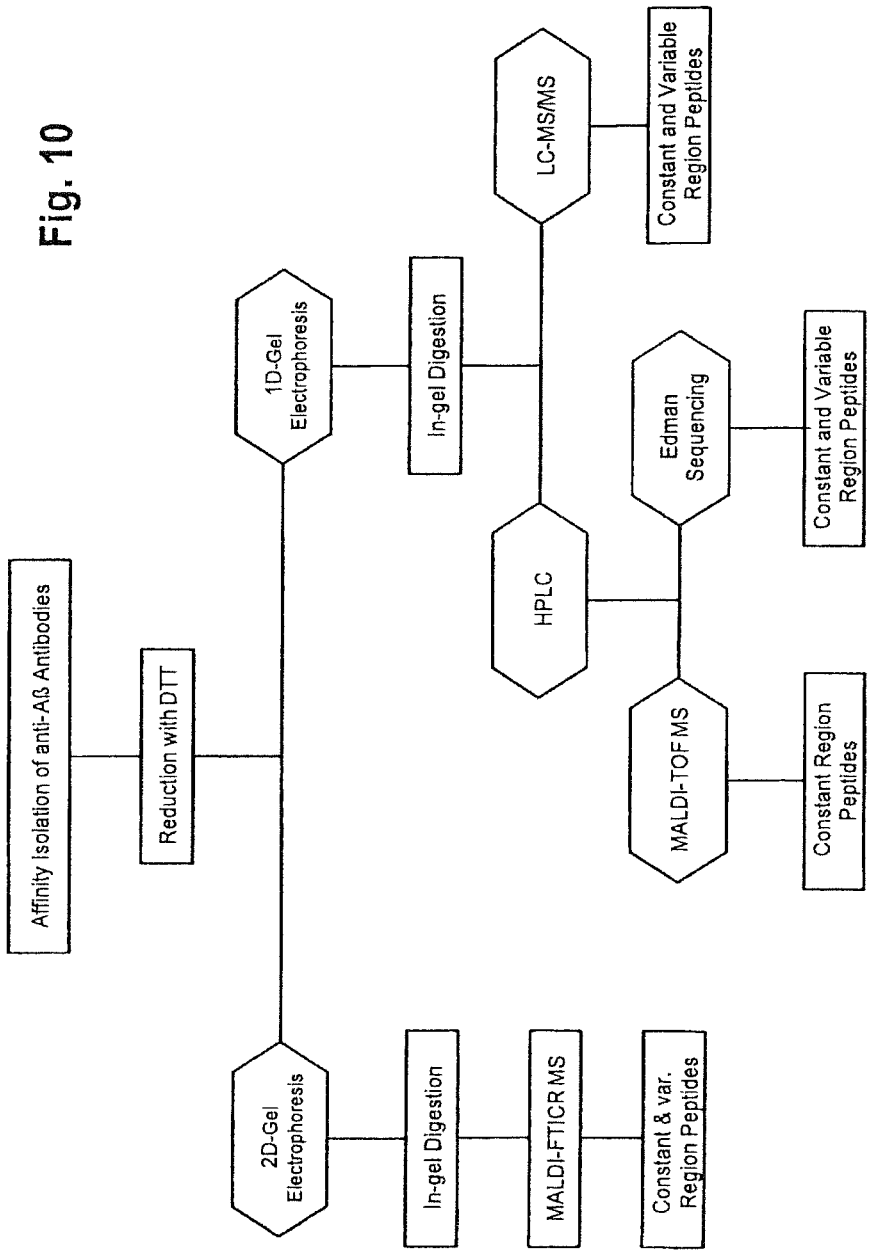
FIG. 10: Analytical scheme and experimental procedures employed for sequence determination of affinity-isolated anti-Aβ(21-37) autoantibodies: N-terminal protein sequence analysis; 2D-electrophoretic separation, in-gel proteolytic digestion and high resolution FTICR-MS identification of constant region sequences; proteolytic digestion and HPLC separation of peptide fragments, followed by a) Edman sequence determinations; b) LC-MS/MS sequence determination; c) MALDI-TOFMS identification of constant region partial sequences; MALDI-FTICR-MS identification of constant/variable partial sequences.
Figure 11:
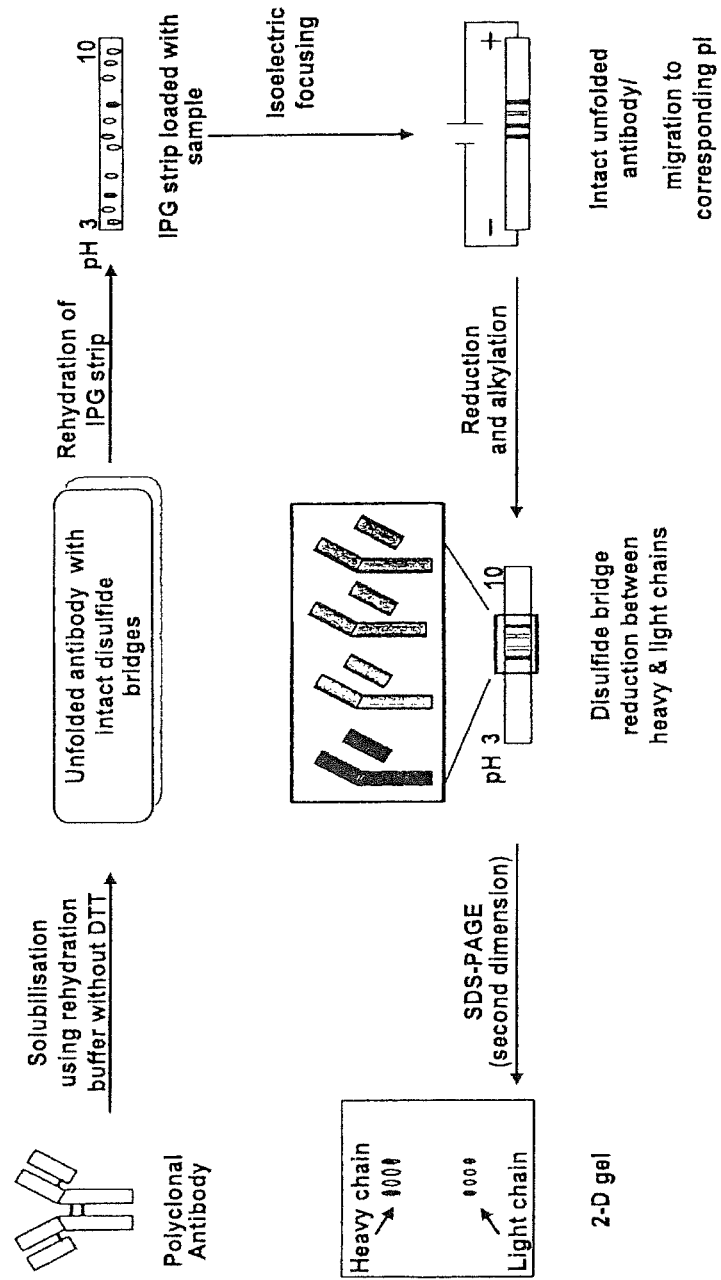
FIG. 11: Analytical scheme of experimental procedure employed for assignment of heavy- and light chain sequence pairs of serum-IVIgG anti-Aβ(21-37) autoantibodies.

E. Overview of Analytical Strategy and Methods for Sequence Determination of Anti-Aβ(21-37)-Autoantibodies The primary structure determinations of antibodies, encompassing amino acid sequences of heavy and light chains, determination and multiplicity of CDR sequences, disulfide linkages, and N-terminal sequences and their variations were performed by a combination of the following complementary and partially overlapping methods (overview in FIG. 10):

(i) Direct Edman N-terminal sequence determinations of intact proteins, heavy and light chains following 1D-electrophoretic isolation and blotting of antibody bands (N-terminus and CDR1 variable domains);
(ii) 1D-Electrophoretic separation of heavy and light chains, followed by tryptic digestion of isolated protein bands, HPLC isolation of tryptic peptides, and Edman sequence determinations of peptide fragments (variable sequences and CDR regions);
(iii) LC-ES I-MS/MS sequence determinations of proteolytic peptides isolated by HPLC, using a combination of de-novo sequencing and sequence determination from NCBI data base search procedures (variable sequences and CDR regions);
(iv) Mass spectrometric sequence assignments of proteolytic digest peptides from 2D-gel electrophoretic separations of antibody-isoforms, using high resolution MALDI-FTICR-MS in conjunction with database search; by performing two or more data base search procedures (e.g., Mascot, Profound search engines); constant domains and partially variable sequence domains;
(v) Mass spectrometric analysis of HPLC-isolated proteolytic peptides, using MALDI-TOF-MS (constant region sequences); in addition, MALDI-MS (MALDI-TOF and MALDI-FTICR-MS) of proteolytic peptide fragments without and with reduction of disulfide bridges was used for assignment and confirmation of correct disulfide linkages;
(vi) assignments of the heavy and light chain connectivities of antibody-isoforms were performed by MALDI-MS (MALDI-TOF- and MALDI-FTICR-MS) of proteolytic peptide mixtures following 2D-gel electrophoretic separation, in which the dithiothreitol (DTT) reduction step was initially omitted, providing intact disulfide-linked antibodies during the isoelectric focusing step. Disulfide reduction and alkylation was then performed in the second electrophoresis step.

F. Detailed Description of Sequences of Anti-Aβ(21-37)-Autoantibodies

Amino acid sequences were determined for anti-Aβ(21-37)-autoantibodies isolated by affinity-purification from a) serum-IVIgG, and b) serum-IgGs isolated from two healthy adult individuals (m, 30 yrs). Sequence determinations for complete antibodies, heavy and light chains, (identified with disulfide-linkages as described above) are shown with assignments of structural details in FIGS. 29, 30 and 32. In the experimental details depicted in FIGS. 25 to 30, the different complementary methods used for completing the sequence determinations by complementary and overlapping partial sequences are shown by different underlining codes for (i), Edman N-terminal protein sequence determinations; and (ii-v), sequence determinations of proteolytic peptides isolated by HPLC using Edman sequencing, LC-MS/MS, MALDI-TOF-MS and high resolution MALDI-FTICR-MS, and MALDI-FTICR-MS of proteolytic peptide mixtures upon 2D-electrophoretic isolation. Furthermore, intra-disulfide linkages of cystinyl residues and heavy chain-light chain-disulfide linkages identified at Cys-224 (HC-LC), Cys-230 and Cys-233 (HC), have been annotated in the heavy chain sequence. In addition to direct assignment of sequence positions of cysteine residues, disulfide linkages were confirmed by mass spectrometric molecular weight determinations from tryptic, non-reduced peptide mixtures (not shown), and subsequent DTT-reduced peptides, showing full agreement with homology comparison from predicted assignment of disulfide linkages from crystallographic data of a reference IgG1 structure (PDB HG, Brookhaven protein structure data base).

From the serum-IVIgG antibodies, sequences were identified for 12 heavy chain isoforms and 5 light chain isoforms of the respective variable regions; the light chain sequences comprised 4 kappa and 1 lambda chain sequences. For a major portion of the amino acid sequences, sequence data were corresponding with, and ascertaining each other by at least two complementary, overlapping partial sequence determinations. All antibody sequences were identified as $IgG_1$ subclass molecules.

Noteworthy results in the heavy and light chain sequences are the identification of several single amino acid variations in the constant domains, each of which was ascertained by several complementing mass spectrometric methods and by Edman sequencing of HLC-isolated tryptic peptides. The N-glycosylation site at N-301, was ascertained by Edman sequence determination of the tryptic peptide (297-304) (EEQYNSTYR) (SEQ ID NO: 163); this peptide provided a blank in the sequencing cycle-5. After N-deglycosylation with PNGaseF, this peptide yielded the sequence determination, N-301; furthermore MALDI-FTICR-MS analysis of the deglycosylated peptide provided identification of the correct molecular mass. In addition a non-glycosylated Fc sequence variation was identified by mutation of N301A and by the presence of partially non-glycosylated N.

Figure 25F:
FIG. 25f: amino acid sequence of light chain kappa variable region of sample IVIG_(8) (SEQ ID NO:52).
Figure 25I:
FIG. 25i: amino acid sequence of light chain kappa variable region of sample Serum_(11) (SEQ ID NO:55).
Figure 26C:
FIG. 26c: amino acid sequence of heavy chain variable region of sample IVIG_(12) (SEQ ID NO:58).
Figure 26D:
FIG. 26d: amino acid sequence of heavy chain variable region of sample IVIG_(13) (SEQ ID NO:59).
Figure 26E:
FIG. 26e: amino acid sequence of heavy chain variable region of sample IVIG_(14) (SEQ ID NO:60).
Figure 26H:
FIG. 26h: amino acid sequence of heavy chain variable region of sample IVIG_(17) (SEQ ID NO:63).
Figure 26O:
FIG. 26o: amino acid sequence of heavy chain variable region of sample Serum_(24) (SEQ ID NO:70).
Figure 26Q:
FIG. 26q: amino acid sequence of heavy chain variable region of sample IVIG_(14) (SEQ ID NO:148).
Figure 28B:
Figure 28C:
Figure 29A:
FIG. 29a: complete amino acid sequence of light chain kappa of sample IVIG_(1)_A', constant region isoform 1 (SEQ ID NO:78).
Figure 29B:
FIG. 29b: complete amino acid sequence of light chain kappa of sample IVIG_(1)_A', constant region isoform 2 (SEQ ID NO:79).
Figure 29E:
FIG. 29e: complete amino acid sequence of light chain lambda of sample IVIG_(3) (SEQ ID NO:82).
Figure 29I:
FIG. 29i: complete amino acid sequence of light chain kappa of sample IVIG_(7), constant region isoform 2 (SEQ ID NO:86).
Figure 29K:
FIG. 29k: complete amino acid sequence of light chain kappa of sample IVIG_(8), constant region isoform 2 (SEQ ID NO:88).
Figure 29I:
Figure 29O:
FIG. 29o: complete amino acid sequence of light chain kappa of sample Serum_(11), constant region isoform 1 (SEQ ID NO:92).

Variable sequences determined for light and heavy chains are summarized in FIGS. 25 and 26, comprising 12 sequence variants (heavy chain) and 5 (light chain). Sequence variations in the heavy chains were considerably more frequent than for light chains, except for the N-terminal sequences which showed several sequence variations for the light chains but complete homogeneity of the heavy chains. N-Terminal sequences were determined by a combination of direct Edman sequence analysis of proteins, Edman sequencing of tryptic N-terminal peptides, and LC-MS/MS sequencing of HPLC-isolated N-terminal peptides. A characteristic feature is the single uniform heavy chain N-terminal heavy chain (1-20), in contrast to the light chain N-terminal mutations. The N-terminal mutations of the light chains were confirmed by a blast homology search using the NCBI data base.

CDR Sequence domains determined for both heavy and light chain regions are summarized in FIG. 24 a to d. In agreement with mutations identified within the variable domains, a higher multiplicity was found for the heavy chain sequences with identifications of up to 7 CDR1, CDR2 and CDR3 sequences; while 4 and 5 sequences were determined for light chain CDR1 and CDR2 domains, and two CDR3 sequence variants. Using a stepwise examination of heavy and light chain CDRs, all CDR sequences were in agreement matching the Kabat rules (Kabat, E. A., Wu, T. T., Perry, H. M., Gottesman, K. S.& Foeller, C. (1991) Sequences of Proteins of Immunological Interest (Department of Health and Human Services, Public Health Service, National Institutes of Health, Bethesda, Md.) NIH Publ. No 91-3442 5th Ed and R. Kontermann, S. Dübel (eds.), Antibody Engineering; Springer Lab Manual Series; Springer, Heidelberg 2001). The CDR sequences identified enabled the derivation of consensus sequences.

G. Detailed Description of Experimental Procedures for Sequence Determinations i) Protein Sample Preparation for Sequence Determinations Anti-Aβ(21-37)-autoantibodies isolated from serum-IVIgG obtained as described in Example 2A were lyophilized and solubilized in denaturation buffer (6 M Urea; 50 mM Tris, pH=7.5) at a concentration of 1 μg/μL. Reduction of disulfide bridges was performed with DTT at a 1000× molar excess, for 2 hrs at 30° C. Subsequent alkylation of free thiol groups was carried out with iodoacetamide at a 3000× molar excess by reaction for 1 hr at 20° C. in subdued light. The samples were subsequently lyophilized before separation of heavy and light chains by 1D-gel electrophoresis.

ii) N-Terminal Edman Protein Sequence Analysis

Automated amino acid sequence analyses were performed with an Applied Biosystems 494 HT Procise Sequencer attached to a 140C Microgradient HPLC system, a 785A Programmable Absorbance Detector and a 610A data analysis system. All solvents and reagents used were of analytical ultragrade purity (supplied by Applied Biosystems Europe, Darmstadt, Germany).

The following reagents and materials (Applied Biosystems) were employed in all analyses: Blotting buffer: 25 mM Tris-HCl, 192 mM glycine, 0.1% SDS, 20% methanol; PVDF membrane: ProBlott, Applied Biosystems; Filter papers: GB005 (Schleicher & Schuell); Blotter: PeqLab PerfectBlue Tank-Elektroblotter Web M; staining solution: 0.1% Coomassie Blue R-250 in 50% methanol; destaining solution: 50% aqueous methanol.

The antibodies were reduced, alkylated and separated by 1D-SDS-PAGE into heavy and light chain components as described in 4). Immediately after electrophoretic separation the fresh gel was equilibrated in transfer buffer for 10 min. The PVDF membrane (10×10 cm, the size of the gel) was wetted in methanol (analytical grade, Normapur) for 1 min and then equilibrated for 20 min in the transfer buffer. Two sheets of filter paper were cut to the dimensions of the gel (10×10 cm), and filter papers were soaked in the transfer buffer.

The blotting sandwich was assembled as follows: A wet filter paper was placed onto the anode (+) side of the blotting cassette. The equilibrated PVDF membrane was placed on top of the filter paper. The equilibrated gel was placed on top of the transfer membrane. The other wet filter paper was placed on top of the gel. Care was taken not to include air bubbles between the sandwich components. The cassette was then closed and immersed into the blotting tank.

The blotting was carried out at constant current 1 mA/cm$^2$ for 4 hours. After the protein transfer was completed, the PVDF membrane was washed twice for 15 min with MilliQ water to remove the SDS and glycine. The PVDF membrane was then washed with methanol for 1 min and then stained for 1 min. The stained membrane was washed with destaining solution until the protein spots were clearly visible from the background. The membrane was then allowed to dry in air. The protein spots were excised, placed in Eppendorf tubes and stored at 4° C. Before sequence analysis the spots were washed with 100% methanol until complete destaining. The protein spots were placed in the sequencer cartridge and sequenced using the standard PL PVDF protein method (pulsed liquid sequencing method for PVDF blotted proteins, Applied Biosystems).

iii) Proteolytic Digestion of Antibodies Following Gel Electrophoretic Separation Heavy and light chains were separated by 1D-gel electrophoresis with 12% separating gel and 5% stacking gel and stained with colloidal Coomassie Blue as described in 4).

For in-gel proteolytic digestion and subsequent HPLC isolation and mass spectrometric analysis of the tryptic peptides, the gel bands were cut out and destained by addition of 60% acetonitrile in MilliQ water for 20 min at 25° C. After removal of the supernatant and lyophilization of the gel spot to dryness, 1 ml of a solution of 50 mM $NH_4HCO_3$ was added for rehydration and incubated for 20 min at 25° C. This procedure was repeated two times and the final rehydration was performed with the protease solution (12.5 ng/μl trypsin in 50 mM $NH_4HCO_3$) at 4° C. for 45 min. The gel spots were then incubated for 12 hrs at 37° C. in 1 ml 50 mM $NH_4HCO_3$ and protein fragments were eluted three times with 1 ml 60% acetonitrile in water for 1 hr. The eluates were lyophilised to dryness and solubilised immediately prior to HPLC and MS analysis.

For protein identification/sequence and data base analyses following 2D-electrophoresis, sequence determinations by LC-MS/MS and Edman N-terminal sequence determinations of proteolytic peptides, the gel spots were excised, subjected to dehydration in acetonitrile, and following removal of acetonitrile in vacuo dried in a vacuum centrifuge. Sample preparation for proteolytic digestion was performed as described above, by reduction with a volume of 10 mM dithiothreitol (DTT) in 50 mM $NH_4HCO_3$ sufficient to cover the gel pieces, and protein was performed for 1 hr at 56° C. After cooling to room temperature, the DTT-containing solution was replaced with the same volume of a solution of 55 mM iodoacetamide in 50 mM $NH_4HCO_3$. After 45 min incubation at room temperature in the dark with occasional shaking (vortexing), the gel pieces were washed for 10 min with 50-100 μL of 50 mM $NH_4HCO_3$, and dehydrated again by addition of the same volume of acetonitrile. The liquid phase was then removed and the gel pieces were completely dried in a vacuum centrifuge.

Excised gel pieces were digested with trypsin either manually or automatically using a DigestPro 96 robot (Intavis Bioanalytical Instruments, Langenfeld, Germany) according to literature procedures. For manual in-gel-digestion and subsequent mass spectrometric analysis, the spots were excised and destained by addition of 60% acetonitrile in MilliQ water for 20 min at 25° C. After removal of supernatant and lyophilization of the gel spot, a solution of 50 mM $NH_4HCO_3$ was added for rehydration and incubated for 20 min at 25° C. This procedure was repeated two times, and final rehydration was then performed for 45 min with the protease solution (12.5 ng/μl trypsin in 50 mM $NH_4HCO_3$) at 4° C. The gel spots were incubated for 12 h at 37° C. in 50 mM $NH_4HCO_3$ and proteolytic peptides were eluted for 3-4 hrs with 60% acetonitrile in water. The eluates were lyophilized to dryness and dissolved immediately before MALDI-MS analysis in 5 μl acetonitrile/0.1% trifluoroacetic acid in water (2:1).

Automated in-gel-digestion for subsequent mass spectrometric analysis was performed with a DigestPro 96 robot (Intavis Bionalytical Instruments). The DigestPro 96 is a commercial digest robot system consisting of a Gilson 221XL robot, equipped with a module containing a temperature-regulated aluminium reactor block. The block can hold up to 96 protein samples and is mounted on rails so that it can be moved by the robot arm to either a washing or a sample collection position. Protein gel pieces were excised from the 2D-PAGE gels and loaded into a clean 96 well PCR plate which contained small holes pierced into the well bottoms. The plate was covered by a silicone membrane held in place by a lid and four mounting screws. The holes in the silicone membrane allow for reagent delivery by a specially designed dispensing needle. This needle has a second, outer channel which delivers nitrogen pressure to the reaction wells. Needle positioning allows either the delivery of liquid to the vial or the ejection from the reactor by 2.6-bar nitrogen pressure. The entire in-gel digestion process, as described below, was implemented on the robot platform, and was controlled by the DigestPro 96 software (version 4.02; INTAVIS). Briefly, the gel pieces were washed four times with 50 μl of 50 mM $NH_4HCO_3$ and after each step dehydrated with 100 μl acetonitrile. After the last shrinking step, 50 μl of enzyme buffer (12.5 ng/μl trypsin in 50 mM $NH_4HCO_3$, pH ~8) were added to the tubes. The enzyme was drawn into the gel pieces for 30 min. Subsequently, 50 μl solution of 50 mM $NH_4HCO_3$ were added to cover the gel pieces, and after 6 hrs at 37° C. the peptides were extracted. The first extraction was performed with 50 μl $NH_4HCO_3$ followed by three extractions with 50 μl of 10% formic acid; between extractions, the gel pieces were dehydrated with acetonitrile as described above. The collected extracts were then dried in a vacuum centrifuge and redissolved immediately before MS analysis, in either 5 μl MALDI-MS solution (acetonitrile:0.1% trifluoroacetic acid in water, 2:1) or 5 μl ESI-MS solution (methanol:water:acetic acid, 50:48:2 (v/v/v)). For in-gel deglycosylation, the gel pieces were swollen in deglycosylation buffer, which was prepared by mixing 100 μL of a commercial N-Glycosidase F (PNGase F) preparation (Roche, Mannheim, Germany) with 100 μL of 0.1 M ammonium bicarbonate buffer to provide a final enzyme concentration of 100 units $mL^{-1}$. If all liquid was taken up by the gel pieces, further digestion buffer (but without PNGase F) was added to the sample to keep the sample wet during overnight incubation at 37° C. To avoid possible interference from PNGase F-related peptides in MALDI-MS analyses, the glycosidase was removed prior to proteolysis, by washing the gel pieces with 0.1% SDS in 0.1 M ammonium bicarbonate (four times 250 μL for 1 hr each). All washing solutions were discarded and SDS was removed by incubation with 50:45:5 (v/v/v) methanol:water:acetic acid (30 min) and three times washing using 50% acetonitrile in 0.1 M ammonium bicarbonate (30 min each). All washings were discarded, and the gel plugs then dried in a vacuum centrifuge. The same procedure was used for in-gel deglycosylation with EndoH glycosidase.

A ZipTip-cleanup procedure was then performed using ZipTip®$_{C18}$ pipette tips from Millipore (Eschbom, Germany). A ZipTip pipette tip is a microcolumn with a resin prepacked into the narrow end of a 10 μl pipette tip. ZipTip pipette tips contain $C_{18}$ or $C_4$ reversed-phase material for concentrating and purifying peptide and protein samples. ZipTip$_{C18}$ pipette tips were applied for peptides and low molecular weight proteins, while ZipTip$_{C4}$ pipette tips were applied for higher molecular weight proteins. The complete ZipTip procedure was carried out according to the instructions of the manufacturer. Briefly, it consists essentially of five steps: wetting; equilibration of the ZipTip pipette tip; binding of peptides and proteins to the pipette tip; washing; and elution.

iv) HPLC Separation and Isolation of Proteolytic Peptides

All analytical HPLC separations were performed with a BIO-RAD (Muenchen, Germany) 2700 HPLC system using a Vydac $C_4$ column (250×4.6 min I.D.) with 5 μm silica (300 Å pore size). Linear gradient elution (0 min 0% solvent B; 5 min 0% solvent B; 135 min 65% solvent B, 150 min 100% solvent B, 160 min 100% B), with eluant A consisting of 0.1% trifluoroacetic acid (TFA) in water, and eluant B of 0.1% TFA in acetonitrile:water (80:20, v/v) at a flow rate of 1 mL/min. The proteolytic peptide samples, typically 50 μg-aliquots were dissolved in 200 μL of eluant A. Detection of peptides was generally performed at 220 nm using a BIO-RAD variable wavelength absorbance detector.

v) N-terminal Edman Sequence Determinations of Proteolytic Peptides

Tryptic peptides were isolated by HPLC as described above, and lyophilized and stored at −20° C. prior to sequence analysis. The sample support used for sequence determinations consisted of a glass fibre filter (Applied Biosystems) which was treated with a 30 μL BioBrene™ Plus (Applied Biosystems) solution (100 μg/μL Biobrene and 6.66 μg/μL NaCl in water), and precycled (3 cycles) using the standard filter precycle method. For sequence analyses the lyophilized HPLC fractions were reconstituted in 15 μL 0.1% TFA, containing 20% (v/v) acetonitrile in water. The reconstituted peptide solution was applied on the precycled glass fiber filter in aliquots of 5 μl to ensure a distribution as close to the centre of the glass fiber filter as possible, each application followed by drying under a stream of Ar for 1 min.

All sequence analyses were performed on an Applied Biosystems 494 HT Procise Sequencer/140C Microgradient System with 785A Programmable Absorbance Detector and 610A Data Analysis System as described above. All solvents and reagents used were from Applied Biosystems. The general method used for the analysis of proteolytic peptides was the standard pulse-liquid method.

vi) Sequence Determinations by ESI-LC-MS/MS of Proteolytic Peptides

All sequence determinations of tryptic peptides isolated by HPLC (see above) were performed with a Bruker Esquire-3000+ ion-trap LC-MS/MS system equipped with nano-ESI/LC ion source systems (Bruker Daltonics, Bremen, Germany). HPLC fractions of proteolytic peptides were collected in 1 ml Eppendorf cups and lyophilized to dryness and stored at −20° C. until LC/MS analysis. The HPLC fractions were dissolved in 16 μl of a solvent mixture containing 1% formic acid in water:acetonitrile (9:1, v/v). The samples were sonicated for 5 min at 20° C. and centrifuged at 13 000 rpm/min for 3 min. The content of a sample was transferred into a 2 ml screw cap vial equipped with an internal microvial (0.1 ml) and placed in the LC/MS tray. A 3 μl aliquot of the sample was injected on the C-18 microcolumn by means of the automatic injection system, and an elution gradient listed in the table below (LC-MS gradient) was employed. The sample flows from the injection loop into the column and is then directed into the electrospray interface and through the ion optics into the ion trap. The total ion current (TIC) was recorded as a function of time, and is converted into the mass spectrum using the Data Analysis software (Bruker Daltonics). The most intensive ions to be used for MS/MS analysis were selected from the mass spectrum resulting from the first LC/MS run. For each precursor ion identified, a separate LC-MS/MS run was performed at identical gradient conditions (see Table). Following start of the pumping system, the isolation and fragmentation of parent ions was switched on in the Esquire Control window, using the specification of precursor mass, isolation width and fragmentation amplitude. The total ion current (TIC) corresponding to the ion fragments was recorded as a function of time; if a single parent ion was subjected to fragmentation during the run, the TIC contains a single peak. The MS/MS spectrum of the precursor ion was generated by the Data Analysis software by averaging the pulses at half peak width. The m/z values of the fragments contained in the MS/MS spectrum and their intensities were exported into a data analysis file type (wearing the extension *mgf). The file was uploaded into the MS/MS Mascot search engine for performing the NCBInr data base search, using the following search parameters: taxonomy, *Homo sapiens*; allowed missed cleavages, −1; peptide search tolerance, 2 Da; MS/MS tolerance, 0.8 Da; fixed modification, carbamidomethyl (cysteine); variable modification, Met-oxidation. The results displayed contain the Mowse probability score in fond, of a chart, providing the peptide sequence and the protein originating for each hit result. If the result for the fragment ions of a given precursor led to direct identification score of a peptide from immunoglobulin heavy- or light-chain, the peptide sequence obtained was taken to be a correct one. If no identification score was directly obtained for a given precursor and its MS/MS spectrum, the peptide sequence was ascertained by de novo sequencing, using the assignment function from the Data Analysis software. This function assigns the mass difference between two fragments into the mass for a specific amino acid. If the peptide sequence data obtained by the de novo procedure was identical with the sequence obtained by the NCBI database search, the sequence result was taken as correct. If the database search performed for a certain precursor ion did not provide any immunoglobulin peptide fragment, the corresponding precursor ion was assigned as unidentified.

Table of LC-MS/MS gradient elution parameters.

| Time (min) | Solvent A | Solvent B |
|---|---|---|
| 0 | 80 | 20 |
| 3 | 80 | 20 |
| 6 | 50 | 50 |
| 16 | 20 | 80 |
| 18 | 2 | 98 |
| 20 | 2 | 98 |
| 22 | 98 | 2 |
| 24 | 98 | 2 | vii) MALDI-TOF Mass Spectrometry of Proteolytic Peptides

MALDI-TOF MS analysis was carried out with a Broker Biflex linear TOF mass spectrometer (Bruker Daltonics, Bremen, Germany) equipped with a nitrogen UV laser ($\lambda$=337 nm), a 26-sample SCOUT source, a video system and a XMASS data system for spectra acquisition and instrument control. A saturated solution of $\alpha$-cyano-4-hydroxy-cinnamic acid (HCCA) in acetonitrile: 0.1% TFA in water (2:1 v/v) was used as the matrix. For all MALDI-MS analyses, 0.8 µL of matrix solution and 0.8 µL of the sample solution (proteolytic peptide mixture or tryptic peptides separated by HPLC) were mixed on the stainless steel MALDI target and allowed to dry. Acquisition of spectra was carried out at an acceleration voltage ($V_{acc}$) of 20 kV and a detector voltage of 1.5 kV. External calibration was carried out using the average masses of singly protonated ion signals of bovine insulin (5734.5 Da), bovine insulin B-chain oxidized (3496.9), human neurotensin (1673.9 Da), human angiotensin I (1297.5 Da), human bradykinin (1061.2) and human angiotensin II (1047.2 Da).

viii) MALDI-FT-ICR-MS of Proteolytic Peptides

MALDI-FTICR mass spectrometric analyses were performed with a Bruker APEX II FTICR instrument (Bruker Daltonics, Bremen, Germany) equipped with an actively shielded 7T superconducting magnet (Magnex, Oxford, UK), a cylindrical infinity ICR analyzer cell, and an external Scout 100 fully automated X-Y target stage MALDI source with pulsed collision gas. The pulsed nitrogen laser was operated at 337 nm.

Analyses of peptide samples were performed with a 100 mg/mL solution of 2,5-dihydroxybenzoic acid (DHB) in acetonitrile/0.1% TFA in water (2:1 v/v) used as the matrix. An aliquot of 0.5 µL of matrix solution and 0.5 µL of sample solution (tryptic peptide or peptide mixture) were mixed on the stainless steel MALDI target and allowed to dry. External calibration was carried out using the monoisotopic masses of singly protonated ion signals of bovine insulin (5730.609 Da), bovine insulin B-chain oxidized (3494.651), human neurotensin (1672.917 Da), human angiotensin I (1296.685 Da), human bradykinin (1060.569) and human angiotensin II (1046.542 Da). Acquisition and processing of spectra were performed with XMASS software (Bruker Daltonics, Bremen, Germany).

MALDI-FTICR-MS/MS analyses were performed with the Bruker ApexII FTICR-MS instrument equipped with SORI-CID (sustained-off-resonance-collision-induced—dissociation) dissociation, IRMPD (Infrared Multiphoton Photodissociation) instrumentation for fragmentation of peptide and protein ions (Damoc et al., 2003). Ions formed by MALDI ionization were trapped in the analyzer cell, and isolation of a precursor ion was performed by ejecting from the ICR cell all ions of higher and lower masses through the application of suitable excitation pulses, using the appropriate frequencies and amplitudes. The following experimental conditions were employed: correlated sweep attenuation: 8-10 dB, ejection safety belt: 500-1000 Hz. For SORI-CID, a low-amplitude rf-excitation was applied for 250 msec to the precursor ion at a frequency that is slightly off-resonance (500-1000 Hz) from the cyclotron frequency. The amplitude of the excitation was kept low so that the ion never went too far from the center of the cell. While this excitation was applied, the pressure was raised in the analyzer cell ($10^{-8}$ mbar) by admitting a collision gas (argon) through a pulse valve for 20-80 msec. Under these conditions, the precursor ion underwent many low-energy collisions, which slowly activated the ion until it reached its threshold for dissociation.

For IRMPD (infrared-multiphoton-dissociation) experiments the mass-selected ions were photodissociated using a 25 W continuous wave $CO_2$ laser (10.6 µm, Synard, Mukilteo, Wash., USA). The laser power was set to 50% threshold and the laser irradiation time to 50-200 msec.

For protein identifications and sequence determinations (constant region sequences) of proteolytic peptide mixtures following 2D-gel electrophoresis, the following (publicly available) data base search engines were employed:

Mascot—Peptide mass fingerprint and MS/MS ion search from Matrix Science Ltd., London.

ProFound—Peptide mass fingerprint from Rockefeller and New York Universities.

MS-Fit—Peptide mass fingerprint from University of California, San Francisco (UCSF).

MS-Tag—MS/MS ion search from University of California, San Francisco (UCSF).

Example 3

Determination of Dissociation Constants of Antigen-Antibody-Complexes by ELISA

The $K_d$ values were determined by a modification of the method of Kim et al. (1990). For the determinations, the antibody concentrations employed were first derived from an initial calibration curve obtained by an indirect ELISA as described in example 9B.

1) For the indirect ELISA, microliter plates were coated with 150 µL/well of streptavidin at 20° C. for 2 hrs. Wells were washed one time with 0.05% (v/v) Tween-20 detergent in phosphate-buffered saline (PBS) ($Na_2HPO_4$ 5 mM, NaCl 150 mM, pH 7.5). Biotinylated-$(G)_5$-A$\beta$(12-40) peptide at concentrations between $1\times10^{-6}$ and $10^{-8}$ M were prepared in PBS and deposited in the wells at a volume of 100 µL/well.

The wells were incubated for 2 hours at 20° C. temperature followed by a 4 times washing step and blocking with blocking buffer (BSA 5% w/v, 0.05% Tween-20 v/v in PBS) for 2 hours. Anti-Aβ(12-40) antibody was diluted to concentrations between $1.4 \times 10^{-7}$ and $10^{-9}$ M with blocking buffer and added at 100 µL/well. The microplate was incubated at 20° C. for 2 hours and then washed with Covabuffer (0.15 M PBS, pH 7.2 containing 2M NaCl, 0.083 M $MgSO_4$ and 0.05% Tween-20). The wells were incubated with peroxidase-conjugated mouse anti-human IgG (1:5.000) for 45 min at 20° C. Antibody binding was detected with a freshly prepared solution of 1,2-Phenylendiamine (OPD) containing 0.1 M citrate-phosphate, 0.1% OPD and 0.006% hydrogen peroxide. The enzyme reaction was monitored as a function of time at 450 nm, using an ELISA plate reader (Victor$^2$, Perkin Elmer Life/Analytical Sciences, Boston, Mass.). For each antibody and antigen concentration triplicate wells were prepared and measured. Direct proportionality was observed between absorbance and antibody concentration over a wide concentration range. This concentration range was used to select the initial concentration for $K_d$ determinations. The initial concentration was selected to be within the linear region of the plot of optical density vs. antibody concentration.

2) For the determination of the $K_d$ values the following conditions were applied. The antigen, Aβ(12-40) peptide at various concentrations ($1 \times 10^{-6}$ M to $4.8 \times 10^{-10}$ M) was mixed with a constant concentration of antibody derived from the preliminary ELISA calibration. The incubation was performed in 5% BSA, 0.05% Tween-20 in PBS using polypropylene test tubes to minimize antibody loss by adsorption on the microreaction tube walls. After 2 hrs, 100 µl of each mixture was transferred and incubated for 30 min into the wells of a microliter plate previously coated with biotinylated-(G)$_5$-Aβ(12-40) (1 µM) and blocked. The concentration of free antibody was then measured by indirect ELISA as described above. The IQ values were obtained by plotting the experimental data using the Sips coordinates. The following mean $K_d$ values were determined for the Aβ-antibody complexes of Aβ(12-40) peptide:

a) Affinity purified IVIgG antibodies from commercially available IVIgG preparation:
 $8 \times 10^{-9}$ M
b) Affinity purified IVIgG antibodies from Serum-A (healthy human individual; age above 30): $14 \times 10^{-9}$ M
c) Affinity purified IVIgG antibodies from Serum-B (healthy human individual; age above 30): $18 \times 10^{-9}$ M Since the range of binding/dissociation constants for the formation of Aβ-fibrils/aggregates has been estimated in the literature to be in the range of $10^{-6}$ M (determined), the binding of antibodies is determined to be specific. For IgG antibodies, typical IQ-values in the range of $10^{-8}$ to $10^{-9}$ M have been determined for a large variety of oligo- and polypeptide antigens and epitopes.

Example 4

Inhibition of plaque formation by affinity purified IVIgG Antibodies

Figure 4:
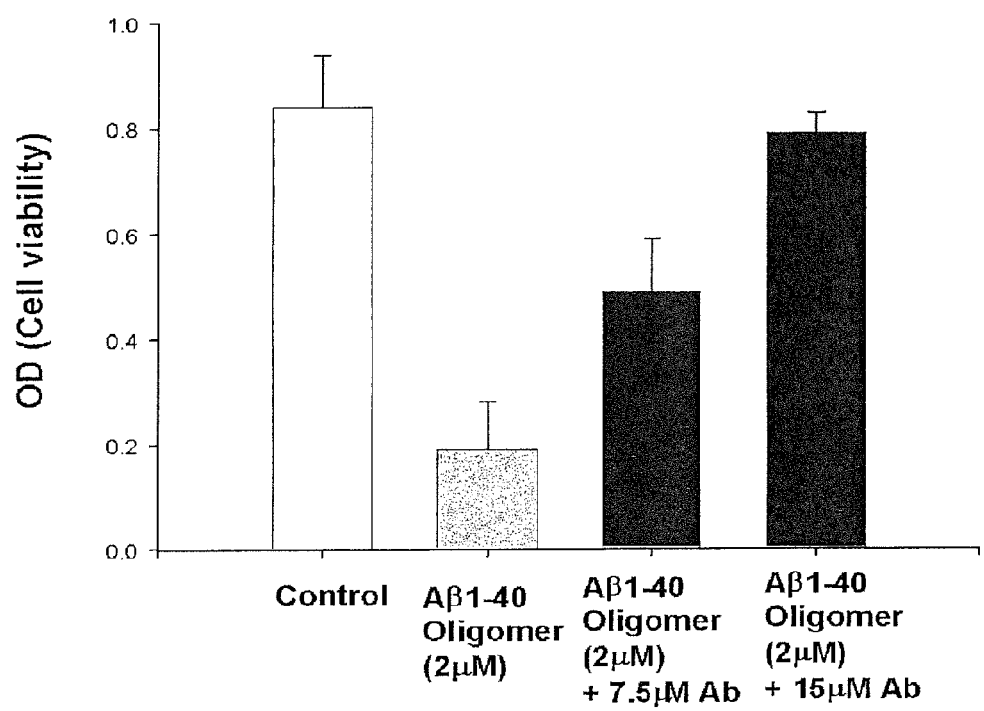
FIG. 4: Toxicity of Aβ-oligomers for human neuroblastoma cells (SH-Sy5y) in absence or presence of anti-Aβ(21-37) autoantibody as described in Example 4. OD: optical density.

Human neuroblastoma cells (SH-Sy5y) were grown in RPMI 1640-Medium supplemented with 10% fetal calf serum, 10 mM Hepes, 4 mM glutamine and penicillin (200 units/ml), streptomycin (200 µg/ml). Cells were incubated at a density of 30,000 cells/well over night in a 96-well microtiter plate. After removal of medium, cells were washed with PBS, and toxic Aβ-oligomers (2 µM final concentration) were added at a volume of 100 µl fresh medium to 7.5 µM or 15 µM of anti-Aβ(21-37)-autoantibody or without anti-Aβ(21-37)-autoantibody. The affinity purified IVIgG antibodies were obtained by purifying antibodies from commercially available IVIgG by affinity chromatography using Aβ(1-40) coupled to a gel using the coupling chemistry described in Example 2A. MTT test was performed after 4-hrs incubation. FIG. 4 shows that the Aβ-mediated toxicity (grey bars) is almost completely antagonized by affinity purified IVIgGs (black bars).

The experiment was repeated with affinity purified IVIgG (purified as described above, mab CSL Clone 7 (see Example 5). As a negative control the antibodies CSL360 (see Example 10) or no antibody was used. A positive control antibody used was ACA (see Example 10). Results as shown in FIG. 49 clearly show a dose dependent effectiveness of protecting cells from the neurotoxic effects of Aβ oligomers for both the affinity purified mab CSL Clone 7 and affinity purified IVIgG.

Soluble toxic Aβ oligomers as used in Examples 4 can be prepared by dissolving 1.0 mg Aβ in 400 µL HFIP for 10-20 min at room temperature. 100 µl of the resulting seedless Aβ solution are then added to 900 µL DD H2O in a siliconized Eppendorf tube. After 10-20 min incubation at room temperature, the samples are centrifuged for 15 min. at 14,000×G and the supernatant fraction (pH 2.8-3.5) is transferred to a new siliconized tube and subjected to a gentle stream of N2 for 5-10 min to evaporate the HFIP. The samples are then stirred at 500 RPM using a Teflon coated micro stir bar for 24-48 hr at 22° C. Aliquots (10 µl) are taken at 6-12 hr intervals for observation by atomic force microscopy or electron microscopy.

Example 5

Recombinant Expression of an Anti-Aβ(21-37) Autoantibodies

A. Mammalian Expression Vector Construction for Transient Expression

Amino acid sequences for both the light chain variable region of CSL Clone 7 (SEQ ID NO: 53) and heavy chain variable region of CSL Clone 7 (SEQ ID NO: 60) were used to synthesize cDNA constructs encoding these sequences by GENEART AG (Regensburg, Germany) The light and heavy chain cDNA constructs were also designed to contain unique flanking restriction enzyme sites to allow cloning into a mammalian expression vector upstream of the human light and heavy chain constant regions respectively. The constructs were also engineered with a Kozak translation initiation sequence, an ATG start codon and signal peptides (MESQTQVLMSLLFWVSGTCG—light chains and MGWSWIFLFLVSGTGGVLS—heavy chains) (SEQ ID NO: 164) and (SEQ ID NO: 165).

Using standard molecular biology techniques, the heavy chain variable region was cloned into the mammalian expression vector pcDNA3.1(+)-hIgG1, which is based on the pcDNA3.1(+) expression vector (Invitrogen) modified to include the human IgG1 constant region and a terminal stop codon downstream of the variable region insertion site. The light chain variable region was cloned into the expression vector pcDNA3.1(+)-hκ, which is based on the pcDNA3.1(+) expression vector modified to include the human kappa constant region and a stop codon downstream of the variable region insertion site.

CSL Clone 7 also was engineered as a "murinized" version to facilitate repetitive use in murine animal models. The heavy chain variable region was cloned into the mammalian expression vector pcDNA3.1(+)-mIgG2a, which is based on the pcDNA3.1(+) expression vector (Invitrogen) modified to include the murine IgG2a constant region and a terminal stop codon downstream of the variable region insertion site. The light chain variable region was cloned into the expression vector pcDNA3.1(+)-mκ, which is based on the pcDNA3.1 (+) expression vector modified to include the murine kappa constant region and a stop codon downstream of the variable region insertion site. Murinized CSL Clone 7 was expressed and purified as described below.

B. Cell Culture

Serum-free suspension adapted 293-T cells were obtained from Genechoice Inc. Cells were cultured in FreeStyle™ Expression Medium (Invitrogen) supplemented with penicillin/streptomycin/fungizone reagent (Invitrogen). Prior to transfection the cells were maintained at 37° C. in humidified incubators with an atmosphere of 8% $CO_2$.

C. Transient Transfection

Transient transfection of the clone 7 expression plasmids using 293-T cells was performed using 293fectin transfection reagent (Invitrogen) according to the manufacturer's instructions. The light and heavy chain expression vectors were combined and co-transfected with the 293-T cells. Cells (1000 ml) were transfected at a final concentration of $1 \times 10^6$ viable cells/ml and incubated in a Cellbag 2L (Wave Biotech/ GE Healthcare) for 5 days at 37° C. with an atmosphere of 8% $CO_2$ on a 2/10 Wave Bioreactor system 2/10 or 20/50 (Wave Biotech/GE Healthcare). The culture conditions were 35 rocks per minute with an angle of 8°. Pluronic® F-68 (Invitrogen), to a final concentration of 0.1% v/v, was added 4 hours post-transfection. 24 hours post-transfection the cell cultures were supplemented with Tryptone N1 (Organotechnie, France) to a final concentration of 0.5% v/v. The cell culture supernatants were harvested by centrifugation at 2500 rpm and were then passed through a 0.45 µM filter (Nalgene) prior to purification.

D. Analysis of Protein Expression

After 5 days 20 µl of culture supernatant was electrophoresed on a 4-20% Tris-Glycine SDS polyacrylamide gel and the antibody was visualized by staining with Coomassie Blue reagent.

E. Antibody Purification

The CSL Clone 7 monoclonal antibody was purified using protein A affinity chromatography at 4° C., where MabSelect resin (5 ml, GE Healthcare, UK) was packed into a 30 ml Poly-Prep empty column (Bio-Rad, CA). The resin was first washed with 10 column volumes of pyrogen free GIBCO Distilled Water (Invitrogen, CA) to remove storage ethanol and then equilibrated with 5 column volumes of pyrogen free phosphate buffered saline (PBS) (GIBCO PBS, Invitrogen, CA). The filtered conditioned cell culture media (1 L) was loaded onto the resin by gravity feed. The resin was then washed with 5 column volumes of pyrogen free PBS to remove non-specific proteins. The bound antibody was eluted with 2 column volumes of 0.1M glycine pH 2.8 (Sigma, Mo.) into a fraction containing 0.2 column volumes of 2M Tris-HCl pH 8.0 (Sigma, Mo.) to neutralize the low pH. The eluted antibody was dialysed for 18 hrs at 4° C. in a 12 ml Slide-A-Lyzer cassette MW cutoff 3.5 kD (Pierce, Ill.) against 5 L PBS. The antibody concentration was determined by measuring the absorbance at 280 nm using an Ultraspec 3000 (GE Healthcare, UK) spectrophotometer. The purity of the antibody was analysed by SDS-PAGE, where 2 µg protein in reducing Sample Buffer (Invitrogen, CA) was loaded onto a Novex 10-20% Tris Glycine Gel (Invitrogen, CA) and a constant voltage of 150V was applied for 90 minutes in an XCell SureLock Mini-Cell (Invitrogen, CA) with Tris Glycine SDS running buffer before being visualized using Coomassie Stain, as per the manufacturer's instructions.

The above-described techniques can be used to express and purify any of the inventive antibodies. In subsequent experiments light chain SEQ ID NOs: 47, 48, 50 to 55, and 145 to 147 were cloned into the expression vector pcDNA3.1(+)-hκ and co-transfected with heavy chain SEQ ID NOs: 56 to 71 and 148 which were cloned into the expression vector pcDNA3.1(+)-hIgG1. A total of 187 transient transfections were performed covering all possible light and heavy chain antibody pairs. The following 42 light and heavy chain antibody pairs (SEQ ID NOs) expressed sufficient antibody for purification and analysis: 47/56, 50/60, 50/61, 50/62, 50/67, 50/68, 50/69, 50/148, 51/60, 51/61, 51/62, 51/68, 51/148, 52/60, 52/148, 53/60, 53/68, 53/148, 54/60, 54/61, 54/62, 54/67, 54/68, 54/69, 54/148, 55/60, 55/61, 55/62, 55/67, 55/68, 55/69, 55/148, 145/60, 145/61, 145/62, 145/68, 145/148, 146/60, 146/61, 146/62, 146/68 and 146/148.

Such methods can also be employed to produce fully human anti-β amyloid antibodies comprising selected individual sequences based on the consensus sequences of the respective CDRs, such as SEQ ID NOs: 6 to 11 and SEQ ID NOs: 153 to 161, or the single sequences of the respective CDRs, such as (a) for CDR I of the heavy chain SEQ ID Nos: 13 to 20, b) for CDR2 of the heavy chain SEQ ID NOs: 21 to 27, c) for CDR3 of the heavy chain SEQ ID NOs: 28 to 32, d) for CDR1 of the light chain SEQ ID NOs: 33 to 37, e) for CDR2 of the light chain SEQ ID NOs: 38 to 43 and SEQ ID NO: 53, f) for CDR3 of the light chain SEQ ID Nos: 44 to 46, g) for the variable heavy chain SEQ ID NOs: 56 to 71 and h) for the variable light chain SEQ ID NOs: 47 to 55.

For use as a control antibody (ACA) in our studies we also cloned the light and heavy chain variable region sequences of the humanized 266 antibody which is known to bind an epitope contained within position 13-28 of the amyloid beta peptide. These sequences were obtained from the U.S. Pat. No. 7,195,761 B2. Specifically the genes for the humanized light chain variable region of 266 (U.S. Pat. No. 7,195,761 B2, SEQ ID NO: 11) and the humanized heavy chain variable region of 266 (U.S. Pat. No. 7,195,761 B2, SEQ ID No:12) were synthesized, cloned into expression vectors, transiently expressed and purified using the above-described methods.

Example 6

Binding of a Recombinantly Expressed Anti-Aβ(21-37)-Autoantibody CSL Clone 7 and Affinity Purified IVIgG to Oligomeric Forms of Aβ

A synthetic amyloid beta 1-40 peptide (PSL GmbH Heidelberg) containing an additional cysteine at the amino terminal (Aβ1-40.Cys) was analyzed in an immunoprecipitation assay against anti-Aβ(21-37) monoclonal antibody (mab) CSL Clone 7 and against affinity purified IVIgG as described in example 4. PBS was employed as a negative control.

Specifically, it was evaluated whether mab CSL Clone 7 would immunoprecipate the synthetic peptide in a monomer or an oligomer form. The peptide, resuspended (1 mg/ml) in phosphate buffered saline (PBS: 10 mM sodium phosphate, 150 mM NaCl, pH 7.4) was used immediately (0 h) or subjected to oligomerisation (15 h) at 37° C., 900 rpm and stored at −80° C. in small aliquots until use. For the immunoprecipitation, aliquots of 30 µl of Protein-G beads (GE Healthcare) were incubated with 5 µg antibody mab CSL Clone 7 or 5 µg anti-Aβ(21-37) autoantibodies purified according to example 2 (Aβ1-40 column, 2 µg Aβ1-40.Cys and 1.5 ml PBS over night at 4° C. Immobilized antibody/peptide were collected. After washing (five times) with PBS, the peptide was eluted by adding 1× non-reducing NuPAGE LDS Sample Buffer (Invitrogen) for 10 min at 95° C. Protein separation was done by electrophoresis on NuPAGE 4-12% Bis-Tris Gels (Invitrogen) and western transfer on nitrocellulose membranes by wet blot according to the supplier (Invitrogen). Membranes were blocked with 1× Roti-Block (Roth) and then successively incubated with the first antibody, 1:6000 Bam90.1 (anti-Aβ) (Sigma) and secondary antibody, goat anti-mouse HRP conjugated (Pierce). A SuperSignal West Dura Extended Duration Substrate (Thermo Scientific/Pierce) was used as chemiluminescent substrate.

The results show that mab CSL Clone 7 (see FIG. 33) and affinity purified IVIgG (see FIG. 37) bind oligomeric forms of Aβ1-40. In particular, mab CSL Clone 7 or affinity purified IVIgG co-incubated either with monomeric (0 h) or oligomeric (15 h) forms of Aβ1-40, Cys precipitated oligomeric forms of the peptide. More results on binding to oligomeric forms of Aβ can be found in Example 12D.

Example 7

Peptide Synthesis

Peptides Biotin-$G_5$-FAEDVGSNKGA-$NH_2$ (Biotin-$G_5$-Aβ20-30) (SEQ ID NO: 166) and Biotin-$G_5$-FAEDVGSNK-GAIIGLMVG-$NH_2$ (Biotin-$G_5$-Aβ20-37) (SEQ ID NO: 167) were synthesized by solid-phase peptide synthesis (SPPS) on a NovaSyn TGR resin, containing a polystyrene-polyethyleneglycol resin and Rink-amide-linker cleavable under acidic conditions, according to commercially available material and published literature procedures. 9-Fluorenyl-methoxycarbonyl/t-butyl (Fmoc/tBu) chemistry was used throughout for synthesis using a semi-automated Economy Peptide Synthesizer EPS-221 (ABIMED, Germany). The following side-chain protected amino acid derivatives were used: Fmoc-Lys(Boc)-OH, Fmoc-Asn(Trt)-OH, Fmoc-Ser (tBu)-OH, Fmoc-Asp(OtBu)-OH, Fmoc-Glu(OtBu)-OH.

The synthesis was performed according to the following general protocol: (i) DMF washing (3×1 min), (ii) Fmoc deprotection with 2% DBU, 2% piperidine in DMF (15 min), (iii) DMF washing (6×1 min), (iv) coupling of 5 equiv of Fmoc amino acid:PyBOP:NMM in DMF (40-60 min), (v) DMF washing (3×1 min) For the synthesis of Aβ (20-37) which has a hydrophobic C-terminal part, double coupling of each amino acid was employed. The biotinylation of the N-terminus was carried out on the resin using D-(+)-Biotin. After completion of the syntheses, the peptides were cleaved from the resin using a TFA, triethylsilane and deionized water mixture (95:2.5:2.5, V/V/V) for 3 h at room temperature. The synthetic peptides were used for example in ELISAs.

Example 8

Amino Acid Sequencing of Aβ(21-37)

Sequence determination of all epitopes either identified (isolated Aβ epitopes Aβ(4-10) and Aβ(21-37)) or used (e.g. synthetic Aβ(21-37)) was carried out by means of
a) Edman sequencing;
b) ESI-Tandem MS/MS-sequencing, and
c) FTICR-MS analysis and fragmentation by means of IRMPD-Fragmentation.

Automated amino acid sequence analysis was performed on an Applied Biosystems Model 494 Procise Sequencer attached to a Model 140C Microgradient System, a 785A Programmable Absorbance Detector and a 610A Data Analysis System.

All solvents and reagents used were of highest analytical grade purity (Applied Biosystems). The sequencing method used was pulsed liquid. Lyophilized samples were dissolved in 10 μL 0.1% To assure a distribution as close to the centre of the glass fiber filter as possible, the sample was applied in aliquots of 2 μL, each application followed by drying under a stream of argon.

Example 9

ELISAs

ELISAs were used for the determination of:
(a) plaque-specific anti-Aβ(4-10) antibodies in the anti-Aβ autoantibodies mixture separated from IVIgG
(b) binding of anti-Aβ autoantibodies from human serum to Aβ(21-37) peptide, Aβ(12-40) peptide, and Aβ(1-40) peptide
(c) binding of anti-Aβ autoantibodies separated from IVIgG and from individual human sera (AD serum and healthy individuals serum) to Aβ(1-40) peptide and to Aβ(21-37) epitope peptide
(d) binding of a recombinantly expressed Aβ(21-37) autoantibody (CSL Clone 7) to Aβ partial sequences A. ELISA for Aβ(4-10) Antibodies In this experiment a standard dilution of the antibody (anti-Aβ antibodies isolated from IVIgG using a Cys-Aβ(1-40) antigen column) was used in combination with 12 serial dilutions of Biotin-GSAβ(4-10) peptide, used as coating antigen. 96-well ELISA plates were coated with 150 μL/well streptavidin solution (c=5 μg/mL in PBS) for 2 hours at room temperature. After washing the wells four times with PBS-T (0.05% Tween-20 v/v in PBS, pH=7.5), 100 μL/well of biotinylated epitope peptides (12 serial dilutions from 50 μM to 0.024 μM in PBS, pH=7.5) was added and incubated for 2 hours at room temperature. After that, the plates were washed four times with 200 μL/well PBS-T and the non-specific adsorption sites were blocked with 5% BSA, 0.05% Tween-20 in PBS (200 μL/well, 2 h incubation at RT). Then, 100 μL/well of the anti-Aβ autoantibodies isolated from IVIgG (1:150 dilution prepared in 5% BSA, 0.05% Tween-20 in PBS) was added to each well. Thereafter, the plates were incubated at room temperature for two hours and subsequently washed six times with PBS-T. 100 μL of peroxidase goat anti-human IgG diluted 5000 times in 5% BSA, 0.05% Tween-20 were added to each well and the plates were incubated at room temperature for one hour, then they were washed three times with PBS-T and once with 0.05 M sodium phosphate-citrate buffer, pH=5. 100 μL of o-phenylenediamine dihydrochloride (OPD) in substrate buffer (phosphate-citrate) at c=1 mg/mL with 2 μL of 30% hydrogen-peroxide per 10 mL of substrate buffer were added. The absorbance at 450 nm was measured on a Wallac 1420 Victor2 ELISA Plate.

B. Antibody Determination in Human Serum by Indirect ELISA 96-well ELISA plates were coated with 100 μL/well of Aβ(1-40) peptide (c=2.5 μg/mL in PBS buffer, pH 7.5) for 2 h at room temperature. Thereafter, the plates were washed four times with 200 μL/well of washing buffer (PBS-T; PBS with 0.05% Tween-20) and blocked for 2 h at room temperature with blocking buffer (5% BSA, 0.1% Tween-20 in PBS). After two times washing with PBS-T, the sera were added at an initial dilution of 1:33.3, then diluted 3 fold serially in blocking buffer and incubated for 2 h at room temperature.

Figure 8:
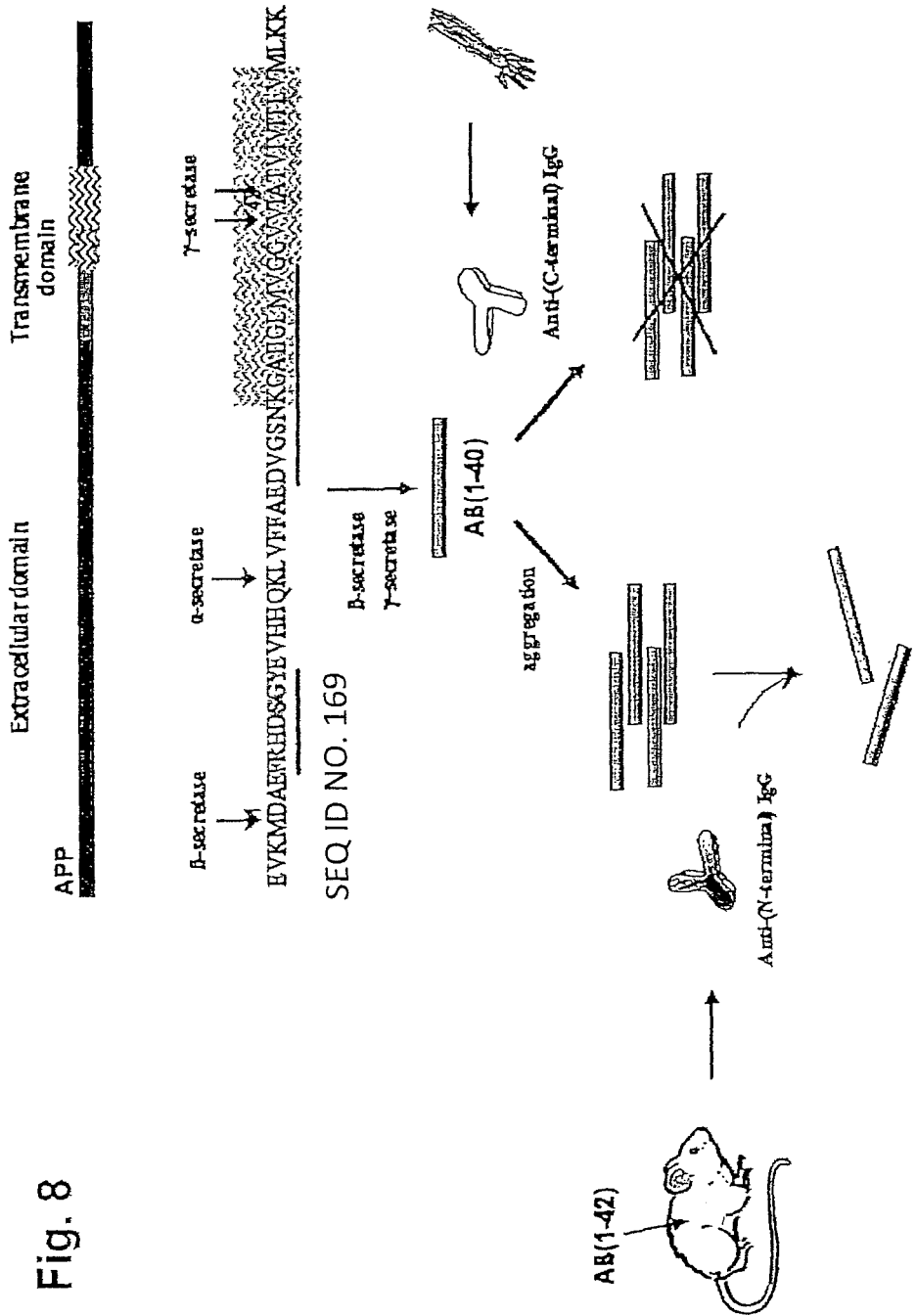
FIG. 8: Molecular recognition mechanism of plaque-specific, plaque-disaggregating Aβ-antibodies recognizing the Aβ(4-10) epitope, and the anti-Aβ(21-37)-autoantibodies recognizing the Aβ(21-37) carboxyterminal epitope.

Then, the plates were washed eight times with PBS-T and goat anti-human IgG conjugated with horseradish peroxidase diluted 1:5000 in blocking buffer was added to the plates and incubated for 1 h at RT. The plates were washed four times with PBS-T and two times with 0.05 M sodium phosphate-citrate buffer, pH=5. 100 μL of o-phenylenediamine dihydrochloride (OPD) in substrate buffer (phosphate-citrate) at c=1 mg/mL with 2 μL of 30% hydrogen-peroxide per 10 mL of substrate buffer were added. The absorbance at 450 nm was measured on a Wallac 1420 Victor2 ELISA Plate. Aβ-antibody quantifications were performed with a 1 μg/μl stock solution, using a BSA reference curve for calibration using the commercial protein quantification kit Pierce micro-BCA. The results obtained are illustrated in FIG. 8. The percentage given illustrates the Aβ-antibody concentrations in IVIgG from two separate ELISA determinations. Similar results were obtained with the Aβ(21-37) affinity chromatography. To the contrary, affinity chromatography with Aβ(4-10) peptide yielded no detectable amounts of polypeptides binding to the N-terminal epitope. Consequently, the results obtained with Aβ(1-40) are equivalent to those obtained with Aβ(21-37) for healthy individuals.

C. Binding of Anti-Aβ Autoantibodies Isolated from IVIgG and from Individual Human Serum to Aβ1-40 Peptide 96-well ELISA plates were coated with 100 μL/well of Aβ1-40 peptide (c=2.5 μg/mL in PBS buffer, pH 7.5) for 2 h at room temperature. Thereafter, the plates were washed four times with 200 μL/well of washing buffer (PBS-T; PBS with 0.05% Tween-20) and blocked for 2 h at room temperature with blocking buffer (5% BSA in PBS). After washing the plates two times with 200 μl/well of PBS-T, 100 μL/well of the 1$^{st}$ antibody (polyclonal anti-Aβ autoantibodies isolated from IVIgG or from individual human serum) (8 serial dilutions prepared in blocking buffer; dilutions from 1:250 to 1:32000) was added and incubated for 2 h at room temperature. Then, the plates were washed four times with 200 μL/well of PBS-T and the 2$^{nd}$ antibody (HRP-goat anti-human IgG; c=1 μg/μL) diluted 2000 times in blocking buffer was added (100 μL/well; 2 h incubation at room temperature). After washing the plates three times with 200 μL/well of PBS-T and once with 200 μL/well of citrate-phosphate buffer, pH=5, 100 μL of o-phenylenediamine dihydrochloride (OPD) in substrate buffer (phosphate-citrate) at c=1 mg/mL with 2 μL of 30% hydrogen-peroxide per 10 mL of substrate buffer were added. The absorbance at 450 nm was measured on a Wallac 1420 Victor$^2$ ELISA Plate.

D. Binding of a Recombinantly Expressed Aβ(21-37) Autoantibody (CSL Clone 7) to Aβ Partial Sequences Peptides Biotin-G$_5$-Aβ(1-40), Biotin-G$_5$-Aβ(12-40) and Biotin-Gs-Aβ(4-10) were compared for binding to a recombinantly expressed Aβ(21-37) autoantibody (CSL Clone 7) by the following indirect ELISA: 96-well ELISA plates were coated with 150 μL/well streptavidin solution (c=2.5 μg/mL in PBS pH7.4) for 2 hours at room temperature. After washing the wells four times with 200 μL/well PBS-T (0.05% Tween-20 v/v in PBS, pH=7.4), 100 μL/well of biotinylated epitope peptides 1 μM in PBS, pH=7.5) were added and incubated for 2 hours at room temperature. After that, the plates were washed four times with 200 μL/well PBS-T and the non-specific adsorption sites were blocked with 5% BSA, 0.1% Tween-20 in PBS (200 μL/well, over night at RT). Then the plates were washed once with 200 μL/well with PBS-T. Then, 8 serial dilutions of CSL Clone 7 prepared in 5% BSA, 0.1% Tween-20, 1% DMSO in PBS) were added to the wells. Thereafter, the plates were incubated at room temperature for two hours and subsequently washed six times with PBS-T. 100 μl, of peroxidase goat anti-human IgG diluted 5000 times in 5% BSA, 0.1% Tween-20 were added to each well and the plates were incubated at room temperature for one hour, then they were washed three times with 200 μL/well PBS-T and once with 0.05 M sodium phosphate-citrate buffer, pH=5. 100 μl of o-phenylenediamine dihydrochloride (OPD) in substrate buffer (phosphate-citrate) at c=1 mg/mL with 2 μL of 30% hydrogen-peroxide per 10 mL of substrate buffer were added. The absorbance at 450 nm was measured on a Wallac 1420 Victor$^2$ ELISA Plate. Background signals of the assay were measured with antibody dilutions incubated in wells lacking the biotinylated peptides.

The recombinantly expressed anti-Aβ(21-37) autoantibody CSL clone 7 (see Example 5) was evaluated as described above using Biotin-G$_5$-Aβ(1-40), Biotin-G$_5$-Aβ(12-40) and Biotin-G$_5$-Aβ(4-10). FIG. 39 shows that CSL clone 7 binds to Aβ(1-40) and Aβ(12-40) but not to Aβ(4-10).

Example 10

Prevention of Fibril Formation by the Antibodies of the Invention 1 mg of Aβ1-40 (PSL Heidelberg) was dissolved in a LoBind tube (Eppendorf) with 100 μl trifluoroacetic acid 0.1% (TFA) and incubated for 1 hour at room temperature. The solution was diluted with PBS to 1 mM Aβ1-40. To 100 μl Aβ fiber formation sample, the antibodies were added to a final concentration of 1.3 μM.

The following antibodies were examined:
affinity purified IVIgG as described in Example 4
recombinant antibody CSL Clone 7 (as described in example 5)
antibody ACA (U.S. Pat. No. 7,195,761 B2)
negative control CSL360 (CSL360 is a chimeric antibody and shows no binding to Aβ(1-40) when tested using biosensor or ELISA analysis)

The incubation was carried out overnight at 37° C. on a heating block. A 2.5 mM Thioflavin T (THT) solution in Glycine buffer pH 9.2 was prepared. The 100 μl Aβ fiber formation sample was transferred into a black –96 well plate (Greiner), and 50 μM THT was added. The fluorescence (excitation 450 nm emission 490 nm) of the samples was measured after 24 hour with a Tecan InfiniTE M200 plate reader. One measurement represents the average of 25 flashes.

As shown in FIG. 40, all tested Aβ antibodies showed an inhibition of fibrilization by about 20% as compared to the negative control.

Example 11

Assay Binding of Sera from an AD Patient and an Age Matched Healthy Control

A: Dot Blot

Dot blots of Aβ$_{1-15Cys}$- and Aβ$_{1-40Cys}$-, (both peptides do have a cysteine do have at the N-terminus) freshly resuspended in PBS buffer (sample-0 h) or subjected to oligomerisation (sample-15 h) were applied on nitrocellulose membrane (0.5 μg/3 μl spot).

The membranes were blocked with Roti-Block (Roth) for 1 h at room temperature and then incubated with 10 μg primary antibody (6E10, Bam90.1, IVIG, CSL-7, ACA), an AD-serum (AD1) and a serum (K4) from a healthy human individual) in 20 ml blocking reagent (RotiBlock) over night at 4° C. Incubation with secondary antibodies (anti-human HRP: 1:100,000; anti-mouse HRP: 1:6,000) was done for 1 h at room temperature. A SuperSignal West Dura Extended Duration Substrate (Thermo Scientific/Pierce) was used as chemiluminescence substrate according to the instructions of the manufacturer. The signal on X-ray films was recorded for 10 s-5 min.

As shown in FIG. 41 all control antibodies showed specificity to the expected epitope (6E10=Aβ(1-17), Bam90.1=Aβ (13-28)). Purified antibodies CSL Clone7, anti Aβ(21-37) autoantibodies (purified according to example 4), ACA (see example 5), but also antibodies from the AD serum and the healthy individual bind to Aβ$_{1-40}$ oligomers (sample 15 h). Only 6E10 and the AD-serum bound to Aβ 1-15 but not the control sera of the healthy patient.

Also, CSL Clone 7 and Aβ(21-37) autoantibodies purified from IVIgG as described in Example 4 exhibited preferential binding to aggregated/oligomeric forms of Aβ (Aβ(1-40) 15 h as opposed to Aβ 1-400 h). By comparison, the control antibodies 6E10, Bam90.1 and ACA showed no such preference, binding instead equally to both species of Aβ.

TABLE 1

Summary data of the Dot Blot analysis

| Peptide | 6E10 | Bam90.1 | CSL-Clone 7 | Affinity purified IVIgG | ACA | serum AD1 | serum K4 |
|---|---|---|---|---|---|---|---|
| Aβ 1-40, 0 h | ++ | ++ | (trace) | – | ++ | – | – |
| Aβ 1-40, 15 h | ++ | ++ | +++ | ++ | ++ | +++ | +++ |
| Aβ 1-15, 0 h | ++ | – | – | – | – | ++ | – |
| Aβ 1-15, 15 h | ++ | – | – | – | – | ++ | – |

B: ELISA

IgG from serum samples (AD1 and an age matched healthy human individual, see above in Example 11A) after purification on Protein G (Pierce) according to the instructions of the manufacturer were loaded on an Aβ(1-16) affinity column (prepared according to Example 1), washed with PBS and 10 mM sodium phosphate pH 6.8 and eluted with 100 mM Glycine pH 2.8.

The eluate was analyzed in an ELISA on Biotin-G$_5$-Aβ(4-10) coated plates as described in Example 9D.

Figure 42:
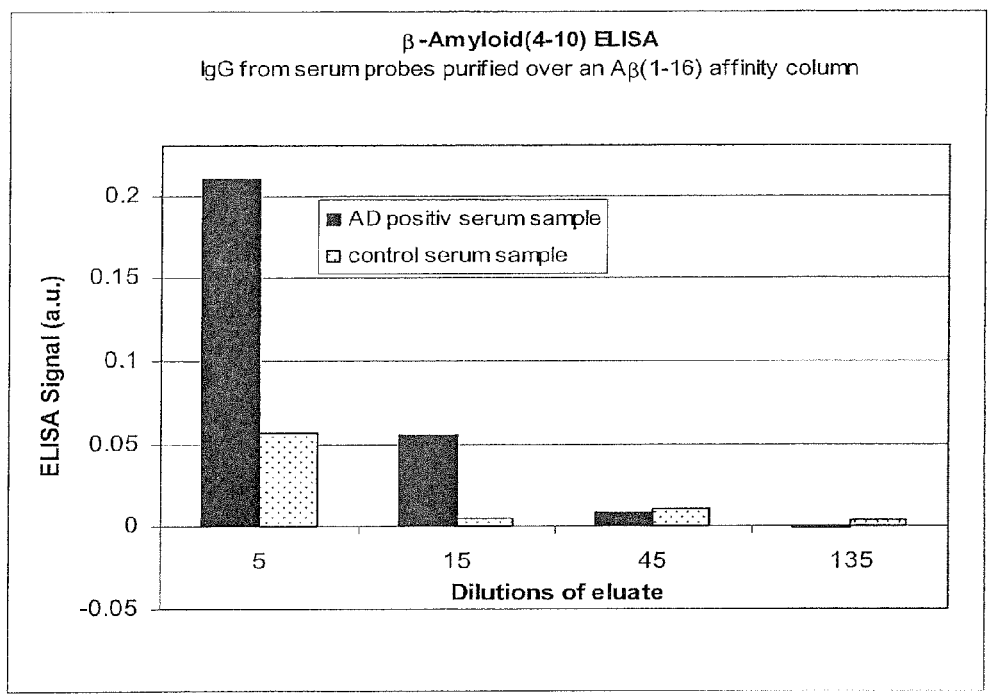

The result shows a higher titer of Aβ(4-10) antibodies in the serum of the AD patient as compared to the signal detected for the control sample from an age matched healthy human individual (see FIG. 42).

Results represent an early experiment which suggests, at least for the single AD1 serum tested, that Aβ(4-10) autoantibodies are present but either in low amount, of low affinity, or possible both. If these results are verified, they indicate that ultra-sensitive assay procedures will be required to permit the procedure to become routine.

Example 12

Binding Characteristics of Recombinantly Expressed Aβ(21-37) Autoantibodies in ELISA, Biacore and Western Blot

TABLE 2

Binding characteristics of recombinantly expressed Aβ(21-37) autoantibodies in ELISA and Biacore

| ANTIBODY | EIA | BIACORE | WESTERN BLOT ANALYSIS |
|---|---|---|---|
| ACA (# 80) | ++++ | ++++ | Binds to all species |
| 53/60 (# 92) | ++++ | ++++ | Dimer binding |
| 53/60 (# 93) | ++++ | ++++ | Dimer binding |
| 50/60 | + | +++ | nt |
| 50/61 | + | ++ | nt |
| 50/62 | – | – | nt |
| 50/67 | – | – | nt |
| 50/68 | – | – | nt |
| 50/69 | – | nt | nt |
| 50/148 | – | + | nt |
| 47/56 | – | – | nt |
| 51/60 | ++++ | +++ | Dimer binding |
| 51/61 | + | + | nt |
| 51/62 | – | – | nt |
| 51/68 | – | + | nt |
| 51/148 | + | + | nt |
| 52/60 | ++++ | ++++ | Dimer binding |
| 52/148 | + | ++ | nt |
| 53/68 | – | – | nt |
| 53/148 | ++++ | ++++ | nt |
| 54/60 | ++ | +++ | nt |
| 54/61 | ++ | ++ | Dimer binding |
| 54/62 | – | – | nt |
| 54/67 | – | No capture | nt |
| 54/68 | – | – | nt |
| 54/69 | – | No capture | nt |
| 55/60 | + | ++ | nt |
| 55/61 | +++ | +++ | Dimer binding |
| 55/62 | – | – | nt |
| 55/67 | – | No capture | nt |
| 55/68 | – | – | nt |
| 55/69 | – | – | nt |
| 55/148 | + | + | nt |
| 145/60 | +++++ | ++++ | nt |
| 145/61 | – | – | nt |
| 145/62 | +++ | + | nt |
| 145/68 | – | – | nt |
| 145/148 | ++ | ++ | nt |
| 146/60 | ++++ | ++++ | nt |
| 146/61 | ++ | ++ | nt |
| 146/62 | + | – | nt |
| 146/68 | +/? | – | nt |
| 146/148 | + | +++ | nt |
| 54/148 | ++ | + | nt |

+/– qualitative assessment of ELISA and biosensor binding where increasing (+) indicates increase binding titre on ELISA and on biosensor indicates an improvement on either off-rate or on rate that would suggest an antibody with comparative higher affinity
(–) indicates either no binding by antibodies to immobilised antibodies
nt denotes not tested All transfectants that expressed immunoglobulin efficiently were tested in an ELISA based on binding to amyloid β peptide. Biosensor data is ranked on a qualitative affinity binding assessment of the antibody to the cys-dimer peptide as described below.

Antibodies which are expressed in high quantities and show binding in ELISA or Biacore or Western blot are preferred embodiments of the invention. A failure to express in high quantity or non-binding in any of the assays described below does not necessarily mean that these antibodies would not be functional if either expression would be improved or more sensitive detection methods were be employed.

A: Aβ Peptide Preparation

Lyophilized 1 mg Aβ(1-40) peptide (Sigma) was resuspended in 200 µl. 1,1,1,3,3,3-hexafluoro-2-propanol (HFIP) (Sigma), aliquoted into 1.5 ml Eppendorf tubes and lyophilized overnight. The aliquoted Aβ(1-40) peptide was resuspended at 1 mg/ml with dimethyl sulphoxide (DMSO, ICN) and stored at 4° C. This material is referred to as Aβ1-40 monomer.

To oligomerize the Aβ(1-40) peptide the Aβ(1-40) monomer was diluted to 0.1 mg/ml in 1×PBS (137 mM NaCl, 10 mM phosphate, 2.7 mM KCl) and incubated for 3 to 6 days at 37° C. and then stored at 4° C., this material is referred to as Aβ(1-40) oligomer.

Aβ(1-40) peptide with an N-terminal cysteine residue (Aβ (1-40 Cys)) was resuspended from a lyophilized state in ddH2O at 5.9 mg/ml and stored at −80° C. The Aβ(1-40 Cys) peptide was then diluted to 0.1 mg/ml in 1×PBS and stored at 4° C., this material is referred to as Aβ(1-40 Cys) oligomer.

B: Anti-Beta Amyloid Antibody ELISA Protocol

Aβ(1-40) monomer, Aβ(1-40) oligomer, Aβ(1-40 Cys) oligomer, and control plate using bovine serum albumin (Sigma) or Aprotinin (Sigma) were immobilized at 1 µg/ml in PBS (50 µl per well) on a Nunc Maxisorb 96-well plate overnight at 4° C. Wells were washed once with 350 µl Wash Buffer (1×PBS, 0.05% (v/v) Tween-20 (Sigma)). Wells were then blocked with Blocking Buffer (2% (w/v) Difco Skim milk (BD) in PBS, 50-150 µl per well) for 2 hours at room-temperature and washed once with 350 µl Wash Buffer.

The primary antibody was serial diluted 1:2 in V-bottom well 96-well plates (Nunc) at starting concentration of 100 µg/ml in Antibody Buffer (1% (w/v) Bovine Serum Albumin (Sigma) in PBS, 0.05% Tween-20 (Sigma)).

The control antibodies (eg. 6E10 mAb (Sigma) and ACA) were analyzed at a starting concentration of 1 µg/ml 100 µl of primary antibody were transferred in serial dilution to Nunc Maxisorb plates and incubated for 2-3 hours at room-temperature. Wells were washed three times with 350 µl Wash Buffer rapidly.

The secondary antibodies sheep anti-human IgG-HRP and sheep anti-mouse IgG-HRP (Chemicon) were added at 1:1000 in Antibody Buffer (50 µl per well) and incubated for 30 minutes at room-temperature.

Wells were then washed three times with 350 µl Wash Buffer and the plates developed with TMB Substrate (Millipore, Australia) (50 µl per well) for 5 minutes. The reaction was stopped with 2M phosphoric acid (25 µl per well) and the plates were read at 450 nm, 0.1 seconds in Wallac Victor 2 plate reader.

C: Biosensor Analysis of Aβ(1-40) Interaction with Recombinantly Expressed Aβ(21-37) Autoantibodies Peptide Sample Preparation:

Preparation of Peptides for Analysis on Captured Monoclonal Antibodies is as Described in section "Aβ preparation of peptides" above Biosensor Immunoglobulin Capture Surface Preparation:

An anti-human immunoglobulin biosensor chip was prepared using a human antibody capture kit (Biacore, Sweden) as per manufacturer's instructions at flow rate of 5 µl/min with a 6 minute contact time during NHS/ECD immobilisation. Approximately 10000 resonance units were achieved on all channels.

Capture Conditions:

All antibodies were captured (25 µg/ml in 0.1 mg/ml BSA, Hepes buffered saline) at a flow rate of 20 µl/min for 2 mins. In all experiments flow cell 1 served as a baseline subtracted control channel using human IgG1 control antibody (Chemicon, Australia).

The 3 remaining channels were used to capture either control antibody (ACA) or human monoclonal antibodies to test for peptide binding. Peptide binding (60 µl) to the captured antibodies was then analysed at a flow rate of 30 µl/min over all channels simultaneously and allowed to dissociate to for 300-600 seconds prior to desorption from the sensor surface using a 5 µl injection of 3M MgCl$_2$ as per instructions.

All samples were cooled prior to analysis at 12'C using a Multitemp (GE, Sweden) attached to the biosensor 2000 (GE, Sweden).

A second control experiment was performed for all monoclonal antibodies where a 60 µl injection of 0.1 mg/ml BSA, Hepes buffered saline was directly injected post antibody capture to take into account dissociation of human monoclonal antibody from immobilised capture antibody. This result was manually subtracted from data generated using peptides using BIAevaluation software (GE, Sweden).

In all experiments Aβ(1-40 Cys) oligomer was analyzed at 20-50 µg/ml in 0.1 mg/ml BSA, Hepes buffered saline. Aβ(1-40) monomer was diluted from a 1 mg/ml stock in 100% DMSO to 10 µg/ml in 0.1 mg/ml BSA, Hepes buffered saline prior to analysis.

Figure 44:
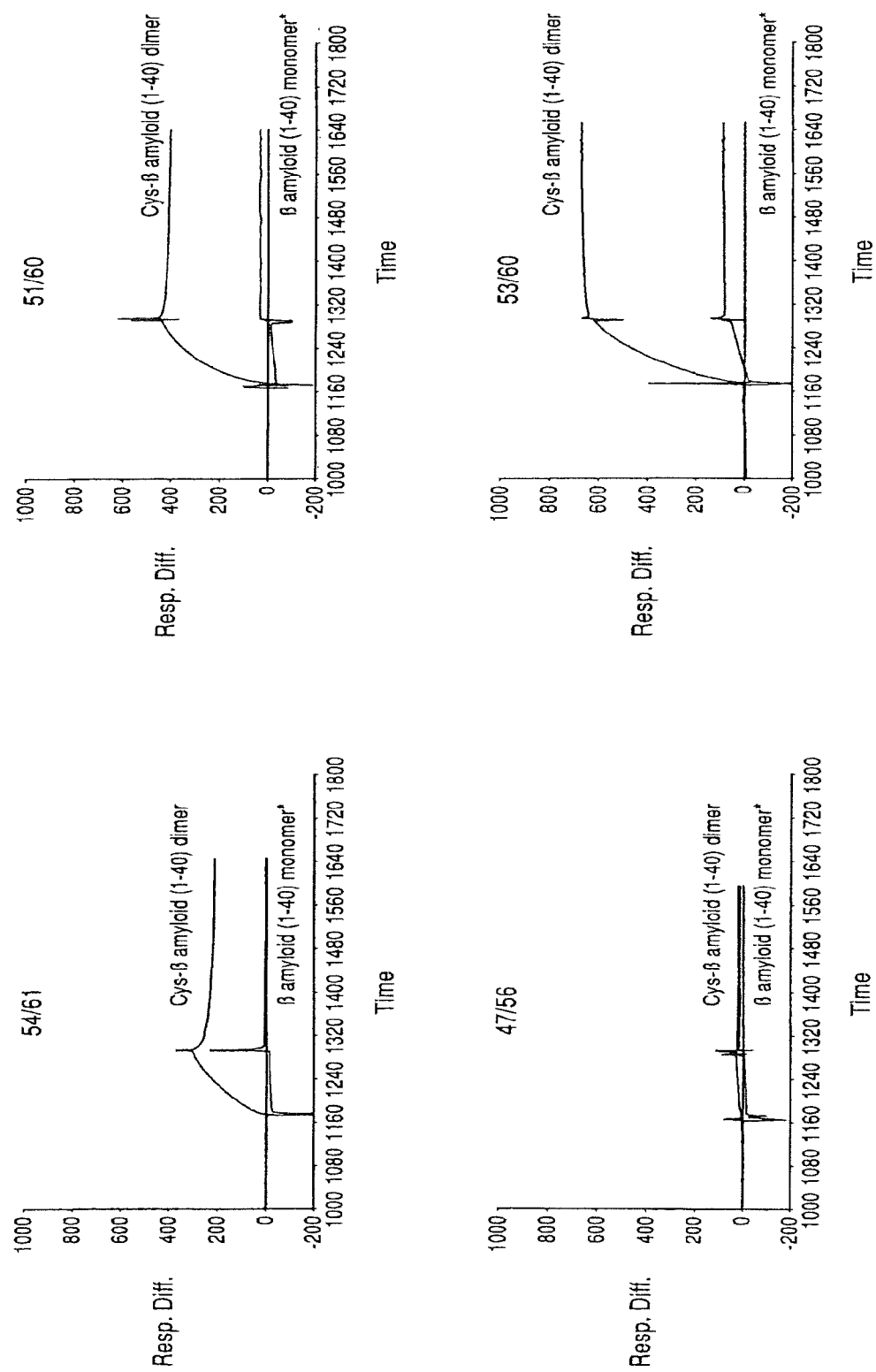

FIGS. 43 to 45 show the results obtained in this analysis. Whereas the ACA control antibody show equal binding to both Aβ(1-40) monomer and Aβ(1-40 Cys) oligomer most antibodies of the invention show a preferential binding to Aβ(1-40 Cys) oligomer.

D: Anti-Beta Amyloid Antibody Tricine SDS-Page and Western Blot Protocol

Novex Pre-cast 10-20% Tricine gels 10-well (Invitrogen) were loaded with 0.5 µg peptide per well in 20 µl (0.5 µg/20 µl=25 µg/ml).

Preparation of molecular weight marker: 20 µl 2× Tricine Sample Buffer—Non-reducing (TSB-NR) (300 mM Tris-HCl, pH 8.45, 24% Glycerol, 8% SDS, 0.005% Coomassie Blue G, 0.005% Phenol Red) were added to 20 µl Pre-stained markers (Bio-Rad), and 20 µl per well were used.

Preparation of the Samples:

100 µl 1×TSB-NR loading samples were prepared as follows

Peptides:

|  | Stock | Dilution | 100 µl |
|---|---|---|---|
| Aβ 1-40 monomer | 1.0 mg/ml | 1/40 | 2.5 µl + 47.5 µl ddH$_2$O + 50 µl 2X TSB-NR |
| Aβ 1-40 oligomer | 0.1 mg/ml | 1/4 | 25 µl + 25 µl ddH$_2$O + 50 µl 2X TSB-NR |
| Aβ 1-40 Cys oligomer | 0.1 mg/ml | 1/4 | 25 µl + 25 µl ddH$_2$O + 50 µl 2X TSB-NR |

Each gel was set up in a 10-lane format as below so that each test antibody was flanked by a molecular weight marker lane and a blank buffer lane. Molecular weight positions have been marked for simplicity.

1) Pre-stained markers
2) Aβ 1-40 monomer
3) Aβ 1-40 oligomer
4) Aβ 1-40 Cys oligomer
5) 1×TSB-NR
6) Pre-stained markers
7) Aβ 1-40 monomer
8) Aβ 1-40 oligomer 9) A/β 1-40 Cys oligomer
10) 1×TSB-NR A further gel was run as above and stained for protein by coomassie and deep purple. The less sensitive Coomassie shows that the peptide is essentially monomer in lanes 2 and 3 and dimer in lane 4 (or lane 7, 8 and 9 respectively which is labeled 1, 2 and 3 in FIGS. 47 and 48). The more sensitive deep purple reveals a ladder of oligomers in each lane, which is consistent with the staining pattern for mabs 6E10 and ACA.

The Tricine gels were run in XCell SureLock Mini-Cell (Invitrogen) with inner and outer buffer chambers containing Tricine SDS Running Buffer (0.1 M Tris Base, 0.1M Tricine, 0.1% SDS). The electrophoretic separation was completed applying 125V for 90 minutes.

The gel was then transferred to nitrocellulose as per Membrane Filter Paper Sandwich (Invitrogen) using the XCell II Blot Module (Invitrogen) in the XCell SureLock Mini-Cell (Invitrogen). The inner XCell H Blot Module chamber was filled with chilled 1× Tris-Glycine Transfer Buffer (12 mM Tris Base, 96 mM glycine, 20% methanol)) and the outer chamber was filled with chilled distilled water.

Transfer was achieved by applying 25V for 1.5 hours and the nitrocellulose membrane was subsequently blocked overnight in 50 ml Blocking Buffer (2% (w/v) Difco Skim milk (BD) in PBS) at 4° C.

The primary antibody, control antibodies 6E10 and ACA were added to the membrane at 0.5 µg/ml and the recombinant Aβ(21-37) antibodies at 10-20 µg/ml in 10 ml, 1% (w/v) Bovine Serum Albumin (Sigma) in PBS, 0.05% Tween-20 (Sigma)) and were incubated with shaking for 2-3 hours. Membranes were washed 3 times for 10 minutes with 50 ml Wash Buffer (IX PBS, 0.05% (v/v) Tween-20 (Sigma)). The secondary antibody, sheep anti-human IgG-HRP and sheep anti-mouse IgG-HRP (Chemicon) was added at 0.5 µg/ml in 10 ml buffer (as above) and incubated with the membrane with shaking for 30 minutes.

The membranes were washed 3 times for 10 minutes with 50 ml Wash Buffer and subsequently developed with ECL Plus (Perkin-Elmer) on Amersham Hyperfilm ECL (GE Lifesciences) (see FIG. 47).

Where the signal was below detection threshold using the above protocol, membranes were washed 3× with Wash buffer and then additionally probed with biotinylated antihuman IgG1 (Sigma Clone 8c/6-39, 1:2000) for 30-60 minute at RT. Membranes were then washed as above. Streptavidin peroxidase (1:4000, Chemicon) was then added for 30 mins and membranes washed again. This additional step amplified the signal and resulted in detection using ECL substrates as indicated above.

An equivalent gel as probed in the western blot analysis was not transferred to nitrocellulose. One half was stained with coomassie blue per manufacturers instructions (Novex, Invitrogen) and the other half was subjected to deep purple high protein sensitivity staining as per manufacturers instructions (GE, Sweden)

Example 13

Plaque Deposition (Taconic Mice)

Antibody Treatment of Transgenic App Mice

APP transgenic mice (Tg2576) at 10 month of age received once a week an i.p. injection of 2041 containing 200 µg (8 g/kg) antibodies for 8 weeks. One animal received an affinity purified Aβ autoantibodies from IVIgG, two animals received a murinized monoclonal antibody against Aβ (CSL Clone 7), and two mice received a negative chimeric monoclonal control antibody (CSL360). At the end of the experimental period, animals were killed by decapitation. The brain was dissected and the hemispheres separated along the midline. One hemisphere was fixed in 4% buffered formaldehyde for 24 h followed by dehydration and paraffin embedding. The other hemisphere was immediately snap-frozen in liquid nitrogen and kept at −80° C.

Plaque Evaluation

Materials:

3 µm thick slices of murine brain tissue mounted on microscope slides from Mentzel Glas and immunostained with 6F3D-Antibody (see protocol: Immunohistochemistry).

Transmitting light microscope: Eclipse 80i, containing Plan Apochromat objectives 2×-40× magnification; Nikon Instruments Europe, Nikon GmbH, Duesseldorf, Germany Imaging Software: NIS-Elements BR software version 2.3, Nikon; Nikon Instruments Europe, Nikon GmbH, Duesseldorf, Germany Digital sight: 2 Megapixel digital camera, Nikon (Nikon Instruments Europe, Nikon GmbH, Duesseldorf, Germany).

Excel Software (Microsoft Office 2003, Microsoft Corp. Redmont, USA.)

Method:

Digital RGB-Pictures were taken using the above-mentioned camera in a 40× magnification. A macro was created by recording every step defining the threshold of intensity, minimum and maximum diameter, excluding e.g. vessels ("objects with holes in the middle") to ensure equal parameters for every analysis. The area of interest was defined by applying a measurement frame. Within this area, the aforementioned criteria were used to identify "objects" (cluster of pixels) fitting into the scheme provided by the macro. A binary picture was created by the software for background subtraction. Five independent fields per location were analyzed (Cortex and Hippocampal formation were evaluated separately). Data of the five analyses were summarized by the software and a small statistical analysis was provided, like number of plaques per measured area, the quotient of plaque area and measured area as percentage. Detailed data of every object were transmitted into an excel file for further analysis.

TABLE 3

| | |
|---|---|
| Number of Fields | 1 |
| Number of Objects | 7 |
| Objects per Field | 7 |
| Measured Area | 33152.5 [µm*µm] |
| Objects per Area | 0.000211146/[µm *µm] |
| Area Fraction | 0.152147 |

| Feature | Mean | St.Dev | Minimum | Maximum |
|---|---|---|---|---|
| Area | 720.58 | 1438.5 | 0.072697 | 4222.5 |
| EqDiameter | 19.112 | 23.499 | 0.30424 | 73.323 |
| Perimeter | 106.58 | 169.48 | 0.94227 | 514.37 |
| Width | 7.5773 | 5.9398 | 0.20097 | 17.626 |
| Circularity | 0.70335 | 0.24485 | 0.20055 | 1 |
| MeasuredArea | 33152 | 0 | 33152 | 33152 |

Of special importance is the "Area fraction" as it equals the percentage of plaque area (the marked area) from the measured area (total area).

Measured Features:

Area

Area is a principal size criterion. In a non-calibrated system, it expresses the number of pixels; in a calibrated one, it expresses the real area (given in µm²).

Area Fraction

Area Fraction is the ratio of the segmented image area and the Measured Area (defined as: square unit over selected fields).

Area Fraction=Area/Measured Area

Circularity

Circularity equals "1" only for circles; all other shapes are characterized by circularity values smaller than "1". It is a derived shape measure, calculated from the area and perimeter. This feature is useful for examining shape characteristics.

Circularity=4*π*Area/Perimeter$^2$

EqDiameter

The equivalent diameter (EqDiameter) is a size feature derived from the area. It determines the diameter of a circle with the same area as the measured object:

EqDiameter=√(4*Area/π)

Object Per Area

Number of objects per square unit over selected fields (measured area),

Perimeter

Perimeter is the total boundary measure. It includes both the outer and inner boundary (if there are holes within an object). The perimeter is calculated from four projections in the directions 0, 45, 90 and 135 degrees using Crofton's formula.

Perimeter=π*(Pr0+Pr45+Pr90+Pr135)/4

Width

Width is a derived feature appropriate for elongated or thin structures. It is based on the rod model and is calculated according to:

Width=Area/Length

Example 14

Evidence that the Antibodies of the Invention do not Show Vessel Staining

Methods:

3 μm paraffin slices were cut from post-mortem brain material of a patient suffering from Alzheimer's disease and cerebral amyloid angiopathy (CAA) using the HM 355 S rotary microtome from Microm (MICROM International GmbH, Walldorf, Germany) and mounted on SuperFrost Plus microscope slides from Menzel-Glaeser (Menzel-Glaeser GmbH & Co. KG Braunschweig, Germany). All protocol steps were performed at room temperature if not stated otherwise.

De-paraffining of the microscope slides was performed according to the following protocol: xylene (4 changes), 96% ethanol (3 changes), 70% ethanol (3 changes) followed by 2 changes of de-ionised water. Each step was performed for 3 minutes.

As pre-treatment for the antigen retrieval, slides were incubated in 70% (v/v) formic acid in PBS for 20 minutes, replaced by de-ionised water and two changes of PBS as washing steps. The endogenous peroxidase was blocked for 30 minutes using 1% (v/v) $H_2O_2$ in Methanol. To prevent unspecific staining, slides were incubated for 30 minutes with diluted goat serum (according to the Vectastain® Elite ABC Kit instructions) or for one hour with diluted mouse IgG (according to the Vectastain® M.O.M.-Kit instructions), respectively. The blocking solutions were removed, no washing step was used.

After the blocking step, primary antibodies were applied to the slides in a dilution of 1:100 in Vectastain® Elite ABC Kit diluent or 1:50 (6F3D, according to the manufacturer's instructions) in Vectastain® M.O.M.-Kit diluent. Negative controls were carried along consisting of one slide without any antibody or detection system, two slides without primary antibody, but with the Vectastain® Elite ABC Kit or the Vectastain® M.O.M.-Kit secondary system, respectively, and two slides with clone 53/60 recombinant human anti β-amyloid immunoglobulin or the 6F3D antibody, respectively, and without any detection system.

The slides were incubated with the primary antibodies overnight (18 hrs) at 4° C. in a humid chamber. The day after, the slides were washed twice for 2 minutes with PBS. Afterwards, the slides were incubated for 30 minutes with biotinylated anti-mouse antibody (6F3D antibody) or biotinylated anti-human antibody (diluted according to the Vectastain® Elite ABC Kit or the Vectastain® M.O.M.-Kit instructions). The slides were washed twice for 2 minutes with PBS. Subsequently, the slides were incubated for 30 minutes with the Vectastain® Elite ABC reagent according to the instructions of the Vectastain® Elite ABC Kit and the Vectastain® M.O.M.-Kit. This step was followed by two washing steps with PBS for 2 minutes. Afterwards, the DAB reagent was applied for 5 minutes (according to the manufacturer's instructions) as chromogen. This reaction was stopped by a washing step in de-ionised water for 5 minutes. A 10 second dip in Mayer's acid haemalaun-solution followed by blueing for 5 minutes in running tap-water served as a counterstain Dehydration was performed by putting the slides into a sequence of 70% (v/v) ethanol (3 times), 96% ethanol (3 times), isopropanol (once), xylene (4 times) for 30 seconds each. The slides were air-dried and mounted with RotiHistokit® and coverslips from Menzel-Glas. Images were taken using the Nikon Eclipse 80i microscope with a Nikon digitalsight 2 Megapixel camera and the Nikon MS-Elements BR version 2.3 software.

The results shown in FIGS. 48a to 48f demonstrate that neither the affinity purified autoantibodies (purified as in Example 4) nor mab CSL Clone 7 (see Example 5) show staining of the vessel walls, whereas the anti-Aβ antibody ACA (see Example 5) shows a staining of the vessel walls, comparable to that of the antibody 6F3D which was used as a positive control. Such results suggest that the antibodies of the invention will not trigger adverse events which are believed to be caused by Aβ antibodies binding to Aβ deposited brain vessels (Pfeifer M, et al. Cerebral hemorrhage after passive anti-Abeta immunotherapy. *Science* 298:1379. Herzig M C, et al (2004): Abeta is targeted to the vasculature in a mouse model of hereditary cerebral hemorrhage with amyloidosis. *Nat Neurosci* 7:954-960).

We claim:

1. A method of treating a neurodementing disease in a patient comprising administering to said patient a therapeutically acceptable amount of an antibody, wherein the antibody comprises:
    a full set of six CDRs, three from the variable heavy chain region (VH) (SEQ ID NOs: 15, 23 and 29) and three from the variable light chain region (VL) (SEQ ID NOs: 33, 41 and 45); or
    a full set of six CDRs, three from the variable heavy chain region (VH) (SEQ ID NOs: 13, 21 and 28) and three from the variable light chain region (VL) (SEQ ID NOs: 34, 38 and 44); or
    a full set of six CDRs, three from the variable heavy chain region (VH) (SEQ ID NOs: 14, 27 and 30) and three from the variable light chain region (VL) (SEQ ID NOs: 33, 42 and 44); or
    the three CDRs from the VL and the three CDRs from the VH amino acid sequence pairs of SEQ ID NO: 53 and SEQ ID NO: 60, SEQ ID NO: 47 and SEQ ID NO: 56, SEQ ID NO: 48 and SEQ ID NO: 57, SEQ ID NO: 145 and SEQ ID NO: 60, SEQ ID NO: 51 and SEQ ID NO: 60, SEQ ID NO: 52 and SEQ ID NO: 60, SEQ ID NO: 146 and SEQ ID NO: 60, SEQ ID NO: 53 and SEQ ID NO: 148, SEQ ID NO: 55 and SEQ ID NO: 61, SEQ ID NO: 145 and SEQ ID NO: 62, SEQ ID NO: 54 and SEQ ID NO: 60, SEQ ID NO: 54 and SEQ ID NO: 61, SEQ ID NO: 54 and SEQ ID NO: 148, SEQ ID NO: 145 and SEQ ID NO: 148, or SEQ ID NO: 146 and SEQ ID NO: 61;
    wherein said antibody binds to dimeric forms of Aβ with higher affinity than to monomeric forms of Aβ;
    and wherein the neurodementing disease is selected from the group consisting of Alzheimer's disease, Down's syndrome, dementia with Lewy bodies, fronto-temporal dementia and cerebral amyloid angiopathy.

2. The method of claim 1, wherein the antibody binds to a peptide comprising Aβ(21-37) (SEQ ID NO: 2).

3. The method of claim 1, wherein the antibody shields residues of Aβ(21-37) from proteolytic digestion when being bound to an Aβ polypeptide comprising Aβ(21-37).

4. The method of claim 1, wherein the antibody binds specifically to Aβ partial polypeptides Aβ(12-40) or Aβ(20-37) when said antibody is coupled to NHS-activated 6-aminohexanoic acid-coupled sepharose, but does not bind specifically to Aβ(17-28), Aβ(25-35) or Aβ(31-40).

5. The method of claim 1, wherein the antibody shields residues of Aβ(21-37) from proteolytic digestion when being bound to an Aβ polypeptide comprising Aβ(21-37).

6. The method of claim 1 wherein the antibody is administered intravenously at a dose between 0.01 mg/kg to 100 mg/kg.

7. The method of claim 1, wherein the antibody is administered to the brain.

* * * * *